US007932257B2

(12) United States Patent
Oslob et al.

(10) Patent No.: US 7,932,257 B2
(45) Date of Patent: Apr. 26, 2011

(54) SUBSTITUTED PYRAZOLO[4,3-D]PYRIMIDINES AS AURORA KINASE INHIBITORS

(75) Inventors: Johan D. Oslob, Sunnyvale, CA (US); Chul Hyun Yu, Foster City, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 11/490,983

(22) Filed: Jul. 21, 2006

(65) Prior Publication Data
US 2007/0027166 A1    Feb. 1, 2007

Related U.S. Application Data

(60) Provisional application No. 60/701,695, filed on Jul. 22, 2005.

(51) Int. Cl.
C07D 487/04     (2006.01)
A61K 31/519    (2006.01)
A61P 35/00      (2006.01)
A61P 25/28      (2006.01)
A61P 29/00      (2006.01)
C07D 487/06     (2006.01)

(52) U.S. Cl. ............ 514/262.1; 544/262; 544/251; 514/250

(58) Field of Classification Search .......... 544/262; 514/262.1, 252.16, 251
See application file for complete search history.

(56) References Cited

U.S. PATENT DOCUMENTS

| 2,980,677 | A | 4/1961 | Druey et al. | |
| 5,654,307 | A | 8/1997 | Bridges | 514/258 |
| 5,723,608 | A | 3/1998 | Yuan | 544/118 |
| 5,760,028 | A | 6/1998 | Jadhav | 514/211 |
| 5,929,046 | A | 7/1999 | McMurry | 514/45 |
| 6,043,228 | A | 3/2000 | McMurry | 514/45 |
| 6,096,724 | A | 8/2000 | McMurry | 514/45 |
| 6,214,834 | B1 | 4/2001 | Jadhav | 514/275 |
| 6,288,078 | B1 | 9/2001 | Walsh | 514/303 |
| 6,506,762 | B1 | 1/2003 | Horvath | 514/259.4 |
| 6,552,192 | B1 | 4/2003 | Hanus | 514/280 |
| 7,119,200 | B2 | 10/2006 | Guzi et al. | |
| 7,148,228 | B2 | 12/2006 | Kasibhatla et al. | |
| 2001/0007867 | A1 | 7/2001 | Chen | 554/183 |
| 2003/0187261 | A1 | 10/2003 | Havlicek | 544/264 |
| 2004/0157851 | A1 | 8/2004 | Haddach et al. | 514/350 |
| 2005/0059650 | A1 | 3/2005 | Jones | 514/262.1 |

FOREIGN PATENT DOCUMENTS

| EP | 1475094 | * 11/2004 |
| WO | WO 94/13668 | 6/1994 |
| WO | WO 95/19774 | 7/1995 |
| WO | WO 97/20843 | 6/1997 |
| WO | WO 97/23480 | 7/1997 |
| WO | WO 98/08847 | 3/1998 |
| WO | WO 98/43962 | 10/1998 |
| WO | WO 00/43394 | 7/2000 |
| WO | WO 00/53185 | 9/2000 |
| WO | WO 00/53602 | 9/2000 |
| WO | WO 01/23389 | 4/2001 |
| WO | WO 01/49688 | 7/2001 |
| WO | WO 03/055491 | 7/2003 |
| WO | WO 03/082872 | 10/2003 |
| WO | WO 2004/065392 | 8/2004 |
| WO | WO 2004/096810 | 11/2004 |
| WO | WO 2004/098698 | 11/2004 |
| WO | WO 2005/07658 | 1/2005 |
| WO | WO 2005/39506 | 5/2005 |
| WO | WO 2005/82865 | 9/2005 |

OTHER PUBLICATIONS

Moravcova et. al. (Bioorg. Med. Chem. Lett. 2003, 13, 2989-2992).*
Dhainaut, et al. "New Purines and Purine Analogs as Modulators of Multidrug Resistance" *Journal of Medicinal Chemistry* (1996), 39(20), 4099-4108.
Kim, et al. "Synthesis and biological evaluations of pyrazolo[3,4-d]pyrimidines as cyclin-dependent kinase 2 inhibitors" *European Journal of Medicinal Chemistry* (2003), 38(5), 525-532.
Quintela, et al. "6-Dimethylamino 1H-Pyrazolo[3,4-d]pyrimidine derivatives as new inhibitors of inflammatory mediators in intact cells" *Bioorganic & Medicinal Chemistry* (2003), 11(6), 863-868.
Quintela, et al. "Pyrazolopyrimidines: synthesis, effect on histamine release from rat peritoneal mast cells and cytotoxic activity" *European Journal of Medicinal Chemistry* (2001), 36(4), 321-332.

* cited by examiner

*Primary Examiner* — Susanna Moore
(74) *Attorney, Agent, or Firm* — Choate, Hall & Stewart LLP; Andrea L. C. Robidoux; Emilie Porter Huck

(57) ABSTRACT

The present invention provides compounds having the formula:

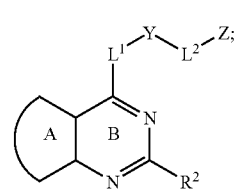

wherein A-B together represent one of the following structures:

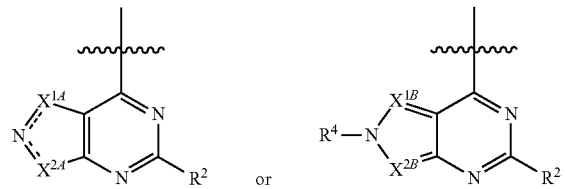

wherein one of ---- is a double bond, as valency permits; and $R^2$, $R^4$, $X^{1A}$, $X^{2A}$, $X^{1B}$, $X^{2B}$, $L^1$, $L^2$, Y and Z are as defined in classes and subclasses herein, and pharmaceutical compositions thereof, as described generally and in subclasses herein, which compounds are useful as inhibitors of protein kinase (e.g., Aurora), and thus are useful, for example, for the treatment of Aurora mediated diseases.

39 Claims, 2 Drawing Sheets

Western Blot of Compound B, 100mpk, 10 (10-12) hour post dose.

| Time (hr) | Animal # | % pHH3 inhibition | Average | STDEV |
|---|---|---|---|---|
| 10 | 10 | 81.28 | 85.58 | 7.16 |
|  | 11 | 81.61 |  |  |
|  | 12 | 93.85 |  |  |

| Compound# | Aurora A (μM) | Aurora B (μM) | HCS CC (μM) | HCS pHH3 (μM) |
|---|---|---|---|---|
| A | 0.010 | 0.021 | 0.016 | 0.035 |
| B | 0.006 | 0.018 | 0.016 | 0.011 |
| C | 0.005 | 0.010 | 0.011 | 0.017 |
| D | 0.069 | 0.032 | 0.190 | 0.210 |
| E | 0.004 | 0.085 | 0.041 | 0.048 |
| F | 0.047 | 0.250 | 0.073 | 0.110 |
| G | 0.024 | 0.003 | 0.054 | 0.008 |

Figure 2

SUBSTITUTED PYRAZOLO[4,3-D]PYRIMIDINES AS AURORA KINASE INHIBITORS

PRIORITY

The present application claims priority under 35 U.S.C. 119(e) to U.S. Provisional Patent Application No. 60/701,695 filed Jul. 22, 2005, the entire contents of which are incorporated herein by reference.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor $\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

The Aurora family of serine/threonine kinases plays an important role in cell proliferation. The three known mammalian family members, Aurora-A ("2"), B ("1") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. Elevated levels of all Aurora family members are observed in a wide variety of tumor cell lines. For example, the Aurora-2 protein has been found to be overexpressed in human colon cancer tissue [Bischoff et al., *EMBO J.* 1998, 17, 3052-3065; Schumacher et al., *J. Cell Biol.* 1998, 143, 1635-1646; Kimura et al., *J. Biol. Chem.* 1997, 272, 13766-13771]. Aurora-2 has been implicated in human cancer, such as colon, breast and other solid tumors. This kinase is involved in protein phosphorylation events that regulate the cell cycle. Specifically, Aurora-2 plays a role in controlling the accurate segregation of chromosomes during mitosis. Thus, Aurora inhibitors have an important role in the treatment of Aurora-mediated diseases.

Accordingly, there is a great need to develop compounds useful as inhibitors of protein kinases. In particular, it would be desirable to develop compounds that are useful as inhibitors of Aurora, particularly given the inadequate treatments currently available for the majority of the disorders implicated in their activation.

SUMMARY OF THE INVENTION

As discussed above, there remains a need for the development of novel therapeutic agents and agents useful for treating disorders mediated by Aurora. In certain embodiments, the present invention provides novel compounds having the structure:

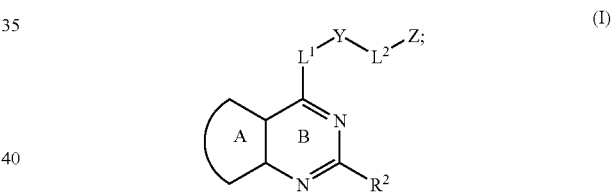

wherein A-B together represent one of the following structures:

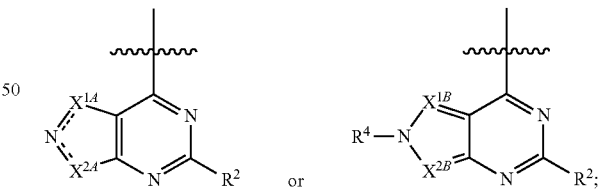

wherein one of ----- is a double bond, as valency permits; and $R^2$, $R^4$, $X^{1A}$, $X^{2A}$, $X^{1B}$, $X^{2B}$, $L^1$, $L^2$, Y and Z are as defined in classes and subclasses herein, and pharmaceutical compositions thereof, as described generally and in subclasses herein, which compounds are useful as inhibitors of protein kinase (e.g., Aurora), and thus are useful, for example, for the treatment of Aurora mediated diseases.

In certain other embodiments, the invention provides pharmaceutical compositions comprising an inventive compound, wherein the compound is present in an amount effective to inhibit Aurora activity. In certain other embodiments, the invention provides pharmaceutical compositions comprising an inventive compound and optionally further comprising an additional therapeutic agent. In yet other embodiments, the additional therapeutic agent is an agent for the treatment of cancer.

In yet another aspect, the present invention provides methods for inhibiting kinase activity (e.g., Aurora) activity in a patient or a biological sample, comprising administering to said patient, or contacting said biological sample with an effective inhibitory amount of a compound of the invention. In still another aspect, the present invention provides methods for treating any disorder involving Aurora activity, comprising administering to a subject in need thereof a therapeutically effective amount of a compound of the invention.

BRIEF DESCRIPTION OF THE DRAWING

FIG. 2 depicts an exemplary western blot experiment of compound B using anti-Histone H3 and anti-phosphorylated Histone H3 antibodies as probes.

DEFINITIONS

Figure 1:
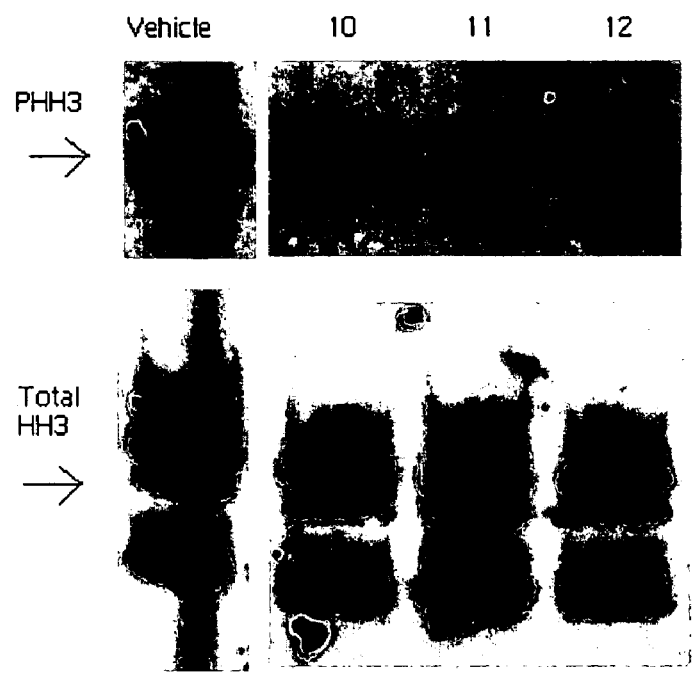
FIG. 1 depicts exemplary biochemical assay data ($IC_{50}$ values) for selected compounds of the invention. The compounds were evaluated in: (i) Aurora A kinase inhibition assay, (ii) Aurora B kinase inhibition assay, (iii) HCS cell cycle assay and (iv) Phospho-Histone H3 HCS assay.

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$;— or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC (=S)—, —SC(=S)S—, —C(=$NR^{G2}$)—, —C(=$NR^{G2}$) O—, —C(=$NR^{G2}$)$NR^{G3}$—, —OC(=$NR^{G2}$)—, $NR^{G2}$C (=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norborbyl moieties and the like, which again, may bear one or more substituents.

The term "cycloalkyl", as used herein, refers specifically to cyclic alkyl groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, i.e., in place of carbon atoms. Thus, a 1-6 atom heteroaliphatic linker having at least one N atom in the heteroaliphatic main chain, as used herein, refers to a $C_{1-6}$ aliphatic chain wherein at least one carbon atom is replaced with a nitrogen atom, and wherein any one or more of the remaining 5 carbon atoms may be replaced by an oxygen, sulfur, nitrogen, phosphorus or silicon atom. As used herein, a 1-atom heteroaliphatic linker having at least one N atom in the heteroaliphatic main chain refers to —NH— or —NR— where R is aliphatic, heteroaliphatic, acyl, aromatic, heteroaromatic or a nitrogen protecting group. Heteroaliphatic moieties may be branched or linear unbranched. In certain embodiments, heteroaliphatic moieties are substituted by independent replacement of one or more of the hydrogen atoms thereon with one or more moieties including, any of the substituents described above.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to stable substituted or unsubstituted unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -(alkyl)aromatic, (heteroalkyl)aromatic, -(alkyl)heteroaromatic, and -heteroalkyl) heteroaromatic moieties. Thus, as used herein, the phrases "aromatic or heteroaromatic moieties" and "aromatic, heteroaromatic, -alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound.

The terms "alkoxy" (or "alkyloxy"), and "thioalkyl" as used herein refers to an alkyl group, as previously defined, attached to the parent molecular moiety through an oxygen atom ("alkoxy") or through a sulfur atom ("thioalkyl"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy. Examples of thioalkyl groups include, but are not limited to, methylthio, ethylthio, propylthio, isopropylthio, n-butylthio, and the like.

The term "amine" refers to a group having the structure —N(R)$_2$ wherein each occurrence of R is independently hydrogen, or an aliphatic, heteroaliphatic, aromatic or heteroaromatic moiety, or the R groups, taken together, may form a heterocyclic moiety.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

The terms "halo" and "halogen" as used herein refer to an atom selected from fluorine, chlorine, bromine and iodine.

The term "halogenated" denotes a moiety having one, two, or three halogen atoms attached thereto.

The term "haloalkyl" denotes an alkyl group, as defined above, having one, two, or three halogen atoms attached thereto and is exemplified by such groups as chloromethyl, bromoethyl, trifluoromethyl, and the like.

The term "acyloxy", as used herein, does not substantially differ from the common meaning of this term in the art, and refers to a moiety of structure —OC(O)Rx, wherein Rx is a substituted or unsubstituted aliphatic, alicyclic, heteroaliphatic, heteroalicyclic, aryl or heteroaryl moiety.

The term "acyl", as used herein, does not substantially differ from the common meaning of this term in the art, and refers to a moiety of structure —C(O)Rx, wherein Rx is a substituted or unsubstituted, aliphatic, alicyclic, heteroaliphatic, heteroalicyclic, aryl or heteroaryl moiety.

The term "imino", as used herein, does not substantially differ from the common meaning of this term in the art, and refers to a moiety of structure —C(=NR$_X$)R$_Y$, wherein R$_X$ is hydrogen or an optionally substituted aliphatic, alicyclic, heteroaliphatic, heteroalicyclic, aryl or heteroaryl moiety; and R$_Y$ is an optionally substituted aliphatic, alicyclic, heteroaliphatic, heteroalicyclic, aryl or heteroaryl moiety.

The term "$C_{1-6}$alkylene", as used herein, refers to a substituted or unsubstituted, linear or branched saturated divalent radical consisting solely of carbon and hydrogen atoms, having from one to six carbon atoms, having a free valence "—" at both ends of the radical.

The term "$C_{2-6}$alkenylene", as used herein, refers to a substituted or unsubstituted, linear or branched unsaturated divalent radical consisting solely of carbon and hydrogen atoms, having from two to six carbon atoms, having a free valence "—" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like, used alone or as part of a larger moiety, encompass both substituted and unsubstituted groups.

As used herein, the term "isolated", when applied to the compounds of the present invention, refers to such compounds that are (i) separated from at least some components with which they are associated in nature or when they are made and/or (ii) produced, prepared or manufactured by the hand of man.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety that is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "Aurora-mediated disease" or "Aurora-mediated condition", as used herein, means any disease or other deleterious condition in which Aurora is known to play a role. The terms "Aurora-mediated disease" or "Aurora-mediated condition" also mean those diseases or conditions that are alleviated by treatment with an Aurora inhibitor. Such conditions include, without limitation, colon, breast, stomach, and ovarian cancer. The term "Aurora-mediated disease", as used herein, means any disease or other deleterious condition or disease in which Aurora is known to play a role. Such diseases or conditions include, without limitation, cancers such as colon and breast cancer.

The term "treating", as used herein generally means that the compounds of the invention can be used in humans or animals with at least a tentative diagnosis of disease. In certain embodiments, compounds of the invention will delay or slow the progression of the disease thereby giving the individual a longer life span.

The term "preventing" as used herein means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of disease, or prevent the individual from developing the disease at all. Preventing also includes administration of the compounds of the invention to those individuals thought to be predisposed to the disease due to familial history, genetic or chromosomal abnormalities, and/or due to the presence of one or more biological markers for the disease.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF CERTAIN PREFERRED EMBODIMENTS OF THE INVENTION

As noted above, there has been increasing interest in recent years in the development of protein kinase inhibitors, particularly Aurora inhibitors, as therapeutic agents for the treatment of diseases/conditions involving protein kinase-mediated events. In one aspect, the present invention provides Aurora inhibitors.

Compounds of this invention include those generally set forth above and described specifically herein, and are illustrated in part by the various classes, subgenera and species disclosed herein. Additionally, the present invention provides pharmaceutically acceptable derivatives of the inventive compounds, and methods of treating a subject using these compounds, pharmaceutical compositions thereof, or either of these in combination with one or more additional therapeutic agents.

1) General Description of Compounds of the Invention

In certain embodiments, the compounds of the invention include compounds of the general formula (I) as further defined below:

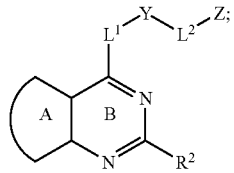

wherein A-B together represent one of the following structures:

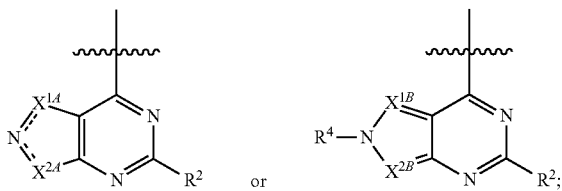

and pharmaceutically acceptable derivatives thereof;

wherein one of ----- is a double bond, as valency permits;

$R^2$ is hydrogen, halogen, cyano, nitro, or an aliphatic, heteroaliphatic, alicyclic, heteroalicyclic, aromatic or heteroaromatic moiety;

$R^4$ is hydrogen, or an aliphatic, heteroaliphatic, alicyclic, heteroalicyclic, aromatic or heteroaromatic moiety;

$X^{1A}$ is $NR^1$ or $—C(R^{X1})—$; wherein $R^1$ taken together with a moiety present on $L^1$ may form an optionally substituted heterocyclic ring;

$X^{2A}$ is $NR^3$ or $—C(R^{X1})—$; wherein one of $X^{1A}$ and $X^{2A}$ is $—C(R^{X1})—$, but not both;

$X^{1B}$ and $X^{2B}$ are $—N—$ or $—C(R^{X1})—$; whereby one of $X^{1B}$ and $X^{2B}$ is $—C(R^{X1})—$, but not both;

wherein $R^1$ and $R^3$ are independently hydrogen, a nitrogen protecting group, or an aliphatic, heteroaliphatic, alicyclic, heteroalicyclic, aromatic or heteroaromatic moiety; and $R^{X1}$ is hydrogen, halogen, cyano, nitro, or an aliphatic, heteroaliphatic, alicyclic, heteroalicyclic, aromatic or heteroaromatic moiety;

$L^1$ is a 2-8 atom heteroaliphatic linker having at least one N, O or S atom in the heteroaliphatic main chain;

$L^2$ is a 1-6 atom heteroaliphatic linker having at least one N atom in the heteroaliphatic main chain;

Y is an alicyclic, heteroalicyclic, aromatic or heteroaromatic moiety; and

Z is an aliphatic, heteroaliphatic, alicyclic, heteroalicyclic, aromatic or heteroaromatic moiety.

In certain embodiments, the following groups do not occur simultaneously as defined: A-B together represent

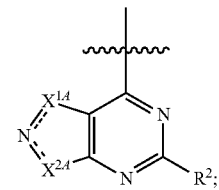

$X^{1A}$ is $NR^1$ and $X^{2A}$ is $CR^{X1}$ or $X^{1A}$ is $CR^{X1}$ and $X^{2A}$ is $NR^3$; $L^1$ is $—X(CHR^x)_{0-2}—$, wherein X is O, S, NH or $NC_{1-4}$alkyl, and $R^x$ is H or $C_{1-4}$alkyl; Y is phenyl, thienyl, furanyl, pyrrolyl, pyridyl, pyrimidyl, imidazolyl, pyrazinyl, oxazolyl, thiazolyl, naphthyl, benzothienyl, benzofuranyl, indolyl, quinolinyl, isoquinolinyl or quinazolinyl; and $L^2$-Z is lower alkyl (1-4 carbon atoms), cycloalkyl (3-8 carbon atoms), lower alkoxy (1-4 carbon atoms), cycloalkoxy (3-8 carbon atoms), lower perfluoroalkyl (1-4 carbon atoms), lower acyloxy (1-4 carbon atoms; —OC(O)R), amino, lower mono or dialkylamino (1-4 carbon atoms), lower mono or dicycloalkylamino (3-8 carbon atoms), hydroxymethyl, lower acyl (1-4 carbon atoms; —C(O)R), lower thioalkyl (1-4 carbon atoms), lower sulfinylalkyl (1-4 carbon atoms), lower sulfonylalkyl (1-4 carbon atoms), thiocycloalkyl (3-8 carbon atoms), sulfinylcycloalkyl (3-8 carbon atoms), sulfonylcycloalkyl (3-8 carbon atoms), sulfonamido, lower mono or dialkylsulfonamido (1-4 carbon atoms), mono or dicycloalkylsulfonamido (3-8 carbon atoms), mercapto, carboxy, carboxamido (—C(O)$NH_2$), lower mono or dialkylcarboxamido (1-4 carbon atoms), mono or dicycloalkylcarboxamido (3-8 carbon atoms), lower alkoxycarbonyl (1-4 carbon atoms), cycloalkoxycarbonyl (3-8 carbon atoms), lower alkenyl (2-4 carbon atoms), cycloalkenyl (4-8 carbon atoms), lower alkynyl (2-4 carbon atoms).

In certain embodiments, the following groups do not occur simultaneously as defined: A-B together represent

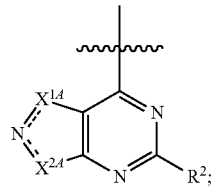

$X^{1A}$ is $NR^1$ and $X^{2A}$ is $CR^{X1}$ or $X^{1A}$ is $CR^{X1}$ and $X^{2A}$ is $NR^3$; $R^{X1}$ is hydrogen, halo, nitro, $C_{1-6}$alkyl, $C_{1-6}$alkoxy, —$CONR^aR^b$, —$O(CH_2)_nNR^aR^b$, —$(CH_2)_nNR^aR^b$ or —$NR^aR^b$; $L^1$ is —$NHCH_2$—; $Y-L^2-Z$ is pyridinyl, pyrimidinyl, indazolyl, dihydroisoindolyl, benzisoxazolyl, oxazolyl, imidazolyl, oxadiazolyl or thiazolyl each optionally substituted with halo, $C_{1-6}$alkyl, $C_{1-6}$alkoxy, —$O(CH_2)_nNR^xR^y$, —$O(CH_2)_nOR^x$, —$NR^xR^y$, $(CH_2)_nNR^xR^y$, —$CH_2OR^x$, —$COOR^x$, —$CONR^xR^y$, —$CH_2SO_2NR^xR^y$, —$SO_2NR^xR^y$, or optionally substituted phenyl; and $R^2$ is pyridin-2-yl, $C_{1-6}$alkylpyridin-2-yl, $C_{1-6}$alkylpyrrol-2-yl or $C_{1-6}$alkylthiazol-2-yl; wherein $R^a$ is H or $C_{1-4}$alkyl, $R^b$ is $C_{1-4}$alkyl, or $R^a$ and $R^b$ together for a 3-7-membered heterocyclic ring; and $R^x$ and $R^y$ are independently H or $C_{1-6}$alkyl.

In certain embodiments, for compounds of formula (I), no occurrence of $R^1$, $R^3$, $R^4$ or $R^{X1}$ is $Q^1$, $Q^2$ or $Q^3$, wherein $Q^1$ is —$(CR^{1A}R^{1B})_mC\equiv C-(CR^{1A}R^{1B})_tR^{1C}$, —$(CR^{1A}R^{1B})_mC\equiv C-(CR^{1A}R^{1B})_tR^{1C}$, —$C=NOR^{1D}$, or —$X^3R^{1D}$ wherein m is an integer from 0 to 3, t is an integer from 0 to 5, and $X^3$ is a divalent group derived from azetidine, oxetane or a $C_{3-4}$carbocyclic group;

$Q^2$ is —$(CR^{1A}R^{1B})_nC\equiv C-(CR^{1A}R^{1B})_kR^{1E}$, —$(CR^{1A}R^{1B})_mC\equiv C-(CR^{1A}R^{1B})_kR^{1E}$ wherein k is an integer from 1 to 3 and m is an integer from 0 to 3; and $Q^3$ is —$(CR^{1A}R^{1B})_tR^{1C}$, wherein t is an integer from 0 to 5 and the attachment point to $R^{1C}$ is through a carbon atom of the $R^{1C}$ group; wherein $R^{1A}$ and $R^{1B}$ are independently H or $C_{1-6}$alkyl; $R^{1C}$ is an optionally substituted non-aromatic monocyclic ring, a fused or bridged bycyclic ring or a spirocyclic ring; $R^{1E}$ is —$NR^{1A}R^{1D}$ or —$OR^{1D}$; $R^{1D}$ is $R^{1F}$, —$C(=O)R^{1F}$, —$SO_2R^{1F}$, —$C(=O)N(R^{1F})_2$, —$SO_2N(R^{1F})_2$, or —$CO_2R^{1F}$, wherein $R^{1F}$ is H, $C_{1-6}$alkyl, $(CR^{1A}R^{1B})_t(C_{6-10}aryl)$ or —$(CR^{1A}R^{1B})_t$(4-10 membered heterocyclic).

In certain embodiments, the present invention defines particular classes of compounds which are of special interest. For example, one class of compounds of special interest includes compounds of formulae ($I^{A1}$) though ($I^{A4}$):

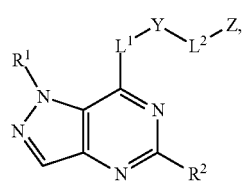

(I^{A1})

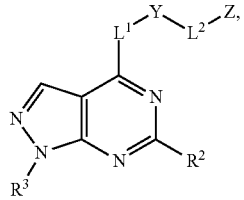

(I^{A2})

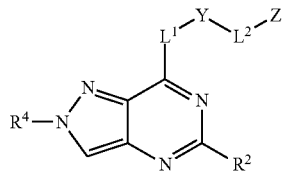

(I^{A3})

or

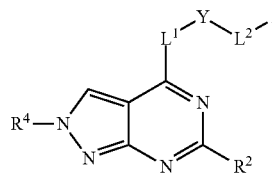

(I^{A4})

Another class of compounds of special interest includes compounds of formula 3 ($I^{B1}$) though ($I^{B4}$):

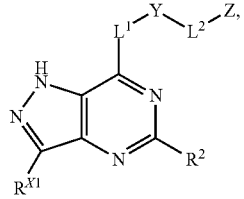

(I^{B1})

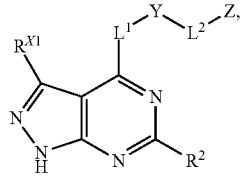

(I^{B2})

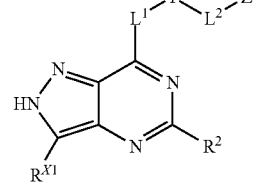

(I^{B3})

or

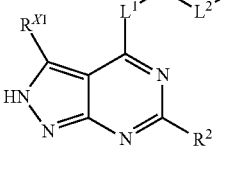

(I^{B4})

Another class of compounds of special interest includes compounds of formulae ($I^{C1}$) through ($I^{C4}$):

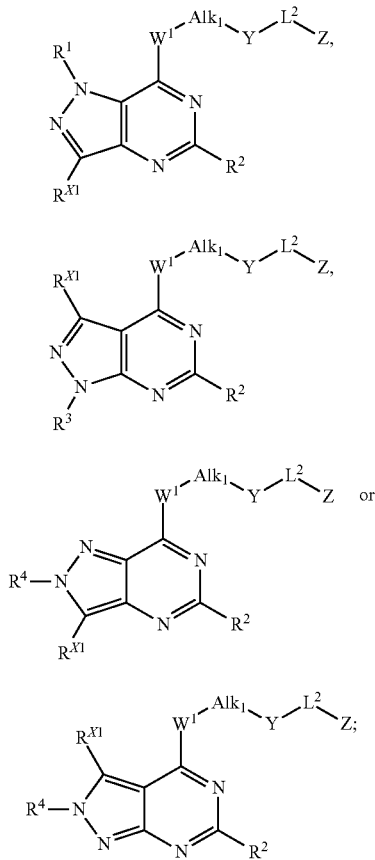

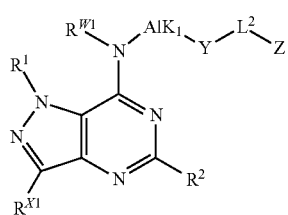

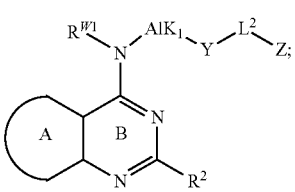

wherein $W^1$ is O or $NR^{W1}$, where $R^{W1}$ is hydrogen, aliphatic, heteroaliphatic, alicyclic, heteroalicyclic, aromatic, heteroaromatic, or acyl; and $Alk_1$ is a $C_{1-6}$alkylene or $C_{2-6}$alkenylene moiety.

Another class of compounds of special interest includes compounds of formula ($I^D$):

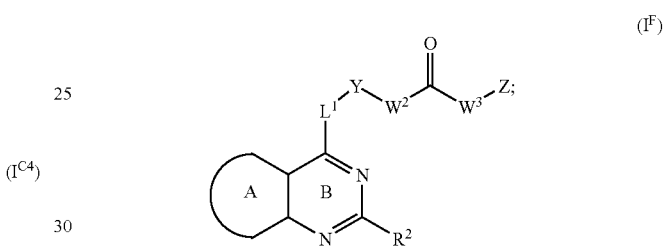

wherein $Alk_1$ is a $C_{1-6}$alkylene or $C_{2-6}$alkenylene moiety; and $R^{W1}$ is hydrogen, aliphatic, heteroaliphatic, alicyclic, heteroalicyclic, aromatic, heteroaromatic, or acyl; or $R^{W1}$ taken together with $R^1$ may form a heterocyclic moiety.

Another class of compounds of special interest includes compounds of formula ($I^E$):

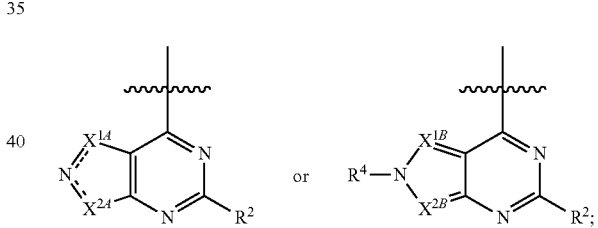

wherein A-B together represent one of the following structures:

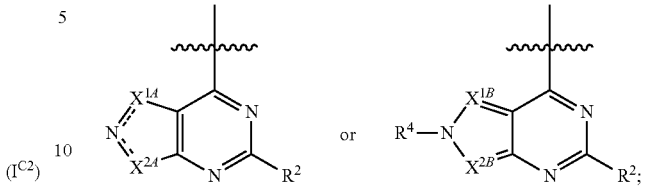

wherein $R^{W1}$ is hydrogen, aliphatic, heteroaliphatic, alicyclic, heteroalicyclic, aromatic, heteroaromatic, or acyl; $Alk_1$ is a $C_{1-6}$alkylene or $C_{2-6}$alkenylene moiety; or $R^{W1}$ taken together with a carbon atom present on $Alk_1$ may form a heterocyclic moiety.

Another class of compounds of special interest includes compounds of formula ($I^F$):

(I^F)

wherein A-B together represent one of the following structures:

wherein $W^2$ and $W^3$ are independently absent, O, $NR^W$, $CR^{W1}R^{W2}$ or $NR^W CR^{W1}R^{W2}$, where $R^W$ is hydrogen, aliphatic, heteroaliphatic, alicyclic, heteroalicyclic, aromatic, heteroaromatic, or acyl; and $R^{W1}$ and $R^{W2}$ are independently hydrogen, aliphatic, heteroaliphatic, alicyclic, heteroalicyclic, aromatic or heteroaromatic; with the proviso that $W^2$ and $W^3$ are not each absent and at least one of $W^2$ and $W^3$ is $NR^W$ or $NR^W CR^{W1}R^{W2}$.

A number of important subclasses of each of the foregoing classes deserve separate mention; these subclasses include subclasses of the foregoing classes in which:

i) $R^2$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

ii) $R^2$ is $C_{1-3}$alkyl or $C_{1-3}$alkoxy;

iii) $R^2$ is methyl or $-CF_3$;

iv) $R^2$ is halogen;

v) $R^2$ is hydrogen;

vi) $X^{1A}$ is $NR^1$ and $X^{2A}$ is $-C(R^{X1})-$, or $X^{2A}$ is $NR^3$ and $X^{1A}$ is $-C(R^{X1})-$, or $X^{1B}$ is N and $X^{2B}$ is $-C(R^{X1})-$, or $X^{2B}$ is N and $X^{1B}$ is $-C(R^{X1})-$; wherein $R^{X1}$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

vii) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is C($R^{X1}$)—; wherein $R^{X1}$ is hydrogen, halogen, or an alkyl, alkenyl, alkynyl, cycloalkyl, cycloalkenyl, heteroalkyl, heteroalkenyl, heteroalkynyl, heterocyclyl, aryl or heteroaryl moiety;

viii) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is hydrogen, halogen, or a lower alkyl, cycloalkyl, cycloalkenyl, lower heteroalkyl, heterocyclyl, aryl or heteroaryl moiety;

ix) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is hydrogen, halogen, or a lower alkyl, cycloalkyl, heterocyclyl, aryl or heteroaryl moiety;

x) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is hydrogen, halogen, $C_{1-5}$alkyl, $C_{1-5}$alkoxy, —CO$_2$H, —CO$_2$C$_{1-5}$alkyl, —CN or —NO$_2$;

xi) $X^{1A}$ is $NR^1$ and $X^{2A}$ is CH;

xii) $X^{2A}$ is $NR^3$ and $X^{1A}$ is CH;

xiii) $X^{1B}$ is N and $X^{2B}$ is CH;

xiv) $X^{2B}$ is N and $X^{1B}$ is CH;

xv) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is hydrogen, halogen, —CN, —NO$_2$, —C(=O)$R^{1A}$, —C(=O)O$R^{1A}$, C(=O)N$R^{1A}R^{1B}$, —S(=O)$_2R^{1C}$, —P(=O)($R^{1C}$)$_2$, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; wherein $R^{1A}$ and $R^{1B}$ are independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5-6-membered heterocyclic ring; and each occurrence of $R^{1C}$ is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

xvi) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is hydrogen, halogen, —NO$_2$, —CN, —C(=O)O$R^{1A}$, —S(=O)$_2R^{1C}$, —P(=O)$_2R^{1C}$)$_2$, alkyl, alkenyl, alkynyl, heteroalkyl, heteroalkenyl, heteroalkynyl, heterocyclyl, aryl or heteroaryl; wherein $R^{1A}$ is hydrogen or $C_{1-6}$alkyl; and each occurrence of $R^{1C}$ is independently $C_{1-6}$alkyl;

xvii) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is hydrogen, halogen, —NO$_2$, —CN, $C_{1-5}$alkyl or $C_{1-5}$alkoxy;

xviii) $X^{1A}$ is NH and $X^{2A}$ is —CH—, or $X^{2A}$ is NH and $X^{1A}$ is —CH—;

xix) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is F, Cl, Br or I;

xx) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is alkyl, alkenyl, alkynyl, heteroalkyl, heteroalkenyl or heteroalkynyl;

xxi) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is one of:

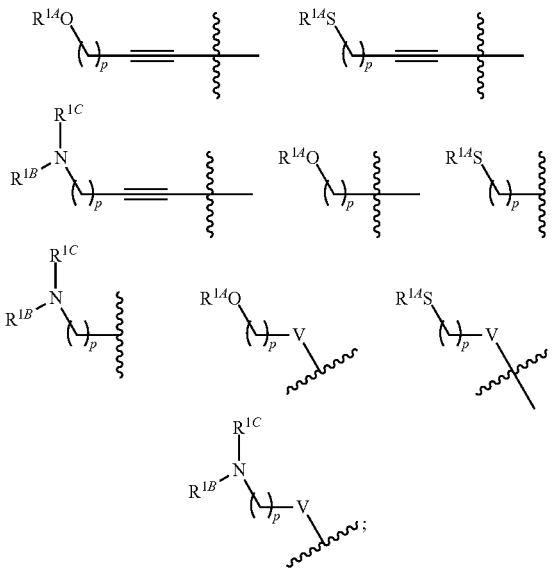

wherein V is O, S or $R^{1B}$; p is an integer from 0 to 6; and $R^{1A}$ is hydrogen, alkyl, heteroalkyl, aryl, heteroaryl, -(alkyl)aryl, -(alkyl)heteroaryl, —C(=O)N($R^{1B}$)$_2$, —C(=O)O$R^{1B}$; wherein each occurrence of RIB and $R^{1C}$ is independently hydrogen, lower alkyl, lower heteroalkyl, aryl, heteroaryl, -(alkyl)aryl, -(alkyl)heteroaryl or acyl; or $R^{1B}$ and $R^{1C}$, taken together with the nitrogen atom to which they are attached, form a substituted or unsubstituted heterocyclic moiety;

xxii) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is —CN, lower alkyl, lower alkynyl, —CO$_2R^{1D}$, or one of:

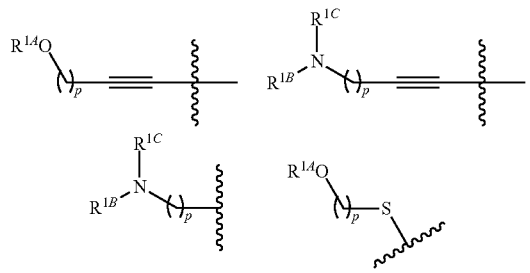

wherein p is an integer from 1 to 4; and $R^{1A}$ is hydrogen, alkyl, heteroalkyl, aryl, heteroaryl, -(alkyl)aryl, -(alkyl)heteroaryl, —C(=O)N($R^{1B}$)$_2$, —C(=O)O$R^{1B}$; wherein each occurrence of $R^{1B}$ and $R^{1C}$ is independently hydrogen, lower alkyl, lower heteroalkyl, aryl, heteroaryl, -(alkyl)aryl, -(alkyl)heteroaryl or acyl; or $R^{1B}$ and $R^{1C}$, taken together with the nitrogen atom to which they are attached, form a substituted or unsubstituted heterocyclic moiety; and RID is hydrogen or lower alkyl;

xxiii) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is —CN, —C≡CH, methyl, —CO$_2$H, —CO$_2$Me, or one of:

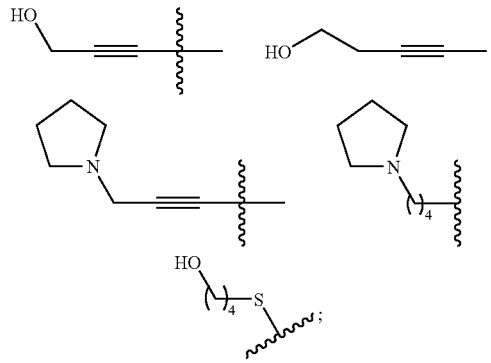

xxiv) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is aryl, heteroaryl or heterocyclyl;

xxv) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is an aryl, heteroaryl or heterocyclyl moiety having one of the structures:

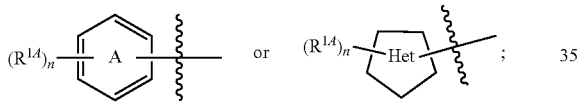

wherein the "A" cyclic moiety is a 6-membered aromatic ring comprising from 0-4 nitrogen atoms; the "Het" moiety represents a fully or partially saturated or unsaturated 5- to 6-membered ring comprising 1-4 heteroatoms selected from N, O and S; n is an integer from 0-6; and each occurrence of $R^{1A}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —O$R^{1B}$, —S$R^{1B}$, —N($R^{1B}$)$_2$, —SO$_2$N($R^{1B}$)$_2$, —SO$_2$$R^{1E}$, —C(═O)N($R^{1B}$)$_2$, halogen, —CN, —NO$_2$, —C(═O)O$R^{1B}$. N($R^{1B}$)C(═O)$R^{1C}$ or —N($R^{1B}$)SO$_2$$R^{1E}$; wherein each occurrence of $R^{1B}$ and $R^{1C}$ is independently hydrogen, lower alkyl, lower heteroalkyl, aryl, heteroaryl, -(alkyl)aryl, -(alkyl)heteroaryl, acyl; or any two occurrences of $R^{1B}$, taken together with the nitrogen atom to which they are attached (e.g., N($R^{1B}$)$_2$), form a substituted or unsubstituted heterocyclic moiety; $R^{1E}$ is alkyl, heteroalkyl, aryl, heteroaryl, -(alkyl)aryl, or -(alkyl)heteroaryl; and wherein any two adjacent occurrence of $R^{1A}$ may form a fused 5- to 6-membered aryl, heteroaryl or heterocyclic ring;

xxvi) $X^{1A}$ is $NR^1$ and $X^{2A}$ is —C($R^{X1}$)—, or $X^{2A}$ is $NR^3$ and $X^{1A}$ is —C($R^{X1}$)—, or $X^{1B}$ is N and $X^{2B}$ is —C($R^{X1}$)—, or $X^{2B}$ is N and $X^{1B}$ is —C($R^{X1}$)—; wherein $R^{X1}$ is one of:

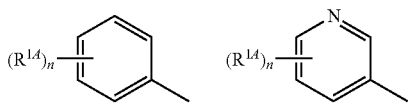

-continued

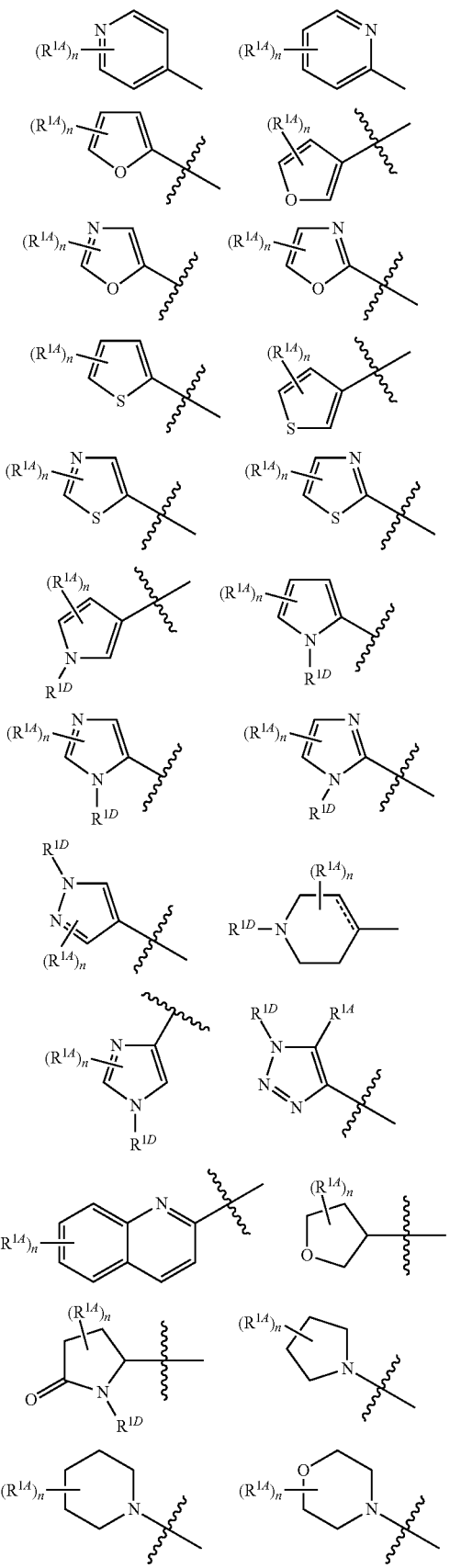

-continued

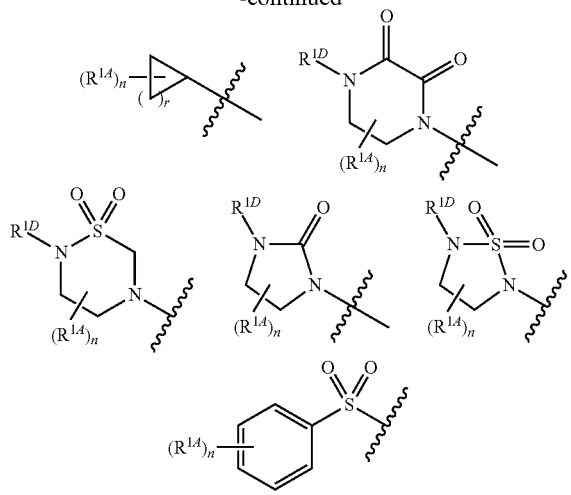

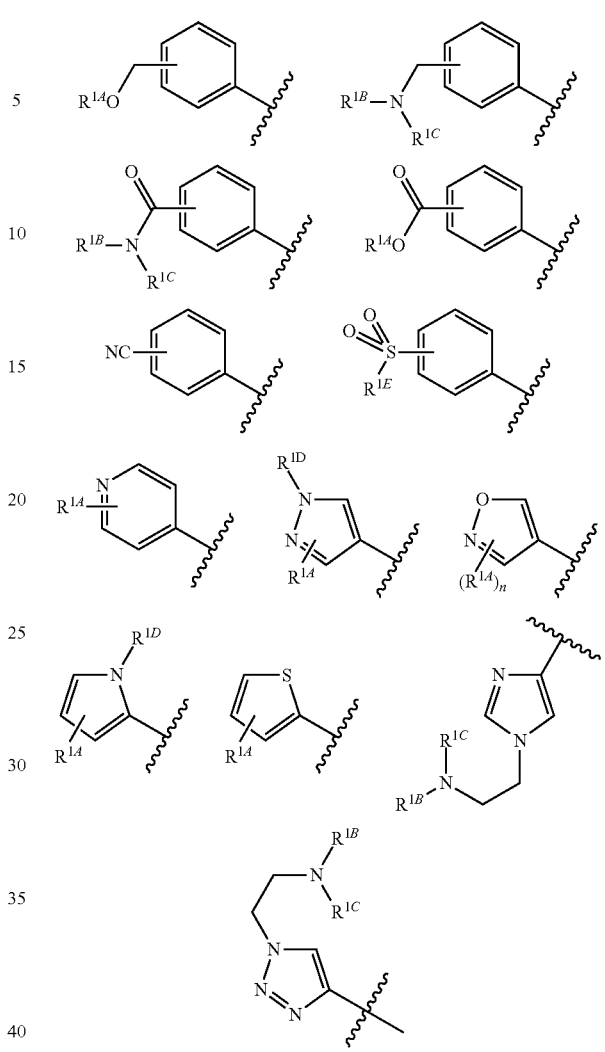

wherein each occurrence of $R^{1A}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, $-OR^{1B}$, $-SR^{1B}$, $-N(R^{1B})_2$, $-SO_2N(R^{1B})_2$, $-SO_2R^{1E}$, $-C(=O)N(R^{1B})_2$, halogen, $-CN$, $-NO_2$, $-C(=O)OR^{1B}$, $-N(R^{1B})C(=O)R^{1C}$ or $-N(R^{1B})SO_2R^{1E}$; wherein each occurrence of $R^{1B}$ and $R^{1C}$ is independently hydrogen, lower alkyl, lower heteroalkyl, aryl, heteroaryl, -(alkyl)aryl, -(alkyl)heteroaryl, acyl; or $R^{1B}$ and $R^{1C}$, taken together with the atoms to which they are attached, form a substituted or unsubstituted heterocyclic moiety; $R^{1D}$ is hydrogen, alkyl, cycloalkyl, heteroalkyl, heterocyclyl, aryl, heteroaryl, -(alkyl)heterocyclyl, -(alkyl)aryl, -(alkyl)heteroaryl, acyl or a nitrogen protecting group; and $R^{1E}$ is lower alkyl, lower heteroalkyl, aryl, heteroaryl, -(alkyl)aryl, or -(alkyl)heteroaryl; wherein n is an integer from 0 to 3 and r is an integer from 1 to 6;

xxvii) $X^{1A}$ is $NR^1$ and $X^{2A}$ is $-C(R^{X1})-$, or $X^{2A}$ is $NR^3$ and $X^{1A}$ is $-C(R^{X1})-$, or $X^{1B}$ is N and $X^{2B}$ is $-C(R^{X1})-$, or $X^{2B}$ is N and $X^{1B}$ is $-C(R^{X1})-$; wherein $R^{X1}$ is one of:

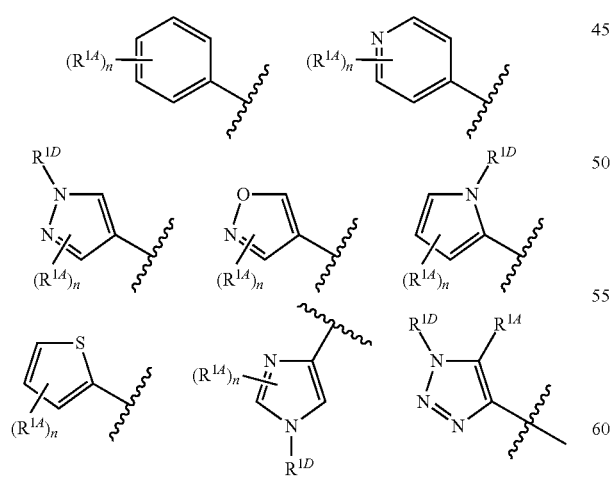

wherein n, $R^{1A}$ and $R^{1D}$ are as defined in xlii) above;

xxviii) $X^{1A}$ is $NR^1$ and $X^{2A}$ is $-C(R^{X1})-$, or $X^{2A}$ is $NR^3$ and $X^{1A}$ is $-C(R^{X1})-$, or $X^{1B}$ is N and $X^{2B}$ is $-C(R^{X1})-$, or $X^{2B}$ is N and $X^{1B}$ is $-C(R^{X1})-$; wherein $R^{X1}$ is one of:

wherein n is 0-2; $R^{1A}$ is hydrogen or lower alkyl; each occurrence of $R^{1B}$ and $R^{1C}$ is independently hydrogen, lower alkyl, or $R^{1B}$ and $R^{1C}$, taken together with the nitrogen atom to which they are attached, form a substituted or unsubstituted 5-6 membered heterocyclic moiety; $R^{1D}$ is hydrogen, or lower alkyl; $R^{1E}$ is hydrogen, or lower alkyl;

xxix) $X^{1A}$ is $NR^1$ and $X^{2A}$ is $-C(R^{X1})-$, or $X^{2A}$ is $NR^3$ and $X^{1A}$ is $-C(R^{X1})-$, or $X^{1B}$ is N and $X^{2B}$ is $-C(R^{X1})-$, or $X^{2B}$ is N and $X^{1B}$ is $-C(R^{X1})-$; wherein $R^{X1}$ is one of:

-continued

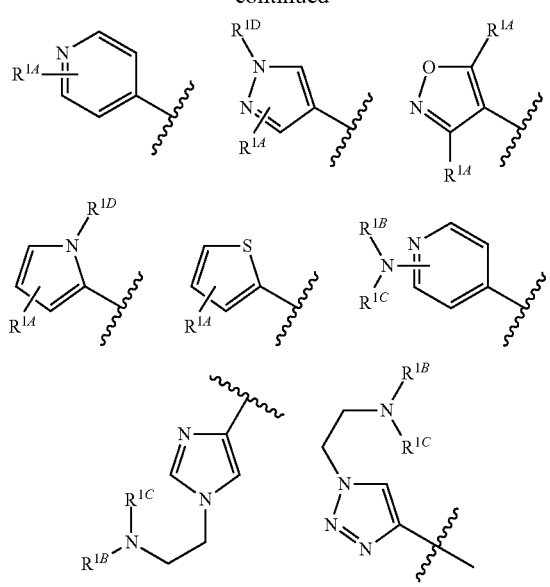

wherein each occurrence of $R^{1A}$ is independently hydrogen or lower alkyl; each occurrence of $R^{1B}$ and $R^{1C}$ is independently hydrogen, lower alkyl, or $R^{1B}$ and $R^{1C}$, taken together with the nitrogen atom to which they are attached, form a substituted or unsubstituted 5-6 membered heterocyclic moiety; $R^{1D}$ is hydrogen, or lower alkyl; $R^{1E}$ is hydrogen, or lower alkyl;

xxx) $X^{1A}$ is $NR^1$ and $X^{2A}$ is —$C(R^{X1})$—, or $X^{2A}$ is $NR^3$ and $X^{1A}$ is $C(R^{X1})$—, or $X^{1B}$ is N and $X^{2B}$ is —$C(R^{X1})$—, or $X^{2B}$ is N and $X^{1B}$ is —$C(R^{X1})$; wherein $R^{X1}$ is one of:

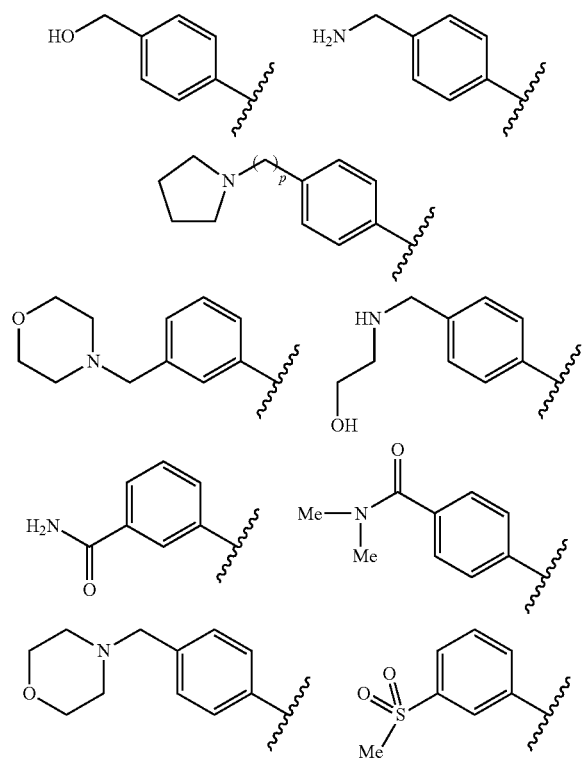

-continued

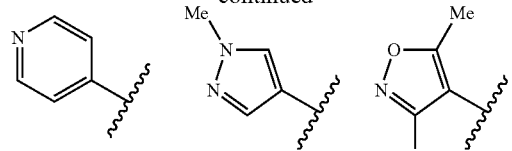

xxxi) $R^1$ is hydrogen, —$C(=O)R^{1A}$, $C(=O)OR^{1A}$, —$C(=O)NR^{1A}R^{1B}$, $S(=O)_2R^{1C}$, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; wherein $R^{1A}$ and $R^{1B}$ are independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5-6-membered heterocyclic ring; and each occurrence of $R^{1C}$ is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

xxxii) $R^1$ is hydrogen, —C(=O)$R^{1A}$, lower alkyl, lower alkenyl, heterocyclyl, aryl or heteroaryl; wherein $R^{1A}$ is hydrogen, or lower alkyl, aryl, or heteroaryl;

xxxiii) $R^1$ is hydrogen or lower alkyl;

xxxiv) $R^1$ is hydrogen;

xxxv) $R^1$ is lower alkyl;

xxxvi) $R^1$ is methyl, ethyl or isopropyl;

xxxvii) $R^1$ is —$C_{1-6}$alkyl-G$R^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G3}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, NR$^{G2}$SO$_2$NR$^{G3}$—, or —SO$_2$NR$^{G2}$—, or -G$R^{G1}$ is halogen, CN or N$_3$; wherein each occurrence of $R^{G1}$, $R^{G2}$ and $R^{G3}$ is independently hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety; and where G is —NR$^{G2}$—, $R^{G1}$ and $R^{G2}$ taken together with the nitrogen atom to which they are attached may form a 4- to 8-membered heterocyclic ring;

xxxviii) $R^1$ is —$C_{1-6}$alkyl-G$R^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$, NR$^{G2}$C(=O)O—, —NR$^{G2}$C(=O)NR$^{G3}$—, —C(=S)—, —C(=S)S—, —SC(=S)—, —SC(=S)S—, —C(=NR$^{G2}$)—, —C(=NR$^{G2}$)O, —C(=NR$^{G2}$)NR$^{G3}$, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, or G$R^{G1}$ is halogen, CN or N$_3$; wherein each occurrence of $R^{G1}$, $R^{G2}$ and $R^{G3}$ is independently hydrogen, halogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; and where G is —NR$^{G2}$—, $R^{G1}$ and $R^{G2}$ taken together with the nitrogen atom to which they are attached may form a 4- to 8-membered heterocyclic ring;

xxxix) $R^1$ is —$C_{1-6}$alkyl-G$R^{G1}$ wherein G is —O—, —S—, —NR$^{G2}$—, —C(=O)O—, —C(=O)NR$^{G2}$—, —S(=O)—, —SO$_2$— or C(=O)NR$^{G2}$—SO$_2$—, or -G$R^{G1}$ is halogen; wherein each occurrence of $R^{G1}$ and $R^{G2}$ is independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; and where G is —NR$^{G2}$—, $R^{G1}$ and $R^{G2}$ taken together with the nitrogen atom to which they are attached may form a 5- to 6-membered heterocyclic ring;

xl) $R^1$ is one of:

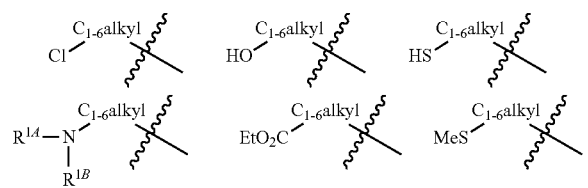

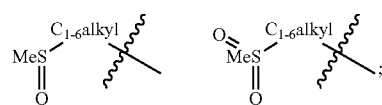

wherein the $C_{1-6}$alkyl moiety is optionally substituted; and $R^{1A}$ and $R^{1B}$ are independently hydrogen or lower alkyl;

xli) $R^1$ is one of:

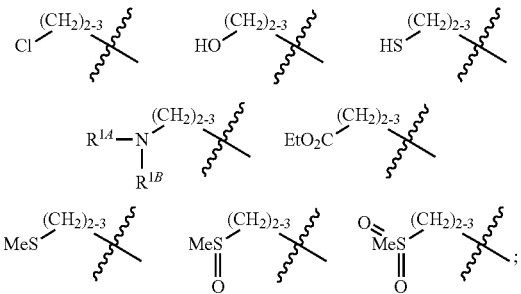

wherein $R^{1A}$ and $R^{1B}$ are independently hydrogen or lower alkyl;

xlii) $R^1$ is one of:

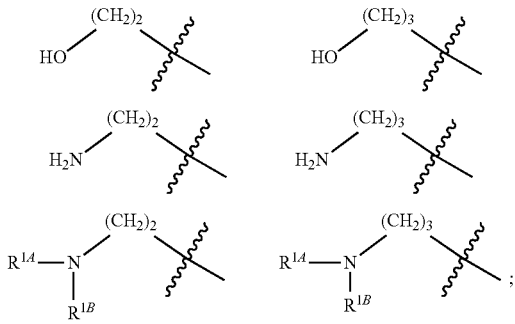

wherein $R^{1A}$ and $R^{1B}$ are independently hydrogen, methyl or ethyl;

xliii) $R^1$ is —$C_{1-6}$alkyl-NR$^{G1}$R$^{G2}$ wherein $R^{G1}$ and $R^{G2}$ taken together with the nitrogen atom to which they are attached may form an optionally substituted 5- to 6-membered heterocyclic ring;

xliv) $R^1$ is

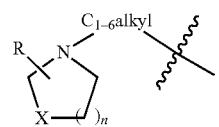

wherein n is 0, 1 or 2; $R^1$ is hydrogen, halogen, lower alkyl or lower alkoxy; and X is O or NR' where R' is hydrogen or lower alkyl;

xlv) R¹ is:

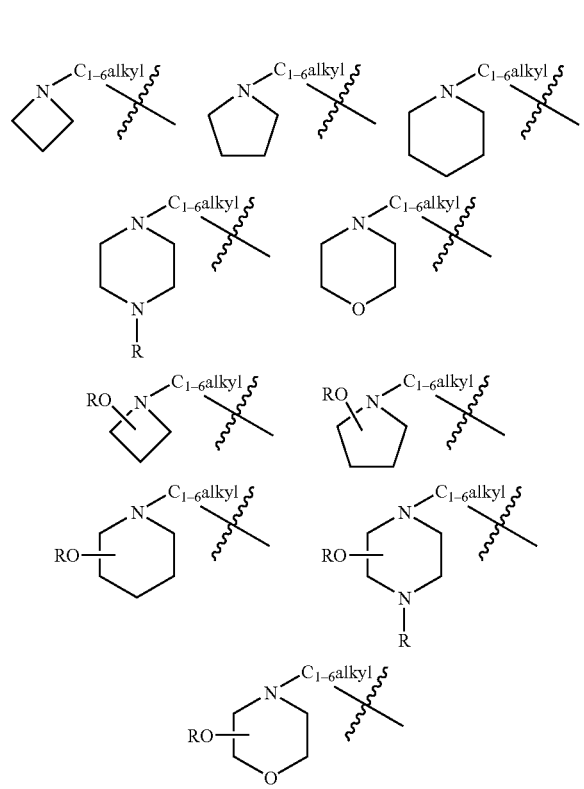

wherein the $C_{1-6}$alkyl moiety is optionally substituted; and R is hydrogen or lower alkyl;

xlvi) R¹ is:

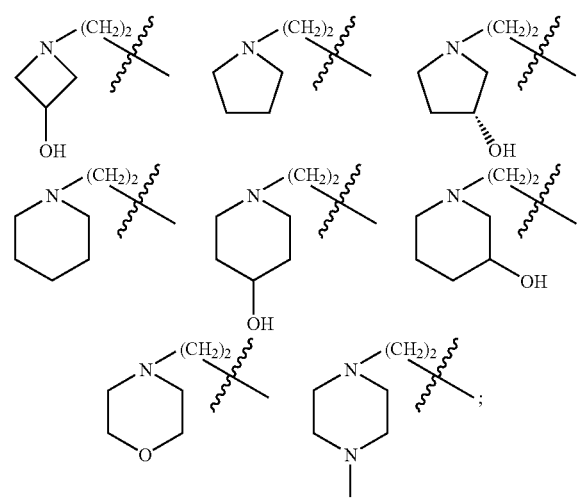

xlvii) R¹ is:

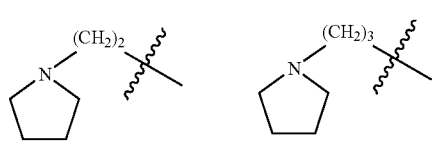

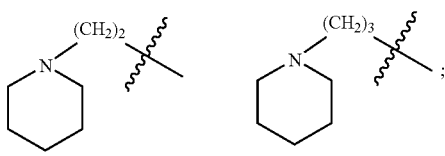

xlviii) R¹ is —$C_{1-6}$alkyl-C(=O)—NR$^{G1}$R$^{G2}$ or —$C_{1-6}$alkyl-C(=O)—NHSO$_2$R$^{G3}$ wherein R$^{G1}$ and R$^{G2}$ taken together with the nitrogen atom to which they are attached may form an optionally substituted 5- to 6-membered heterocyclic ring; and R$^{G3}$ is lower alkyl;

xlix) R¹ is:

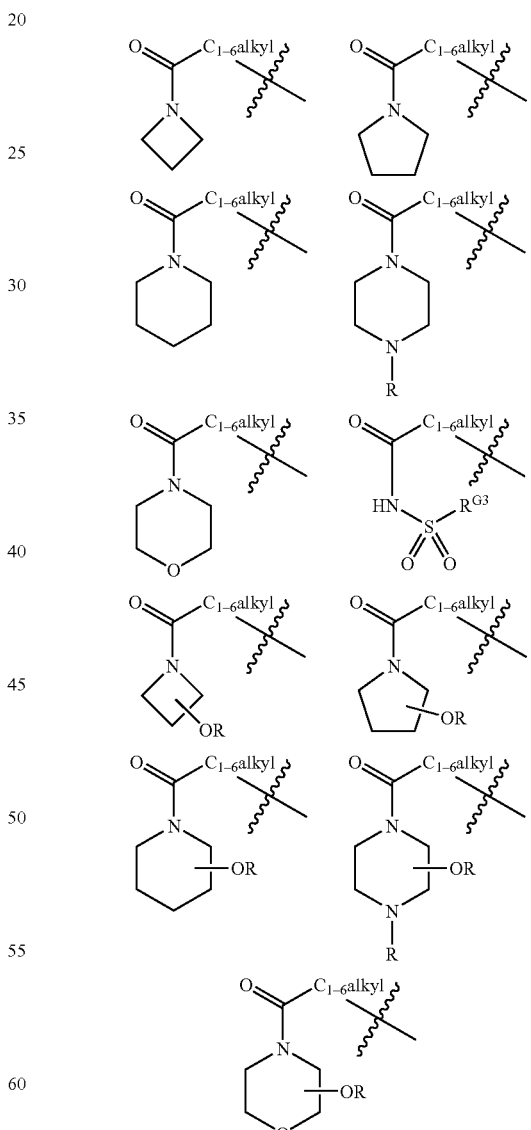

wherein the $C_{1-6}$alkyl moiety is optionally substituted; R is hydrogen or lower alkyl; and R$^{G3}$ is lower alkyl;

1) $R^1$ is:

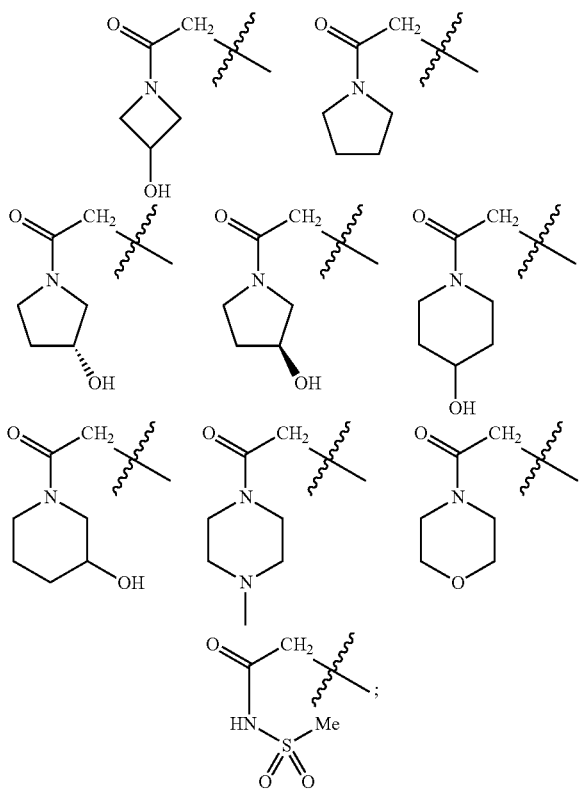

li) Compounds of subsets vi) through xxx) wherein $R^1$ has the definition given in subsets xxxi)-1);

lii) $R^3$ is hydrogen, —C(=O)$R^{3A}$, —C(=O)O$R^{3A}$, —C(=O)N$R^{3A}R^{3B}$, —S(=O)$_2R^{3C}$, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; wherein $R^{3A}$ and $R^{3B}$ are independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5-6-membered heterocyclic ring; and each occurrence of $R^{3C}$ is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

liii) $R^3$ is hydrogen, —C(=O)$R^{3A}$, lower alkyl, lower alkenyl, heterocyclyl, aryl or heteroaryl; wherein $R^{3A}$ is hydrogen, or lower alkyl, aryl, or heteroaryl;

liv) $R^3$ is hydrogen or lower alkyl;

lv) $R^3$ is hydrogen;

lvi) $R^3$ is lower alkyl;

lvii) $R^3$ is methyl, ethyl or isopropyl;

lviii) $R^3$ is —$C_{1-6}$alkyl-G$R^{G3}$ wherein G is —O—, —S—, —N$R^{G4}$—, —C(=O)—, —S(=O)—, —SO$_2$—, —C(=O)O—, —C(=O)N$R^{G4}$, —OC(=O)—, —N$R^{G2}$C(=O)—, —OC(=O)O—, —OC(=O)N$R^{G4}$—, —N$R^{G4}$C(=O)O—, —N$R^{G4}$C(=O)N$R^{G4}$)—, —C(=S)—, —C(=S)S—, —SC(=S)—, —SC(=S)S—, —C(=N$R^{G4}$)—, —C(=N$R^{G4}$)O—, —C(=N$R^{G2}$)N$R^{G5}$—, —OC(=N$R^{G4}$)—, —N$R^{G4}$C(=N$R^{G5}$)—, —N$R^{G4}$SO$_2$—, —N$R^{G4}$SO$_2$N$R^{G5}$—, or —SO$_2$N$R^{G4}$—, or -G$R^{G3}$ is halogen, CN or N$_3$; wherein each occurrence of $R^{G3}$, $R^{G4}$ and $R^{G5}$ is independently hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety; and where G is —N$R^{G4}$—, $R^{G3}$ and $R^{G4}$ taken together with the nitrogen atom to which they are attached may form a 4- to 8-membered heterocyclic ring;

lix) $R^3$ is —$C_{1-6}$alkyl-G$R^{G3}$ wherein G is —O—, —S—, —N$R^{G4}$—, —C(=O)—, —S(=O)—, —SO$_3$—, —C(=O)O—, —C(=O)N$R^{G4}$—, —OC(=O)—, —N$R^{G4}$C(=O)—, —OC(=O)O—, —OC(=O)N$R^{G4}$—, —N$R^{G4}$C(=O)O—, —N$R^{G4}$C(=O)N$R^{G5}$—, —C(=S)—, —C(=S)S—, —SC(=S)—, —SC(=S)S—, —C(=N$R^{G4}$)—, —C(=N$R^{G4}$)O—, —C(=N$R^{G4}$)N$R^{G5}$—, —OC(=N$R^{G4}$)—, —N$R^{G4}$C(=N$R^{G5}$)—, —N$R^{G4}$SO$_2$—, N$R^{G4}$SO$_2$N$R^{G5}$, or —SO$_2$N$R^{G4}$—, or -G$R^{G3}$ is halogen, CN or N$_3$; wherein each occurrence of $R^{G3}$, $R^{G4}$ and $R^{G5}$ is independently hydrogen, halogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; and where G is —N$R^{G4}$—, $R^{G3}$ and $R^{G4}$ taken together with the nitrogen atom to which they are attached may form a 4- to 8-membered heterocyclic ring;

lx) $R^3$ is —$C_{1-6}$alkyl-G$R^{G3}$ wherein G is —O—, —S—, —N$R^{G4}$—, —C(=O)O—, —C(=O)N$R^{G4}$—, —S(=O)—, —SO$_2$— or —C(=O)N$R^{G4}$—SO$_2$—, or -G$R^{G3}$ is halogen; wherein each occurrence of $R^{G3}$ and $R^{G4}$ is independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; and where G is —N$R^{G4}$—, $R^{G3}$ and $R^{G4}$ taken together with the nitrogen atom to which they are attached may form a 5- to 6-membered heterocyclic ring;

lxi) $R^3$ is one of:

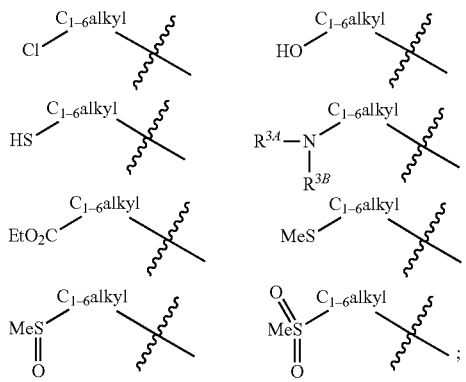

wherein the $C_{1-6}$alkyl moiety is optionally substituted; and $R^{3A}$ and $R^{3B}$ are independently hydrogen or lower alkyl;

lxii) $R^3$ is one of:

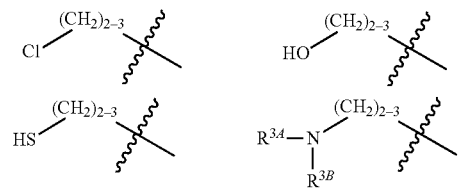

-continued

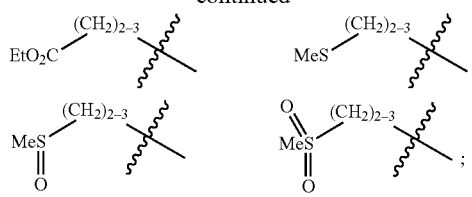

wherein $R^{3A}$ and $R^{3B}$ are independently hydrogen or lower alkyl;

lxiii) $R^3$ is one of:

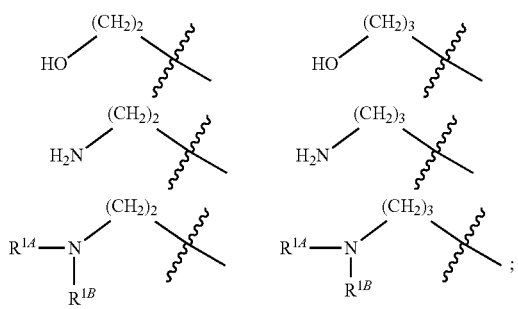

wherein $R^{3A}$ and $R^{3B}$ are independently hydrogen, methyl or ethyl;

lxiv) $R^3$ is —$C_{1-6}$alkyl-$NR^{G1}GR^{G2}$ wherein $R^{G1}$ and $R^{G2}$ taken together with the nitrogen atom to which they are attached may form an optionally substituted 5- to 6-membered heterocyclic ring;

lxv) $R^3$ is

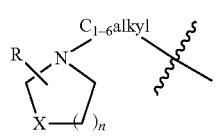

wherein n is 0, 1 or 2; R is hydrogen, halogen, lower alkyl or lower alkoxy; and X is O or NR' where R' is hydrogen or lower alkyl;

lxvi) $R^3$ is:

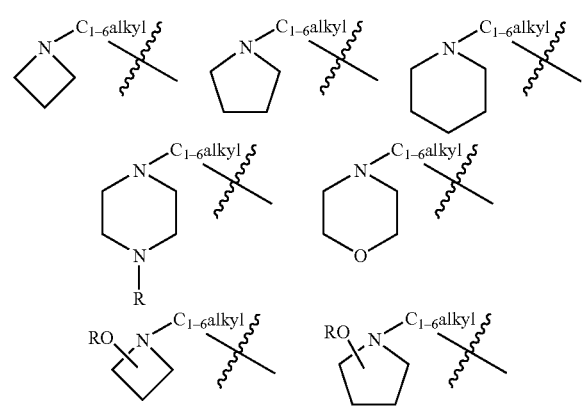

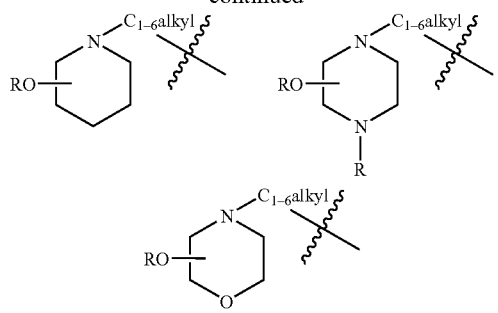

wherein the $C_{1-6}$alkyl moiety is optionally substituted; and R is hydrogen or lower alkyl;

lxvii) $R^3$ is:

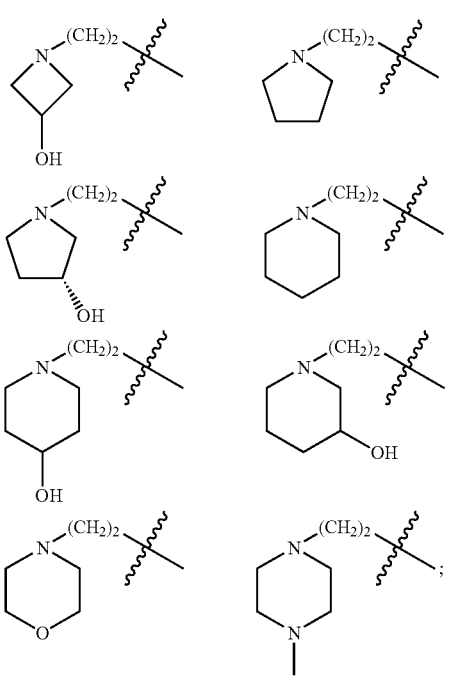

lxviii) $R^3$ is:

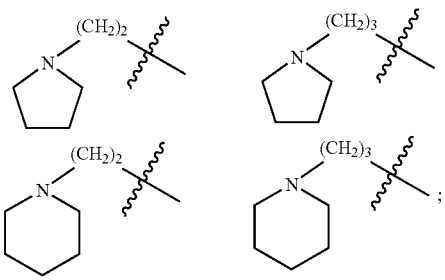

lxix) $R^3$ is —$C_{1-6}$alkyl-C(=O)—$NR^{G1}R^{G2}$ or —$C_{1-6}$alkyl-C(=O)—$NHSO_2R^{G3}$ wherein $R^{G1}$ and $R^{G2}$ taken together with the nitrogen atom to which they are attached may form an optionally substituted 5- to 6-membered heterocyclic ring; and $R^{G3}$ is lower alkyl;

lxx) R³ is:

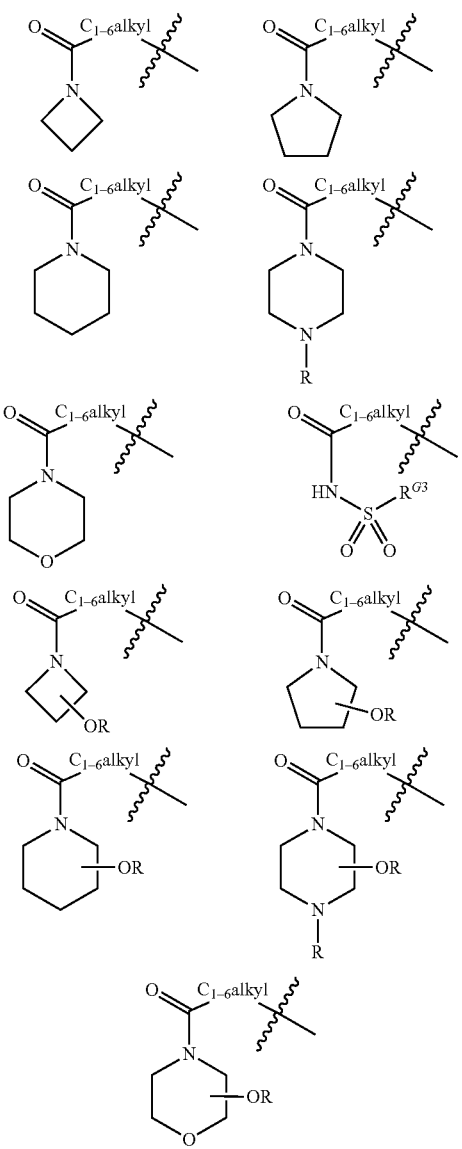

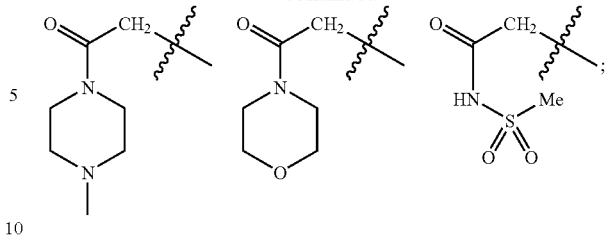

wherein the C₁₋₆alkyl moiety is optionally substituted; R is hydrogen or lower alkyl; and R^{G3} is lower alkyl;

lxxi) R³ is:

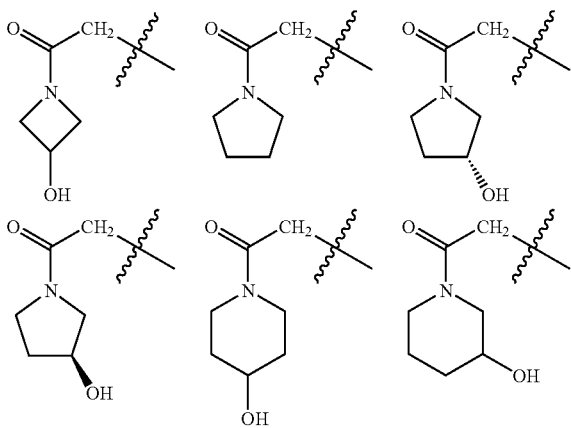

lxxii) Compounds of subsets vi) through xxx) wherein R³ has the definition given in subsets lii)-lxxi);

lxxiii) R⁴ is hydrogen, —C(=O)R^{4A}, —C(=O)OR^{4A}, —C(=O)NR^{4A}R^{4B}, —S(=O)₂R^{4C}, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; wherein R^{4A} and R^{4B} are independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5-6-membered heterocyclic ring; and each occurrence of R^{4C} is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

lxxiv) R⁴ is hydrogen, —C(=O)R^{4A}, lower alkyl, lower alkenyl, heterocyclyl, aryl or heteroaryl; wherein R^{4A} is hydrogen, or lower alkyl, aryl, or heteroaryl;

lxxv) R⁴ is hydrogen or lower alkyl;

lxxvi) R⁴ is hydrogen;

lxxvii) R⁴ is lower alkyl;

lxxviii) R⁴ is methyl, ethyl or isopropyl;

lxxix) R⁴ is —C₁₋₆alkyl-GR^{G3} wherein G is —O—, —S—, —NR^{G4}—, —C(=O)—, —S(=O)—, SO₂—, —C(=O)O—, —C(=O)NR^{G4}—, —OC(=O)—, —NR^{G2}C(=O)—, —OC(=O)O—, —OC(=O)NR^{G4}—, —NR^{G4}C(=O)O—, NR^{G4}C(=O)NR^{G4}—, —C(=S)—, —C(=S)S—, —SC(=S)—, —SC(=S)S—, —C(=NR^{G4})—, —C(=NR^{G4})O, —C(=NR^{G2})NR^{G5}—, —C(=NR^{G4})—, —NR^{G4}C(=NR^{G5})—, —NR^{G4}SO₂—, —NR^{G4}SO₂NR^{G5}—, or —SO₂NR^{G4}—, or -GR^{G3} is halogen, CN or N₃; wherein each occurrence of R^{G3}, R^{G4} and R^{G5} is independently hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety; and where G is —NR^{G4}—, R^{G3} and R^{G4} taken together with the nitrogen atom to which they are attached may form a 4- to 8-membered heterocyclic ring;

lxxx) R⁴ is —C₁₋₆alkyl-GR^{G3} wherein G is —O—, —S—, —NR^{G4}—, —C(=O)—, —S(=O)—, —SO₂—, —C(=O)O—, —C(=O)NR^{G4}—, —OC(=O)—, —NR^{G4}C(=O)—, —OC(=O)O—, —OC(=O)NR^{G4}—, —NR^{G4}C(=O)O—, —NR^{G4}C(=O)NR^{G5}—, —C(=S)—, —C(=S)S—, —SC(=S)—, —SC(=S)S—, —C(=NR^{G4})—, C(=NR^{G4})O—, —C(=NR^{G4})NR^{G5}—, —C(=NR^{G4})—, —NR^{G4}C(=NR^{G5})—, —NR^{G4}SO₂—, NR^{G4}SO₂NR^{G5}—, or —SO₂NR^{G4}—, or -GR^{G3} is halogen, CN or N₃; wherein each occurrence of R^{G3}, R^{G4} and R^{G5} is independently hydrogen, halogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; and where G is —NR^{G4}—, R^{G3} and $R^{G4}$ taken together with the nitrogen atom to which they are attached may form a 4- to 8-membered heterocyclic ring;

lxxxi) $R^4$ is —$C_{1-6}$alkyl-$GR^{G3}$ wherein G is —O—, —S—, —$NR^{G4}$—, —C(=O)O—, —C(=O)$NR^{G4}$—, —S(=O)—, —$SO_2$— or —C(=O)$NR^{G4}$—$SO_2$—, or -$GR^{G3}$ is halogen; wherein each occurrence of $R^{G3}$ and $R^{G4}$ is independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; and where G is —$NR^{G4}$—, $R^{G3}$ and $R^{G4}$ taken together with the nitrogen atom to which they are attached may form a 5- to 6-membered heterocyclic ring;

lxxxii) $R^4$ is aryl or heteroaryl;

lxxxiii) $R^4$ is one of:

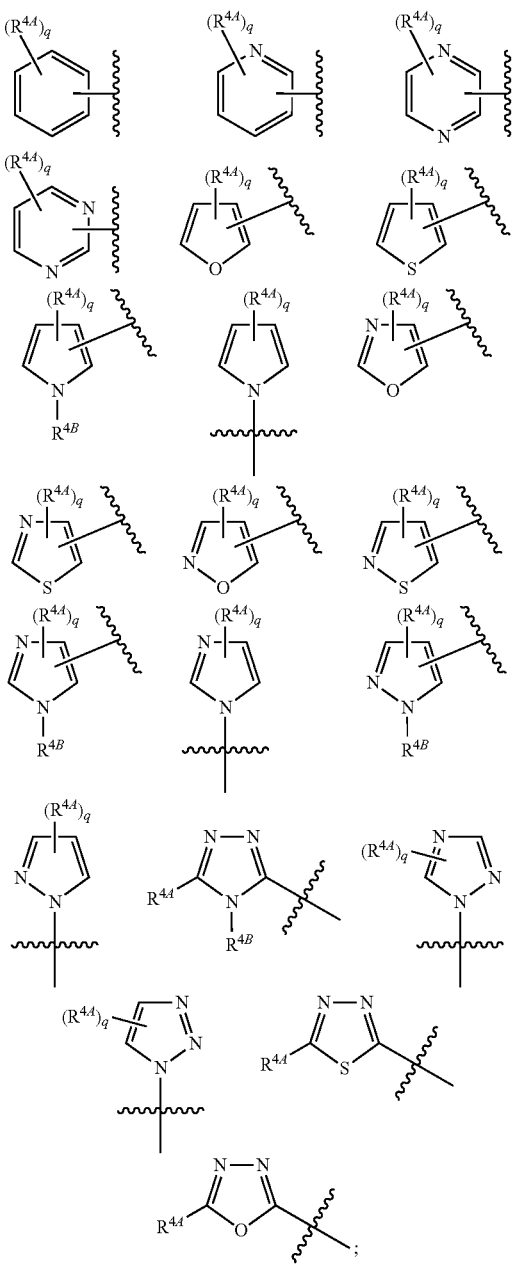

wherein q is an integer from 0 to 3; each occurrence of $R^{4A}$ is independently hydrogen, alkyl, heteroalkyl, aryl, heteroaryl, -(alkyl)aryl or -(alkyl)heteroaryl, —$OR^{4C}$, —$SR^{4C}$, —$NR^{4B}R^{4C}$, —$SO_2NR^{4B}R^{4C}$, —C(=O)$NR^{4B}R^{4C}$, halogen, —CN, —$NO_2$, —C(=O)$OR^{4C}$, —N($R^{4B}$)C(=O)$R^{4C}$, wherein each occurrence of $R^{4B}$ and $R^{4C}$ is independently hydrogen, lower alkyl, lower heteroalkyl, aryl, heteroaryl, -(alkyl)aryl, -(alkyl)heteroaryl or acyl, or $R^{4B}$ and $R^{4C}$ taken together with the nitrogen atom to which they are attached form a 5-6 membered heterocyclic ring;

lxxxiv) $R^4$ is

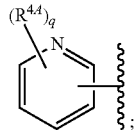

lxxxv) $R^4$ is

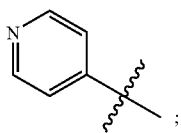

lxxxvi) $R^4$ is one of:

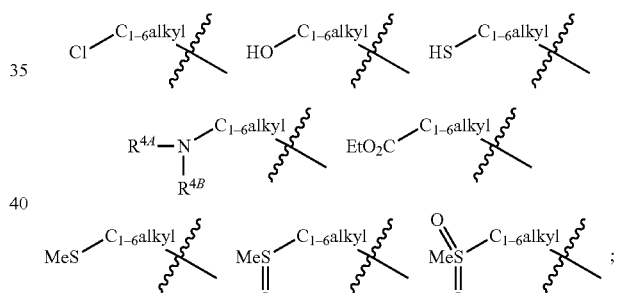

wherein the $C_{1-6}$alkyl moiety is optionally substituted; and $R^{4A}$ and $R^{4B}$ are independently hydrogen or lower alkyl;

lxxxvii) $R^4$ is one of:

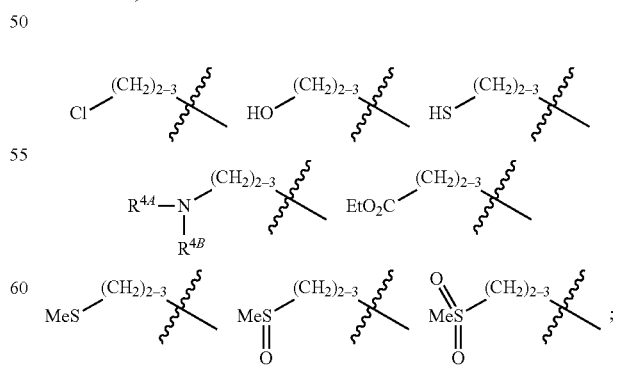

wherein $R^{4A}$ and $R^{4B}$ are independently hydrogen or lower alkyl;

lxxxviii) $R^4$ is one of:

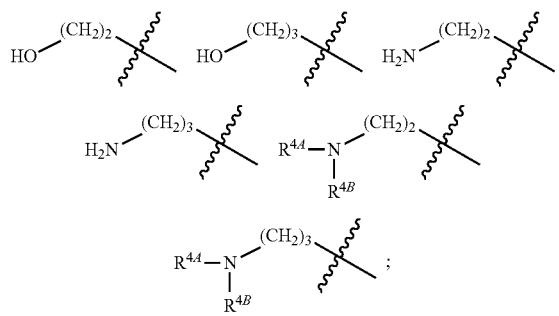

wherein $R^{4A}$ and $R^{4B}$ are independently hydrogen, methyl or ethyl;

lxxxix) $R^4$ is —$C_{1-6}$alkyl-$NR^{G1}R^{G2}$ wherein $R^{G1}$ and $R^{G2}$ taken together with the nitrogen atom to which they are attached may form an optionally substituted 5- to 6-membered heterocyclic ring;

xc) $R^4$ is

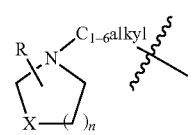

wherein n is 0, 1 or 2; R is hydrogen, halogen, lower alkyl or lower alkoxy; and X is O or NR' where R' is hydrogen or lower alkyl;

xci) $R^4$ is:

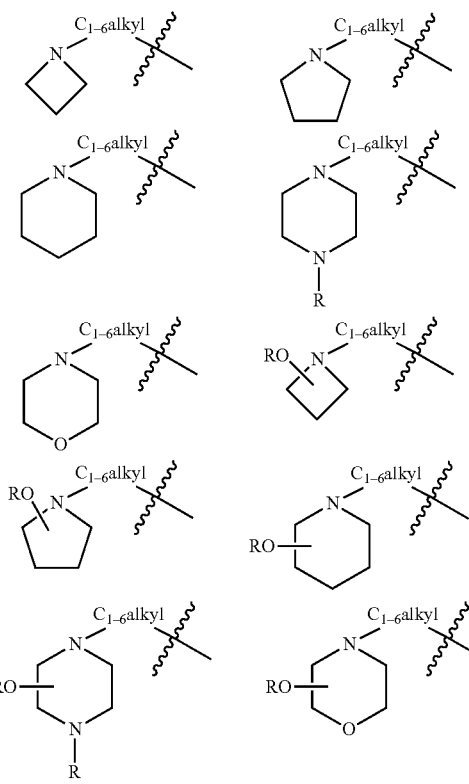

wherein the $C_{1-6}$alkyl moiety is optionally substituted; and R is hydrogen or lower alkyl;

xcii) $R^4$ is:

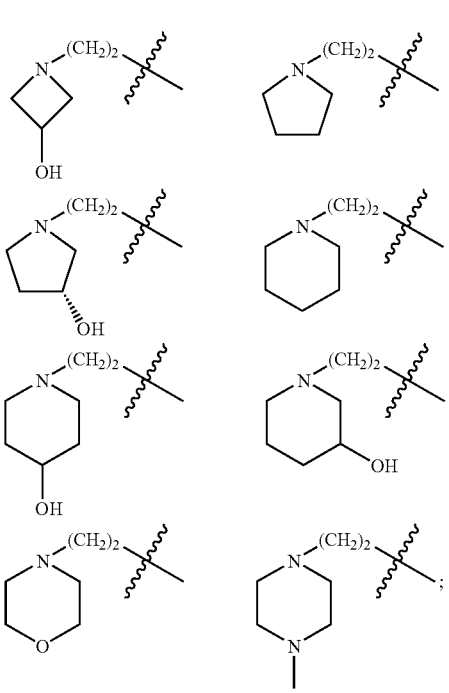

xciii) $R^4$ is:

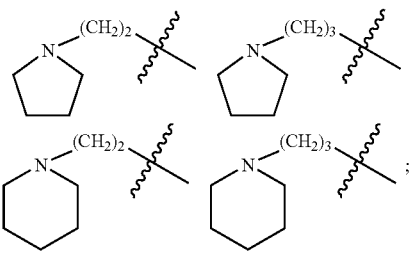

xciv) $R^4$ is —$C_{1-6}$alkyl-C(=O)—$NR^{G1}R^{G2}$ or —$C_{1-6}$alkyl-C(=O)—$NHSO_2R^{G3}$ wherein $R^{G1}$ and $R^{G2}$ taken together with the nitrogen atom to which they are attached may form an optionally substituted 5- to 6-membered heterocyclic ring; and $R^{G3}$ is lower alkyl;

xcv) $R^4$ is:

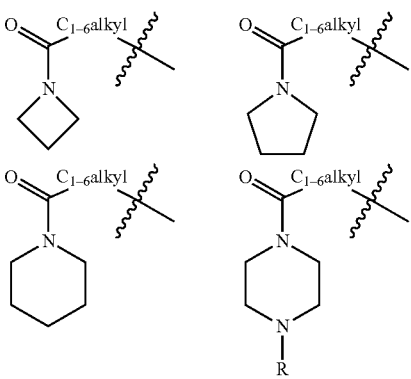

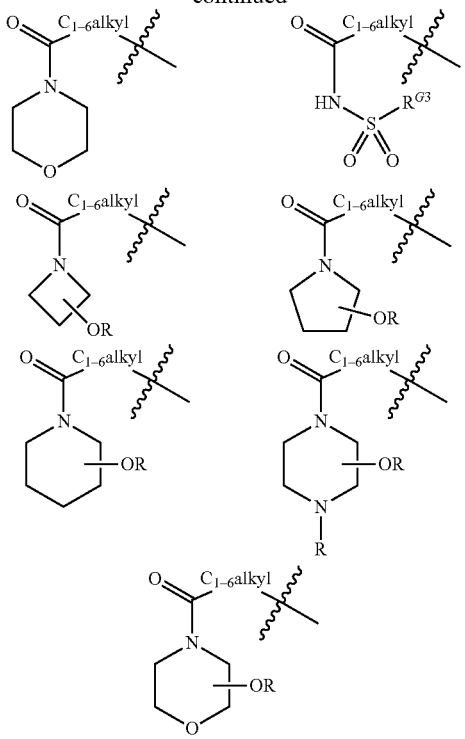

wherein the $C_{1-6}$alkyl moiety is optionally substituted; R is hydrogen or lower alkyl; and $R^{G3}$ is lower alkyl;

xcvi) $R^4$ is:

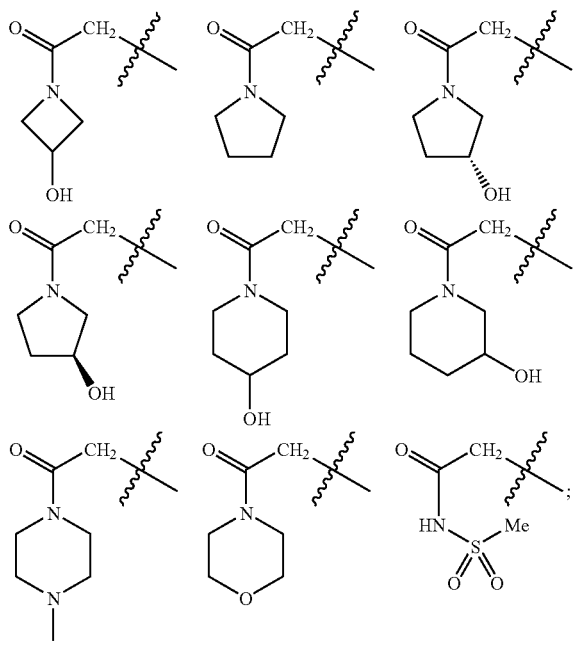

xcvii) Compounds of subsets vi) through xxx) wherein $R^4$ has the definition given in subsets lxxiii)-xcvi);

xcviii) $L^1$ is —$W^1$-$Alk_1$-; wherein $W^1$ is O, S, $NR^{W1}$ or —C(=O)$NR^{W1}$ where $R^{W1}$ is hydrogen, alkyl, cycloalkyl, heteroalkyl, heterocyclyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O)—, —$NR^{L1A}CO_2$—, $NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, alkyl, heteroalkyl, heterocyclyl, aromatic, heteroaromatic or acyl;

xcix) $L^1$ is —$W^1$-$Alk_1$-; wherein $W^1$ is O, S, $NR^{W1}$ or —C(=O)$NR^{W1}$ where $R^{W1}$ is hydrogen, lower alkyl, $C_{3-6}$cycloalkyl, lower heteroalkyl, heterocyclyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O)—, —$NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, lower alkyl, lower heteroalkyl, heterocyclyl, aryl, heteroaryl or acyl;

c) Compounds of subset xcix) above wherein $W^1$ is S;

ci) Compounds of subset xcix) above wherein $W^1$ is O or $NR^{W1}$;

cii) $L^1$ is —O-$Alk_1$-; wherein $Alk_1$ is a substituted or unsubstituted $C_2$alkylene chain;

ciii) $L^1$ is —O-cyclopropyl-;

civ) $L^1$ is —O—$CH_2CH_2$—;

cv) $L^1$ is —$NR^{W1}$-$Alk_1$-; wherein $R^{W1}$ is hydrogen, lower alkyl, $C_{3-6}$cycloalkyl, lower heteroalkyl, aryl, heteroaryl, -(alkyl)aryl, -(alkyl)heteroaryl or acyl; and $Alk_1$ is a substituted or unsubstituted $C_{2-6}$alkylene chain wherein up to two non-adjacent methylene units are independently optionally replaced by —C(=O)—, —S(=O)—, —$SO_2$—, —O—, —S—, or —$NR^{L1A}$—; wherein $R^{L1A}$ is hydrogen or lower alkyl;

cvi) $L^1$ is —$NR^{W1}$-$Alk_1$-; wherein $R^{W1}$ is hydrogen, lower alkyl or lower heteroalkyl; and $Alk_1$ is a substituted or unsubstituted $C_2$alkylene chain;

cvii) $L^1$ is —NH-cyclopropyl-;

cviii) $L^1$ is —NH—$CH_2CH_2$—;

cix) $L^1$ is —NH—$CH_2CF_2$—;

cx) $L^1$ is —NH—$CH_2$CH[$(CH_2)_pOR^{W2}$]—; wherein p is 1 or 2 and $R^{W2}$ is hydrogen or lower alkyl;

cxi) $L^1$ is —NH—$CH_2$CH($CH_2$OH)—;

cxii) $L^1$ is —NH—$CH_2$CH($CH_2CH_2$OH)—;

cxiii) $L^1$ is —$NR^{W1}$-$Alk_1$-; wherein $R^{W1}$ is lower heteroalkyl; and $Alk_1$ is a substituted or unsubstituted $C_2$alkylene chain;

cxiv) $L^1$ is —$NR^{W1}$-$Alk_1$-; wherein $R^{W1}$ is —$(CH_2)_2$$NR^{W2}R^{W3}$; $Alk_1$ is a substituted or unsubstituted $C_2$alkylene chain; and $R^{W2}$ and $R^{W3}$ are independently hydrogen or lower alkyl;

cxv) $L^1$ is —$NR^{W1}$—$(CH_2)_2$—; wherein $R^{W1}$ is —$(CH_2)_2$$NR^{W2}R^{W3}$; and $R^{W2}$ and $R^{W3}$ are independently hydrogen or lower alkyl;

cxvi) $L^1$ is —$NR^{W1}$—$(CH_2)_2$—; wherein $R^{W1}$ is —$(CH_2)_2$$NMe_2$;

cxvii) $L^1$ is —$NR^{W1}$-$Alk_1$-; wherein $R^{W1}$ together with a carbon atom present on $Alk_1$ forms an optionally substituted 5- to 6-membered heterocyclic moiety;

cxviii) L¹ has the structure:

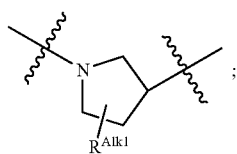

wherein $R^{Alk1}$ is hydrogen, halohen, hydroxy, CN, nitro, lower alkyl, lower alkoxy, aryl, or heteroaryl;

cxix) L¹ has the structure:

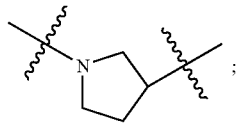

cxx) L¹ has the structure:

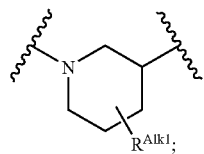

wherein $R^{Alk1}$ is hydrogen, halohen, hydroxy, CN, nitro, lower alkyl, lower alkoxy, aryl, or heteroaryl;

cxxi) L¹ has the structure:

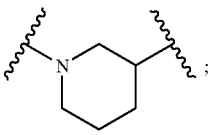

cxxii) $X^{1A}$ is $NR^1$ and L¹ is —$NR^{W1}$-$Alk_1$-; wherein $R^{W1}$ together with $R^1$ forms an optionally substituted 5- to 6-membered heterocyclic moiety;

cxxiii) Compounds of subset cxxii) above wherein $R^{W1}$, $R^1$ and the pyrazolo pyrimidine to which they are attached form the structure:

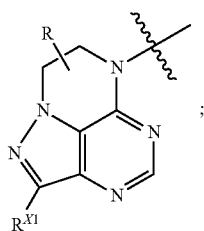

wherein R is hydrogen, halohen, hydroxy, CN, nitro, lower alkyl, lower alkoxy, aryl, or heteroaryl;

cxxiv) Compounds of subset cxxii) above wherein $R^{W1}$, $R^1$ and the pyrazolo pyrimidine to which they are attached form the structure:

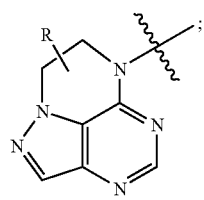

cxxv) Compounds of subset cxxii) above wherein $R^{W1}$, $R^1$ and the pyrazolo pyrimidine to which they are attached form the structure:

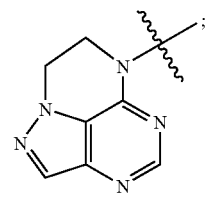

cxxvi) L¹ is —C(=O)$NR^{W1}$-$Alk_1$-; wherein $R^{W1}$ is hydrogen or lower alkyl; and $Alk_1$ is a substituted or unsubstituted $C_1$alkylene moiety;

cxxvii) L¹ is —C(=O)NH—$CH_2$—;

cxxviii) Y is a saturated or unsaturated cyclic ring system optionally comprising one or more heteroatoms selected from S, N and O;

cxxix) Y is a saturated or unsaturated monocyclic cyclic ring system optionally comprising one or more heteroatoms selected from S, N and O;

cxxx) Y is a cycloalkyl, cycloalkenyl, heterocyclic, aryl or heteroaryl moiety;

cxxxi) Y is a 5-6 membered cycloalkyl, 5-6 membered cycloalkenyl, 5-6 membered heterocylic, 6-membered aryl or 6-membered heteroaryl moiety;

cxxxii) Y is one of:

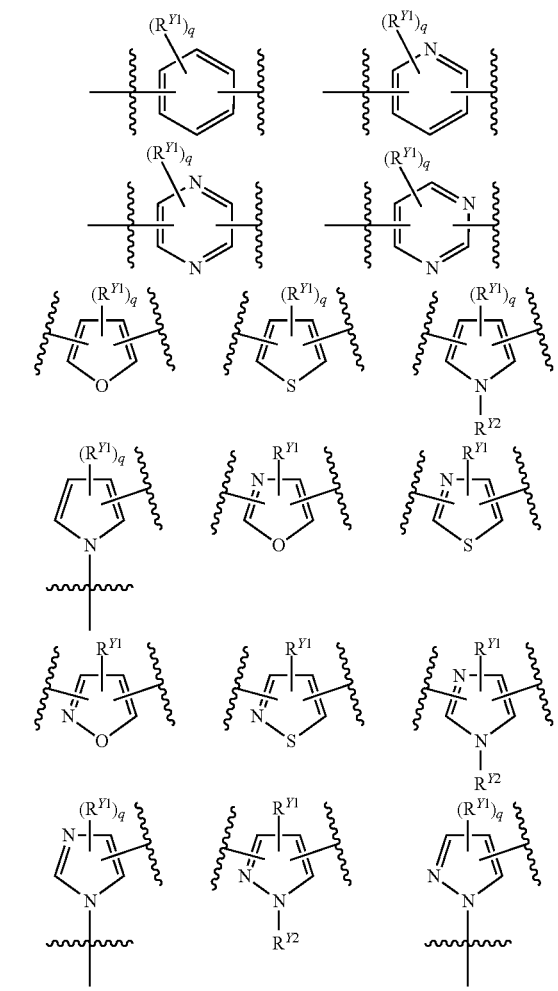

-continued

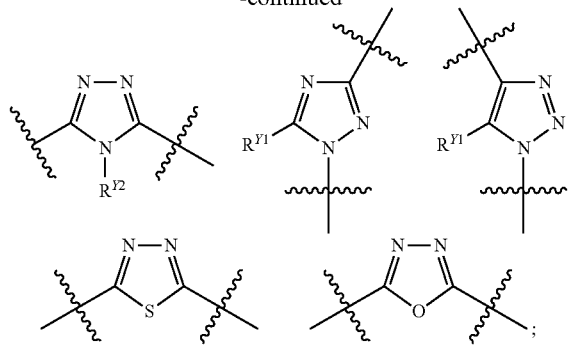

wherein q is an integer from 0 to 3; each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —$C(=O)NR^{Y2}R^{Y3}$, halogen, —CN, —$NO_2$, —$C(=O)OR^{Y3}$, —$N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring;

cxxxiii) Y is one of:

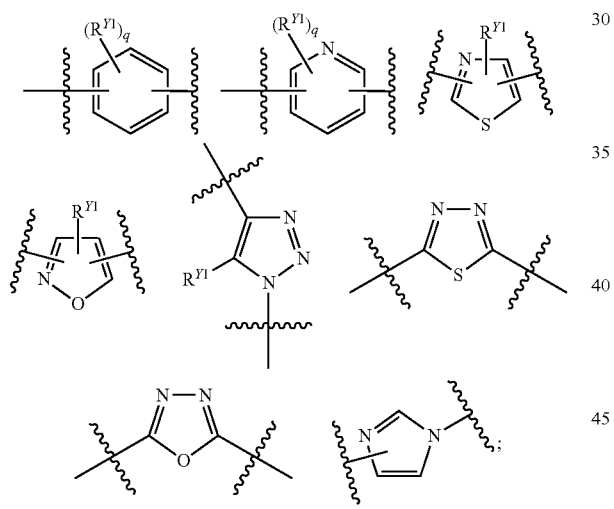

wherein q and $R^{Y1}$ are as defined directly above;

cxxxiv) Y is one of:

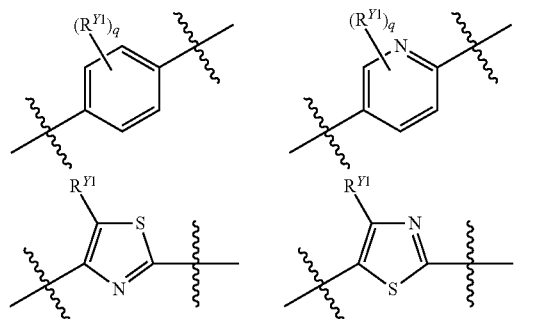

-continued

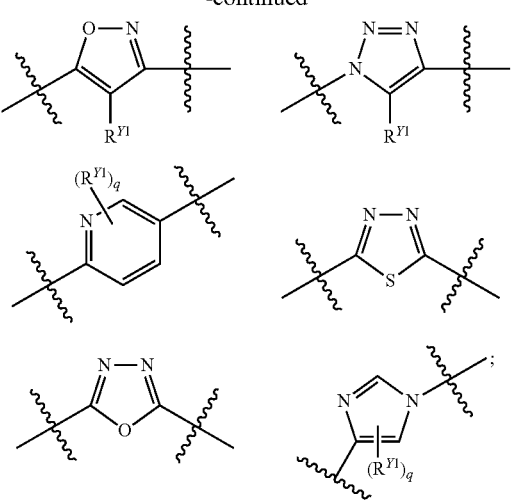

wherein q is 0-3; and $R^{Y1}$ is hydrogen, halogen or lower alkyl;

cxxxv) Y is one of:

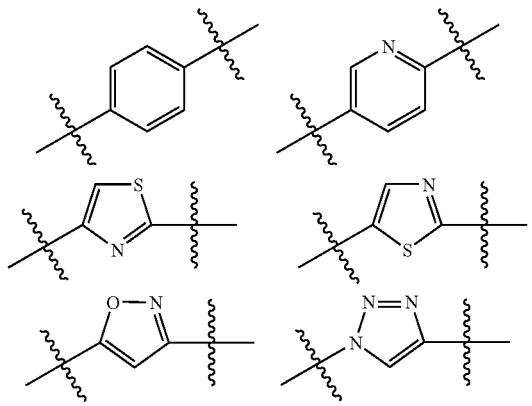

cxxxvi) Y is one of:

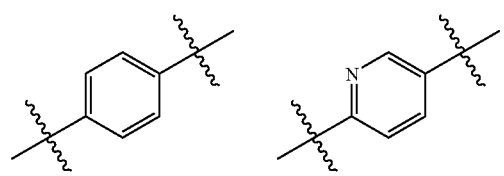

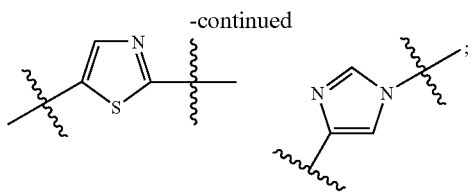

cxxxvii) Y is:

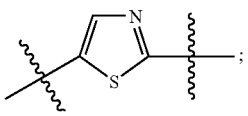

cxxxviii) Y is:

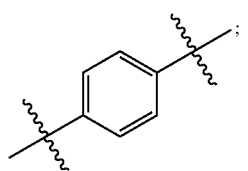

cxxxix) Y is:

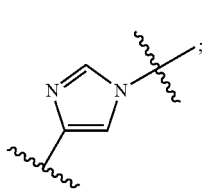

cxl) Y is:

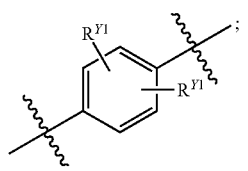

wherein at least one $R^{Y1}$ is halogen, the other is hydrogen or halogen;

cxli) Y is:

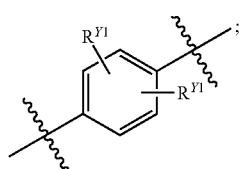

wherein at least one $R^{Y1}$ is fluoro, the other is hydrogen or fluoro;

cxlii) $L^2$ is —$NR^{L2A}$— or a substituted or unsubstituted $C_{1-6}$alkylene or $C_{2-6}$alkenylene chain interrupted with at least one nitrogen atom wherein up to two non-adjacent methylene units are independently optionally replaced by —C(=O)—, —$CO_2$—, —C(=O)C(=O)—, —C(=O)$NR^{L2A}$, —OC(=O)—, OC(=O)$NR^{L2A}$, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(=O)$NR^{L2B}$—, —S(=O)—, —$SO_2$—, —$NR^{L2A}SO_2$—, —$SO_2NR^{L2A}$—, —$NR^{L2A}SO_2NR^{L2B}$, —O—, —S—, or —$NR^{L2A}$—; wherein each occurrence of $R^{L2A}$, $R^{L2B}$, $R^{L2C}$ and $R^{L2D}$ is independently hydrogen, alkyl, heteroalkyl, heterocyclyl, aromatic, heteroaromatic or acyl;

cxliii) $L^2$ is —$NR^{L2A}$— or a substituted or unsubstituted $C_{1-6}$alkylene or $C_{2-6}$alkenylene chain interrupted with at least one nitrogen atom wherein up to two non-adjacent methylene units are independently optionally replaced by —C(=O)—, —$CO_2$—, —C(=O)C(=O)—, —C(=O)$NR^{L2A}$, —OC(=O)—, —OC(=O)$NR^{L2A}$, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(=O)$NR^{L2B}$—, —S(=O)—, —$SO_2$—, —$NR^{L2A}SO_2$—, —$SO_2NR^{L2A}$—, —$NR^{L2A}SO_2NR^{L2B}$, —O—, —S—, or —$NR^{L2A}$; wherein each occurrence of $R^{L2A}$, $R^{L2B}$, $R^{L2C}$ and $R^{L2D}$ is independently hydrogen, lower alkyl, lower heteroalkyl, heterocyclyl, aryl, heteroaryl or acyl;

cxliv) $L^2$ is —$(CH_2)_mNR^{L2A}(CH_2)_m$—, —$(CH_2)_mC(=O)NR^{L2A}(CH_2)_m$—, —$(CH_2)_mOC(=O)NR^{L2A}(CH_2)_m$—, —$(CH_2)_mNR^{L2A}NR^{L2B}(CH_2)_m$—, —$(CH_2)_mNR^{L2A}NR^{L2B}C(=O)(CH_2)_m$—, —$(CH_2)_mNR^{L2A}C(=O)(CH_2)_m$—, —$(CH_2)_mNR^{L2A}C(=O)O(CH_2)_m$—, —$(CH_2)_mNR^{L2A}C(=O)NR^{L2B}(CH_2)_m$—, —$(CH_2)_mNR^{L2A}C(=O)NR^{L2B}CR^{L2C}R^{L2D}(CH_2)_m$—, —$(CH_2)_mCR^{L2C}R^{L2D}C(=O)NR^{L2B}(CH_2)_m$, —$(CH_2)_mNR^{L2A}SO_2(CH_2)_m$—, —$(CH_2)_mSO_2NR^{L2A}(CH_2)_m$—, —$(CH_2)_mNR^{L2A}SO_2NR^{L2B}(CH_2)_m$—; wherein each occurrence of m is independently 0-4; and each occurrence of $R^{L2A}$, $R^{L2B}$, $R^{L2C}$ and $R^{L2D}$ is independently hydrogen, lower alkyl, lower heteroalkyl, heterocyclyl, aryl, heteroaryl or acyl;

cxlv) $L^2$ is —$NR^{L2A}$—, —C(=O)$NR^{L2A}$—, —OC(=O)$NR^{L2A}$—, —$NR^{L2A}NR^{L2B}$—, —$NR^{L2A}NR^{L2B}$C(=O), —$NR^{L2A}$C(=O)—, —$NR^{L2A}CO_2$—, —$NR^{L2A}$C(=O)$NR^{L2B}$, —$NR^{L2A}$C(=O)$NR^{L2B}CR^{L2C}R^{L2D}$, —$CR^{L2C}R^{L2D}$C(=O)$NR^{L2B}$, $NR^{L2A}SO_2$—, —$SO_2NR^{L2A}$—, —$NR^{L2A}SO_2NR^{L2B}$, wherein each occurrence of $R^{L2A}$, $R^{L2B}$, $R^{L2C}$ and $R^{L2D}$ is independently hydrogen, lower alkyl, lower heteroalkyl, heterocyclyl, aryl, heteroaryl or acyl;

cxlvi) $L^2$ is —$NR^{L2A}$—, C(=O)$NR^{L2A}$—, —$NR^{L2A}$C(=O)—, —OC(=O)$NR^{L2A}$, —$NR^{L2A}CO_2$—, —$NR^{L2A}$C(=O)$NR^{L2B}$—, —$NR^{L2A}$C(=O)$NR^{L2B}CR^{L2C}R^{L2D}$ or —$CR^{L2C}R^{L2D}$C(=O)$NR^{L2B}$, wherein each occurrence of $R^{L2A}$, $R^{L2B}$, $R^{L2C}$ and $R^{L2D}$ is independently hydrogen, lower alkyl, lower heteroalkyl, heterocyclyl, aryl, heteroaryl or acyl;

cxlvii) $L^2$ is —$NR^{L2A}$—, —$NR^{L2A}$C(=O), —$NR^{L2A}$C(=O)$NR^{L2B}$, —$NR^{L2A}$C(=O)$NR^{L2B}CR^{L2C}R^{L2D}$ or $CR^{L2C}R^{L2D}$C(=O)$NR^{L2B}$, wherein each occurrence of $R^{L2A}$, $R^{L2B}$, $R^{L2C}$ and $R^{L2D}$ is independently hydrogen, lower alkyl, lower heteroalkyl, heterocyclyl, aryl, heteroaryl or acyl;

cxlviii) $L^2$ is —NH—, —NHC(=O)—, —NHC(=O)O—, —NHC(=O)NH—, —$CH_2$—C(=O)NH— or —NHC(=O)NHCH$_2$—;

cl) $L^2$ is —NH—;

cli) $L^2$ is —NHC(=O)NH—;

clii) $L^2$ is —$CH_2$—C(=O)NH—;

cliii) $L^2$ is —NHC(=O)NHCH$_2$—;

cliv) Z is an alkyl, alkenyl, alkynyl, cycloalkyl, cycloalkenyl, heteroalkyl, heteroalkenyl, heteroalkynyl, heterocyclyl, aryl or heteroaryl moiety;

clv) Z is a branched alkyl, alkenyl, alkynyl, heteroalkyl or heteroalkenyl moiety;

clvi) Z is one of:

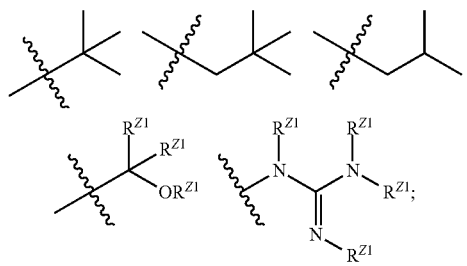

wherein each occurrence of $R^{Z1}$ is independently hydrogen, lower alkyl, lower alkenyl, aryl, heteroaryl or acyl;

clvii) Z is a cycloalkyl, cycloalkenyl, heterocyclyl, aryl or heteroaryl moiety;

clviii) Z is cycloalkyl, cycloalkenyl, or a heterocyclyl, aryl or heteroaryl moiety having one of the structures:

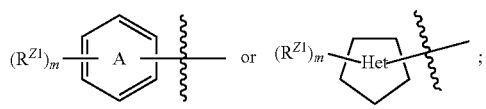

wherein the "A" cyclic moiety is a 6- to 10-membered mono- or fused bicyclic aromatic ring comprising from 0-4 nitrogen atoms; the "Het" moiety represents a fully or partially saturated or unsaturated 5- to 8-membered mono- or fused bicyclic ring comprising 1-4 heteroatoms selected from N, O and S; m is an integer from 0-6; and each occurrence of $R^{Z1}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —$C(=O)N(R^{Z2})_2$, halogen, —CN, —$NO_2$, —$C(=O)OR^{Z2}$, —$N(R^{Z2})C(=O)R^{Z3}$ or —$N(R^{Z2})SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached (e.g., $N(R^{Z2})_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring;

clix) Z is one of:

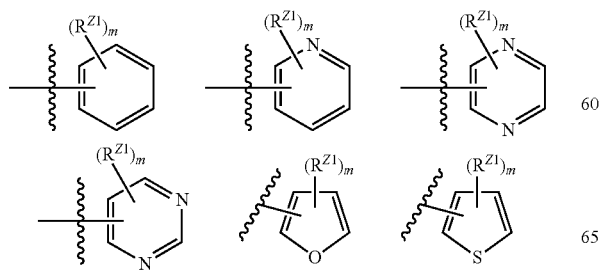

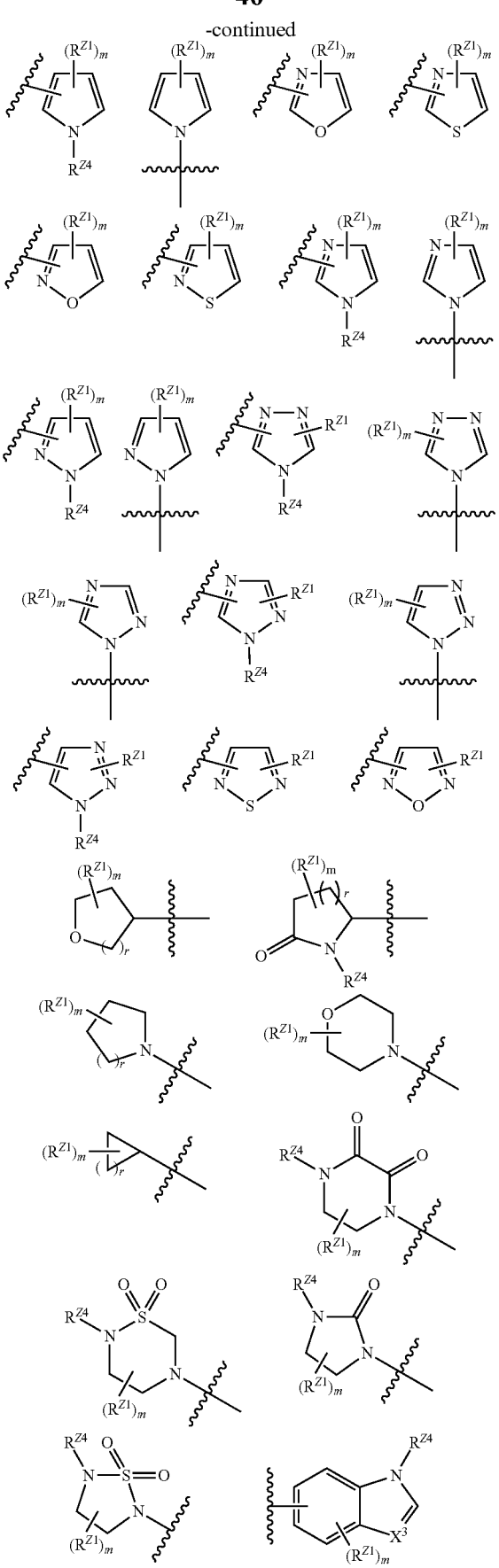

-continued

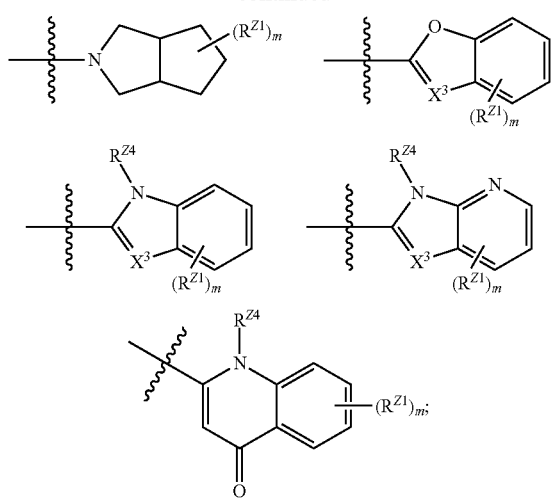

wherein m is an integer from 0 to 3; r is an integer from 1 to 4; $X^3$ is N or $CR^{Z1}$; each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, —$SO_2NR^{Z2}R^{Z3}$, —$SO_2R^{Z1}$, —C(=O)$NR^{Z2}R^{Z3}$, halogen, —CN, —$NO_2$, C(=O)$OR^{Z3}$, N($R^{Z2}$)C(=O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is hydrogen, lower alkyl, lower heteroalkyl, aryl, heteroaryl, -(alkyl)aryl, -(alkyl)heteroaryl or acyl;

clx) Z is one of:

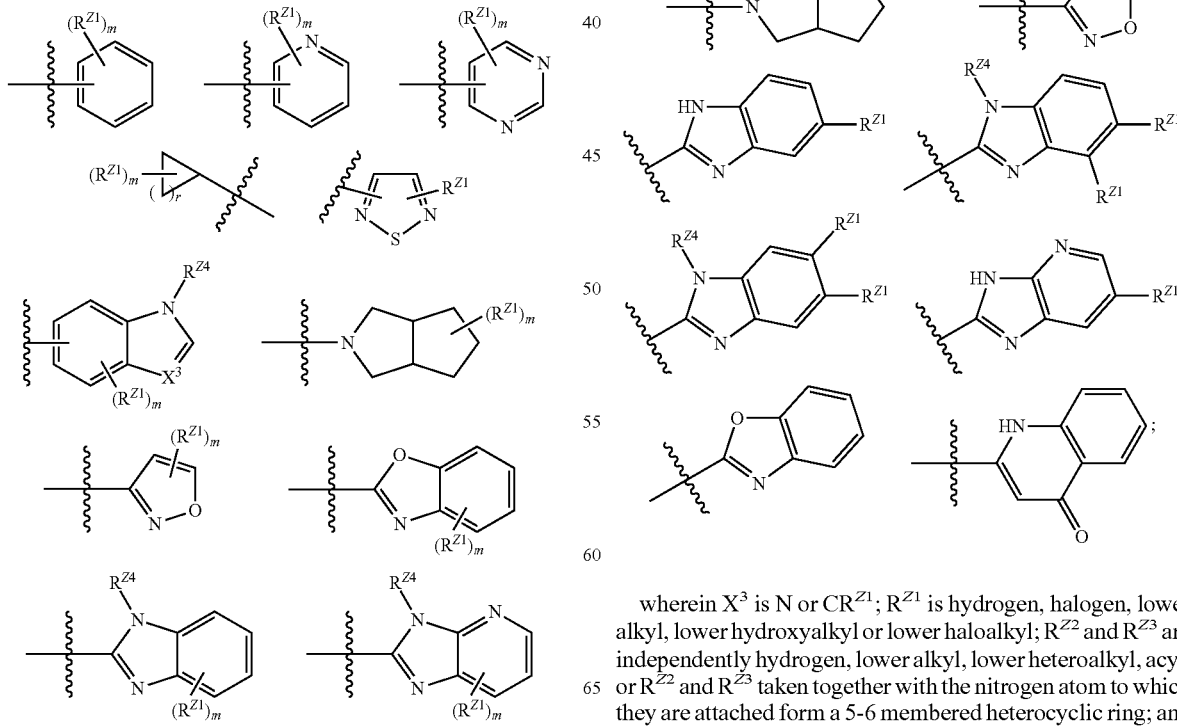

clxi) Z is one of:

wherein $X^3$ is N or $CR^{Z1}$; $R^{Z1}$ is hydrogen, halogen, lower alkyl, lower hydroxyalkyl or lower haloalkyl; $R^{Z2}$ and $R^{Z3}$ are independently hydrogen, lower alkyl, lower heteroalkyl, acyl, or $R^{Z2}$ and $R^{Z3}$ taken together with the nitrogen atom to which they are attached form a 5-6 membered heterocyclic ring; and $R^{Z4}$ is hydrogen or lower alkyl;

clxii) Z is one of:

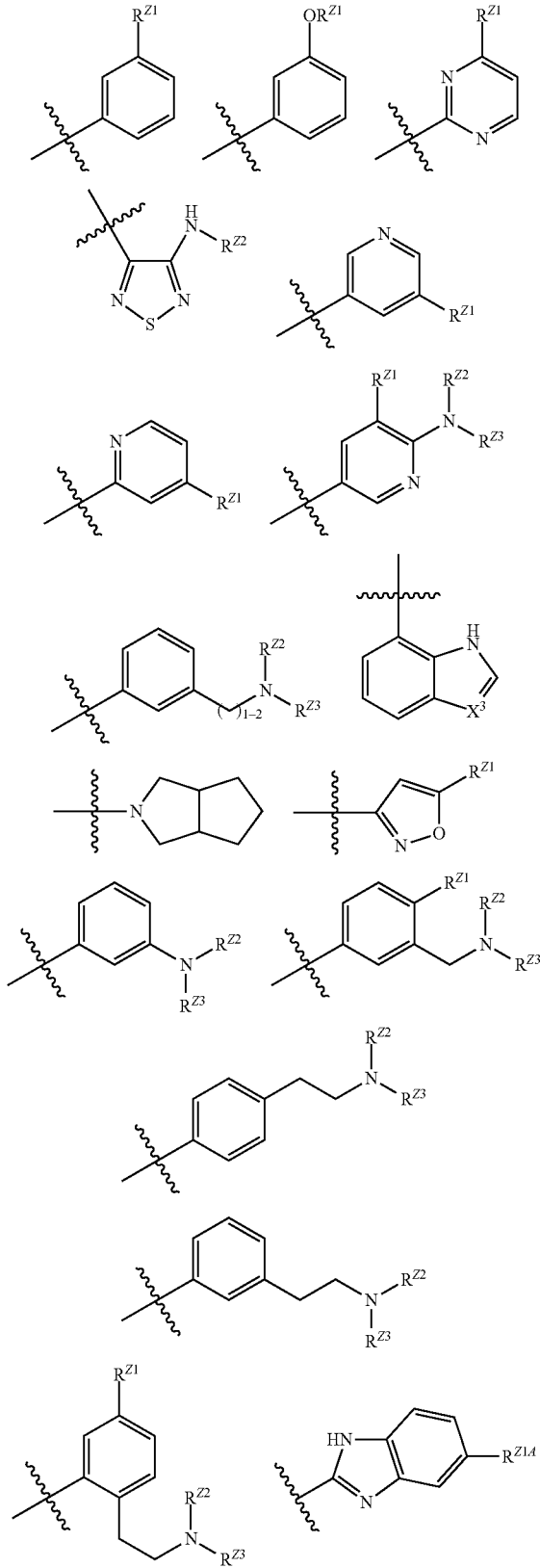

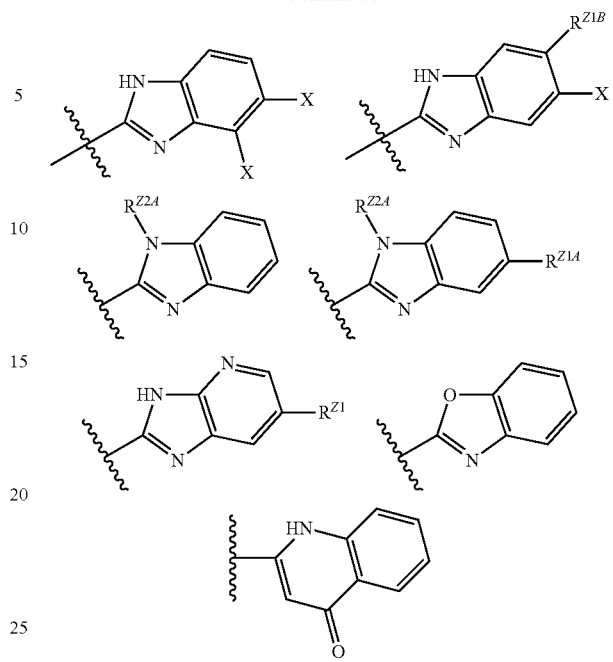

wherein $X^3$ is N or $CR^{Z1}$; $R^{Z1}$ is hydrogen, halogen, lower alkyl or lower haloalkyl; and $R^{Z2}$ and $R^{Z3}$ are independently hydrogen, lower alkyl, lower heteroalkyl, acyl, or $R^{Z2}$ and $R^{Z3}$ taken together with the nitrogen atom to which they are attached form a 5-6 membered heterocyclic ring; X is halogen, $R^{Z1A}$ is hydrogen, halogen, —CN, lower alkyl, lower alkoxy, lower haloalkyl or —SO$_2$R$^{Z4}$; wherein $R^{Z4}$ is lower alkyl; $R^{Z1B}$ is hydrogen or halogen; and $R^{Z2A}$ is hydrogen or lower alkyl;

clxiii) Z is one of:

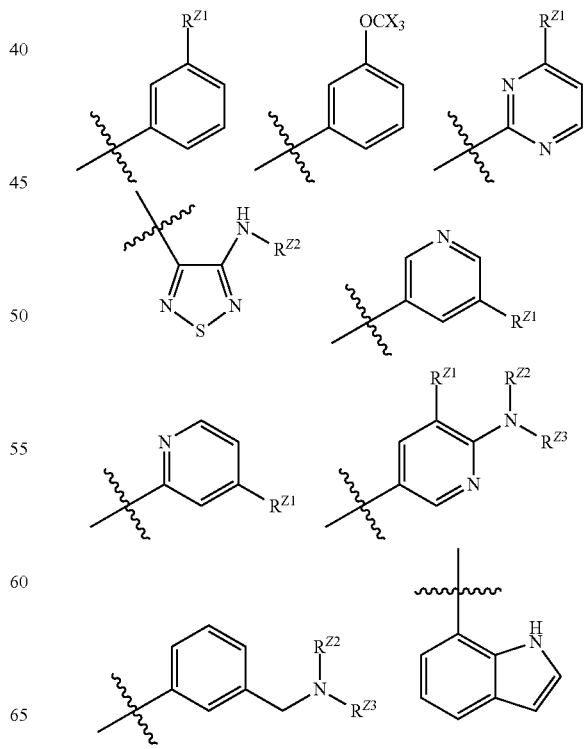

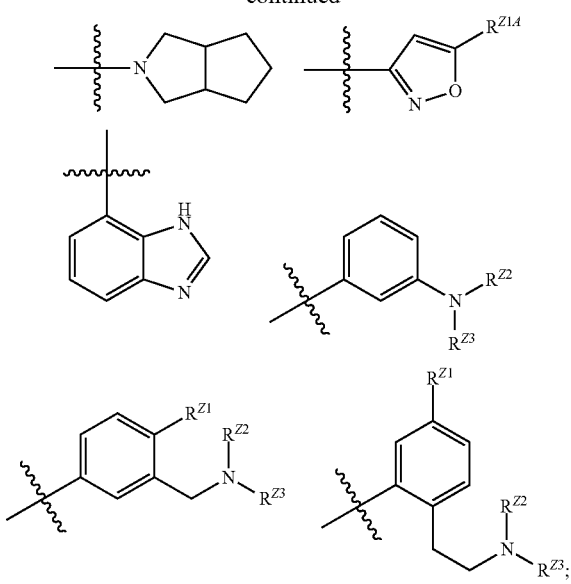

wherein X is halogen; $R^{Z1A}$ is lower alkyl; $R^{Z1}$ is halogen, lower alkyl or lower haloalkyl; and $R^{Z2}$ and $R^{Z3}$ are independently lower alkyl, or $R^{Z2}$ and $R^{Z3}$ taken together with the nitrogen atom to which they are attached form a 5-6 membered heterocyclic ring;

clxiv) Z is one of:

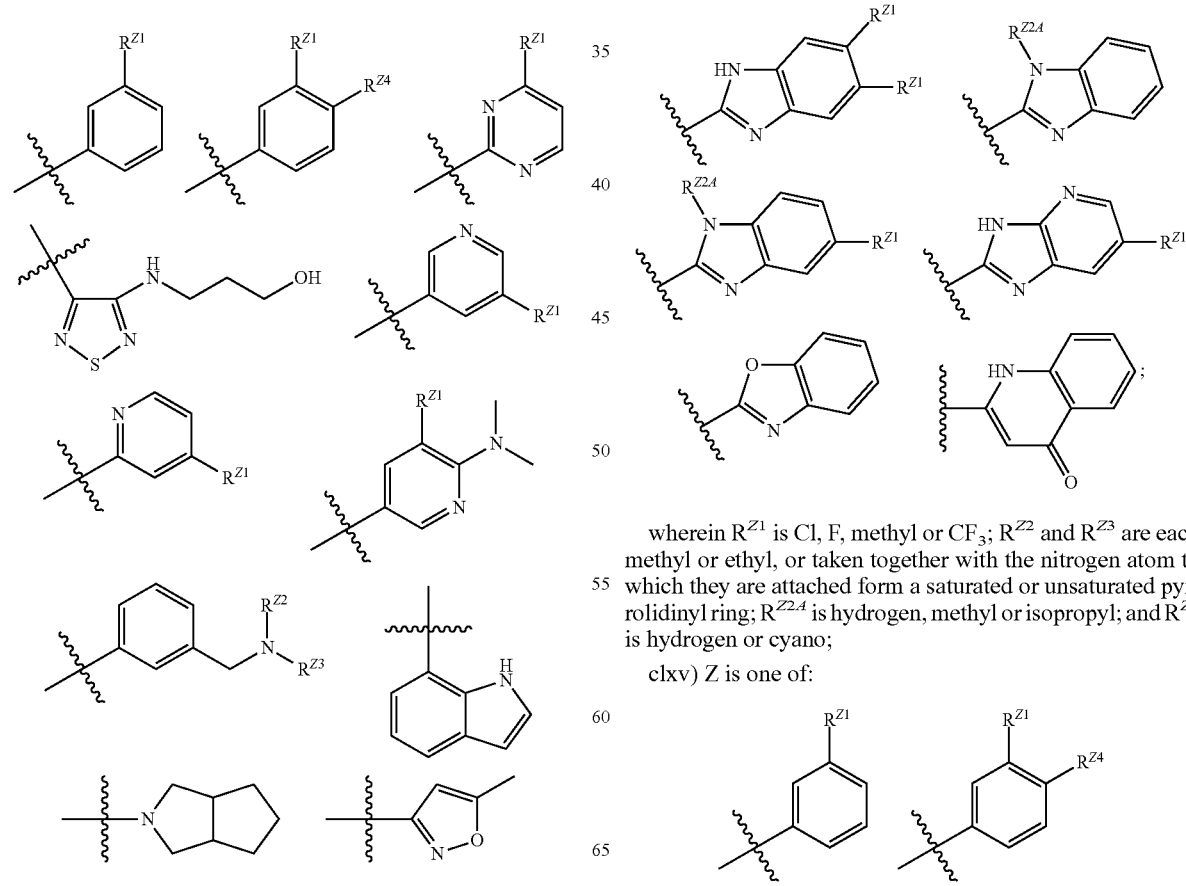

wherein $R^{Z1}$ is Cl, F, methyl or $CF_3$; $R^{Z2}$ and $R^{Z3}$ are each methyl or ethyl, or taken together with the nitrogen atom to which they are attached form a saturated or unsaturated pyrrolidinyl ring; $R^{Z2A}$ is hydrogen, methyl or isopropyl; and $R^{Z4}$ is hydrogen or cyano;

clxv) Z is one of:

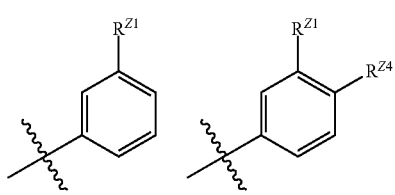

-continued

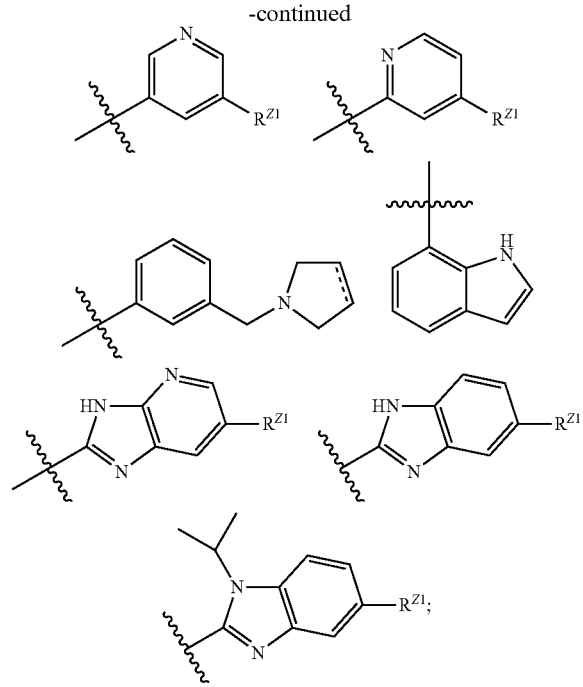

wherein $R^{Z1}$ is Cl, F, methyl or $CF_3$; and $R^{Z4}$ is hydrogen or cyano;

clxvi) $-L^2$-Z together represent a moiety having one of the following structures:

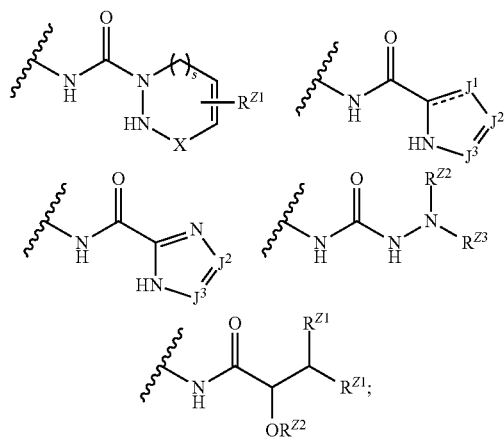

wherein s is 0 or 1; X is $-C(R^{Z1})_2$, $-C(=O)-$ or $-SO_2-$; $J^1$, $J^2$ and $J^3$ are independently N, S, O, $NR^{Z1}$ or $CR^{Z1}$; each occurrence of $R^{Z1}$ is independently hydrogen, alkyl, heteroalkyl, aryl, heteroaryl, -(alkyl)aryl or -(alkyl)heteroaryl, $-OR^{Z2}$, $-SR^{Z2}$, $-NR^{Z2}R^{Z3}$, $-SO_2NR^{Z2}R^{Z3}$, $-SO_2R^{Z1}$, $-C(=O)NR^{Z2}R^{Z3}$, halogen, $-CN$, $-NO_2$, $-C(=O)OR^{Z3}$, $-N(R^{Z2})C(=O)R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring;

clxvii) $-L^2$-Z together represent $-CH_2-Cy$ or $-NH-Cy$ where Cy is an optionally substituted bicyclic heterocycle;

clxviii) $-L^2$-Z together represent a moiety having one of the following structures:

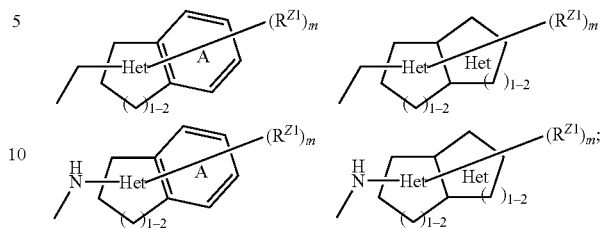

wherein the "A" cyclic moiety is a 6-membered aromatic ring comprising from 0-4 nitrogen atoms; each "Het" moiety independently represents a fully or partially saturated or unsaturated 5- to 6-membered ring comprising 1-4 heteroatoms selected from N, O and S; m is an integer from 0-6; and each occurrence of $R^{Z1}$ is independently hydrogen, alkyl, heteroalkyl, aryl, heteroaryl, -(alkyl)aryl, -(alkyl)heteroaryl, $-OR^{Z2}$, $-SR^{Z2}$, $N(R^{Z2})_2$, $-SO_2N(R^{Z2})_2$, $-SO_2R^{Z4}$, $-C(=O)N(R^{Z2})_2$, halogen, $-CN$, $-NO_2$, $-C(=O)OR^{Z2}$, $-N(R^{Z2})C(=O)R^{Z3}$ or $-N(R^{Z2})SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached (e.g., $N(R^{Z2})_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring;

clxix) $-L^2$-Z together represent a moiety having one of the following structures:

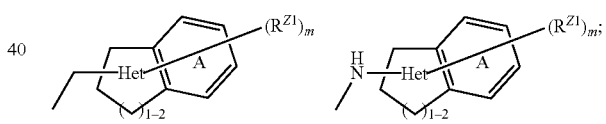

wherein the "A" cyclic moiety is a 6-membered aromatic ring comprising from 0-4 nitrogen atoms; each "Het" moiety independently represents a fully or partially saturated or unsaturated 5- to 6-membered ring comprising 1-4 heteroatoms selected from N, O and S; m is an integer from 0-6; and each occurrence of $R^{Z1}$ is independently hydrogen, lower alkyl, lower alkoxy, $-SO_2R^{Z4}$, halogen or $-CN$; wherein $R^{Z4}$ is lower alkyl;

clxx) $-L^2$-Z together represent a moiety having one of the following structures:

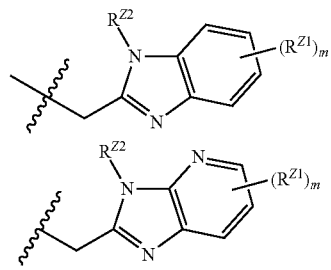

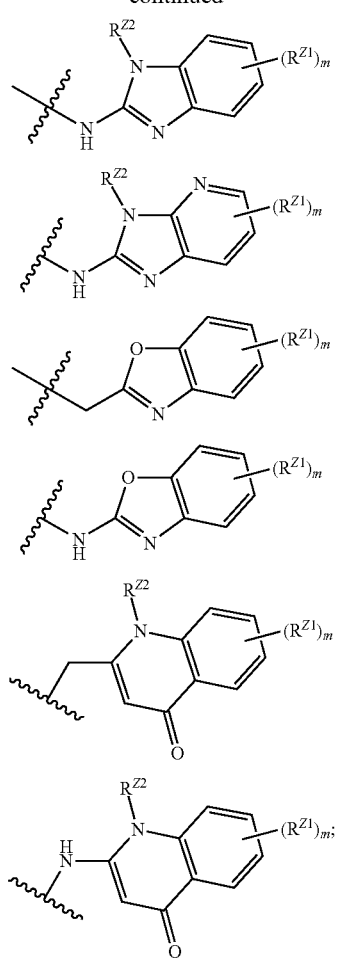

wherein m is an integer from 0-4; each occurrence of $R^{Z1}$ is independently hydrogen, alkyl, heteroalkyl, aryl, heteroaryl, -(alkyl)aryl, -(alkyl)heteroaryl, —$OR^{Z2}$, $SR^{Z2}$, $N(R^{Z2})_2$, —$SO_2N(R^{Z2})_2$, —$SO_2R^{Z4}$, —C(=O)$N(R^{Z2})_2$, halogen, —CN, —$NO_2$, —C(=O)$OR^{Z2}$, —$N(R^{Z2})$C(=O)$R^{Z3}$ or —$N(R^{Z2})SO_2R^{Z4}$; wherein each occurrence of $R^{Z2}$ is hydrogen, lower alkyl, lower heteroalkyl, aryl, heteroaryl, -(alkyl)aryl, -(alkyl)heteroaryl or acyl; and wherein any two adjacent occurrence of $R^{Z1}$ may form a fused 5- to 6-membered aryl, heteroaryl or heterocyclic ring;

clxxi) -$L^2$-Z together represent a moiety having one of the following structures:

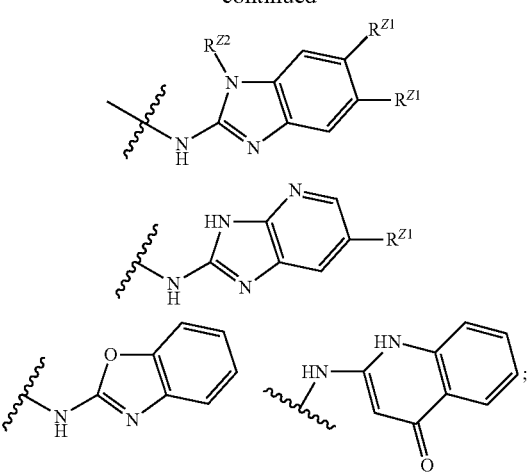

wherein $R^{Z2}$ is hydrogen or lower alkyl; each occurrence of $R^{Z1}$ is independently hydrogen, halogen, —CN, lower alkyl, lower alkoxy, lower haloalkyl or —$SO_2R^{Z4}$; wherein $R^{Z4}$ is lower alkyl;

clxxii) -$L^2$-Z together represent a moiety having one of the following structures:

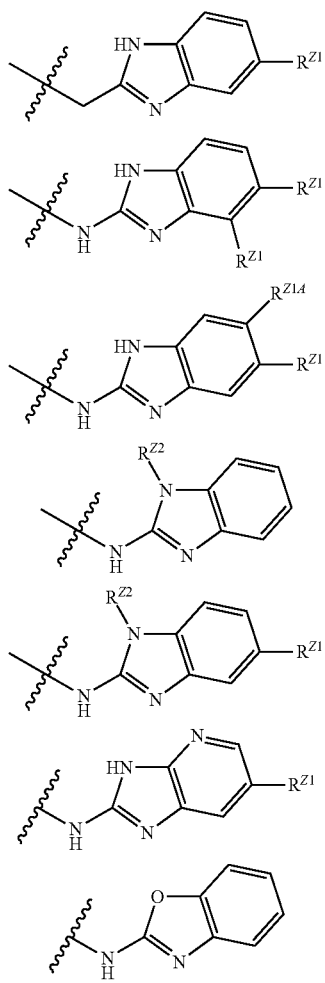

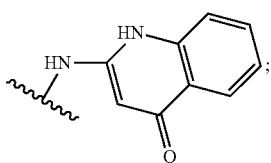

wherein X is halogen, $R^{Z1A}$ is hydrogen, halogen, —CN, lower alkyl, lower alkoxy, lower haloalkyl or —SO$_2$R$^{Z4}$; wherein $R^{Z4}$ is lower alkyl; and $R^{Z2}$ is hydrogen or lower alkyl;

clxxiii) -L$^2$-Z together represent a moiety having one of the following structures:

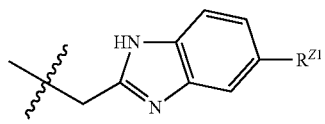
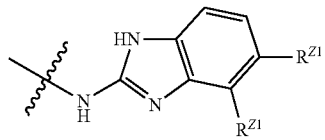
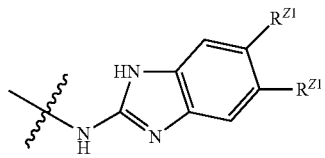
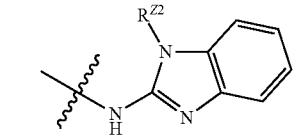
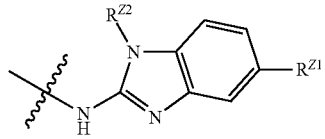
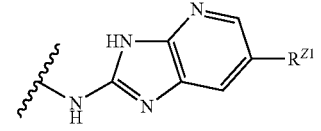
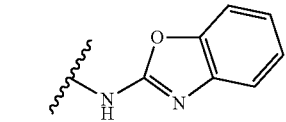
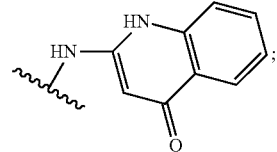

wherein $R^{Z1}$ is Cl, F, methyl or CF$_3$; and $R^{Z2}$ is hydrogen, methyl or isopropyl; and/or clxxiv) -L$^2$-Z together represent a moiety having one of the following structures:

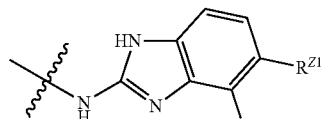
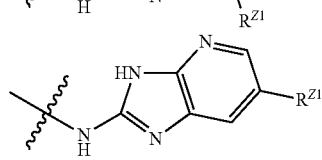
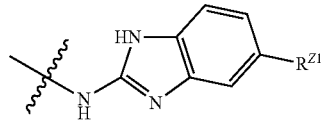
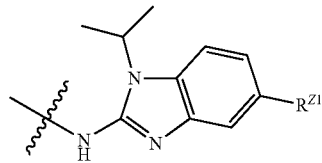

wherein $R^{Z1}$ is Cl, F, methyl or CF$_3$.

It will be appreciated that for each of the classes and subclasses described above and herein, any one or more occurrences of aliphatic or heteroaliphatic may independently be substituted or unsubstituted, cyclic or acyclic, linear or branched, saturated or unsaturated and any one or more occurrences of aryl, heteroaryl, cycloaliphatic, cycloheteroaliphatic may be substituted or unsubstituted.

The reader will also appreciate that any and all possible combinations of the variables described in i)-through clxxiv) above (e.g., R$^2$, L$^1$, L$^2$, X$^1$, X$^2$, Y and Z, among others) are considered part of the invention. Thus, the invention encompasses any and all compounds of formula I generated by taking any possible permutation of variables R$^2$, L$^1$, L$^2$, X$^1$, X$^2$, Y and Z, and other variables/substituents (e.g., R$^1$, R$^3$, R$^{X1A}$, R$^{X2A}$, R$^{X1B}$, R$^{X2B}$, R$^{Y1}$, R$^{Z1}$ etc.) as further defined for R$^2$, L$^1$, L$^2$, X$^1$, X$^2$, Y and Z, described in i)-through lii) above.

For example, an exemplary combination of variables described in i)-through clxxiv) above includes those compounds of Formula I wherein:

R$^2$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

R$^4$ is hydrogen, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

X$^{1A}$ is NR$^1$ or —C(R$^{X1}$)—; wherein R$^1$ taken together with a moiety present on L$^1$ may form an optionally substituted heterocyclic ring;

X$^{2A}$ is NR$^3$ or —C(R$^{X1}$)—; wherein one of X$^{1A}$ and X$^{2A}$ is —C(R$^{X1}$)—, but not both;

X$^{1B}$ and X$^{2B}$ are —N— or —C(R$^{X1}$)—; whereby one of X$^{1B}$ and X$^{2B}$ is —C(R$^{X1}$)—, but not both;

wherein R$^1$ and R$^3$ are independently hydrogen, a nitrogen protecting group, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety; and $R^{X1}$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

$L^1$ is —$W^1$-$Alk_1$-; wherein $W^1$ is O or $NR^{W1}$, where $R^{W1}$ is hydrogen, alkyl, heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O), —$NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, alkyl, heteroalkyl, heterocyclyl, aromatic, heteroaromatic or acyl;

$L^2$ is —C(=O)$NR^{L2A}$—, —C(=O)$NR^{L2A}$, —$NR^{L2A}NR^{L2B}$—, $NR^{L2A}NR^{L2B}$C(=O)—, $NR^{L2A}$C(=O)—, $NR^{L2A}CO_2$—, $NR^{L2A}$C(=O)$NR^{L2B}$—, —$NR^{L2A}SO_2$—, —$SO_2NR^{L2A}$—, —$NR^{L2A}SO_2NR^{L2B}$—, or a substituted or unsubstituted $C_{1-6}$alkylene or $C_{2-6}$alkenylene chain interrupted with at least one nitrogen atom wherein up to two non-adjacent methylene units are independently optionally replaced by —C(=O)—, —$CO_2$—, —C(=O)C(=O)—, —C(=O)$NR^{L2A}$—, —OC(=O)—, —OC(=O)$NR^{L2A}$—, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(=O)$NR^{L2B}$—, —S(=O)—, —$SO_2$—, $NR^{L2A}SO_2$—, $SO_2NR^{L2A}$—, —$NR^{L2A}SO_2NR^{L2B}$—, —O—, —S—, or —$NR^{L2A}$—; wherein each occurrence of $R^{L2A}$ and $R^{L2B}$ is independently hydrogen, alkyl, heteroalkyl, heterocyclyl, aromatic, heteroaromatic or acyl;

Y is a saturated or unsaturated cyclic ring system optionally comprising one or more heteroatoms selected from S, N and O;

Z is an alkyl, alkenyl, alkynyl, cycloalkyl, cycloalkenyl, heteroalkyl, heteroalkenyl, heteroalkynyl, heterocyclyl, aryl or heteroaryl moiety.

Other exemplary combinations are illustrated by compounds of the following subgroups I through XVI:

I. Compounds Having the Structure (and Pharmaceutically Acceptable Derivatives Thereof):

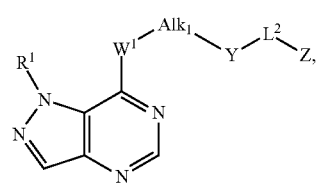

(SP 1)

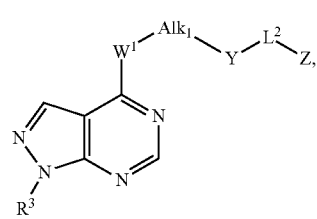

(SP 2)

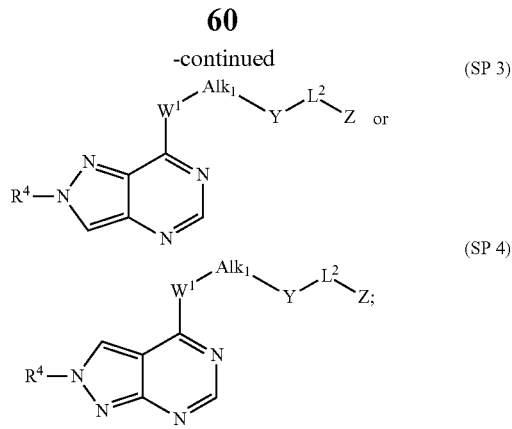

(SP 3)

(SP 4)

wherein $R^1$, $R^3$, $R^4$, $L^2$, Y and Z are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; and $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O), —$NR^{L1A}CO_2$, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$, —O—, —S—, or —$NR^{L1A}$—; wherein each occurrence of $R^{L1A}$ and $R^{L1B}$ is independently hydrogen, lower alkyl, lower heteroalkyl, heterocyclyl, aryl, heteroaryl or acyl.

In certain embodiments, compounds of the invention have one of the structures (SP $1^A$) through (SP $4^A$) below:

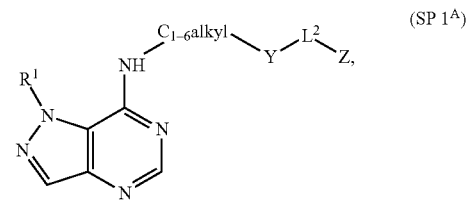

(SP $1^A$)

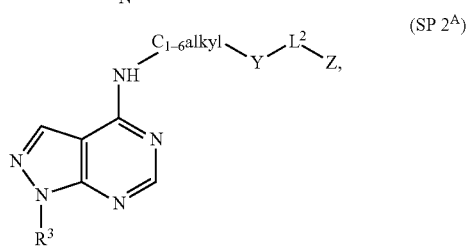

(SP $2^A$)

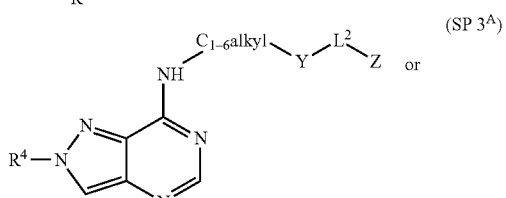

(SP $3^A$)

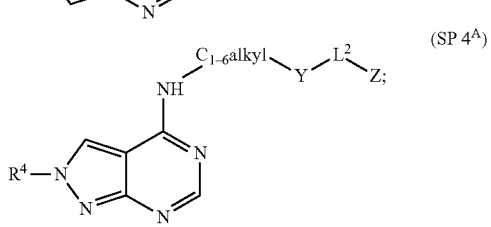

(SP $4^A$)

wherein the $C_{1-6}$alkyl moiety may be substituted or unsubstituted.

In certain embodiments, compounds of the invention have one of the structures ($1^B$) through ($4^B$) below:

(SP $1^B$)

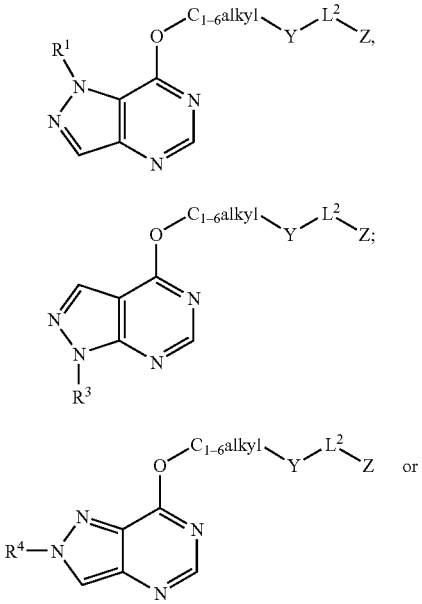

(SP $2^B$)

(SP $3^B$)

(SP $4^B$)

wherein the $C_{1-6}$alkyl moiety may be substituted or unsubstituted.

In certain embodiments, for compounds of formulae ($1^A$)-($4^A$) and ($1^B$)-($4^B$), the $C_{1-6}$alkyl moiety is a substituted or unsubstituted $C_2$alkyl moiety. In certain exemplary embodiments, the $C_{1-6}$alkyl moiety is —$CH_2CH_2$—.

II. Compounds Having the Structure (and Pharmaceutically Acceptable Derivatives Thereof):

(SP 5)

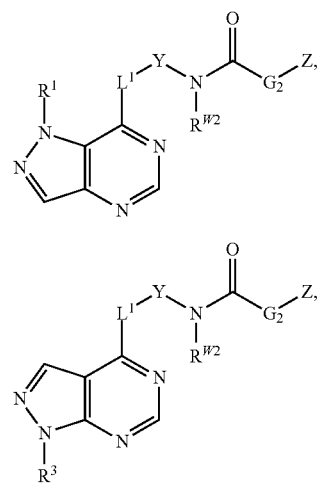

(SP 6)

(SP 7)

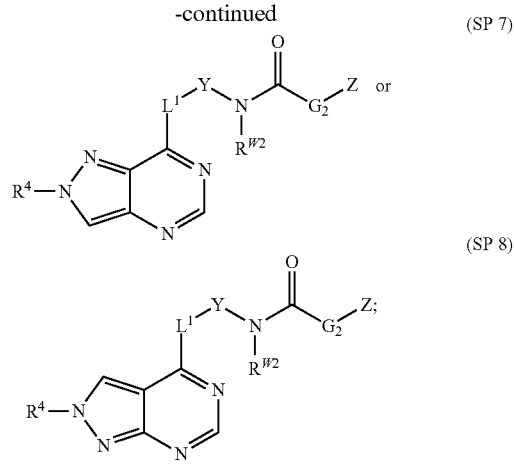

(SP 8)

wherein $R^1$, $R^3$, $R^4$, $L^1$, Y and Z are as defined generally and in classes and subclasses herein; $G_2$ is absent, O or $NR^{G2}$; and $R^{W2}$ and $R^{G2}$ are independently hydrogen, lower alkyl, lower heteroalkyl, aryl, heteroaryl, -(alkyl)aryl, -(alkyl)heteroaryl or acyl.

In certain embodiments, —N($R^{W2}$)C(═O)$G_2$- is —NHC(═O)—, —NHC(═O)O—, or —NHC(═O)NH—. In certain embodiments, compounds of the invention have one of the structures (SP $5^A$)-(SP $8^A$) below:

(SP $5^A$)

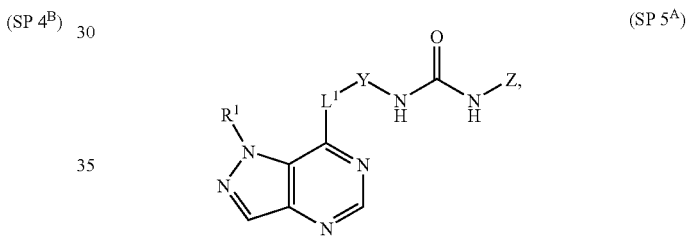

(SP $6^A$)

(SP $7^A$)

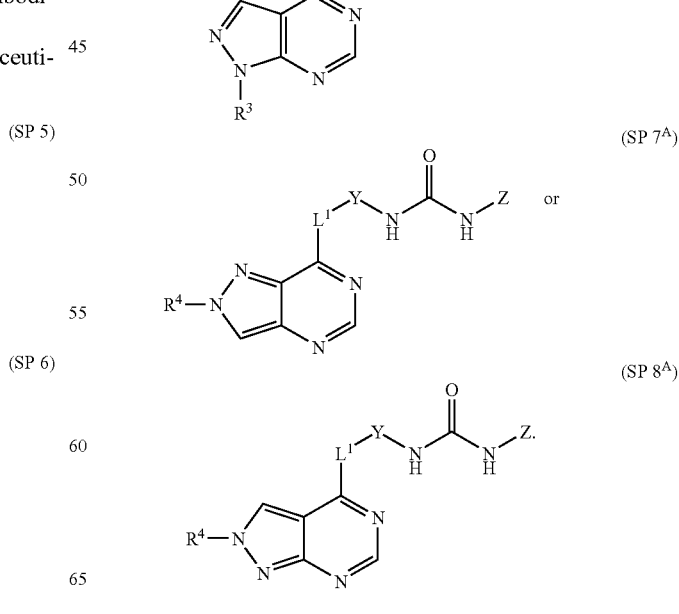

(SP $8^A$)

II. Compounds Having the Structure (and Pharmaceutically Acceptable Derivatives Thereof):

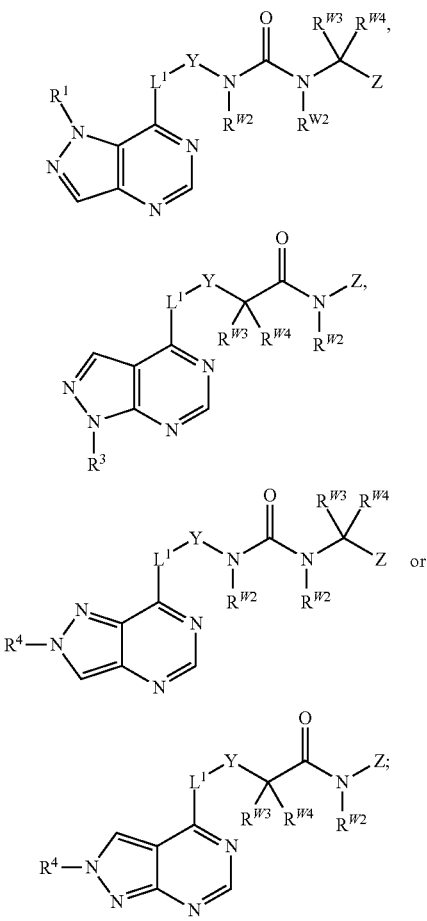

(SP 9)

(SP 10)

(SP 11)

(SP 12)

wherein $R^1$, $R^3$, $R^4$, $L^1$, Y and Z are as defined generally and in classes and subclasses herein; and $R^{W2}$, $R^{W3}$ and $R^{W4}$ are independently hydrogen, lower alkyl, lower heteroalkyl, heterocyclyl, aryl, heteroaryl, -(alkyl)aryl, -(alkyl)heteroaryl or acyl.

In certain embodiments, compounds of the invention have one of the structures (SP $9^A$)-(SP $12^A$) below:

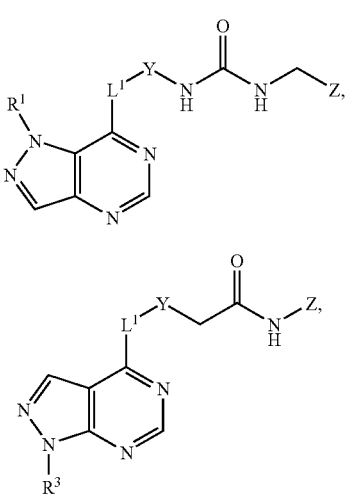

(SP $9^A$)

(SP $10^A$)

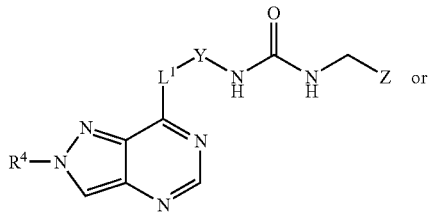

(SP $11^A$)

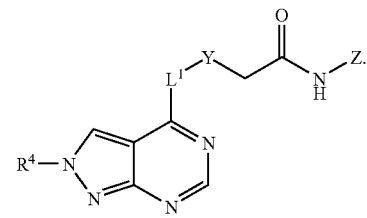

(SP $12^A$)

IV. Compounds Having the Structure (and Pharmaceutically Acceptable Derivatives Thereof):

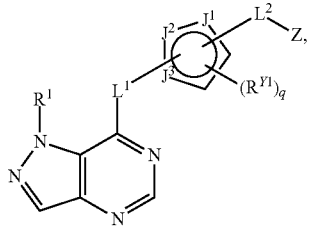

(SP 13)

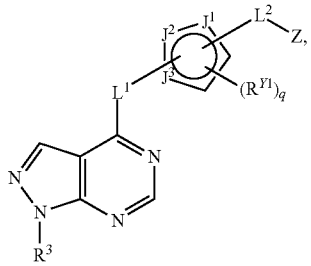

(SP 14)

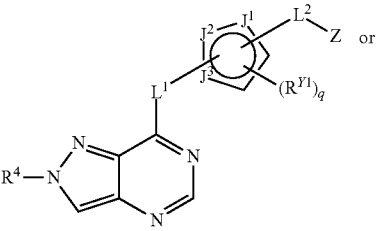

(SP 15)

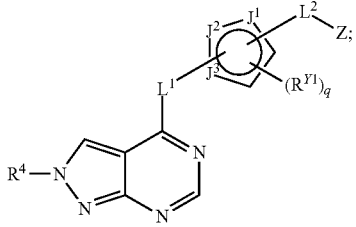

(SP 16)

wherein q is an integer from 0-2; $R^1$, $R^3$, $R^4$, $L^1$, $L^2$ and Z are as defined generally and in classes and subclasses herein; and $J^1$, $J^2$ and $J^3$ are independently O, S, N, $NR^{Y1}$, or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of R$^{Y2}$ and R$^{Y3}$ is independently hydrogen, lower alkyl, lower heteroalkyl, aryl, heteroaryl, -(alkyl)aryl, -(alkyl)heteroaryl or acyl, or R$^{Y2}$ and R$^{Y3}$ taken together with the nitrogen atom to which they are attached form a 5-6 membered heterocyclic ring.

In certain embodiments, compounds of the invention have one of the structures (SP 13$^{A1}$)-(SP 16$^{A1}$) below:

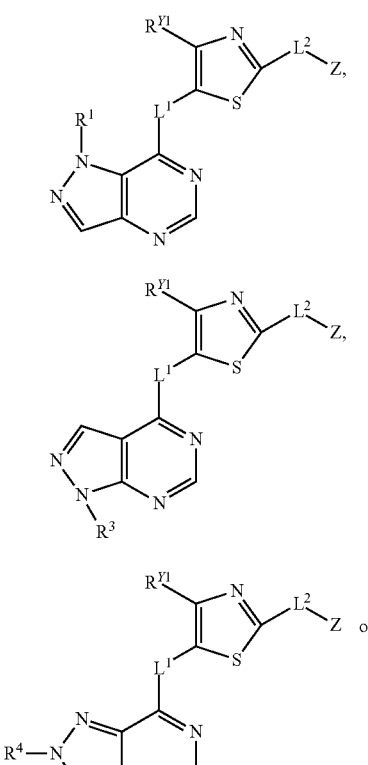

(SP 13$^{A1}$)

(SP 14$^{A1}$)

(SP 15$^{A1}$)

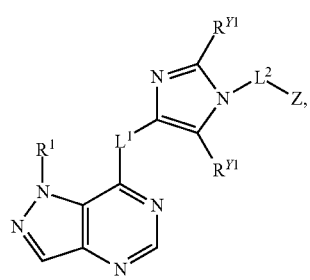

(SP 16$^{A1}$)

In certain embodiments, compounds of the invention have one of the structures (SP 13$^{A2}$)-(SP 16$^{A2}$) below:

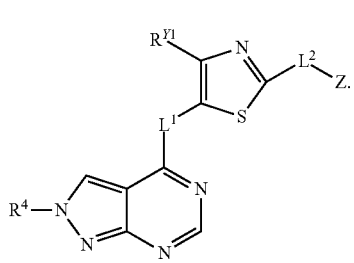

(SP 13$^{A2}$)

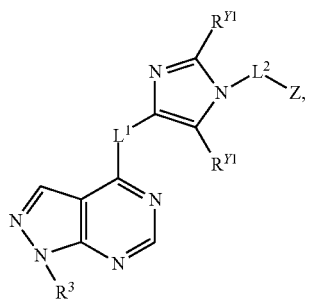

(SP 14$^{A2}$)

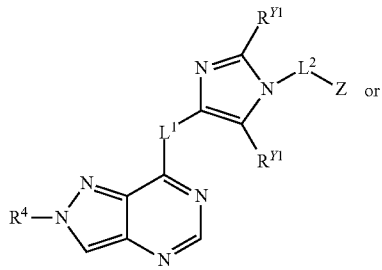

(SP 15$^{A2}$) or

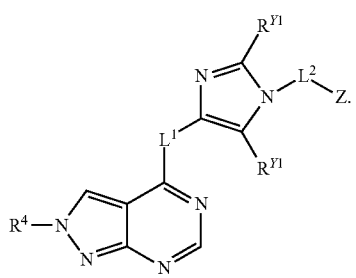

(SP 16$^{A2}$)

V. Compounds Having the Structure (and Pharmaceutically Acceptable Derivatives Thereof):

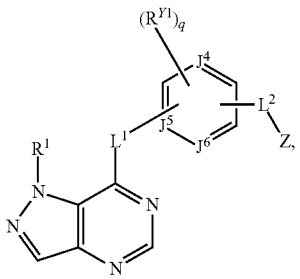

(SP 17)

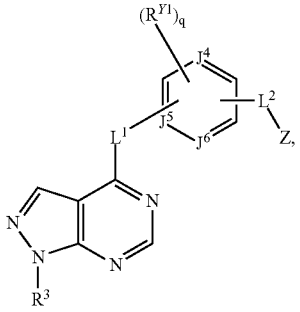

(SP 18)

-continued (SP 19)

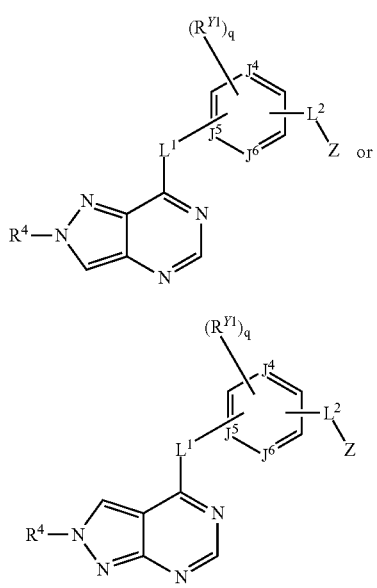

(SP 20)

wherein q is an integer from 0-3; $R^1$, $R^3$, $R^4$, $L^1$, $L^2$ and Z are as defined generally and in classes and subclasses herein; and $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring.

In certain embodiments, compounds of the invention have one of the structures (SP $17^A$)-(SP $20^A$) below:

(SP 17$^A$)

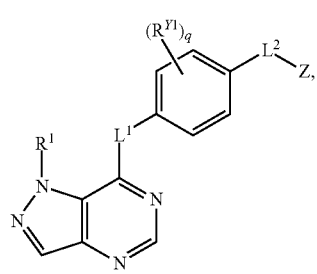

(SP 18$^A$)

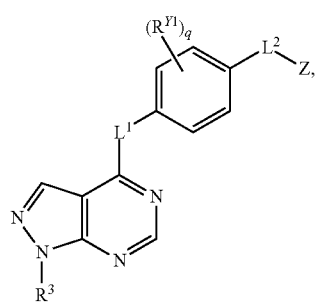

In certain embodiments, compounds of the invention have one of the structures (SP $17^B$)-(SP $20^B$) below:

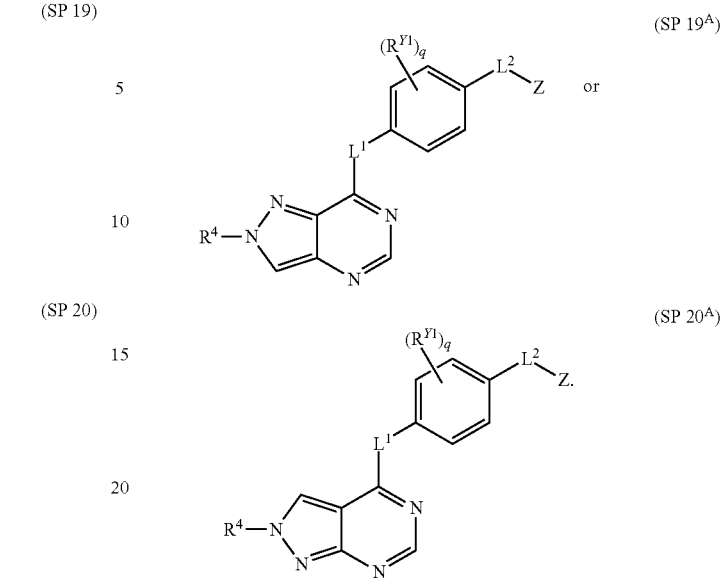

(SP 17$^B$)

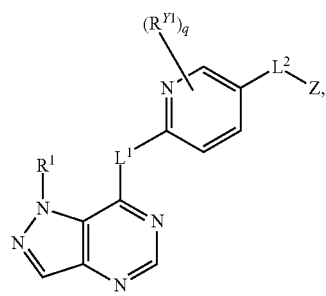

(SP 18$^B$)

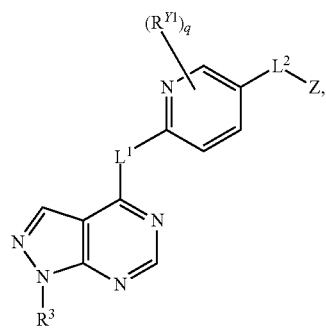

(SP 19$^B$)

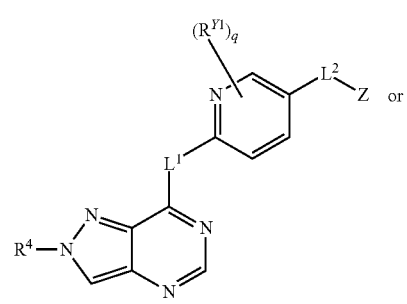

-continued

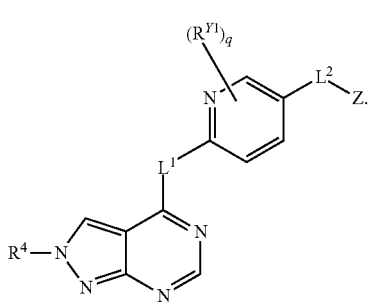
(SP 20$^B$)

VI. Compounds Having the Structure (and Pharmaceutically Acceptable Derivatives Thereof):

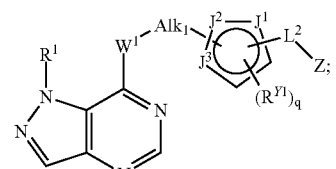
(SP 21)

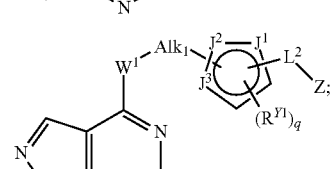
(SP 22)

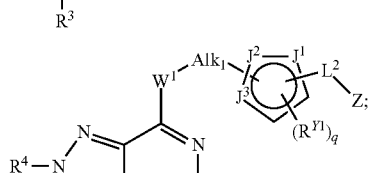
(SP 23)

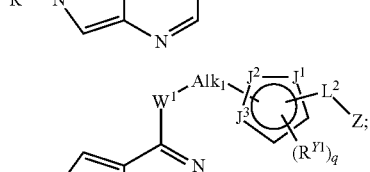
(SP 24)

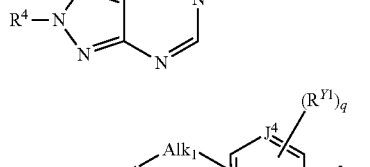
(SP 25)

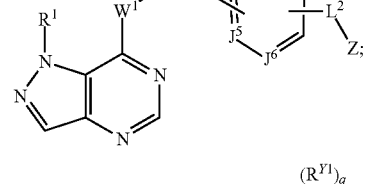
(SP 26)

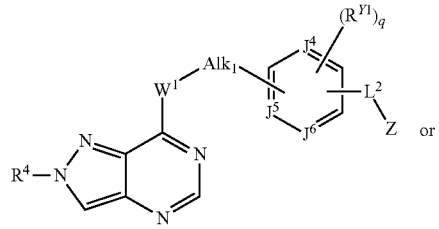
(SP 27)

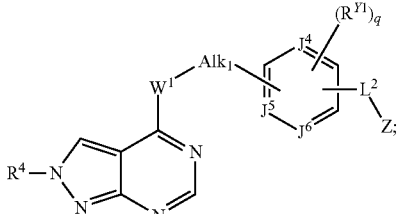
(SP 28)

wherein $R^1$, $R^3$, $R^4$, $L^2$ and Z are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O)—, $NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^1$, $J^2$ and $J^3$ are independently O, S, N, $NR^{Y1}$ or $CR^{Y1}$; $J^4$, $J^5$ and $J^6$ are N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —C(=O)$NR^{Y2}R^{Y3}$, halogen, —CN, —$NO_2$, —C(=O)$OR^{Y3}$, —N($R^{Y2}$)C(=O)$R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring.

In certain embodiments, in compounds of the formulae (SP 21)-(SP 24) the 5-membered ring having the structure:

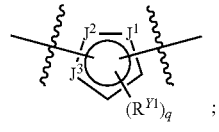

has one of the following structures:

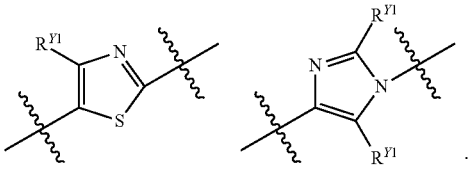

In certain embodiments, in compounds of the formulae (SP 25)-(SP 28) the 6-membered ring having the structure:

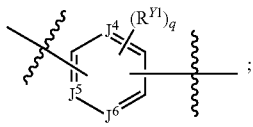

has one of the following structures:

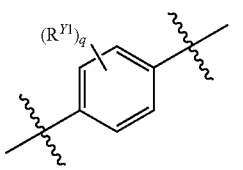 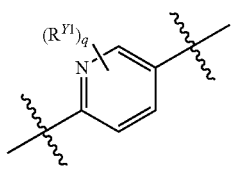

In certain embodiments, —W$^1$-Alk$_1$- is —NHC$_{1-6}$alkyl- or —OC$_{1-6}$alkyl-. In certain embodiments, —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

VII. Compounds Having the Structure (and Pharmaceutically Acceptable Derivatives Thereof):

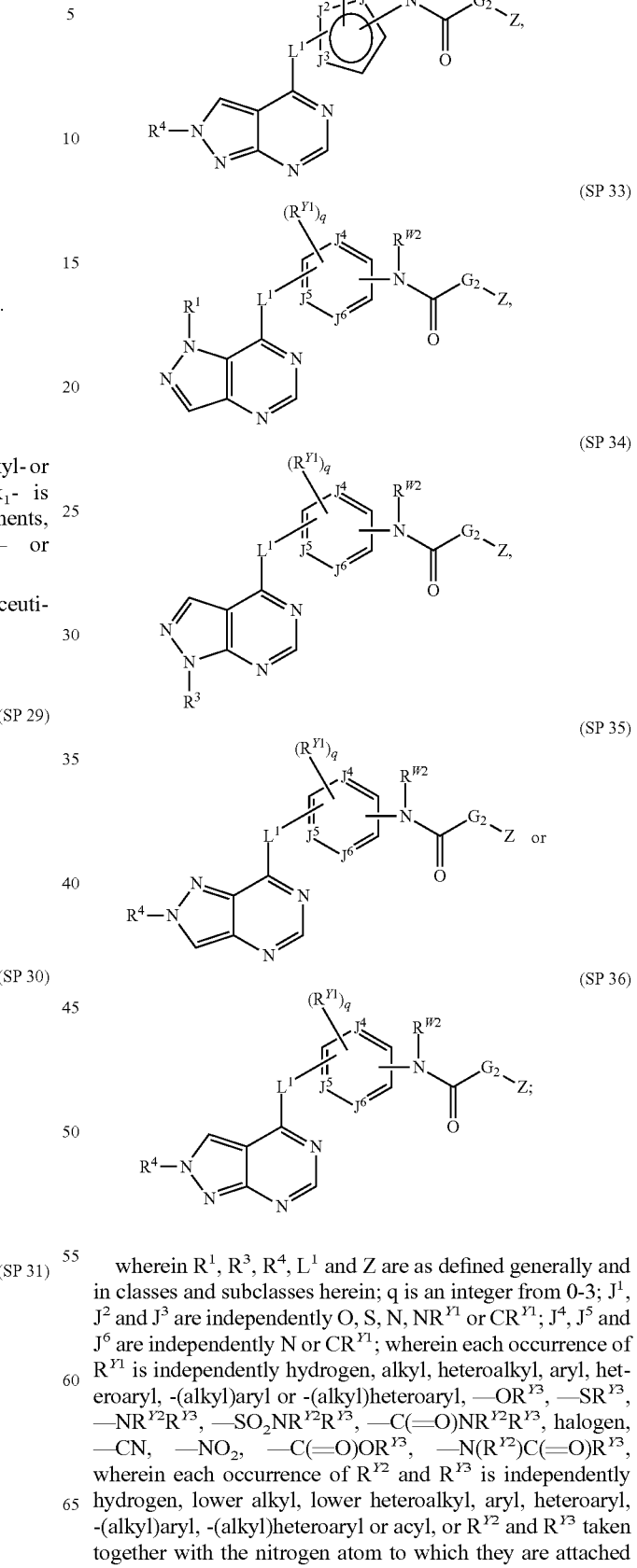

wherein R$^1$, R$^3$, R$^4$, L$^1$ and Z are as defined generally and in classes and subclasses herein; q is an integer from 0-3; J$^1$, J$^2$ and J$^3$ are independently O, S, N, NR$^{Y1}$ or CR$^{Y1}$; J$^4$, J$^5$ and J$^6$ are independently N or CR$^{Y1}$; wherein each occurrence of R$^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of R$^{Y2}$ and R$^{Y3}$ is independently hydrogen, lower alkyl, lower heteroalkyl, aryl, heteroaryl, -(alkyl)aryl, -(alkyl)heteroaryl or acyl, or R$^{Y2}$ and R$^{Y3}$ taken together with the nitrogen atom to which they are attached form a 5-6 membered heterocyclic ring; $G_2$ is absent, O or $NR^{G2}$; and $R^{W2}$ and $R^{G2}$ are independently hydrogen, lower alkyl, lower heteroalkyl, heterocyclyl, aryl, heteroaryl, -(alkyl)aryl, -(alkyl)heteroaryl or acyl.

In certain embodiments, in compounds of formulae (SP 29)-(SP 32) the 5-membered ring having the structure:

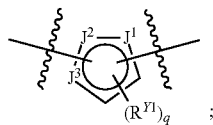

has one of the following structures:

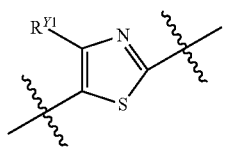 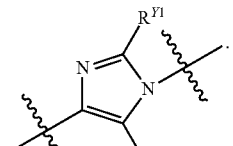

In certain embodiments, in compounds of formulae (SP 33)-(SP 36) the 6-membered ring having the structure:

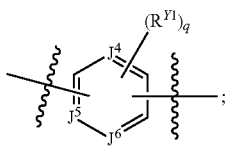

has one of the following structures:

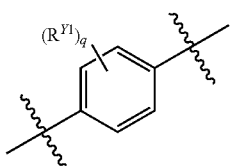 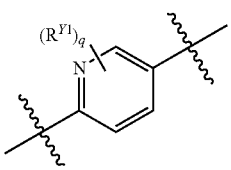

In certain embodiments, $-N(R^{W2})C(=O)G_2-$ is $-NHC(=O)-$, $-NHC(=O)O-$, or $-NHC(=O)NH-$.

VIII. Compounds Having the Structure (and Pharmaceutically Acceptable Derivatives Thereof):

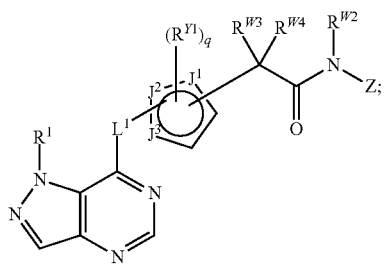

(SP 37$^A$)

-continued

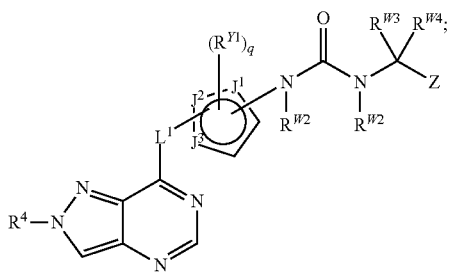

(SP 38$^A$)

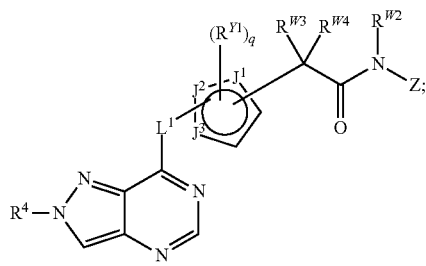

(SP 39$^A$)

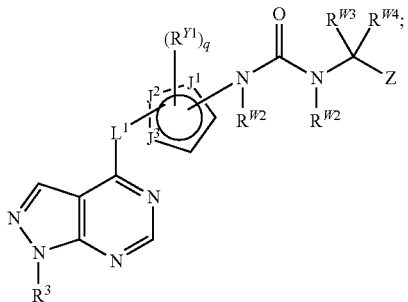

(SP 40$^A$)

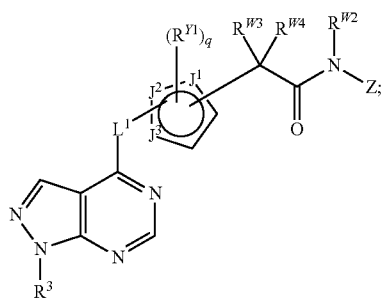

(SP 37$^B$)

(SP 38$^B$)

(SP 39^B)
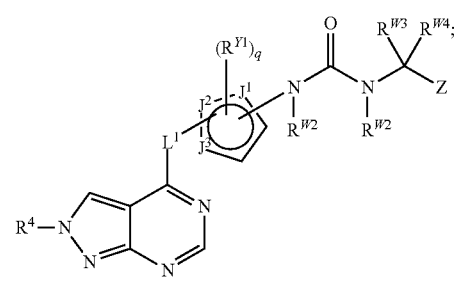

(SP 40^B)
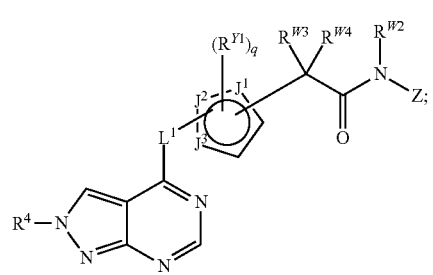

(SP 41^A)
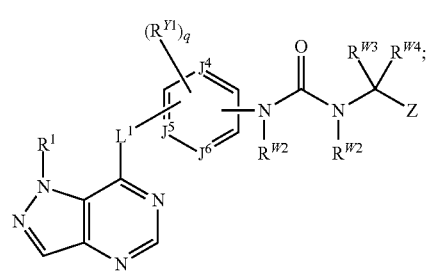

(SP 42^A)
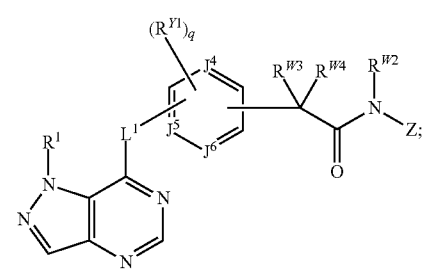

(SP 43^A)
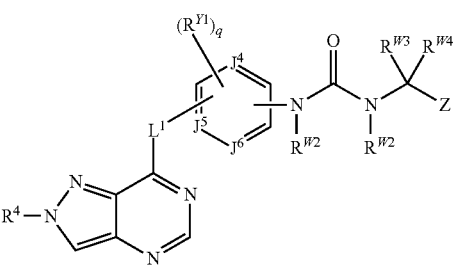

(SP 44^A)
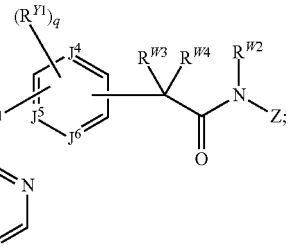

(SP 41^B)
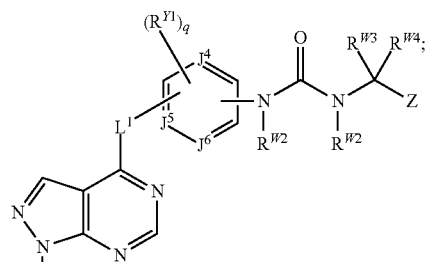

(SP 42^B)
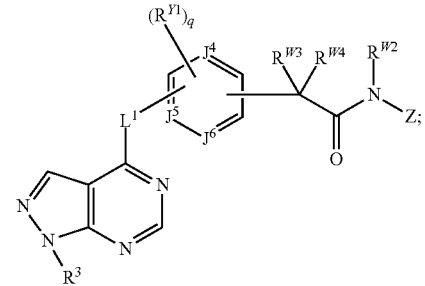

(SP 43^B) or
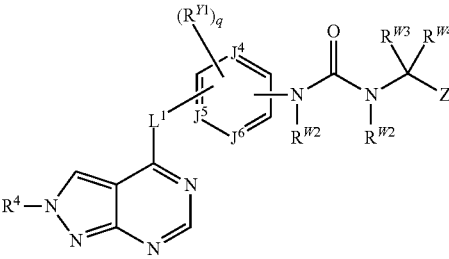

(SP 44^B)
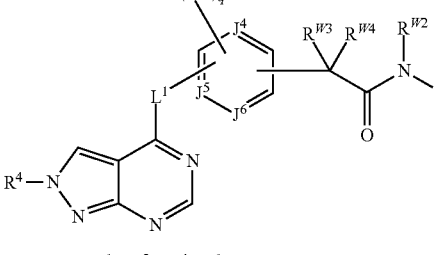

wherein $R^1$, $R^3$, $R^4$, $L^1$ and Z are as defined generally and in classes and subclasses herein; q is an integer from 0-3; $J^1$, $J^2$ and $J^3$ are independently O, S, N, $NR^{Y1}$ or $CR^{Y1}$; $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $R^{W3}$ and $R^{W4}$ are independently hydrogen, lower alkyl, lower heteroalkyl, heterocyclyl, aryl, heteroaryl or acyl; and $R^{W2}$ is hydrogen, lower alkyl, lower heteroalkyl, heterocyclyl, aryl, heteroaryl, -(alkyl)aryl, -(alkyl)heteroaryl or acyl.

In certain embodiments, in compounds of formulae (SP $37^{A-B}$) through (SP $40^{A-B}$) the 5-membered ring having the structure:

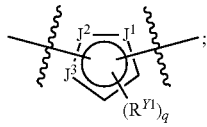

has one of the following structures:

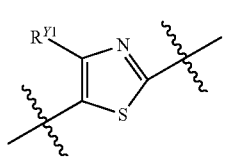 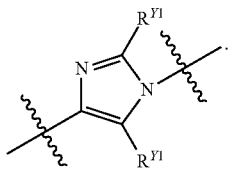

In certain embodiments, in compounds of formulae (SP $41^{A-B}$) through (SP $44^{A-B}$) the 6-membered ring having the structure:

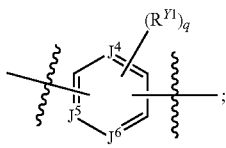

has one of the following structures:

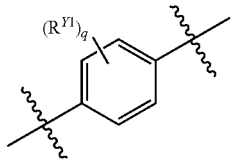 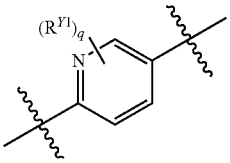

In certain embodiments, —N($R^{W2}$)C(=O)N($R^{W2}$)C$R^{W3}R^{W4}$— is —NHC(=O)NHCH$_2$—, and —C$R^{W3}R^{W4}$C(=O)N($R^{W2}$)— is —CH$_2$C(=O)NH—.

IX. Compounds Having the Structure (and Pharmaceutically Acceptable Derivatives Thereof):

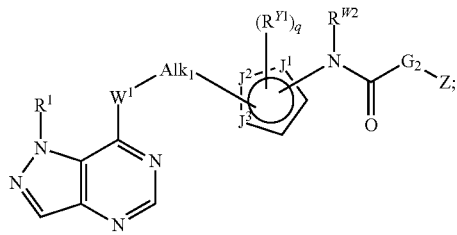
(SP 45)

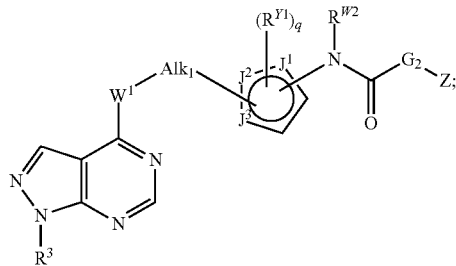
(SP 46)

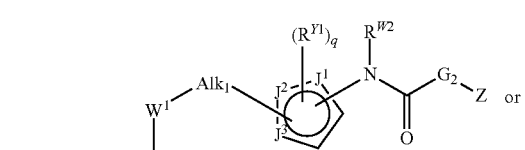
(SP 47)

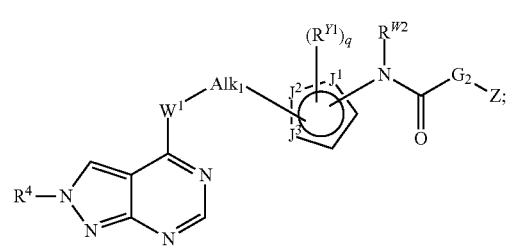
(SP 48)

wherein $R^1$, $R^3$, $R^4$ and Z are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, NR$^{L1A}$NR$^{L1B}$—, —NR$^{L1A}$NR$^{L1B}$C(=O)—, —NR$^{L1A}$C(=O)—, —NR$^{L1A}$C(=O)—, —NR$^{L1A}$CO$_2$—, NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^1$, $J^2$ and $J^3$ are independently O, S, N, NR$^{Y1}$ or CR$^{Y1}$; wherein each occurrence of $R^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}R^{Y3}$— SO$_2$NR$^{Y2}R^{Y3}$, —C(=O)NR$^{Y2}R^{Y3}$, halogen, —CN, —NO$_2$, —C(=O)OR$^{Y3}$, —N(R$^{Y2}$)C(=O)R$^{Y3}$, wherein each occurrence of R$^{Y2}$ and R$^{Y3}$ is independently hydrogen, lower alkyl, lower heteroalkyl, aryl, heteroaryl, -(alkyl)aryl, -(alkyl)heteroaryl or acyl, or R$^{Y2}$ and R$^{Y3}$ taken together with the nitrogen atom to which they are attached form a 5-6 membered heterocyclic ring; G$_2$ is absent, O or NR$^{G2}$; and R$^{W2}$ and R$^{G2}$ are independently hydrogen, lower alkyl, lower heteroalkyl, heterocyclyl, aryl, heteroaryl, -(alkyl)aryl, -(alkyl)heteroaryl or acyl.

In certain embodiments, compounds of this class have the structure (SP $45^{A-B}$), (SP $46^{A-B}$), (SP $47^{A-B}$) or (SP $48^{A-B}$) below:

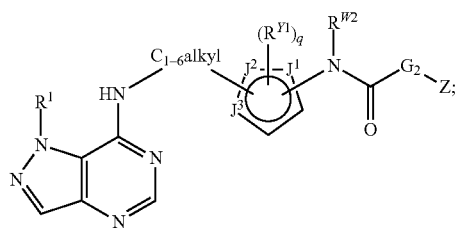
(SP 45^A)

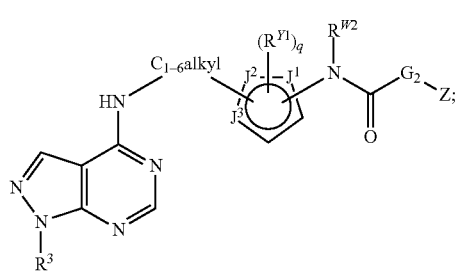
(SP 46^A)

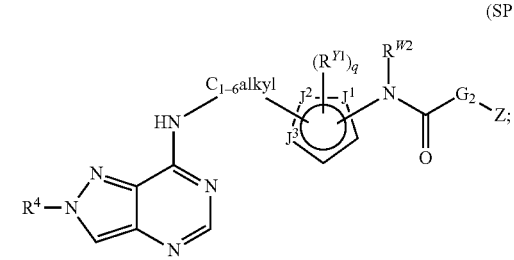
(SP 47^A)

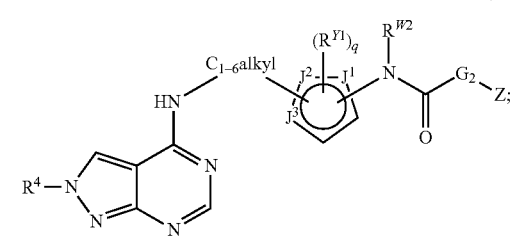
(SP 48^A)

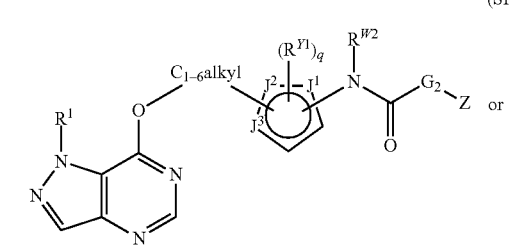
(SP 45^B)

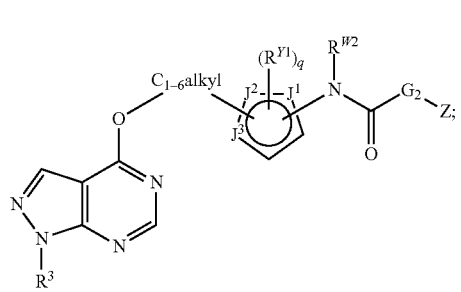
(SP 46^B)

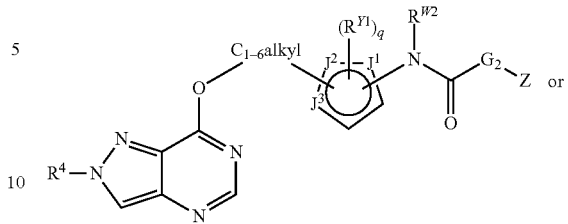
(SP 47^B) or

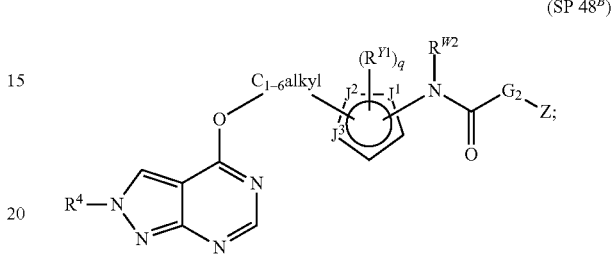
(SP 48^B)

wherein the $C_{1-6}$alkyl moiety may be substituted or unsubstituted.

In certain embodiments, for compounds of formulae (SP 45)-(SP 48), —$W^1$-Alk1- is —NHC$_2$alkyl- or —OC$_2$alkyl-. In certain embodiments, —$W^1$-Alk$_1$- is —NHCH$_2$CH$_2$—, —OCH$_2$CH$_2$— or —NH—CH$_2$CH(CH$_2$OH)—.

In certain embodiments, for compounds of formulae (SP 45^{A-B})-(SP 48^{A-B}) the $C_{1-6}$alkyl moiety is a substituted or unsubstituted C$_2$alkyl moiety. In certain exemplary embodiments, the $C_{1-6}$alkyl moiety is —CH$_2$CH$_2$—.

In certain embodiments, in compounds of formulae (SP 45)-(SP 48), and (SP 45^{A-B})-(SP 48^{A-B}) the 5-membered ring having the structure:

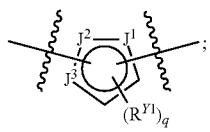

has one of the following structures:

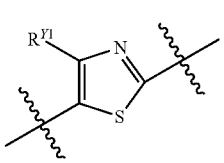 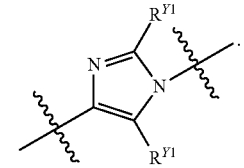

In certain embodiments, —N(R^{W2})C(=O)G$_2$- is —NHC(=O)—, —NHC(=O)O—, or —NHC(=O)NH—.

X. Compounds Having the Structure (and Pharmaceutically Acceptable Derivatives Thereof):

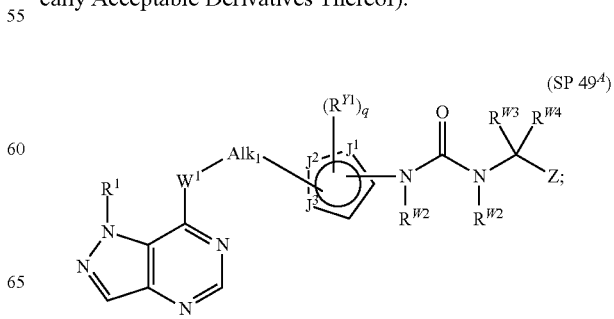
(SP 49^A)

-continued

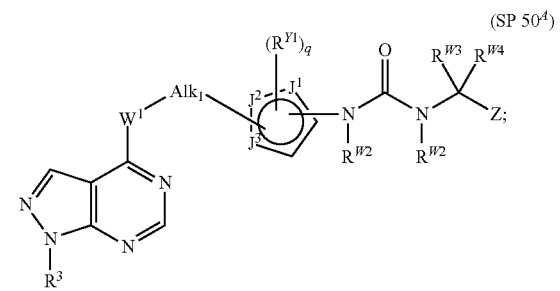
(SP 50^A)

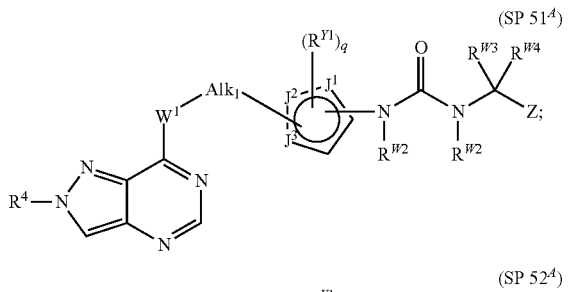
(SP 51^A)

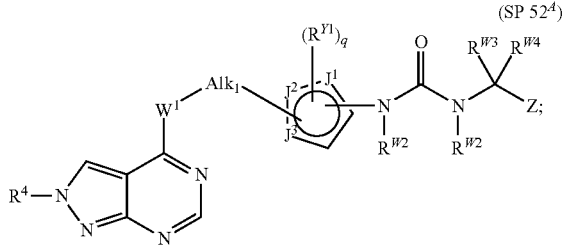
(SP 52^A)

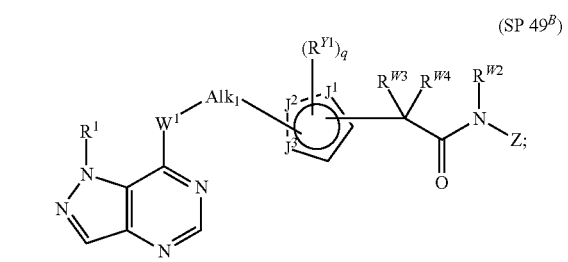
(SP 49^B)

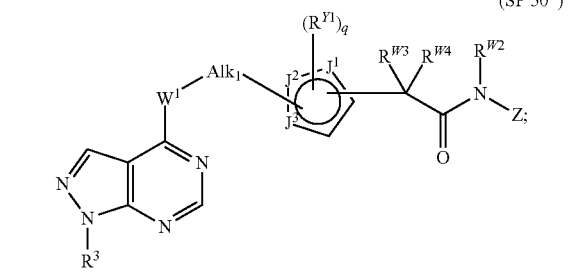
(SP 50^B)

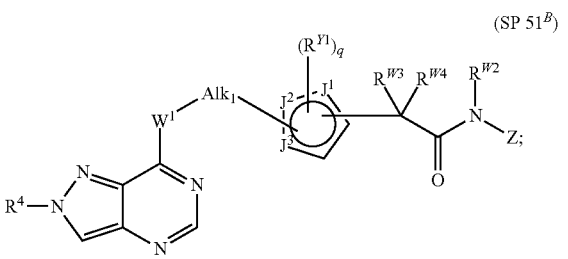
(SP 51^B)

-continued

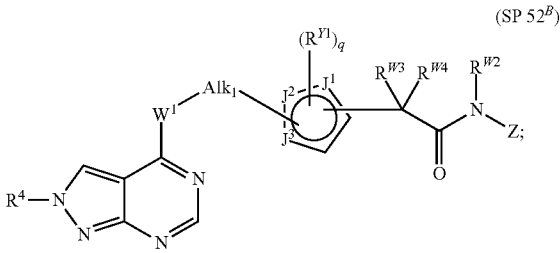
(SP 52^B)

wherein $R^1$, $R^3$, $R^4$ and Z are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^1$, $J^2$ and $J^3$ are independently O, S, N, $NR^{Y1}$ or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $R^{W3}$ and $R^{W4}$ are independently hydrogen, lower alkyl, lower heteroalkyl, heterocyclyl, aryl, heteroaryl or acyl; and $R^{W2}$ is hydrogen, lower alkyl, lower heteroalkyl, heterocyclyl, aryl, heteroaryl, -(alkyl)aryl, -(alkyl)heteroaryl or acyl.

In certain embodiments, —$W^1$-$Alk_1$- is —NHC$_{1-6}$alkyl- or —OC$_{1-6}$alkyl-. In certain embodiments, —$W^1$-$Alk_1$- is —NHC$_2$alkyl- or —OC$_2$alkyl-. In certain embodiments, —$W^1$-$Alk_1$- is —NHCH$_2$CH$_2$—, —OCH$_2$CH$_2$— or —NH—CH$_2$CH(CH$_2$OH)—.

In certain embodiments, in compounds of the formulae (SP 49$^{A-B}$) through (SP 52$^{A-B}$), the 5-membered ring having the structure:

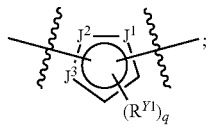

has one of the following structures:

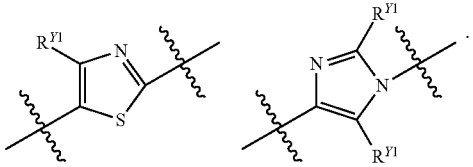

In certain embodiments, —N(R$^{W2}$)C(=O)N(R$^{W2}$)CR$^{W3}$R$^{W4}$ is —NHC(=O)NHCH$_2$—, and —CR$^{W3}$R$^{W4}$C(=O)N(R$^{W2}$)— is —CH$_2$C(=O)NH—.

XI. Compounds Having the Structure (and Pharmaceutically Acceptable Derivatives Thereof):

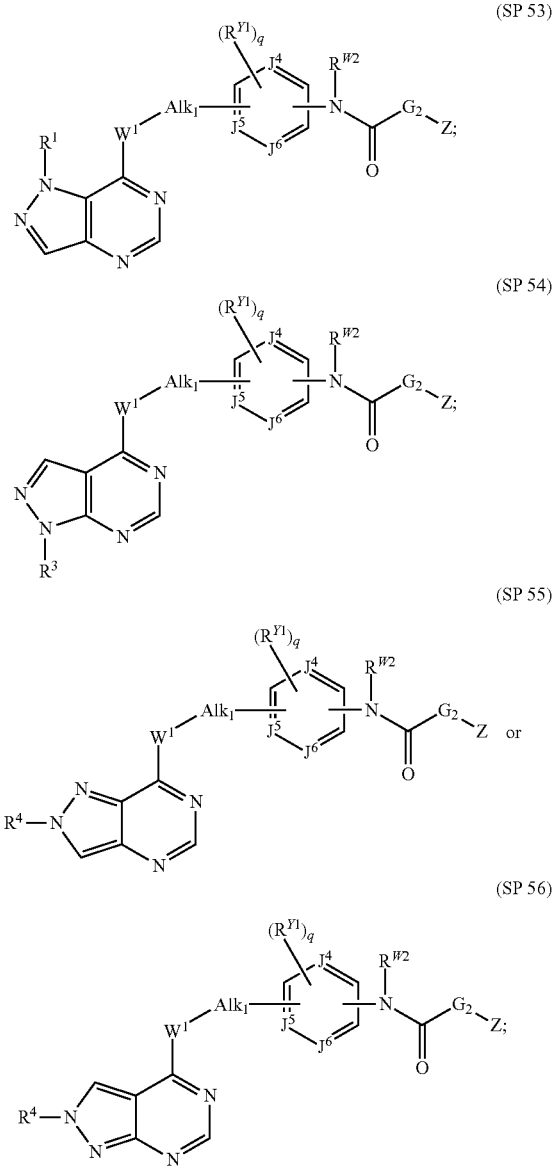

wherein $R^1$, $R^3$, $R^4$ and Z are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$, —OC(=O)—, —OC(=O)NR$^{L1A}$—, NR$^{L1A}$NR$^{L1B}$—, —NR$^{L1A}$NR$^{L1B}$C(=O)—, —NR$^{L1A}$C(=O)—, —NR$^{L1A}$CO$_2$—, NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —OR$^3$, —SR$^3$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of R$^{Y2}$ and R$^{Y3}$ is independently hydrogen, lower alkyl, lower heteroalkyl, aryl, heteroaryl, -(alkyl)aryl, -(alkyl)heteroaryl or acyl, or R$^{Y2}$ and R$^{Y3}$ taken together with the nitrogen atom to which they are attached form a 5-6 membered heterocyclic ring; G$_2$ is absent, O or NR$^{G2}$; and R$^{W2}$ and R$^{G2}$ are independently hydrogen, lower alkyl, lower heteroalkyl, heterocyclyl, aryl, heteroaryl, -(alkyl)aryl, -(alkyl)heteroaryl or acyl.

In certain embodiments, the compounds have the following structures:

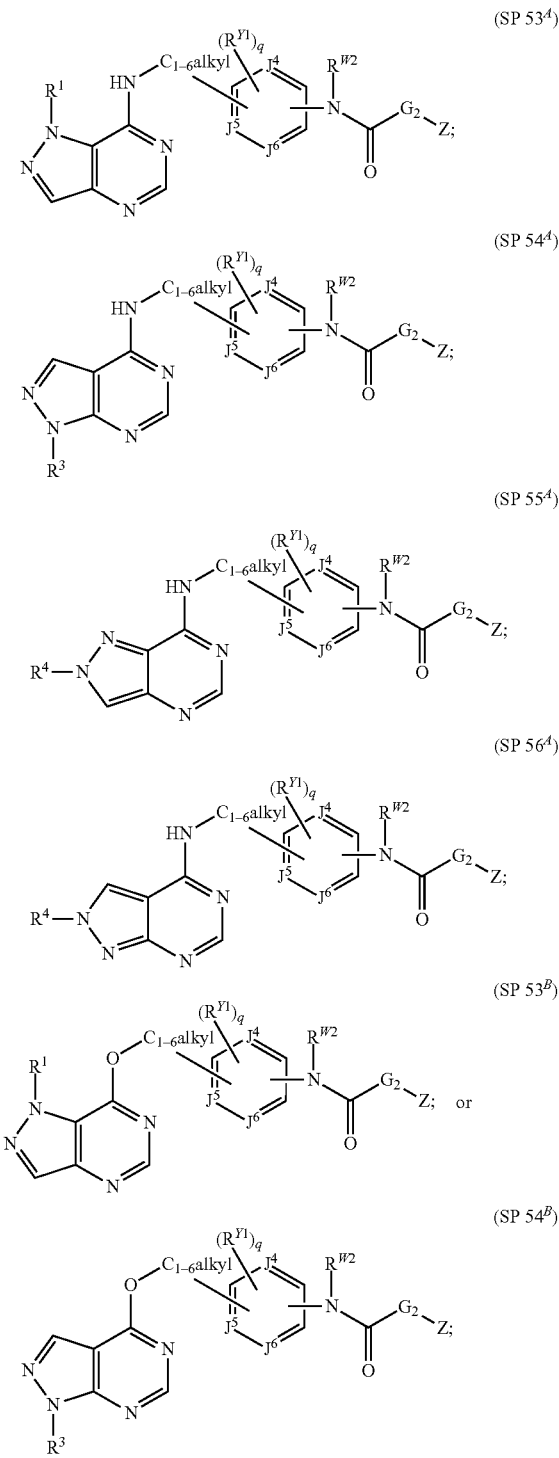

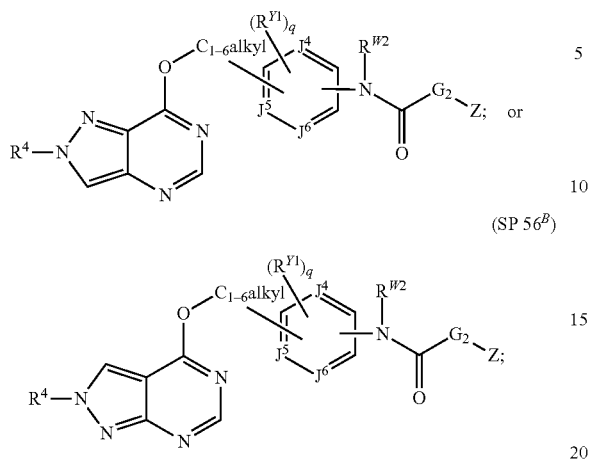

(SP 55$^B$)

(SP 56$^B$)

wherein the $C_{1-6}$alkyl moiety may be substituted or unsubstituted.

In certain embodiments, for compounds of formulae (SP 53)-(SP 56), —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, for compounds of formulae (SP 53$^{A-B}$) through (SP 56$^{A-B}$), the $C_{1-6}$alkyl moiety is a substituted or unsubstituted $C_2$alkyl moiety. In certain exemplary embodiments, the $C_{1-6}$alkyl moiety is —CH$_2$CH$_2$—.

In certain embodiments, in compounds of the formulae (SP 53)-(SP 56) and (SP 53$^{A-B}$) through (SP 56$^{A-B}$), the 6-membered ring having the structure:

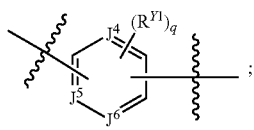

has one of the following structures:

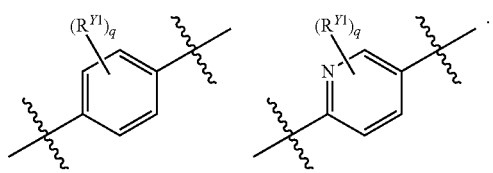

In certain embodiments, —N(R$^{W2}$)C(=O)G$_2$- is —NHC(=O)—, —NHC(=O)O—, or —NHC(=O)NH—.

XII. Compounds Having the Structure (and Pharmaceutically Acceptable Derivatives Thereof):

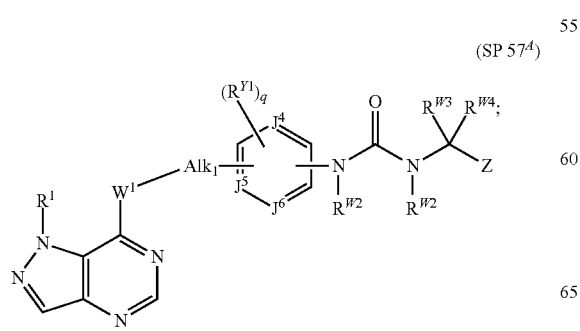

(SP 57$^A$)

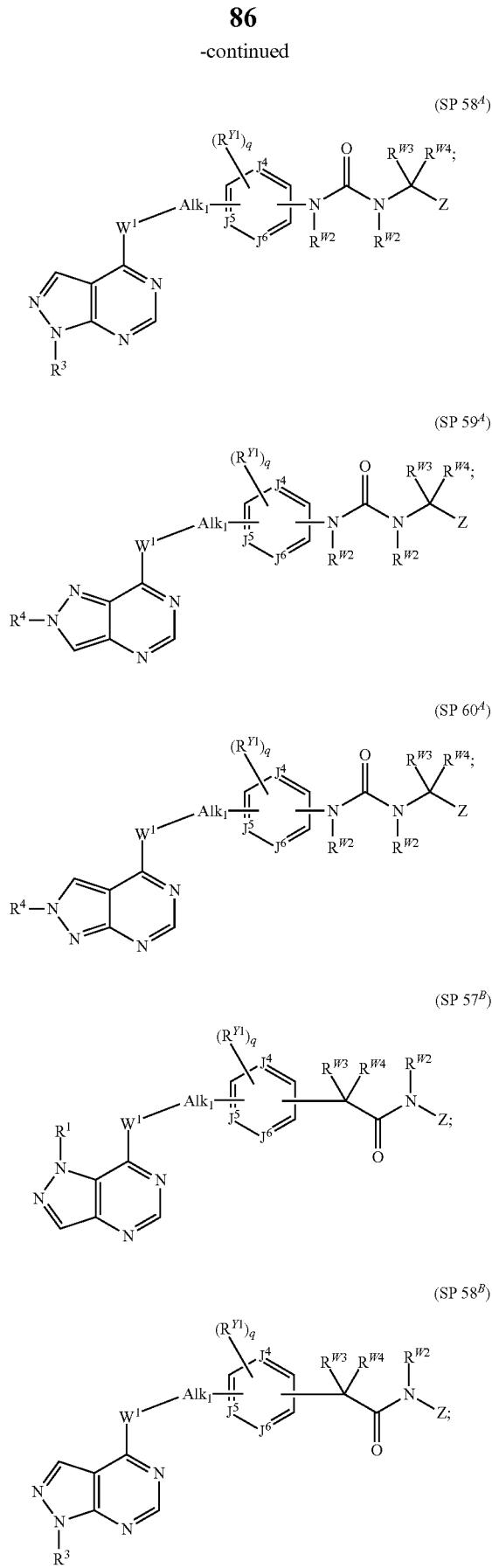

(SP 58$^A$)

(SP 59$^A$)

(SP 60$^A$)

(SP 57$^B$)

(SP 58$^B$)

-continued (SP 59^B)

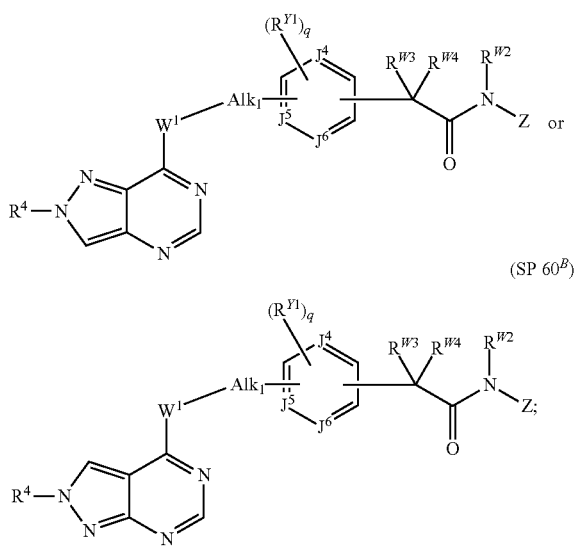

(SP 60^B)

has one of the following structures:

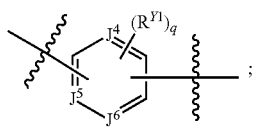

In certain embodiments, —N(R^{W2})C(=O)G_2- is —NHC(=O)—, —NHC(=O)O—, or —NHC(=O)NH—.

In certain embodiments, —N(R^{W2})C(=O)N(R^{W2})CR^{W3}R^{W4}— is —NHC(=O)NHCH_2—, and CR^{W3}R^{W4}C(=O)N(R^{W2})— is —CH_2C(=O)NH—.

XIII. Compounds Having the Structure (and Pharmaceutically Acceptable Derivatives Thereof):

wherein $R^1$, $R^3$, $R^4$ and Z are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —CO_2—, —C(=O)C(=O)—, —C(=O)NR^{L1A}, —OC(=O)—, —OC(=O)NR^{L1A}—, —NR^{L1A}NR^{L1B}—, —NR^{L1A}NR^{L1B}C(=O)—, —NR^{L1A}C(=O)—, —NR^{L1A}CO_2—, NR^{L1A}C(=O)NR^{L1B}—, —S(=O)—, —SO_2—, —NR^{L1A}SO_2—, —SO_2NR^{L1A}—, —NR^{L1A}SO_2NR^{L1B}—, —O—, —S—, or —NR^{L1A}—; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —OR^3, —SR^3, —NR^2R^3, —SO_2NR^{Y2}R^{Y3}, —C(=O)NR^{Y2}R^{Y3}, halogen, —CN, —NO_2, —C(=O)OR^{Y3}, —N(R^{12})C(=O)R^{Y3}, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $R^{W3}$ and $R^{W4}$ are independently hydrogen, lower alkyl, lower heteroalkyl, heterocyclyl, aryl, heteroaryl or acyl; and $R^{W2}$ is hydrogen, lower alkyl, lower heteroalkyl, heterocyclyl, aryl, heteroaryl, -(alkyl)aryl, -(alkyl)heteroaryl or acyl.

In certain embodiments, —$W^1$-$Alk_1$- is —$NHC_{1-6}$-alkyl- or —$OC_{1-6}$alkyl-. In certain embodiments, —$W^1$-$Alk_1$- is —NHC_2alkyl- or —OC_2alkyl-. In certain embodiments, —$W^1$-$Alk_1$- is —NHCH_2CH_2—, —OCH_2CH_2— or —NH—CH_2CH(CH_2OH)—.

In certain embodiments, in compounds of the formulae (SP 57^{A-B}) (SP 60^{A-B}) the 6-membered ring having the structure:

-continued (SP 62$^B$)

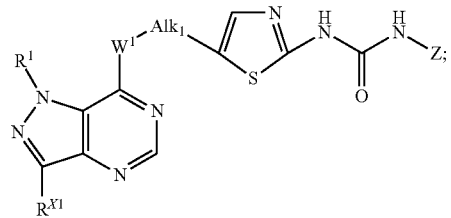

(SP 63$^B$)

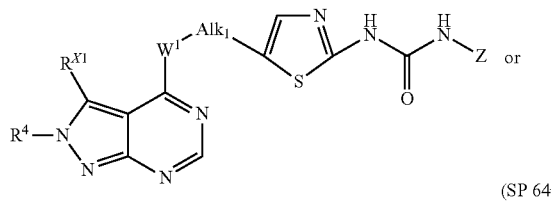

or (SP 64$^B$)

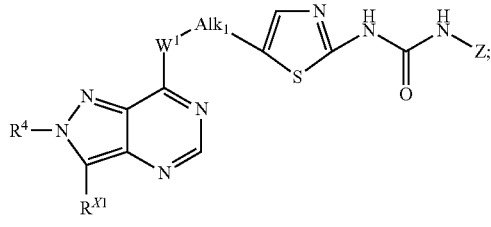

wherein R$^1$, R$^3$, R$^4$ and R$^{X1}$ are as defined generally and in classes and subclasses herein; Z is an aryl, heteroaryl or heterocyclic moiety; W$^1$ is O or NR$^{W1}$, where R$^{W1}$ is hydrogen, lower alkyl, lower heteroalkyl, aryl, heteroaryl, -(alkyl)aryl, -(alkyl)heteroaryl or acyl; Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl; m is an integer from 0 to 3; r is an integer from 1 to 4; and each occurrence of R$^{Z1}$ is independently hydrogen, alkyl, heteroalkyl, aryl, heteroaryl, -(alkyl)aryl or -(alkyl)heteroaryl, —OR$^{Z2}$, —SR$^{Z2}$, —NR$^{Z2}$R$^{Z3}$, —SO$_2$NR$^{Z2}$R$^{Z3}$, —SO$_2$R$^{Z1}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl or acyl, or R$^{Z2}$ and R$^{Z3}$ taken together with the nitrogen or carbon atom to which they are attached form a 5-6 membered heterocyclic, aryl or heteroaryl ring.

XIV. Compounds Having the Structure (and Pharmaceutically Acceptable Derivatives Thereof):

(SP 65$^A$)

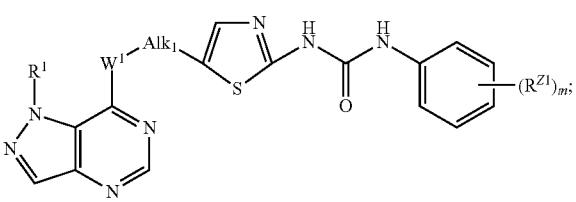

(SP 66$^A$)

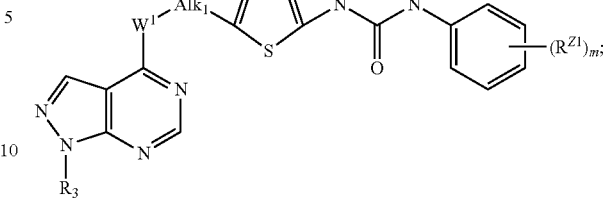

(SP 67$^A$)

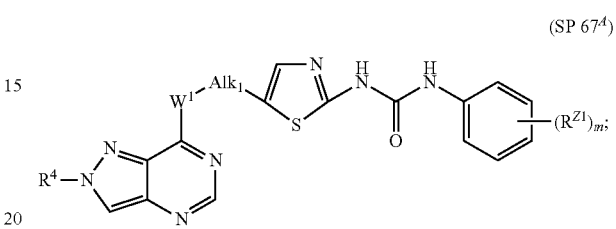

(SP 68$^A$)

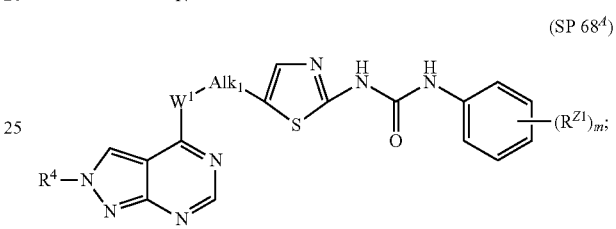

(SP 65$^B$)

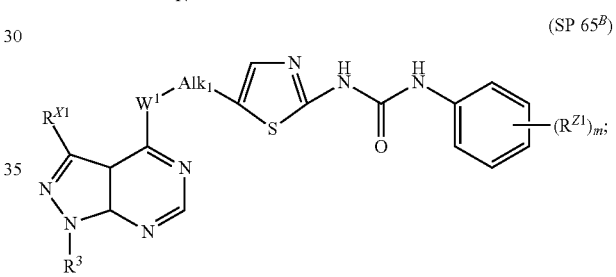

(SP 66$^B$)

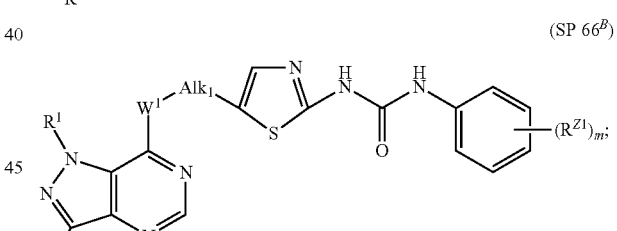

(SP 67$^B$)

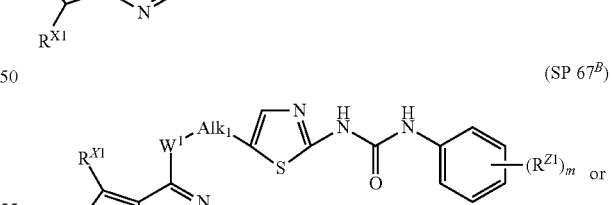

or (SP 68$^B$)

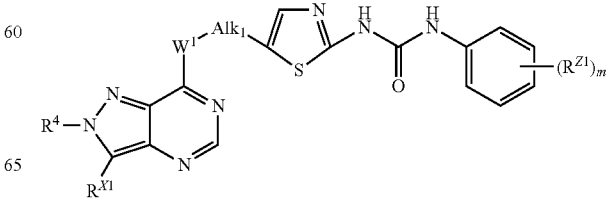

wherein $R^1$, $R^3$, $R^4$ and $R^{X1}$ are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)$NR^{L1A}$—, —OC(=O)—, —OC(=O)$NR^{L1A}$—, $NR^{L1A}NR^{L1B}$—, —$NR^{L1A}NR^{L1B}$C(=O)—, —$NR^{L1A}$C(=O), $NR^{L1A}$CO$_2$—, —$NR^{L1A}$C(=O)$NR^{L1B}$, —S(=O)—, —SO$_2$—, —$NR^{L1A}$SO$_2$—, —SO$_2NR^{L1A}$, —$NR^{L1A}$SO$_2NR^{L1B}$—, —O—, —S—, or —$NR^{L1A}$—; wherein each occurrence of $R^{L1A}$ and $R^{L1B}$ is independently hydrogen, lower alkyl, lower heteroalkyl, heterocyclyl, aryl, heteroaryl or acyl; m is an integer from 0 to 3; r is an integer from 1 to 4; each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, —$SO_2NR^{Z2}R^{Z3}$, —$SO_2R^{Z1}$, —C(=O)$NR^{Z2}R^{Z3}$, halogen, —CN, —NO$_2$, —C(=O)$OR^{Z3}$, —$N(R^{Z2})$C(=O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring.

In certain embodiments, for compounds of groups XIII and XIV, —$W^1$-$Alk_1$- is —$NHC_{1-6}$alkyl- or —$OC_{1-6}$alkyl-; wherein the $C_{1-6}$alkyl moiety may be substituted or unsubstituted. In certain embodiments, —$W^1$-$Alk_1$- is —$NHC_2$alkyl- or —$OC_2$alkyl-. In certain embodiments, —$W^1$-$Alk_1$- is —NHCH$_2$CH$_2$—, —OCH$_2$CH$_2$— or —NH—CH$_2$CH(CH$_2$OH)—.

In certain embodiments, for compounds of group XIV, $R^{Z1}$ is hydrogen, halogen, lower alkyl or lower haloalkyl. In certain embodiments, m is 1 and $R^{Z1}$ is halogen, lower alkyl or lower haloalkyl. In certain embodiments, m is 1 and $R^{Z1}$ is Cl, F, methyl or —CF$_3$. In certain embodiments, m is 1 and $R^{Z1}$ is lower haloalkyl. In certain embodiments, m is 1 and $R^{Z1}$ is —CF$_3$. In certain embodiments, m is 2 and each occurrence of $R^{Z1}$ is independently CN, Cl, F, methyl or —CF$_3$. In certain embodiments, m is 2 and each occurrence of $R^{Z1}$ is CN, Cl, F, methyl or —CF$_3$. In certain embodiments, m is 2 and one occurrence of $R^{Z1}$ is Cl, F, methyl or —CF$_3$ and the other is CN.

In certain embodiments, compounds of group XIV have the structure:

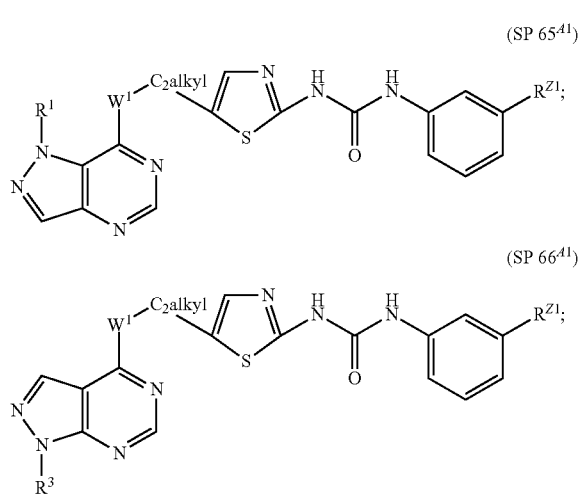

(SP 65$^{41}$)

(SP 66$^{41}$)

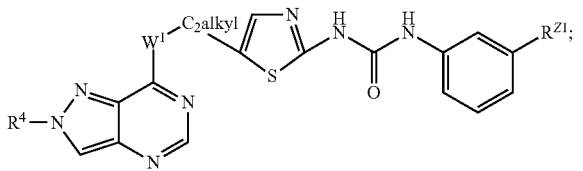

(SP 67$^{41}$)

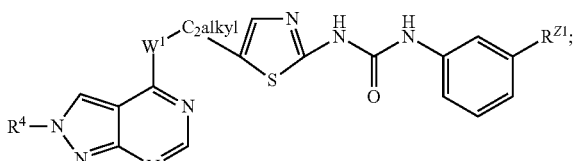

(SP 68$^{41}$)

wherein $W^1$ is NH or O; the $C_2$alkyl moiety is optionally substituted; $R^1$, $R^3$ and $R^4$ are independently hydrogen, lower alkyl or —$CO_2R^{L4}$ where $R^{L4}$ is hydrogen or lower alkyl; $R^{Z1}$ is halogen, lower alkyl or lower haloalkyl. In certain exemplary embodiments, $R^{Z1}$ is Cl, F, methyl or —CF$_3$. In certain exemplary embodiments, $R^{Z1}$ is Cl or —CF$_3$. In certain exemplary embodiments, the $C_2$alkyl moiety is —CH$_2$CH$_2$—.

In certain embodiments, compounds of group XIV have the structure:

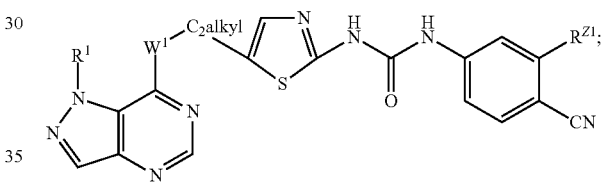

(SP 65$^{42}$)

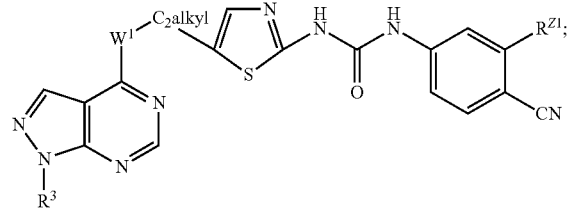

(SP 66$^{42}$)

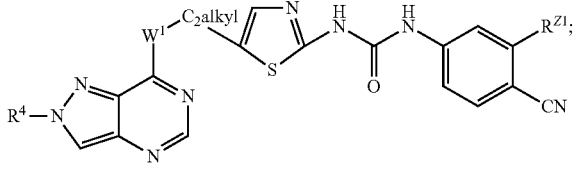

(SP 67$^{42}$)

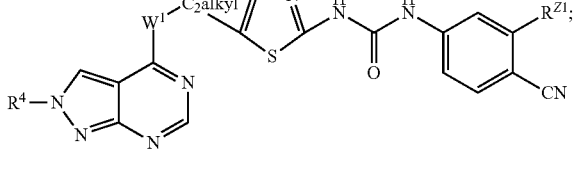

(SP 68$^{42}$)

wherein $W^1$ is NH or O; the $C_2$alkyl moiety is optionally substituted; $R^1$, $R^3$ and $R^4$ are independently hydrogen, lower alkyl or —$CO_2R^{L4}$ where $R^{L4}$ is hydrogen or lower alkyl; $R^{Z1}$ is halogen, lower alkyl or lower haloalkyl. In certain exemplary embodiments, $R^{Z1}$ is Cl, F, methyl or —CF$_3$. In certain exemplary embodiments, $R^{Z1}$ is Cl or —$CF_3$. In certain exemplary embodiments, the $C_2$alkyl moiety is —$CH_2CH_2$—.

In certain embodiments, compounds of group XIV have the structure:

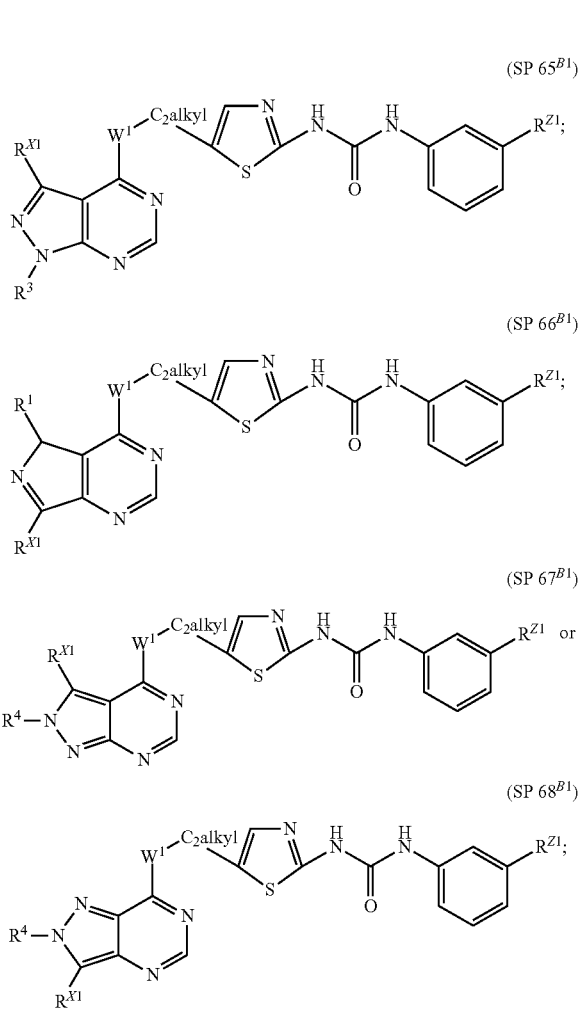

(SP 65$^{B1}$)

(SP 66$^{B1}$)

(SP 67$^{B1}$)

(SP 68$^{B1}$)

wherein $W^1$ is NH or O; the $C_2$alkyl moiety is optionally substituted; $R^1$, $R^3$ and $R^4$ are independently hydrogen, lower alkyl or —$CO_2R^{1A}$ where $R^{1A}$ is hydrogen or lower alkyl; $R^{X1}$ is hydrogen, lower alkyl or heterocyclyl; and $R^{Z1}$ is halogen, lower alkyl or lower haloalkyl. In certain exemplary embodiments, $R^{X1}$ is hydrogen, methyl or thienyl; $R^{Z1}$ is Cl, F, methyl or —$CF_3$. In certain exemplary embodiments, the $C_2$alkyl moiety is —$CH_2CH_2$—.

In certain embodiments, compounds of group XIV have the structure:

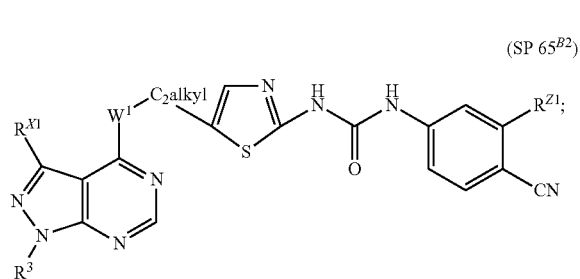

(SP 65$^{B2}$)

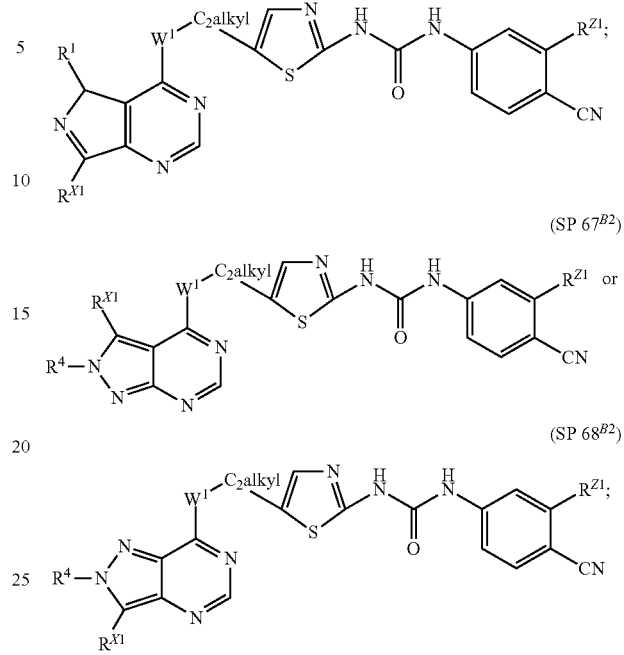

(SP 66$^{B2}$)

(SP 67$^{B2}$)

(SP 68$^{B2}$)

wherein $W^1$ is NH or O; the $C_2$alkyl moiety is optionally substituted; $R^1$, $R^3$ and $R^4$ are independently hydrogen, lower alkyl or —$CO_2R^{1A}$ where $R^{1A}$ is hydrogen or lower alkyl; $R^{X1}$ is hydrogen, lower alkyl or heterocyclyl; and $R^{Z1}$ is halogen, lower alkyl or lower haloalkyl. In certain exemplary embodiments, $R^{X1}$ is hydrogen, methyl or thienyl; and $R^{Z1}$ is Cl, F, methyl or —$CF_3$. In certain exemplary embodiments, the $C_2$alkyl moiety is —$CH_2CH_2$—.

XV. Compounds Having the Structure (and Pharmaceutically Acceptable Derivatives Thereof):

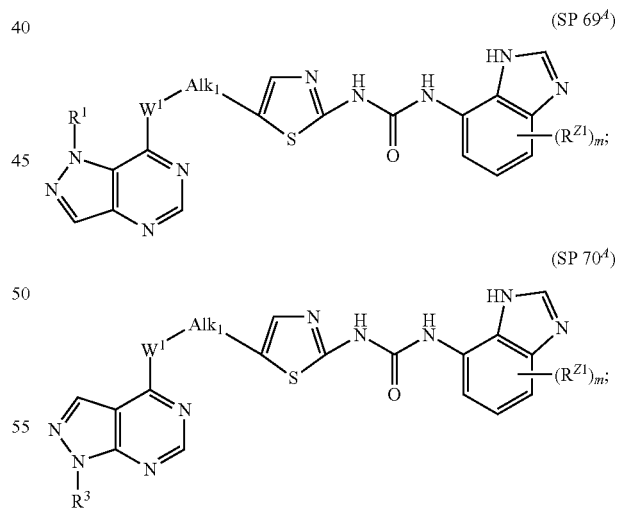

(SP 69$^A$)

(SP 70$^A$)

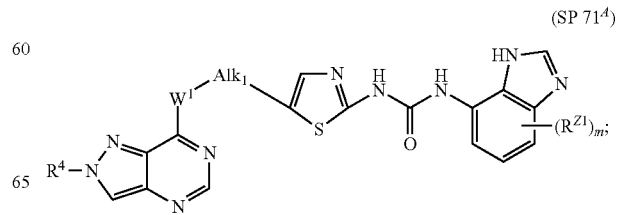

(SP 71$^A$)

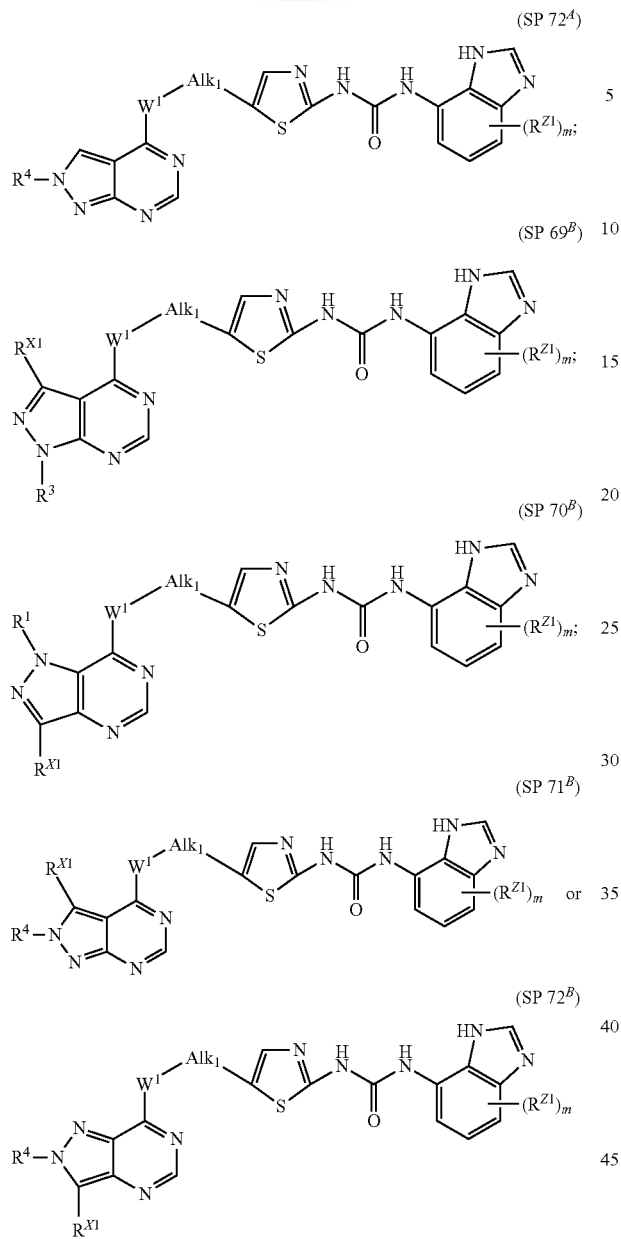

wherein R¹, R³, R⁴ and $R^{X1}$ are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —CO₂—, —C(=O)C(=O)—, —C(=O)$NR^{L1A}$—, —OC(=O)—, —OC(=O)$NR^{L1A}$—, $NR^{L1A}NR^{L1B}$—, —$NR^{L1A}NR^{L1B}$C(=O)—, —$NR^{L1A}$C(=O), $NR^{L1A}CO_2$—, —$NR^{L1A}$C(=O)$NR^{L1B}$, —S(=O)—, —SO₂—, —$NR^{L1A}SO_2$—, —$SO_2NR^{L1A}$, —$NR^{L1A}SO_2NR^{L1B}$—, —O—, —S—, or —$NR^{L1A}$—; wherein each occurrence of $R^{L1A}$ and $R^{L1B}$ is independently hydrogen, lower alkyl, lower heteroalkyl, heterocyclyl, aryl, heteroaryl or acyl; m is an integer from 0 to 3; r is an integer from 1 to 4; each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, —$SO_2NR^{Z2}R^{Z3}$, —$SO_2R^{Z1}$, —C(=O)$NR^{Z2}R^{Z3}$, halogen, —CN, —NO₂, —C(=O)$OR^{Z3}$, —N($R^{Z2}$)C(=O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring.

In certain embodiments, for compounds of group XV, —$W^1$-$Alk_1$- is —$NHC_{1-6}$alkyl- or —$OC_{1-6}$alkyl-. In certain embodiments, —$W^1$-$Alk_1$- is —$NHC_2$alkyl- or —$OC_2$alkyl-. In certain embodiments, —$W^1$-$Alk_1$- is —$NHCH_2CH_2$—, —$OCH_2CH_2$— or —NH—$CH_2CH(CH_2OH)$—.

In certain embodiments, for compounds of group XV, $R^{Z1}$ is hydrogen, halogen, lower alkyl or lower haloalkyl. In certain embodiments, m is 0.

In certain embodiments, compounds of group XV have the structure:

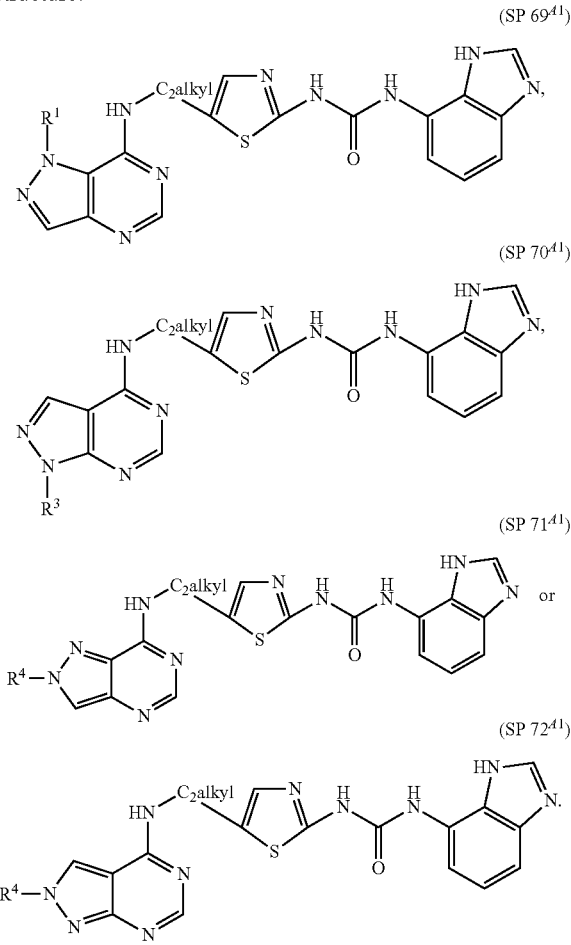

In certain embodiments, compounds of group XV have the structure:

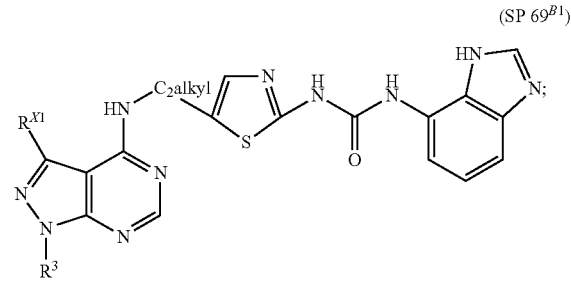

-continued (SP 70^B1)

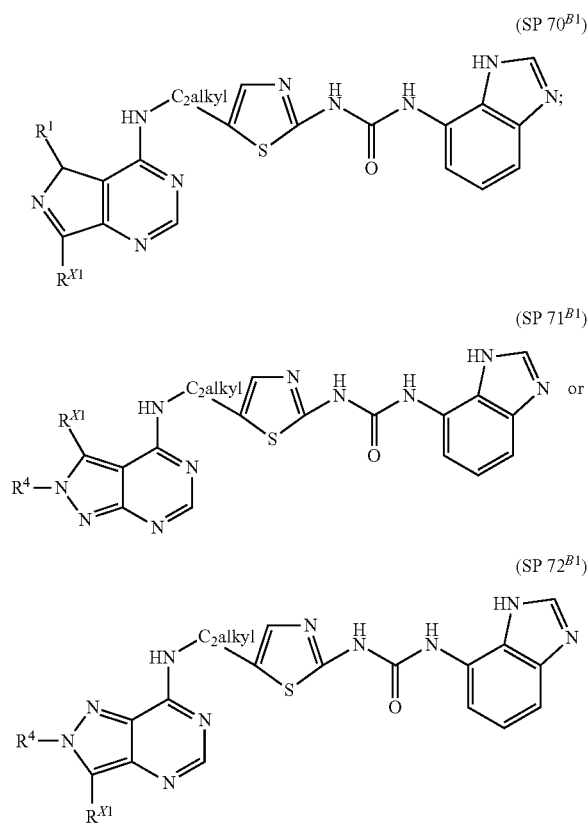

(SP 71^B1)

(SP 72^B1)

In certain embodiments, in the compounds having one of the structures (SP 69^A1) through (SP 72^A1) and (SP 69^B1) through (SP 72^B1) above, the C₂alkyl moiety is optionally substituted; $R^1$, $R^3$ and $R^4$ are independently hydrogen, lower alkyl or —CO₂$R^{1A}$ where $R^{1A}$ is hydrogen or lower alkyl; and $R^{X1}$ is hydrogen, lower alkyl or heterocyclyl. In certain exemplary embodiments, $R^1$, $R^3$ and $R^4$ are independently hydrogen or methyl; and $R^{X1}$ is hydrogen, methyl or thienyl. In certain exemplary embodiments, the C₂alkyl moiety is —CH₂CH₂—.

XVI. Compounds Having the Structure (and Pharmaceutically Acceptable Derivatives Thereof):

(SP 72^A)

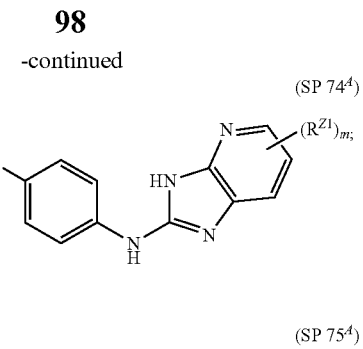

(SP 73^A)

-continued (SP 74^A)

(SP 75^A)

(SP 72^B)

(SP 73^B)

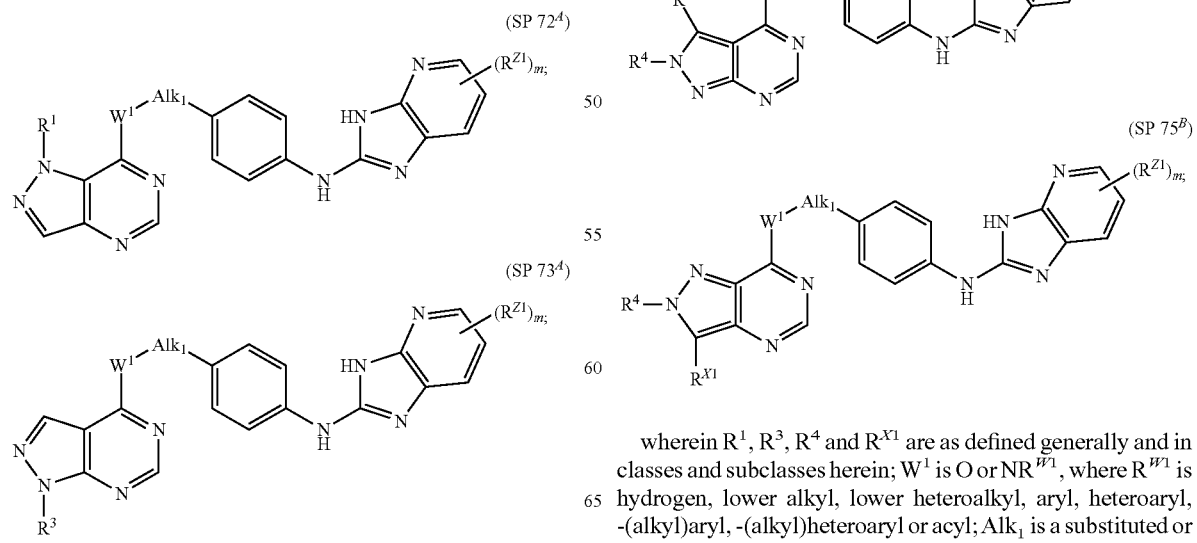

(SP 74^B)

(SP 75^B)

wherein $R^1$, $R^3$, $R^4$ and $R^{X1}$ are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; Alk₁ is a substituted or unsubstituted C₁₋₆alkylene or C₂₋₆alkenylene chain wherein up to two non-adjacent methylene units are independently optionally replaced by —C(=O)—, —CO$_2$—, —C(=O)C(=O)—, NC(=O)NR$^{L1A}$—, —OC(=O)—, —OC(=O)NR$^{L1A}$, —NR$^{L1A}$NR$^{L1B}$—, NR$^{L1A}$NR$^{L1B}$C(=O)—, NR$^{L1A}$C(=O), —NR$^{L1A}$CO$_2$, NR$^{L1A}$—C(=O)NR$^{L1B}$—, —S(=O)—, —SO$_2$—, —NR$^{L1A}$SO$_2$—, —SO$_2$NR$^{L1A}$—, NR$^{L1A}$SO$_2$NR$^{L1B}$—, —O—, —S—, or —NR$^{L1A}$; wherein each occurrence of R$^{L1A}$, and R$^{L1B}$ is independently hydrogen, lower alkyl, lower heteroalkyl, heterocyclyl, aryl, heteroaryl or acyl; m is an integer from 0 to 3; r is an integer from 1 to 4; each occurrence of R$^{Z1}$ is independently hydrogen, alkyl, heteroalkyl, aryl, heteroaryl, -(alkyl)aryl or -(alkyl)heteroaryl, —OR$^{Z2}$, —SR$^{Z2}$, —NR$^{Z2}$R$^{Z3}$, —SO$_2$NR$^{Z2}$R$^{Z3}$, —SO$_2$R$^{Z1}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl or acyl, or R$^{Z2}$ and R$^{Z3}$ taken together with the nitrogen or carbon atom to which they are attached form a 5-6 membered heterocyclic, aryl or heteroaryl ring.

In certain embodiments, for compounds of group XVI, —W$^1$-Alk$_1$- is —NHC$_{1-6}$alkyl- or —OC$_{1-6}$alkyl-. In certain embodiments, —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, for compounds of group XVI, R$^{Z1}$ is hydrogen, halogen, lower alkyl or lower haloalkyl. In certain embodiments, m is 1 and R$^{Z1}$ is Cl, F, methyl or —CF$_3$. In certain embodiments, m is 1 and R$^{Z1}$ is lower haloalkyl. In certain embodiments, m is 1 and R$^{Z1}$ is —CF$_3$.

In certain embodiments, compounds of group XVI have the structure:

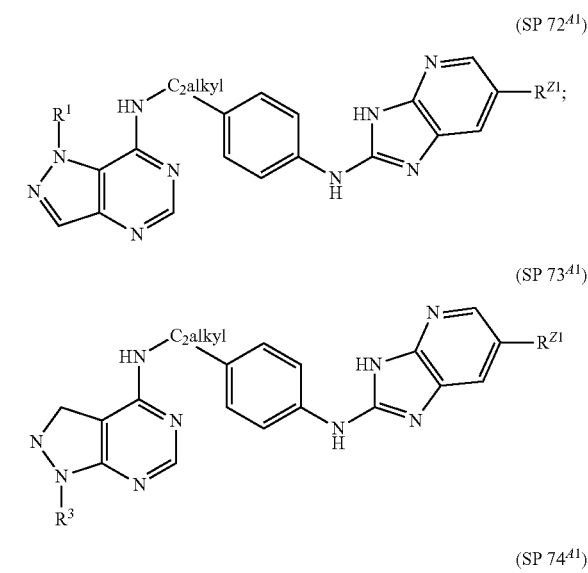

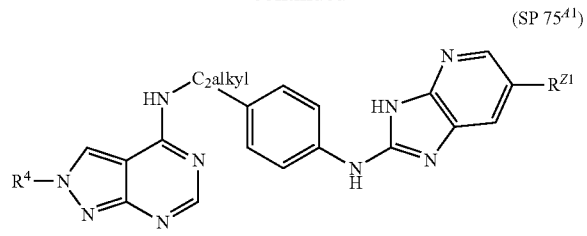

wherein the C$_2$alkyl moiety is optionally substituted; R$^1$, R$^3$ and R$^4$ are independently hydrogen, lower alkyl or —CO$_2$R$^{14}$ where R$^{14}$ is hydrogen or lower alkyl; R$^{Z1}$ is halogen, lower alkyl or lower haloalkyl. In certain exemplary embodiments, R$^{Z1}$ is Cl, F, methyl or —CF$_3$. In certain exemplary embodiments, the C$_2$alkyl moiety is —CH$_2$CH$_2$—.

In certain embodiments, compounds of group XVI have the structure:

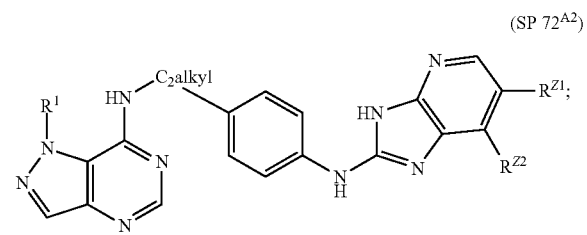

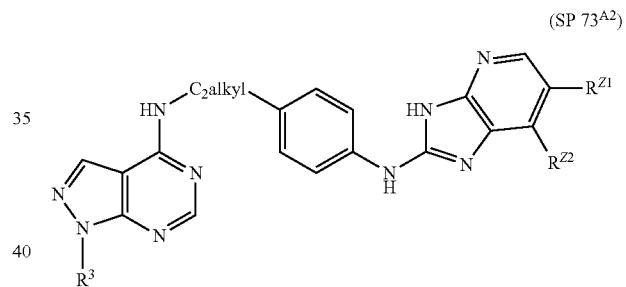

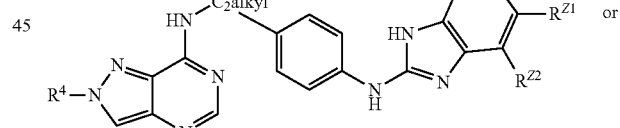

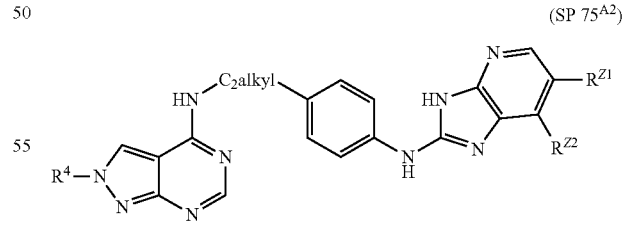

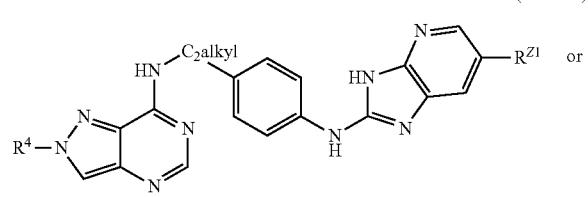

wherein the C$_2$alkyl moiety is optionally substituted; R$^1$, R$^3$ and R$^4$ are independently hydrogen, lower alkyl or —CO$_2$R$^{14}$ where R$^{14}$ is hydrogen or lower alkyl; R$^{Z1}$ and R$^{Z2}$ are independently halogen, lower alkyl or lower haloalkyl. In certain exemplary embodiments, R$^{Z1}$ and R$^{Z2}$ are independently Cl, F, methyl or —CF$_3$. In certain exemplary embodiments, the C$_2$alkyl moiety is —CH$_2$CH$_2$—. In certain embodiments, R$^{Z1}$ and R$^{Z2}$ are each Cl, F, methyl or —CF$_3$.

In certain embodiments, compounds of group XVI have the structure:

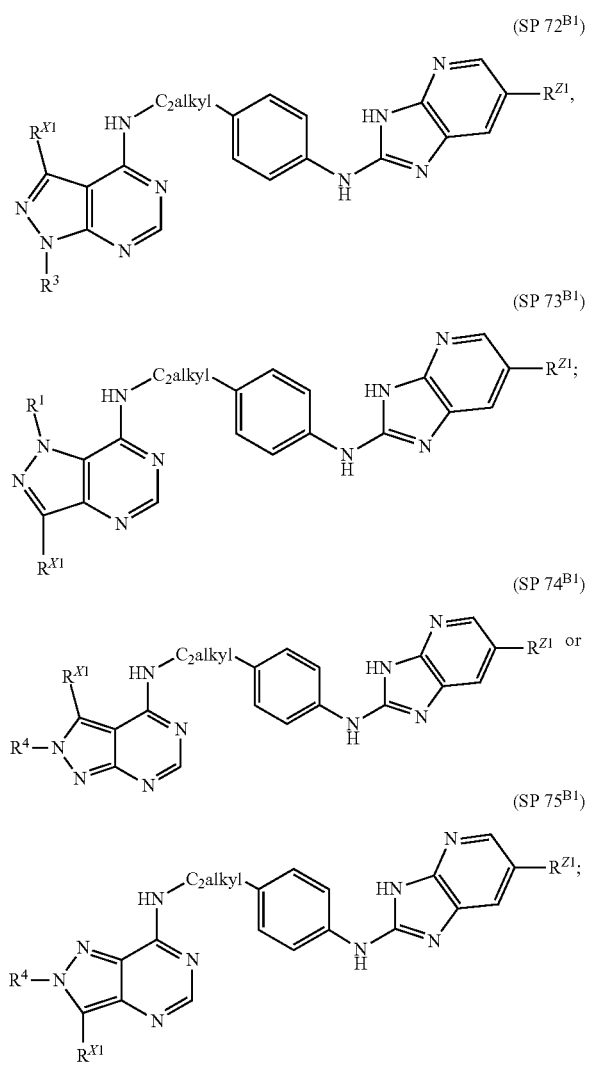

wherein the $C_2$alkyl moiety is optionally substituted; $R^1$, $R^3$ and $R^4$ are independently hydrogen, lower alkyl or —$CO_2R^{14}$ where $R^{14}$ is hydrogen or lower alkyl; $R^{X1}$ is hydrogen, lower alkyl or heterocyclyl; and $R^{Z1}$ is halogen, lower alkyl or lower haloalkyl. In certain exemplary embodiments, $R^{X1}$ is hydrogen, methyl or thienyl; and $R^{Z1}$ is Cl, F, methyl or —$CF_3$. In certain exemplary embodiments, the $C_2$alkyl moiety is —$CH_2CH_2$—.

In certain embodiments, compounds of group XVI have the structure:

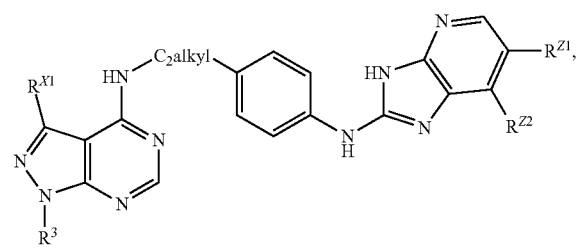
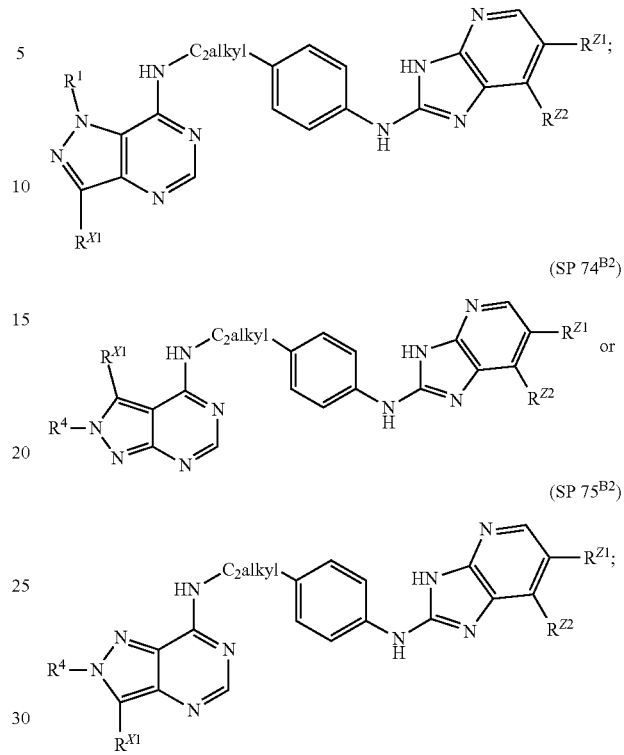

wherein the $C_2$alkyl moiety is optionally substituted; $R^1$, $R^3$ and $R^4$ are independently hydrogen, lower alkyl or —$CO_2R^{14}$ where $R^{14}$ is hydrogen or lower alkyl; $R^{X1}$ is hydrogen, lower alkyl or heterocyclyl; and $R^{Z1}$ and $R^{Z2}$ are independently halogen, lower alkyl or lower haloalkyl. In certain exemplary embodiments, $R^{X1}$ is hydrogen, methyl or thienyl; and $R^{Z1}$ and $R^{Z2}$ are independently Cl, F, methyl or —$CF_3$. In certain exemplary embodiments, the $C_2$alkyl moiety is —$CH_2CH_2$—. In certain embodiments, $R^{Z1}$ and $R^{Z2}$ are each Cl, F, methyl or —$CF_3$.

XVII. Compounds Having the Structure (and Pharmaceutically Acceptable Derivatives Thereof):

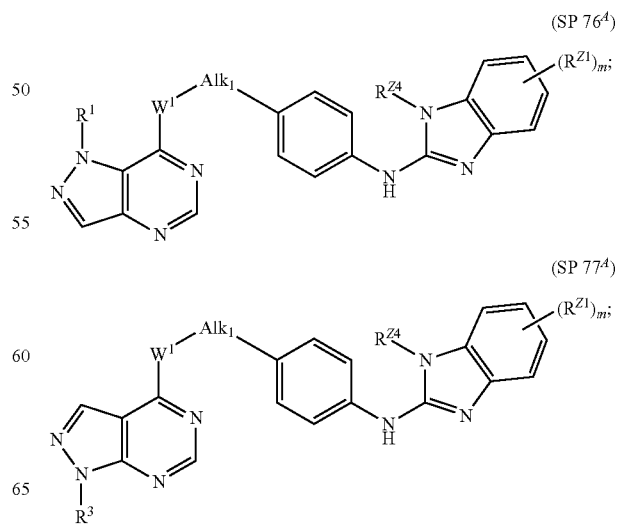

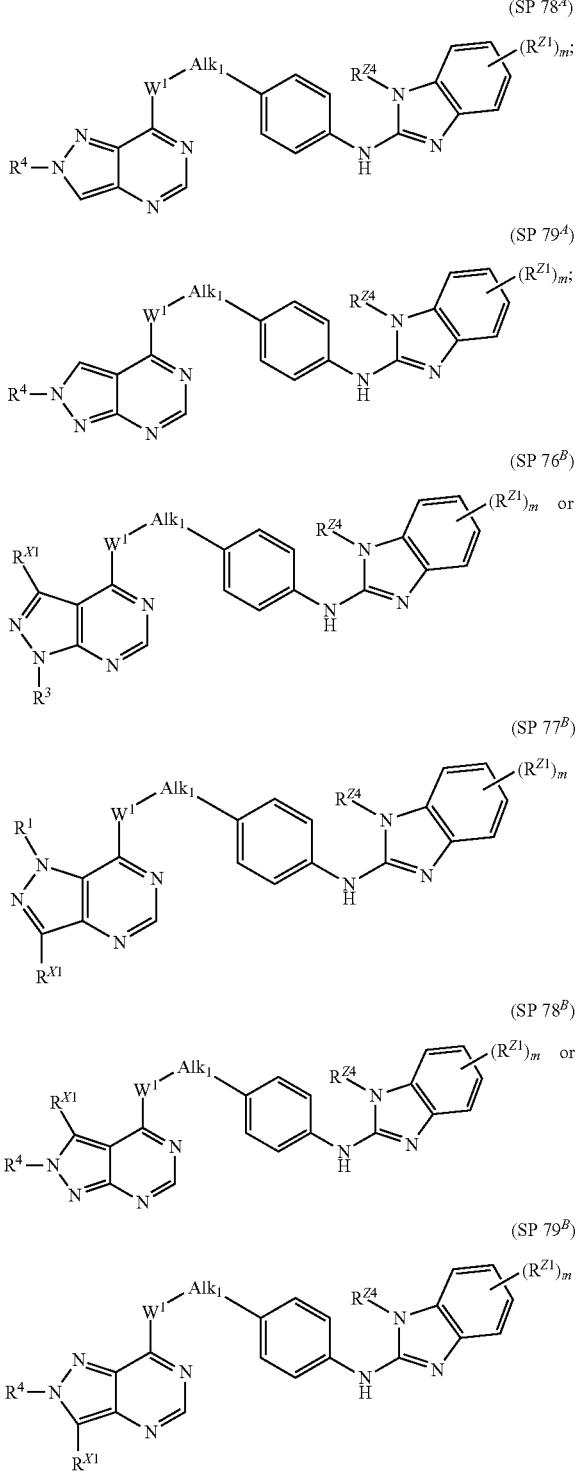

(SP 78^A)

(SP 79^A)

(SP 76^B)

(SP 77^B)

(SP 78^B)

(SP 79^B)

wherein R¹, R³, R⁴ and R^X1 are as defined generally and in classes and subclasses herein; W¹ is O or NR^W1, where R^W1 is hydrogen, lower alkyl, lower heteroalkyl, aryl, heteroaryl, -(alkyl)aryl, -(alkyl)heteroaryl or acyl; Alk₁ is a substituted or unsubstituted $C_{1-6}$alkylene or $C_{2-6}$alkenylene chain wherein up to two non-adjacent methylene units are independently optionally replaced by —C(=O)—, —CO₂—, —C(=O)C(=O)—, —C(=O)NR^{L1A}—, —OC(=O)—, —OC(=O)NR^{L1A}—, —NR^{L1A}NR^{L1B}—, —NR^{L1A}NR^{L1B}C(=O)—, —NR^{L1A}C(=O)—, —NR^{L1A}CO₂—, —NR^{L1A}C(=O)NR^{L1B}, S(=O)—, —SO₂—, —NR^{L1A}SO₂—, —SO₂NR^{L1A}—, —NR^{L1A}SO₂NR^{L1B}—, —O—, —S—, or —NR^{L1A}—; wherein each occurrence of R^{L1A} and R^{L1B} is independently hydrogen, lower alkyl, lower heteroalkyl, heterocyclyl, aryl, heteroaryl or acyl; m is an integer from 0 to 3; r is an integer from 1 to 4; each occurrence of R^{Z1} is independently hydrogen, alkyl, heteroalkyl, aryl, heteroaryl, -(alkyl)aryl or -(alkyl)heteroaryl, —OR^{Z2}, —SR^{Z2}, —NR^{Z2}R^{Z3}, —SO₂NR^{Z2}R^{Z3}, —SO₂R^{Z1}, —C(=O)NR^{Z2}R^{Z3}, halogen, —CN, —NO₂, —C(=O)OR^{Z3}, —N(R^{Z2})C(=O)R^{Z3}, and wherein each occurrence of R^{Z2}, R^{Z3} and R^{Z4} is independently hydrogen, lower alkyl, lower heteroalkyl, aryl, heteroaryl, -(alkyl)aryl, -(alkyl)heteroaryl or acyl, or R^{Z2} and R^{Z3} taken together with the nitrogen or carbon atom to which they are attached form a 5-6 membered heterocyclic, aryl or heteroaryl ring.

In certain embodiments, for compounds of group XVII, —W¹-Alk₁- is —NHC$_{1-6}$alkyl- or —OC$_{1-6}$alkyl-. In certain embodiments, —W¹-Alk1- is —NHC₂alkyl- or —OC₂alkyl-. In certain embodiments, —W¹-Alk₁- is —NHCH₂CH₂—, —OCH₂CH₂— or —NH—CH₂CH(CH₂OH)—.

In certain embodiments, for compounds of group XVII, R^{Z1} is hydrogen, halogen, lower alkyl or lower haloalkyl. In certain embodiments, m is 1 and R^{Z1} is Cl, F, methyl or —CF₃. In certain embodiments, m is 1 and R^{Z1} is lower haloalkyl. In certain embodiments, m is 1 and R^{Z1} is —CF₃. In certain embodiments, m is 2 and each occurrence of R^{Z1} is independently Cl, F, methyl or —CF₃—In certain embodiments, m is 2 and each occurrence of R^{Z1} is Cl, F, methyl or —CF₃. In certain embodiments, m is 2 and each occurrence of R^{Z1} is F.

In certain embodiments, for compounds of group XVII, R^{Z4} is hydrogen, or lower alkyl. In certain embodiments, R^{Z4} is lower alkyl. In certain embodiments, R^{Z4} is isopropyl.

In certain embodiments, compounds of group XVII have the structure:

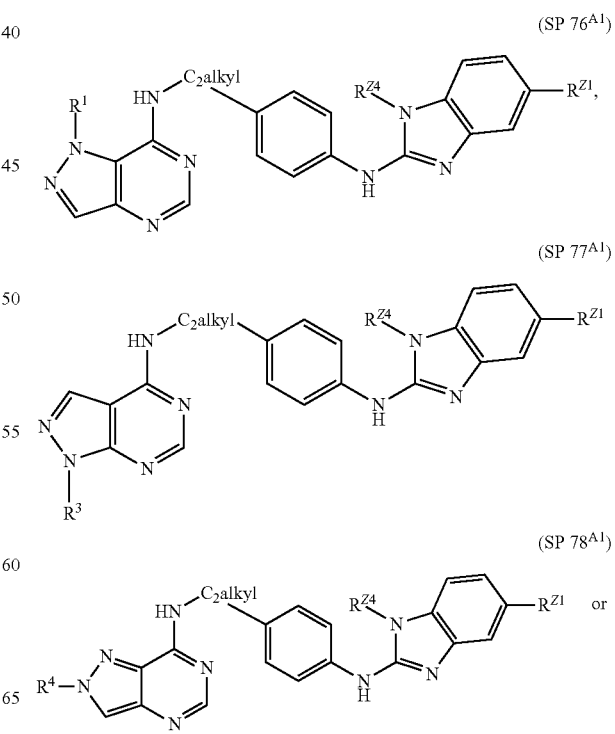

(SP 76^{A1})

(SP 77^{A1})

(SP 78^{A1}) or

-continued

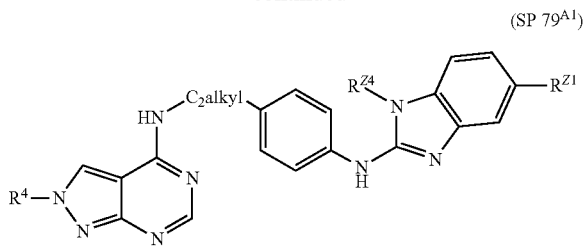
(SP 79^{A1})

wherein the $C_2$alkyl moiety is optionally substituted; $R^1$, $R^3$ and $R^4$ are independently hydrogen, lower alkyl or —$CO_2R^{1A}$ where $R^{1A}$ is hydrogen or lower alkyl; $R^{Z1}$ is halogen, lower alkyl or lower haloalkyl and $R^{Z4}$ is hydrogen or lower alkyl. In certain exemplary embodiments, $R^{Z1}$ is Cl, F, methyl or —$CF_3$ and $R^{Z4}$ is hydrogen or isopropyl. In certain exemplary embodiments, the $C_2$alkyl moiety is —$CH_2CH_2$—.

In certain embodiments, compounds of group XVII have the structure:

(SP 76^{A2})

(SP 77^{A2})

(SP 78^{A2})

(SP 79^{A2})

wherein the $C_2$alkyl moiety is optionally substituted; $R^1$, $R^3$ and $R^4$ are independently hydrogen, lower alkyl or —$CO_2R^{1A}$ where $R^{1A}$ is hydrogen or lower alkyl; $R^{Z1}$ and $R^{Z2}$ are independently halogen, lower alkyl or lower haloalkyl and $R^{Z4}$ is hydrogen or lower alkyl. In certain exemplary embodiments, $R^{Z1}$ and $R^{Z2}$ are independently Cl, F, methyl or —$CF_3$; and $R^{Z4}$ is hydrogen or isopropyl. In certain exemplary embodiments, the $C_2$alkyl moiety is —$CH_2CH_2$—. In certain embodiments, $R^{Z1}$ and $R^{Z2}$ are each Cl, F, methyl or —$CF_3$.

In certain embodiments, compounds of group XVII have the structure:

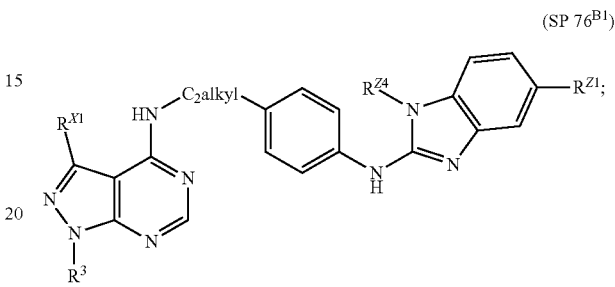
(SP 76^{B1})

(SP 77^{B1})

(SP 78^{B1})

(SP 79^{B1})

wherein the $C_2$alkyl moiety is optionally substituted; $R^1$, $R^3$ and $R^4$ are independently hydrogen, lower alkyl or —$CO_2R^{1A}$ where $R^{1A}$ is hydrogen or lower alkyl; $R^{X1}$ is hydrogen, lower alkyl or heterocyclyl; $R^{Z1}$ is halogen, lower alkyl or lower haloalkyl and $R^{Z4}$ is hydrogen or lower alkyl. In certain exemplary embodiments, $R^{X1}$ is hydrogen, methyl or thienyl; $R^{Z1}$ is Cl, F, methyl or —$CF_3$; and $R^{Z4}$ is hydrogen or isopropyl. In certain exemplary embodiments, the $C_2$alkyl moiety is —$CH_2CH_2$—.

In certain embodiments, compounds of group XVII have the structure:

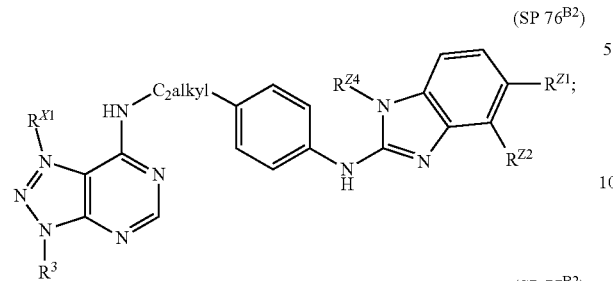
(SP 76^{B2})

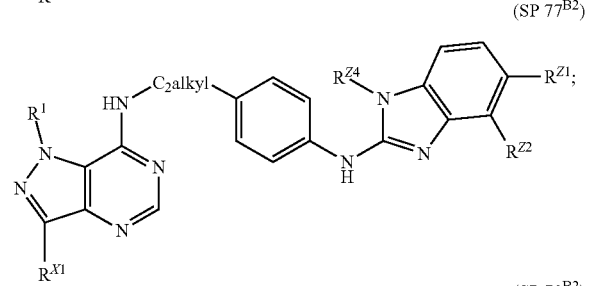
(SP 77^{B2})

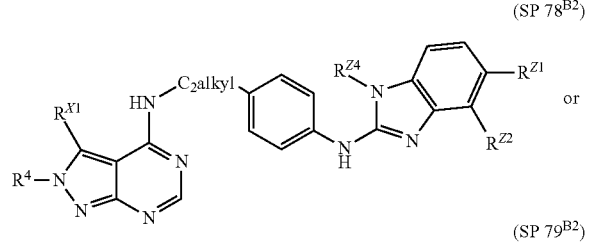
(SP 78^{B2}) or

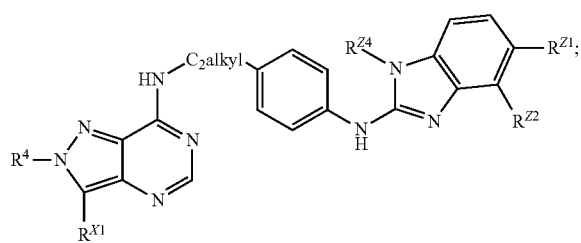
(SP 79^{B2})

wherein the $C_2$alkyl moiety is optionally substituted; $R^1$, $R^3$ and $R^4$ are independently hydrogen, lower alkyl or —$CO_2R^{14}$ where $R^{14}$ is hydrogen or lower alkyl; $R^{X1}$ is hydrogen, lower alkyl or heterocyclyl; $R^{Z1}$ and $R^{Z2}$ are independently halogen, lower alkyl or lower haloalkyl and $R^{Z4}$ is hydrogen or lower alkyl. In certain exemplary embodiments, $R^{X1}$ is hydrogen, methyl or thienyl; $R^{Z1}$ and $R^{Z2}$ are independently Cl, F, methyl or —$CF_3$ and $R^{Z4}$ is hydrogen or isopropyl. In certain exemplary embodiments, the $C_2$alkyl moiety is —$CH_2CH_2$—. In certain embodiments, $R^{Z1}$ and $R^{Z2}$ are each Cl, F, methyl or —$CF_3$.

XVIII. Compounds Having the Structure (and Pharmaceutically Acceptable Derivatives Thereof):

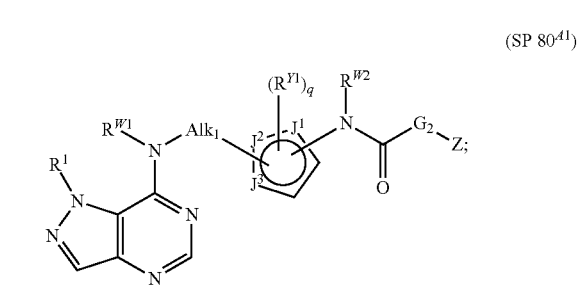
(SP 80^{A1})

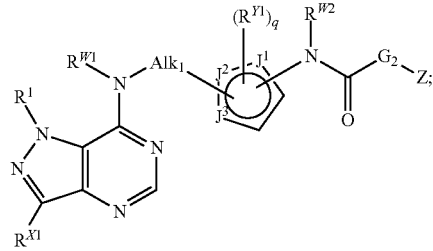
(SP 80^{B1})

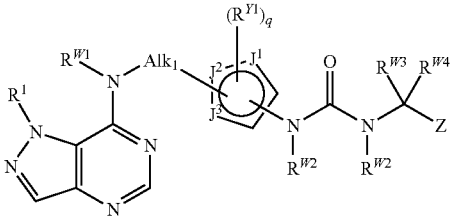
(SP 80^{A2})

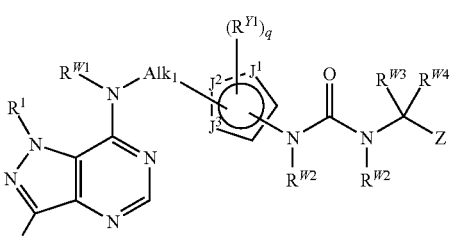
(SP 80^{B2})

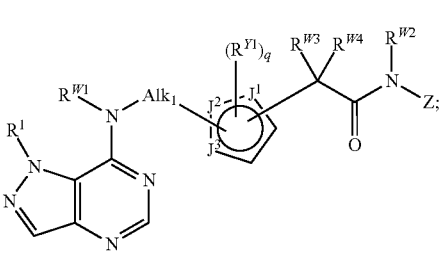
(SP 80^{A3})

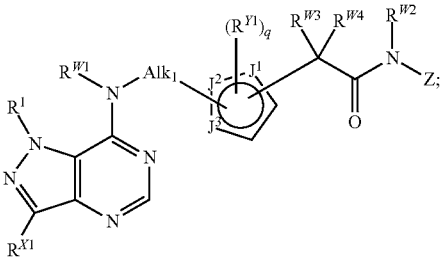
(SP 80^{B3})

wherein $R^{X1}$ and Z are as defined generally and in classes and subclasses herein; $R^1$ and $R^{W1}$ taken together form an optionally substituted 5- to 6-membered ring; $Alk_1$ is a substituted or unsubstituted $C_{1-6}$alkylene or $C_{2-6}$alkenylene chain wherein up to two non-adjacent methylene units are independently optionally replaced by —C(=O)—, —$CO_2$—, —C(=O)C(=O)—, —C(=O)$NR^{L1A}$—, —OC(=O)—, —OC(=O)$NR^{L1A}$—, —$NR^{L1A}NR^{L1B}$—, —$NR^{L1A}NR^{L1B}$C(=O), —$NR^{L1A}$C(=O)—, $NR^{L1A}CO_2$—, —$NR^{L1A}$C(=O)$NR^{L1B}$—, —S(=O)—, —$SO_2$—, —$NR^{L1A}SO_2$—, $SO_2NR^{L1A}$—, $NR^{L1A}SO_2NR^{L1B}$—, —O—, —S—, or —$NR^{L1A}$—; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^1$, $J^2$ and $J^3$ are independently O, S, N, $NR^{Y1}$ or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $—OR^{Y3}$, $—SR^{Y3}$, $—NR^{Y2}R^{Y3}$, $—SO_2NR^{Y2}R^{Y3}$, $—C(=O)NR^{Y2}R^{Y3}$, halogen, —CN, $—NO_2$, $—C(=O)OR^{Y3}$, $—N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $G_2$ is absent, O or $NR^{G2}$; $R^{W3}$ and $R^{W4}$ are independently hydrogen, lower alkyl, lower heteroalkyl, heterocyclyl, aryl, heteroaryl or acyl; and $R^{W2}$ and $R^{G2}$ are independently hydrogen, lower alkyl, lower heteroalkyl, heterocyclyl, aryl, heteroaryl, -(alkyl)aryl, -(alkyl)heteroaryl or acyl.

In certain embodiments, for compounds of group XVIII, $—W^1-Alk_1-$ is $—NHC_{1-6}alkyl-$ or $—OC_{1-6}alkyl-$. In certain embodiments, $—W^1-Alk_1-$ is $—NHC_2alkyl-$ or $—OC_2alkyl-$. In certain embodiments, $—W^1-Alk_1-$ is $—NHCH_2CH_2—$, $—OCH_2CH_2—$ or $—NH—CH_2CH(CH_2OH)—$.

In certain embodiments, compounds of this class have the structure (SP $80^{A4-6}$), or (SP $80^{B4-6}$) below:

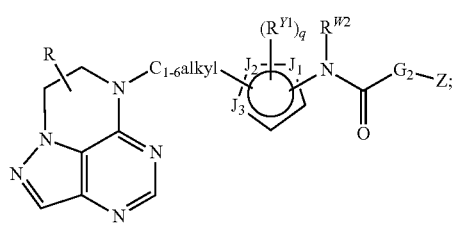
(SP $80^{A4}$)

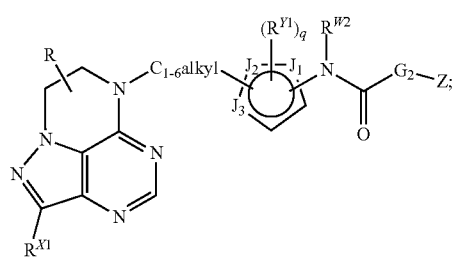
(SP $80^{B4}$)

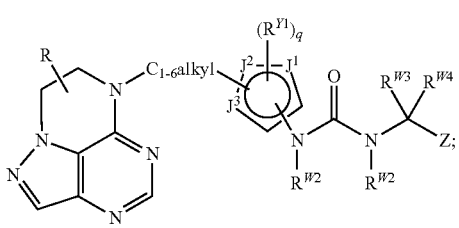
(SP $80^{A5}$)

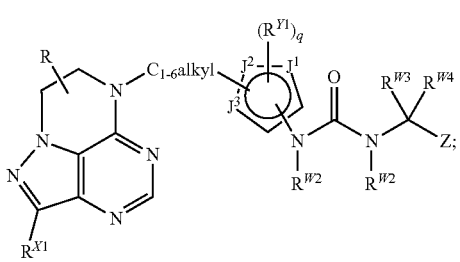
(SP $80^{B5}$)

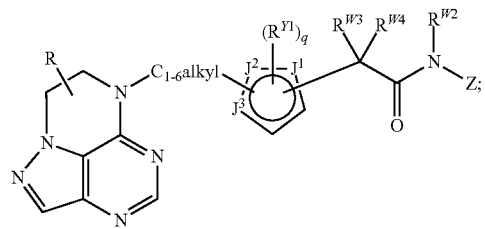
(SP $80^{A6}$)

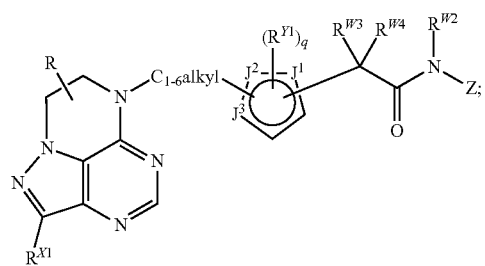
(SP $80^{B6}$)

wherein the $C_{1-6}$alkyl moiety may be substituted or unsubstituted.

In certain embodiments, for compounds of formulae (SP $80^{A4-6}$) and (SP $80^{B4-6}$) the $C_{1-6}$alkyl moiety is a substituted or unsubstituted $C_2$alkyl moiety. In certain exemplary embodiments, the $C_{1-6}$alkyl moiety is $—CH_2CH_2—$.

In certain embodiments, in compounds of formulae (SP $80^{A1-6}$) and (SP $80^{B1-6}$) the 5-membered ring having the structure:

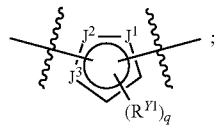

has one of the following structures:

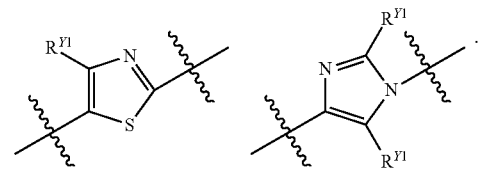

In certain embodiments, $—N(R^{W2})C(=O)G_2-$ is —NHC(=O)—, —NHC(=O)O—, or —NHC(=O)NH—. In certain embodiments, $—N(R^{W2})C(=O)N(R^{W2})CR^{W3}R^{W4}—$ is $—NHC(=O)NHCH_2—$ and $CR^{W3}R^{W4}C(=O)N(R^{W2})—$ is $—CH_2C(=O)NH—$.

XIX. Compounds Having the Structure (and Pharmaceutically Acceptable Derivatives Thereof):

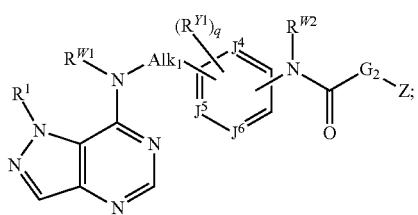
(SP $81^{A1}$)

-continued

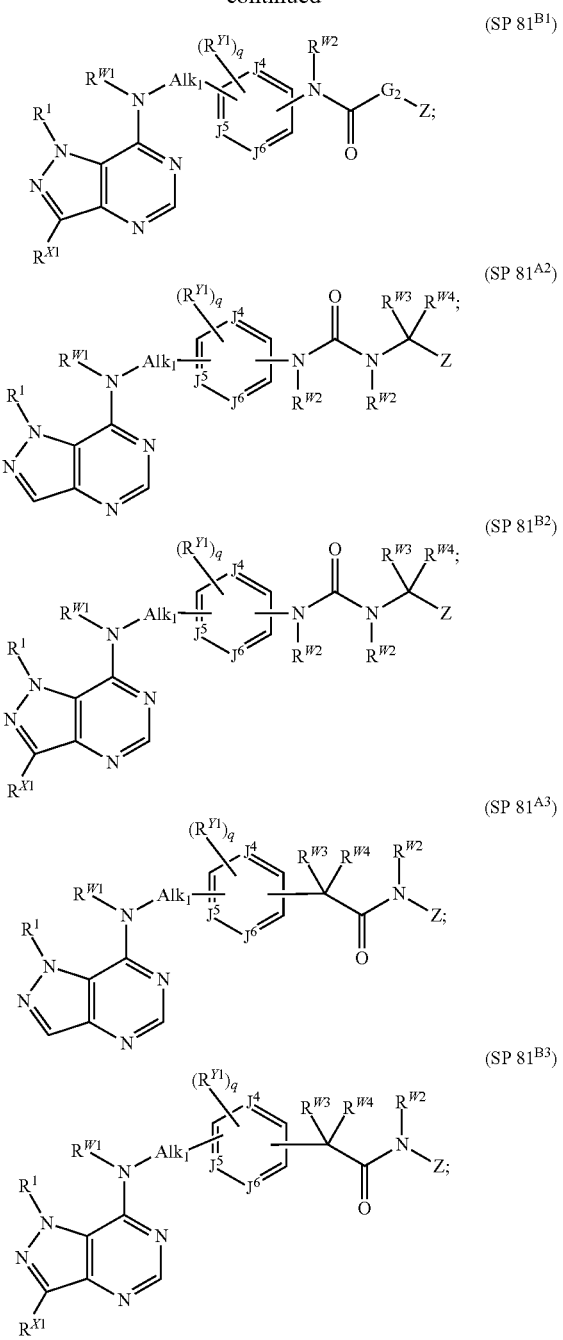

wherein $R^{X1}$ and Z are as defined generally and in classes and subclasses herein; $R^1$ and $R^{W1}$ taken together form an optionally substituted 5- to 6-membered ring; $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $G_2$ is absent, O or NR$^{G2}$; $R^{W3}$ and $R^{W4}$ are independently hydrogen, lower alkyl, lower heteroalkyl, heterocyclyl, aryl, heteroaryl or acyl; and $R^{W2}$ and $R^{G2}$ are independently hydrogen, lower alkyl, lower heteroalkyl, heterocyclyl, aryl, heteroaryl, -(alkyl)aryl, -(alkyl)heteroaryl or acyl.

In certain embodiments, for compounds of group XVIII, —W$^1$-Alk$_1$- is —NHC$_{1-6}$alkyl- or —OC$_{1-6}$alkyl-. In certain embodiments, —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, compounds of this class have the structure (SP 80$^{A4-6}$), or (SP 80$^{B4-6}$) below:

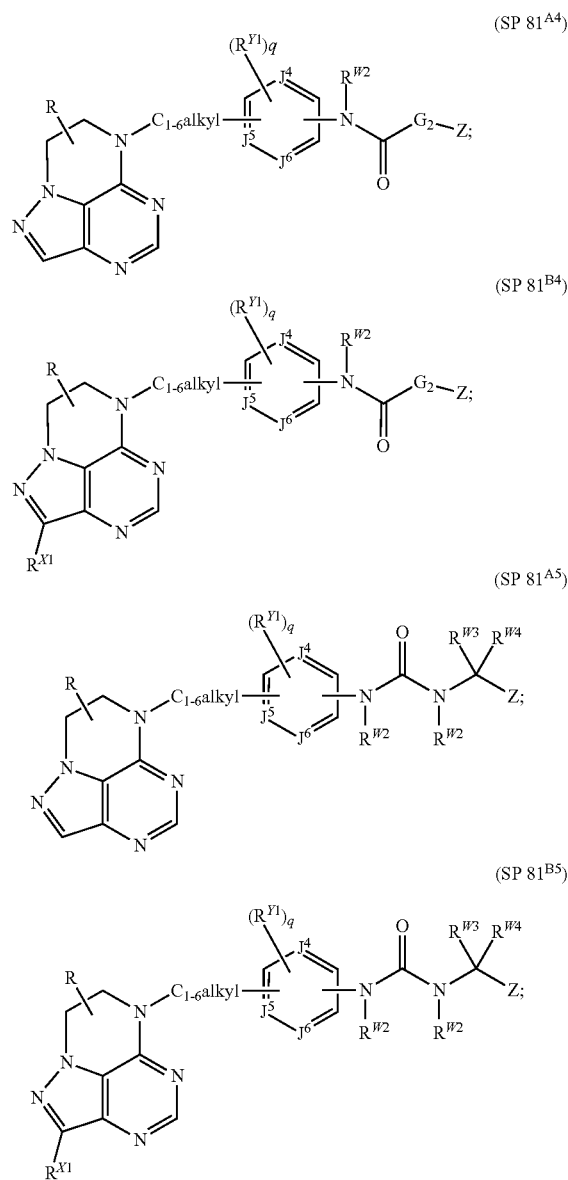

-continued (SP 81^{A6})

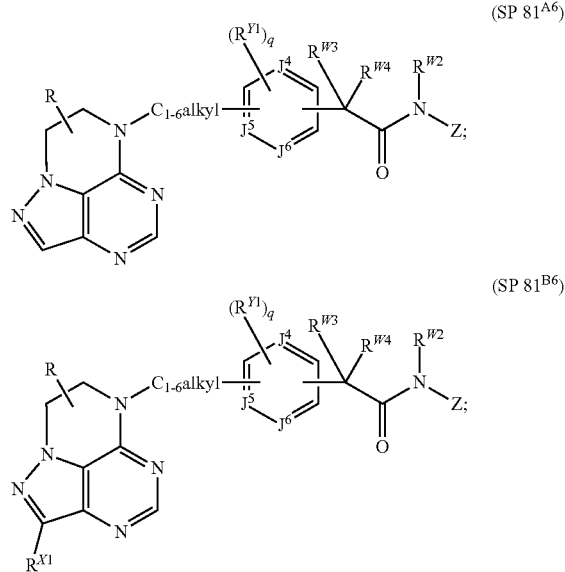

(SP 81^{B6})

wherein the $C_{1-6}$alkyl moiety may be substituted or unsubstituted.

In certain embodiments, for compounds of formulae (SP 81$^{A4-6}$) and (SP 81$^{B4-6}$) the $C_{1-6}$alkyl moiety is a substituted or unsubstituted $C_2$alkyl moiety. In certain exemplary embodiments, the $C_{1-6}$alkyl moiety is —CH$_2$CH$_2$—.

In certain embodiments, in compounds of formulae (SP 81$^{A1-6}$) and (SP 81$^{B1-6}$) the 6-membered ring having the structure:

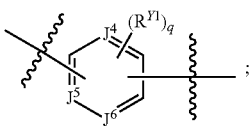

has one of the following structures:

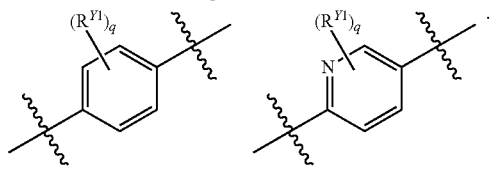

In certain embodiments, —N(R$^{W2}$)C(=O)G$_2$- is —NHC(=O)—, —NHC(=O)O—, or —NHC(=O)NH—. In certain embodiments, —N(R$^{W2}$)C(=O)N(R$^{W2}$)CR$^{W3}$R$^{W4}$— is —NHC(=O)NHCH$_2$—, and CR$^{W3}$R$^{W4}$C(=O)N(R$^{W2}$)— is —CH$_2$C(=O)NH—.

XX. Compounds having the Structure (and Pharmaceutically Acceptable Derivatives Thereof):

(SP 82)

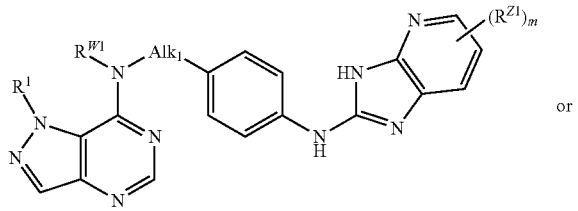

or (SP 83)

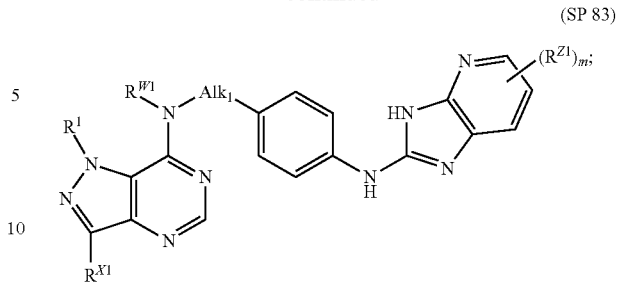

wherein R$^{X1}$ is as defined generally and in classes and subclasses herein; R$^1$ and R$^{W1}$ taken together form an optionally substituted 5- to 6-membered ring; Alk$_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$, —NR$^{L1A}$NR$^{L1B}$, —NR$^{L1A}$NR$^{L1B}$C(=O)—, —NR$^{L1A}$C(=O)—, —NR$^{L1A}$CO$_2$, —NR$^{L1A}$C(=O)NR$^{L1B}$, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl; m is an integer from 0 to 3; r is an integer from 1 to 4; each occurrence of R$^{Z1}$ is independently hydrogen, alkyl, heteroalkyl, aryl, heteroaryl, -(alkyl)aryl or -(alkyl)heteroaryl, —OR$^{Z2}$, —SR$^{Z2}$, —NR$^{Z2}$R$^{Z3}$, SO$_2$NR$^{Z2}$R$^{Z3}$, —SO$_2$R$^{Z1}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl or acyl, or R$^{Z2}$ and R$^{Z3}$ taken together with the nitrogen or carbon atom to which they are attached form a 5-6 membered heterocyclic, aryl or heteroaryl ring.

In certain embodiments, for compounds of group XX, —W$^1$-Alk$_1$- is —NHC$_{1-6}$alkyl- or —OC$_{1-6}$alkyl-. In certain embodiments, —W$^1$-Alk1- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, for compounds of group XX, R$^{Z1}$ is hydrogen, halogen, lower alkyl or lower haloalkyl. In certain embodiments, m is 1 and R$^{Z1}$ is H, Cl, F, methyl or —CF$_3$. In certain embodiments, m is 1 and R$^{Z1}$ is hydrogen.

In certain embodiments, compounds of group XX have the structure:

(SP 82$^4$)

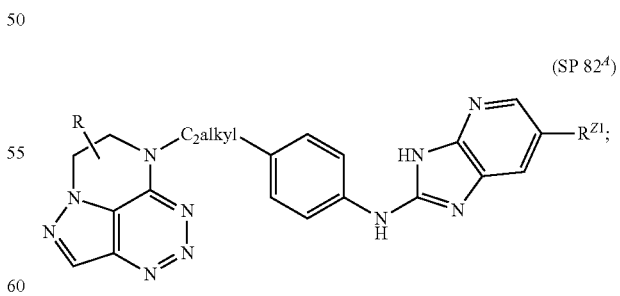

wherein R is hydrogen, halogen, hydroxyl, lower alkyl or lower alkoxy; and R$^{Z1}$ is hydrogen, halogen, lower alkyl or lower haloalkyl. In certain exemplary embodiments, R$^{Z1}$ is hydrogen, Cl, F, methyl or —CF$_3$. In certain exemplary embodiments, R$^{Z1}$ is hydrogen. In certain embodiments, R is hydrogen.

In certain embodiments, compounds of group XX have the structure:

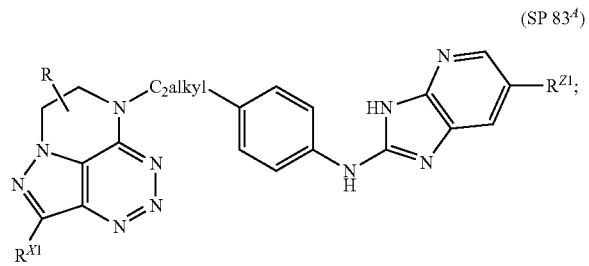

(SP 83^A)

wherein R is hydrogen, halogen, hydroxyl, lower alkyl or lower alkoxy; $R^{X1}$ is hydrogen, lower alkyl or heterocyclyl; and $R^{Z1}$ is hydrogen, halogen, lower alkyl or lower haloalkyl. In certain exemplary embodiments, R is hydrogen or lower alkyl; $R^{X1}$ is hydrogen, methyl or thienyl; and $R^{Z1}$ is hydrogen, Cl, F, methyl or —CF$_3$. In certain exemplary embodiments, R and $R^{Z1}$ are each hydrogen; and $R^{X1}$ is hydrogen, methyl or thienyl.

XXI. Compounds Having the Structure (and Pharmaceutically Acceptable Derivatives Thereof):

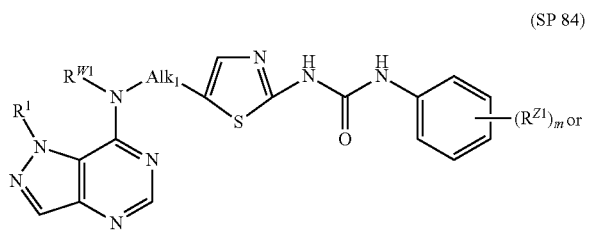

(SP 84)

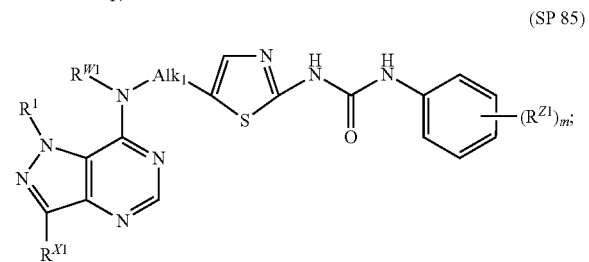

(SP 85)

wherein $R^{X1}$ is as defined generally and in classes and subclasses herein; $R^1$ and $R^{W1}$ taken together form an optionally substituted 5- to 6-membered ring; Alk$_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1B}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, lower alkyl, lower heteroalkyl, heterocyclyl, aryl, heteroaryl or acyl; m is an integer from 0 to 3; r is an integer from 1 to 4; each occurrence of $R^{Z1}$ is independently hydrogen, alkyl, heteroalkyl, aryl, heteroaryl, -(alkyl)aryl or -(alkyl)heteroaryl, —OR$^{Z2}$, —SR$^{Z2}$, —NR$^{Z2}$R$^{Z3}$, —SO$_2$NR$^{Z2}$R$^{Z3}$, —SO$_2$R$^{Z1}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring.

In certain embodiments, for compounds of group XXI, —W$^1$-Alk$_1$- is —NHC$_{1-6}$alkyl- or —OC$_{1-6}$alkyl-. In certain embodiments, —W$^1$-Alk1- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, for compounds of group XXI, $R^{Z1}$ is hydrogen, halogen, lower alkyl or lower haloalkyl. In certain embodiments, m is 1 and $R^{Z1}$ is Cl, F, methyl or —CF$_3$. In certain embodiments, m is 1 and $R^{Z1}$ is lower haloalkyl. In certain embodiments, m is 1 and $R^{Z1}$ is —CF$_3$. In certain embodiments, m is 2 and each occurrence of $R^{Z1}$ is independently CN, Cl, F, methyl or —CF$_3$. In certain embodiments, m is 2 and each occurrence of $R^{Z1}$ is CN, Cl, F, methyl or —CF$_3$. In certain embodiments, m is 2 and one occurrence of $R^{Z1}$ is Cl, F, methyl or —CF$_3$ and the other is CN.

In certain embodiments, compounds of group XXI have the structure:

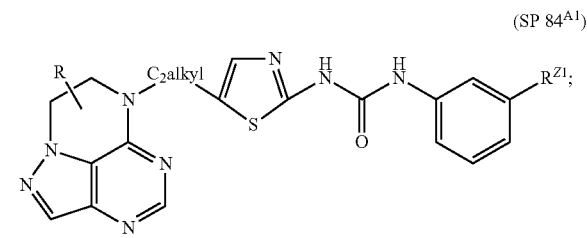

(SP 84$^{A1}$)

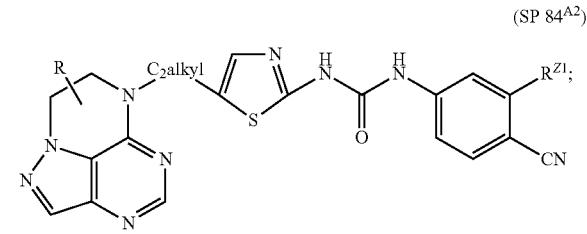

(SP 84$^{A2}$)

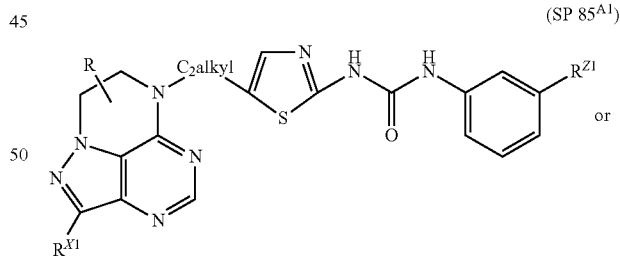

(SP 85$^{A1}$)

or

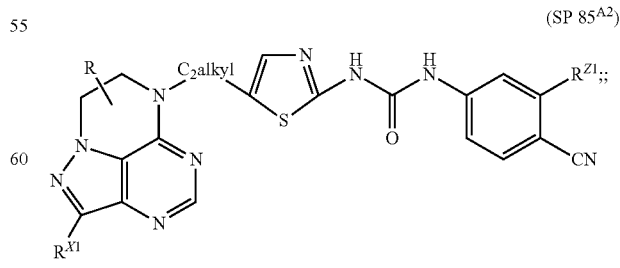

(SP 85$^{A2}$)

wherein the C$_2$alkyl moiety is optionally substituted; R is hydrogen, halogen, hydroxyl, lower alkyl or lower alkoxy;

$R^{X1}$ is hydrogen, lower alkyl or heterocyclyl; and $R^{Z1}$ is hydrogen, halogen, lower alkyl or lower haloalkyl. In certain exemplary embodiments, $R^{X1}$ is hydrogen, methyl or thienyl; and $R^{Z1}$ is hydrogen, Cl, F, methyl or —$CF_3$. In certain exemplary embodiments, in compounds of formulae (SP 84$^{A1}$) and (SP 85$^{A1}$), $R^{Z1}$ is hydrogen. In certain exemplary embodiments, in compounds of formulae (SP 84$^{A2}$) and (SP 85$^{A2}$), $R^{Z1}$ is Cl or —$CF_3$. In certain embodiments, R is hydrogen. In certain exemplary embodiments, the $C_2$alkyl moiety is —$CH_2CH_2$—.

XXII. Compounds Having the Structure (and Pharmaceutically Acceptable Derivatives Thereof):

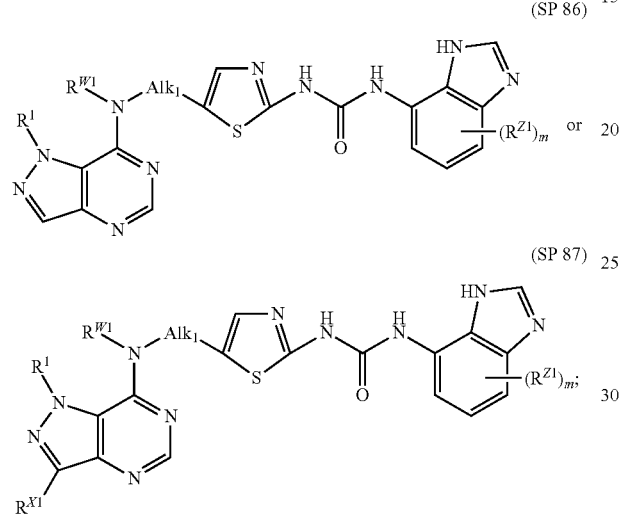

(SP 86)

(SP 87)

wherein $R^{X1}$ is as defined generally and in classes and subclasses herein; $R^1$ and $R^{W1}$ taken together form an optionally substituted 5- to 6-membered ring; $Alk_1$ is a substituted or unsubstituted $C_{1-6}$alkylene or $C_{2-6}$alkenylene chain wherein up to two non-adjacent methylene units are independently optionally replaced by —C(═O)—, —$CO_2$—, —C(═O)C(═O)—, —C(═O)$NR^{L1A}$—, —OC(═O)—, —OC(═O)$NR^{L1A}$, —$NR^{L1A}NR^{L1B}$, —$NR^{L1A}NR^{L1B}$C(═O)—, —$NR^{L1A}$C(═O)—, —$NR^{L1A}CO_2$—, —$NR^{L1A}$C(═O)$NR^{L1B}$—, —S(═O)—, —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, lower alkyl, lower heteroalkyl, heterocyclyl, aryl, heteroaryl or acyl; m is an integer from 0 to 3; r is an integer from 1 to 4; each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, $SO_2NR^{Z2}R^{Z3}$, —$SO_2R^{Z1}$, —C(═O)$NR^{Z2}R^{Z3}$, halogen, —CN, —$NO_2$, —C(═O)$OR^{Z3}$, —N($R^{Z2}$)C(═O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring.

In certain embodiments, for compounds of group XXII, —$W^1$-$Alk_1$- is —$NHC_{1-6}$alkyl- or —$OC_{1-6}$alkyl-. In certain embodiments, —$W^1$-Alk1- is —$NHC_2$alkyl- or —$OC_2$alkyl-. In certain embodiments, —$W^1$-$Alk_1$- is —$NHCH_2CH_2$—, —$OCH_2CH_2$— or —NH—$CH_2CH$($CH_2OH$)—.

In certain embodiments, for compounds of group XXII, $R^{Z1}$ is hydrogen, halogen, lower alkyl or lower haloalkyl. In certain embodiments, m is 0.

In certain embodiments, compounds of group XXII have the structure:

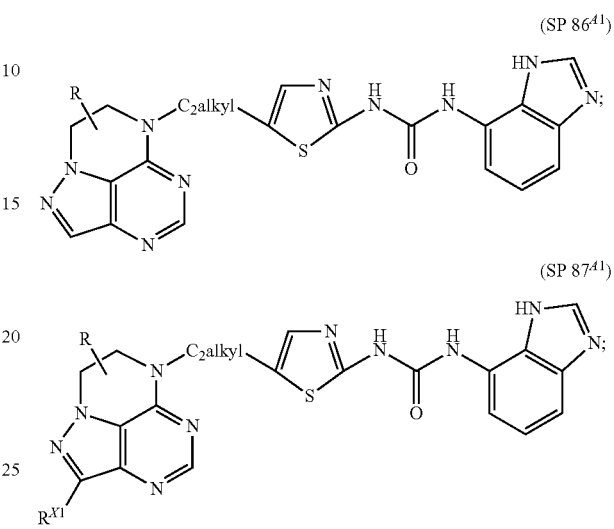

(SP 86$^{A1}$)

(SP 87$^{A1}$)

wherein the $C_2$alkyl moiety is optionally substituted; R is hydrogen, halogen, hydroxyl, lower alkyl or lower alkoxy; and $R^{X1}$ is hydrogen, lower alkyl or heterocyclyl. In certain exemplary embodiments, $R^{X1}$ is hydrogen, methyl or thienyl. In certain embodiments, R is hydrogen. In certain exemplary embodiments, the $C_2$alkyl moiety is —$CH_2CH_2$—.

XXIII. Compounds Having the Structure (and Pharmaceutically Acceptable Derivatives Thereof):

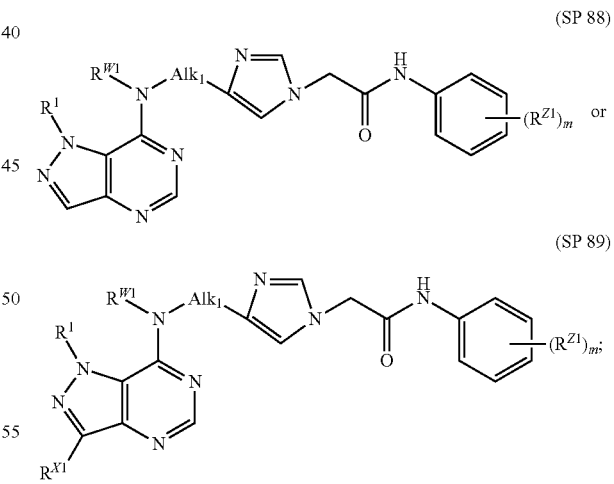

(SP 88)

(SP 89)

wherein $R^{X1}$ is as defined generally and in classes and subclasses herein; $R^1$ and $R^{W1}$ taken together form an optionally substituted 5- to 6-membered ring; $Alk_1$ is a substituted or unsubstituted $C_{1-6}$alkylene or $C_{2-6}$alkenylene chain wherein up to two non-adjacent methylene units are independently optionally replaced by —C(═O)—, —$CO_2$—, —C(═O)C(═O)—, —C(═O)$NR^{L1A}$—, —OC(═O)—, —OC(═O)$NR^{L1A}$, —$NR^{L1A}NR^{L1B}$—, —$NR^{L1A}NR^{L1B}$C(═O)—, —$NR^{L1A}$C(═O)—, —$NR^{L1A}CO_2$, —$NR^{L1A}$C(═O)

$NR^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl; m is an integer from 0 to 3; r is an integer from 1 to 4; each occurrence of R$^{Z1}$ is independently hydrogen, alkyl, heteroalkyl, aryl, heteroaryl, -(alkyl)aryl or -(alkyl)heteroaryl, —OR$^{Z2}$, —SR$^{Z2}$, NR$^{Z2}$R$^{Z3}$, —SO$_2$NR$^{Z2}$R$^{Z3}$, SO$_2$R$^{Z1}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl or acyl, or R$^{Z2}$ and R$^{Z3}$ taken together with the nitrogen or carbon atom to which they are attached form a 5-6 membered heterocyclic, aryl or heteroaryl ring.

In certain embodiments, for compounds of group XXIII, —W$^1$-Alk$_1$- is —NHC$_{1-6}$alkyl- or —OC$_{1-6}$alkyl-. In certain embodiments, —W$^1$-Alk1- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, for compounds of group XXIII, R$^{Z1}$ is hydrogen, halogen, lower alkyl or lower haloalkyl. In certain embodiments, m is 1 and R$^{Z1}$ is Cl, F, methyl or —CF$_3$. In certain embodiments, m is 1 and R$^{Z1}$ is lower haloalkyl. In certain embodiments, m is 1 and R$^{Z1}$ is —CF$_3$. In certain embodiments, m is 2 and each occurrence of R$^{Z1}$ is independently CN, Cl, F, methyl or —CF$_3$. In certain embodiments, m is 2 and each occurrence of R$^{Z1}$ is CN, Cl, F, methyl or —CF$_3$. In certain embodiments, m is 2 and one occurrence of R$^{Z1}$ is Cl, F, methyl or —CF$_3$ and the other is CN.

In certain embodiments, compounds of group XXIII have the structure:

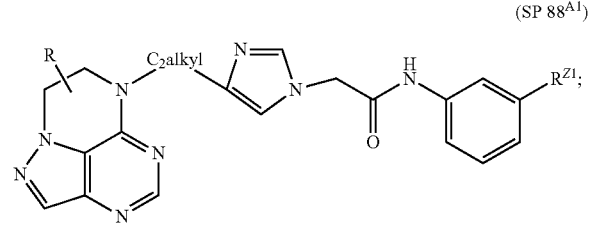

(SP 88$^{A1}$)

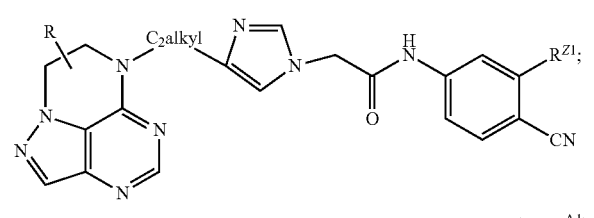

(SP 88$^{A2}$)

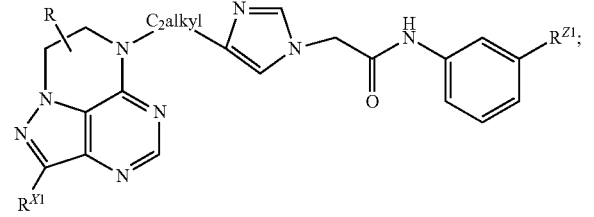

(SP 89$^{A1}$)

-continued

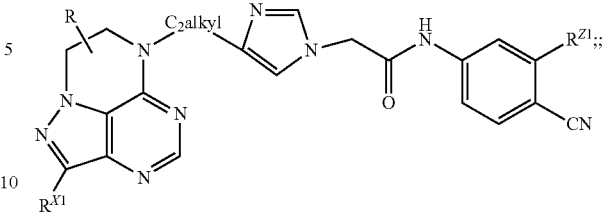

(SP 89$^{A2}$)

wherein the C$_2$alkyl moiety is optionally substituted; R is hydrogen, halogen, hydroxyl, lower alkyl or lower alkoxy; R$^{X1}$ is hydrogen, lower alkyl or heterocyclyl; and R$^{Z1}$ is hydrogen, halogen, lower alkyl or lower haloalkyl. In certain exemplary embodiments, R$^{X1}$ is hydrogen, methyl or thienyl; and R$^{Z1}$ is hydrogen, Cl, F, methyl or —CF$_3$. In certain exemplary embodiments, in compounds of formulae (SP 88$^{A1}$) and (SP 89$^{A1}$), R$^{Z1}$ is hydrogen. In certain exemplary embodiments, in compounds of formulae (SP 88$^{A2}$) and (SP 89$^{A2}$), R$^{Z1}$ is Cl or —CF$_3$. In certain embodiments, R is hydrogen. In certain exemplary embodiments, the C$_2$alkyl moiety is —CH$_2$CH$_2$—.

XXIV. Compounds Having the Structure (and Pharmaceutically Acceptable Derivatives Thereof):

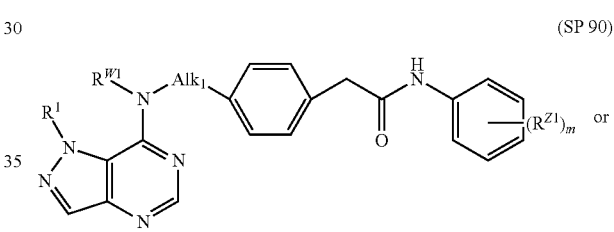

(SP 90)

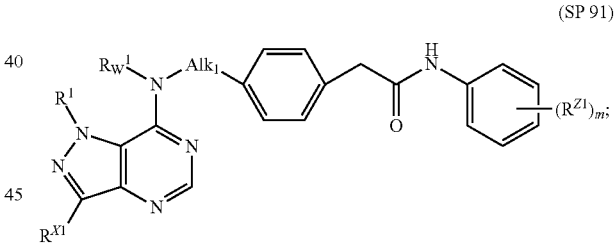

(SP 91)

wherein R$^{X1}$ is as defined generally and in classes and subclasses herein; R$^1$ and R$^{W1}$ taken together form an optionally substituted 5- to 6-membered ring; Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, OC(=O)NR$^{L1A}$—, NR$^{L1A}$NR$^{L1B}$—, —NR$^{L1A}$NR$^{L1B}$C(=O), —NR$^{L1A}$C(=O)—, NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl; m is an integer from 0 to 3; r is an integer from 1 to 4; each occurrence of R$^{Z1}$ is independently hydrogen, alkyl, heteroalkyl, aryl, heteroaryl, -(alkyl)aryl or -(alkyl)heteroaryl, —OR$^{Z2}$, —SR$^{Z2}$, —NR$^{Z2}$R$^{Z3}$, —SO$_2$NR$^{Z2}$R$^{Z3}$, SO$_2$R$^{Z1}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring.

In certain embodiments, for compounds of group XXIV, —$W^1$-$Alk_1$- is —$NHC_{1-6}alkyl$- or —$OC_{1-6}alkyl$-. In certain embodiments, —$W^1$-Alk1- is —$NHC_2alkyl$- or —$OC_2alkyl$-. In certain embodiments, —$W^1$-$Alk_1$- is —$NHCH_2CH_2$—, —$OCH_2CH_2$— or —$NH$—$CH_2CH(CH_2OH)$—.

In certain embodiments, for compounds of group XXIV, $R^{Z1}$ is hydrogen, halogen, lower alkyl or lower haloalkyl. In certain embodiments, m is 1 and $R^{Z1}$ is Cl, F, methyl or —$CF_3$. In certain embodiments, m is 1 and $R^{Z1}$ is lower haloalkyl. In certain embodiments, m is 1 and $R^{Z1}$ is —$CF_3$. In certain embodiments, m is 2 and each occurrence of $R^{Z1}$ is independently CN, Cl, F, methyl or —$CF_3$. In certain embodiments, m is 2 and each occurrence of $R^{Z1}$ is CN, Cl, F, methyl or —$CF_3$. In certain embodiments, m is 2 and one occurrence of $R^{Z1}$ is Cl, F, methyl or —$CF_3$ and the other is CN.

In certain embodiments, compounds of group XXIV have the structure:

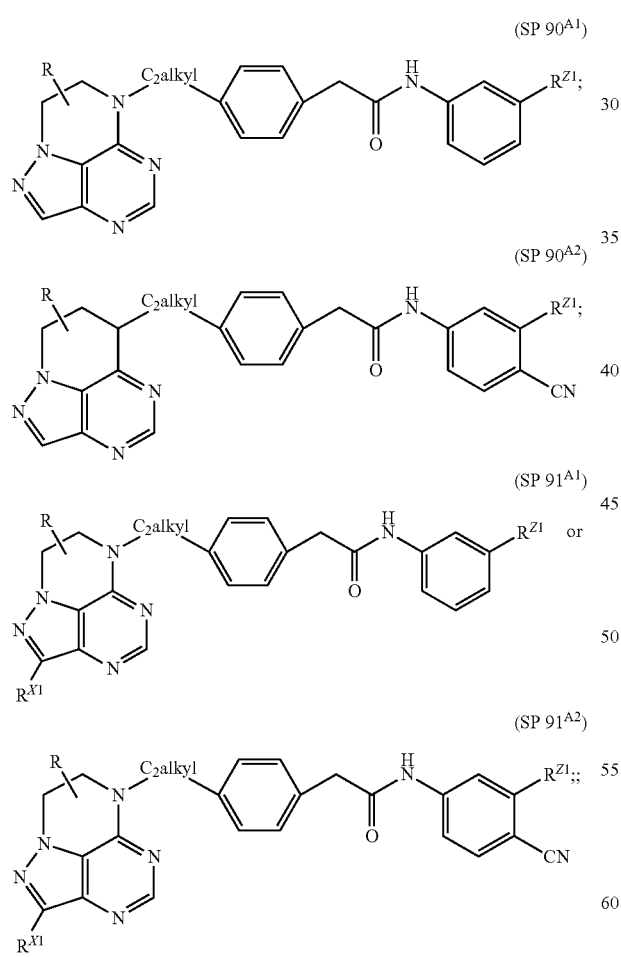

wherein the $C_2$alkyl moiety is optionally substituted; R is hydrogen, halogen, hydroxyl, lower alkyl or lower alkoxy; $R^{X1}$ is hydrogen, lower alkyl or heterocyclyl; and $R^{Z1}$ is hydrogen, halogen, lower alkyl or lower haloalkyl. In certain exemplary embodiments, $R^{X1}$ is hydrogen, methyl or thienyl; and $R^{Z1}$ is hydrogen, Cl, F, methyl or —$CF_3$. In certain exemplary embodiments, in compounds of formulae (SP $90^{A1}$) and (SP $91^{A1}$), $R^{Z1}$ is hydrogen. In certain exemplary embodiments, in compounds of formulae (SP $90^{A2}$) and (SP $91^{A2}$), $R^{Z1}$ is Cl or —$CF_3$. In certain embodiments, R is hydrogen. In certain exemplary embodiments, the $C_2$alkyl moiety is —$CH_2CH_2$—.

XXV. Compounds Having the Structure (and Pharmaceutically Acceptable Derivatives Thereof):

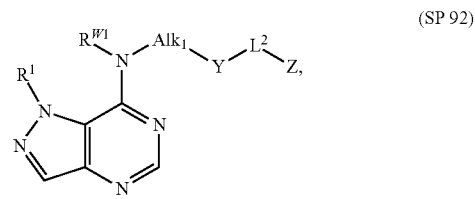
(SP 92)

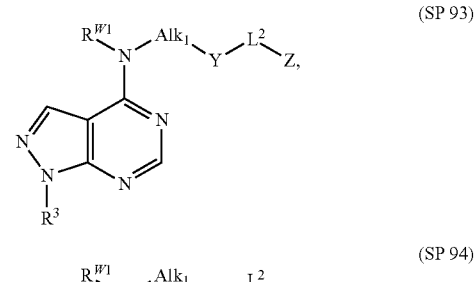
(SP 93)

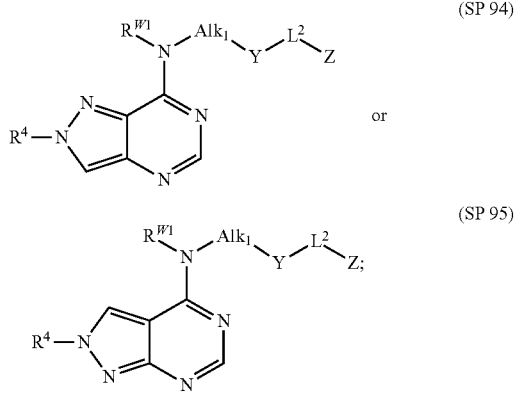
(SP 94)

or

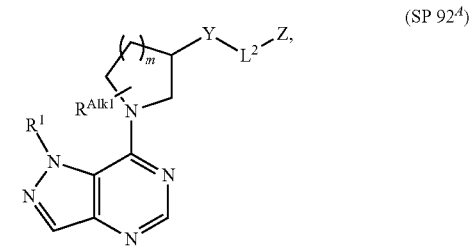
(SP 95)

wherein $R^1$, $R^3$, $R^4$, $L^2$, Y and Z are as defined generally and in classes and subclasses herein; and $R^{W1}$ together with a carbon atom present on $Alk_1$ forms an optionally substituted 5- to 6-membered heterocyclic ring.

In certain embodiments, compounds of the invention have one of the structures (SP $92^A$)-(SP $95^A$) below:

(SP $92^A$)

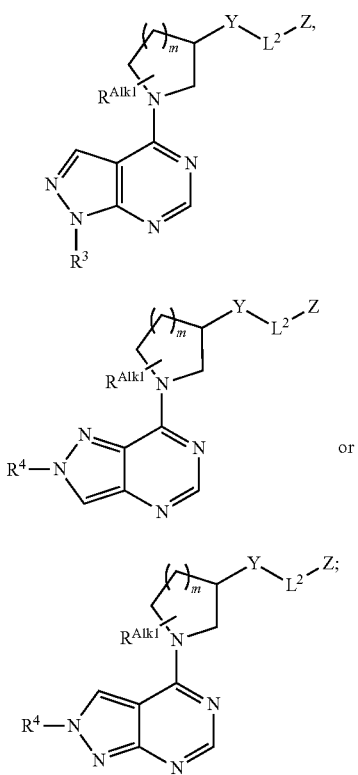

wherein m is 1 or 2 and $R^{Alk1}$ is hydrogen, halohen, hydroxy, CN, nitro, lower alkyl, lower alkoxy, aryl, or heteroaryl. In certain embodiments, $R^{Alk1}$ is hydrogen.

In certain embodiments for compounds as described in subgroups I-XVII and XXV above, $R^1$, $R^3$ and $R^4$ are independently hydrogen or lower alkyl. In certain embodiments, $R^1$, $R^3$ and $R^4$ are independently hydrogen. In certain embodiments, $R^1$, $R^3$ and $R^4$ are independently hydrogen, methyl, ethyl, isopropyl or one of:

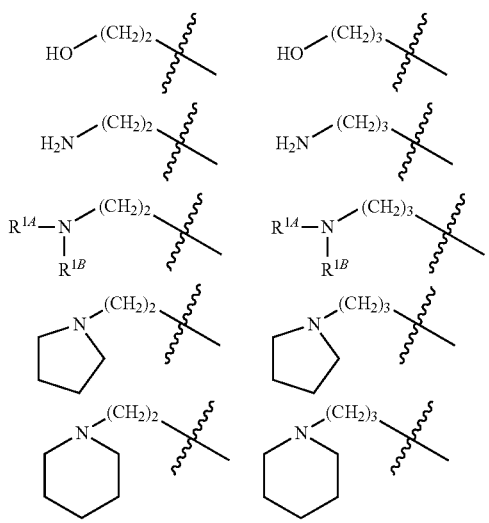

wherein $R^{1A}$ and $R^{1B}$ are independently hydrogen, methyl or ethyl.

In certain embodiments, for compounds as described in subgroups I-XXV above, $R^{W1}$ together with a carbon atom present on $Alk_1$ forms an optionally substituted 5- to 6-membered heterocyclic ring.

In certain embodiments, for compounds as described in subgroups I-XIII, XVIII-XIX and XXV above, Z is a branched alkyl, alkenyl, alkynyl, heteroalkyl or heteroalkenyl moiety. In certain exemplary embodiments, Z has one of the following structures:

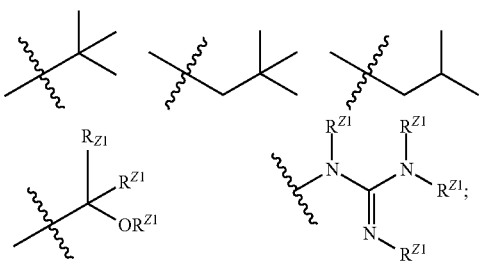

wherein each occurrence of $R^{Z1}$ is independently hydrogen, lower alkyl, lower alkenyl, aryl, heteroaryl or acyl. In certain embodiments, Z has one of the following structures:

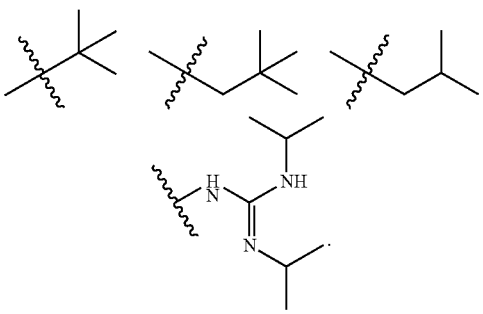

In certain embodiments, for compounds as described in subgroups I-XIII, XVIII-XIX and XXV above, Z is a cycloalkyl, cycloalkenyl, heterocyclyl, aryl or heteroaryl moiety. In certain exemplary embodiments, Z has one of the following structures:

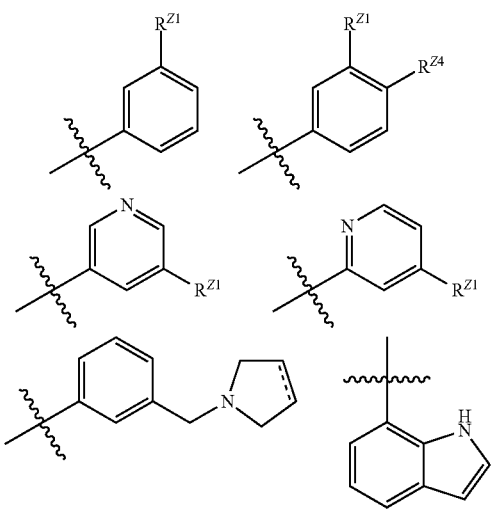

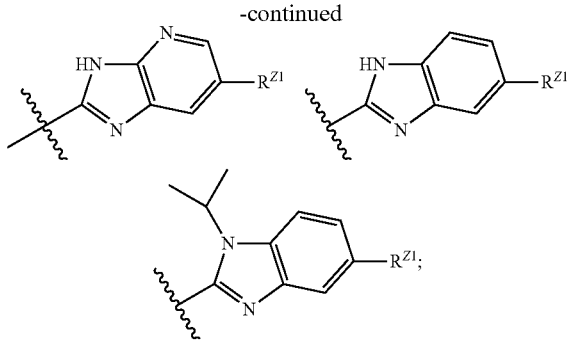

wherein $R^{Z1}$ is Cl, F, methyl or $CF_3$; and $R^{Z4}$ is hydrogen or cyano.

In certain embodiments, for compounds as described in subgroups I, IV-VI and XXV above, $-L^2-Z$ together represent a moiety having one of the following structures:

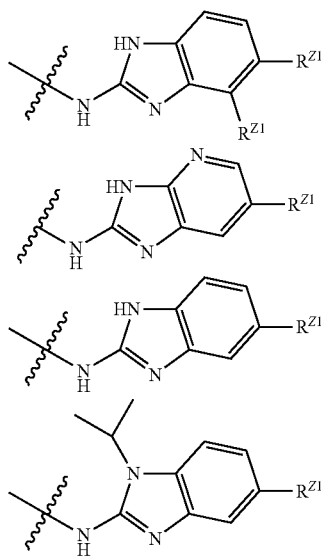

wherein $R^{Z1}$ is Cl, F, methyl or $CF_3$.

It will also be appreciated that for each of the subgroups I-XXV described above, a variety of other subclasses are of special interest, including, but not limited to those classes described above i)-clxxiv) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Synthetic Overview:

The practitioner has a well-established literature of pyrazolo pyrimidine chemistry to draw upon, in combination with the information contained herein, for guidance on synthetic strategies, protecting groups, and other materials and methods useful for the synthesis of the compounds of this invention, including compounds containing the various $R^2$ and $R^3$ substituents and $L^1$, $L^2$, Y and Z moieties.

Moreover, the practitioner is directed to the specific guidance and examples provided in this document relating to various exemplary compounds and intermediates thereof.

As described above, the present invention provides novel compounds, specifically compounds having the following general structure:

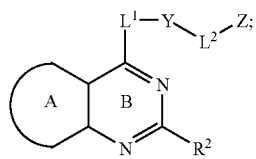

(I)

wherein A-B together represent one of the following structures:

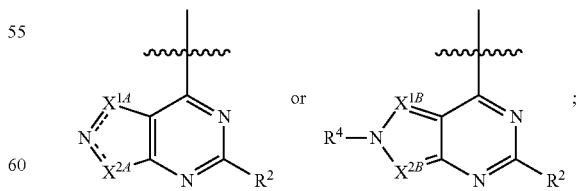

and pharmaceutically acceptable derivatives thereof;
wherein $R^2$, $R^4$, $X^{1A}$, $X^{2A}$, $X^{1B}$, $X^{2B}$, $L^1$, $L^2$, Y and Z are as defined in classes and subclasses herein.

It will be appreciated that for compounds as generally described above, certain classes of compounds are of special interest. For example, one class of compounds of special interest includes pyrazolo pyrimidines having formulae ($I^{A1}$) though ($I^{A4}$):

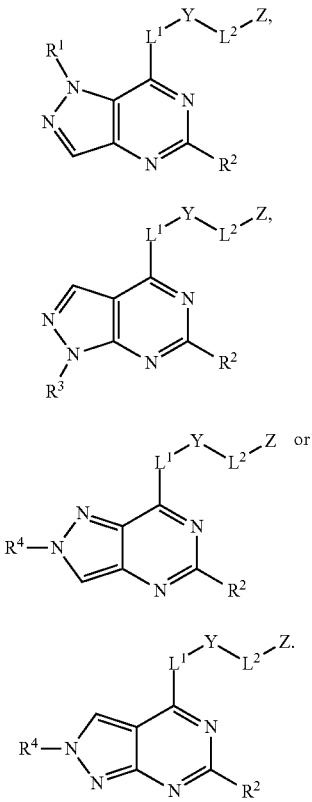

In yet another aspect of the invention, methods for producing intermediates useful for the preparation of compounds of formulae (1) and ($I^{A1}$) though ($I^{A4}$) are provided, embodiments of said methods being depicted generally in Scheme A:

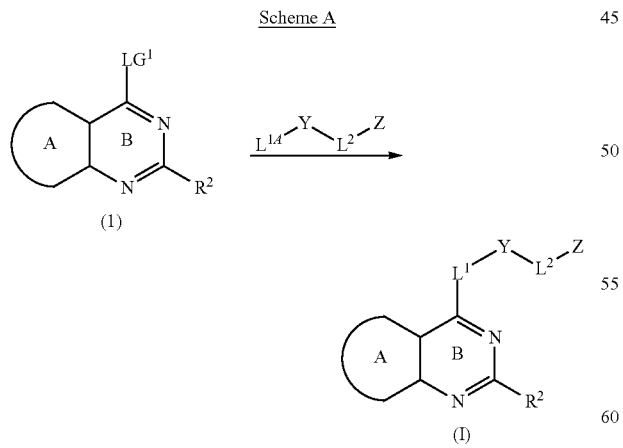

where $LG^1$ is a suitable leaving group and $L^{1A}$ is adapted to displace $LG^1$ upon reaction with pyrazolo pyrimidine (1).

In certain embodiments, the methodology may be used to generate inventive compounds of the general formula ($I^B$):

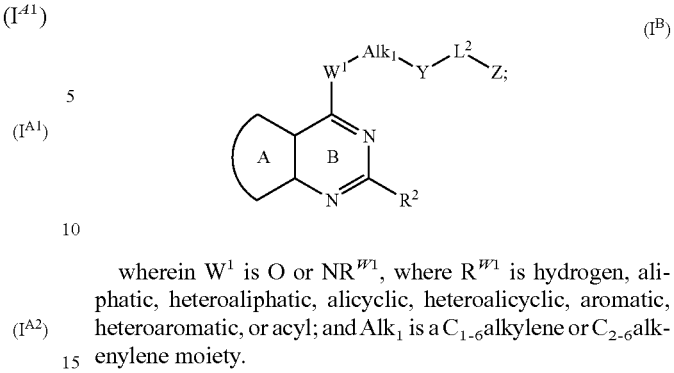

wherein $W^1$ is O or $NR^{W1}$, where $R^{W1}$ is hydrogen, aliphatic, heteroaliphatic, alicyclic, heteroalicyclic, aromatic, heteroaromatic, or acyl; and $Alk_1$ is a $C_{1-6}$alkylene or $C_{2-6}$alkenylene moiety.

In yet another aspect of the invention, methods for producing intermediates useful for the preparation of compounds of Formula ($I^{C1}$) and ($I^{C2}$) wherein $W^1$ is $-C(=O)N(R^{W1})-$, where $R^{W1}$ is as defined above, are provided, embodiments of said methods being depicted generally in Scheme B:

Scheme B

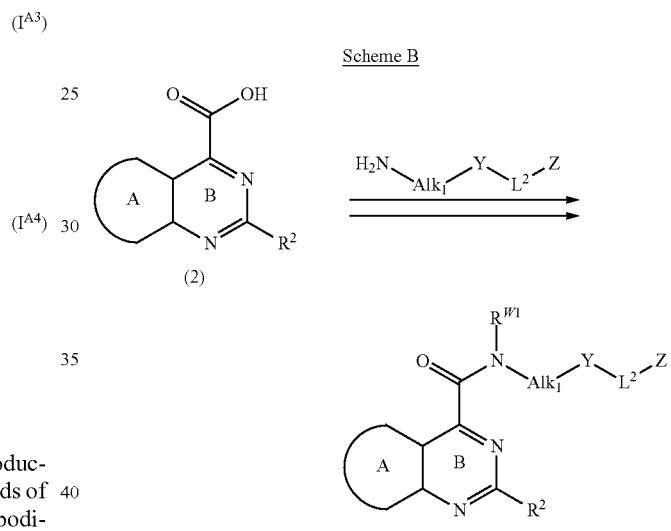

Numerous suitable prodrug moieties, and information concerning their selection, synthesis and use are well known in the art. Examples of prodrug moieties of interest include, among others, prodrug moieties that can be attached to primary or secondary amine-containing functionalities. For instance, prodrug moieties of interest include those that can be attached to group $-NH_2$. Examples of such prodrug moieties include the following:

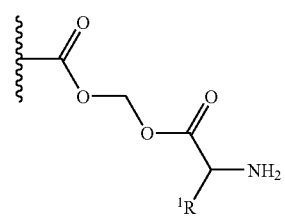

For the synthesis of the prodrug groups, see Borchardt, R. T. et al., J. Org. Chem. 1997, 62, 1356-1362 and 1363-1367.

$R^1$=all natural,
unnatural amino acids

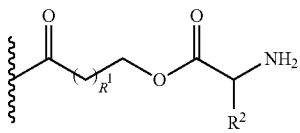

For the synthesis of the prodrug groups, see Zhou, X-X. et. al., PCT WO 99/51613.
$R^1$=C1-C4 alkyl, cycloalkyl, oxyalkyl, aminoalkyl, etc.
$R^2$=all natural, unnatural amino acids

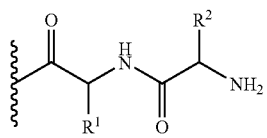

For the synthesis of the prodrug groups, see Ezra, A. et. al., *J. Med. Chem.* 2000, 43, 3641-3652.
$R^1$, $R^2$=all natural, unnatural amino acids The present invention encompasses any prodrug form of the compounds described herein. Although certain other exemplary prodrug moieties generated from the inventive compounds amino group are detailed herein, it will be appreciated that the present invention is not intended to be limited to these prodrug moieties; rather, a variety of additional prodrug moieties can be readily identified by a person skilled in the relevant art.

3) Pharmaceutical Compositions

As discussed above, the present invention provides compounds that are inhibitors of protein kinases (e.g., Aurora kinase), and thus the present compounds are useful for the treatment of diseases, disorders, and conditions including, but not limited to melanoma, leukemia, or cancers such as colon, breast, gastric, ovarian, cervical, renal, prostate, lymphoma, neuroblastoma, pancreatic and bladder cancer. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a Aurora kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; cyclodextrin-type compounds such as Captisol®; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

Research Uses

According to the present invention, the inventive compounds may be assayed in any of the available assays known in the art for identifying compounds having protease inhibitory activity. For example, the assay may be cellular or non-cellular, in vivo or in vitro, high- or low-throughput format, etc.

In certain exemplary embodiments, compounds of this invention were assayed for their ability to inhibit protein kinases, more specifically Aurora.

Thus, in one aspect, compounds of this invention which are of particular interest include those which:

are inhibitors of protein kinases;
exhibit the ability to inhibit Aurora kinase;
are useful for treating mammals (e.g., humans) or animals suffering from an Aurora-mediated disease or condition, and for helping to prevent or delay the onset of such a disease/condition;
exhibit a favorable therapeutic profile (e.g., safety, efficacy, and stability).

In certain embodiments, compounds of the invention are Aurora kinase inhibitors. In certain exemplary embodiments, inventive compounds are Aurora-A inhibitors. In certain exemplary embodiments, inventive compounds have $^{Cell}IC_{50}$ values $\leq 100$ µM. In certain other embodiments, inventive compounds have $^{Cell}IC_{50}$ values $\leq 75$ µM. In certain other embodiments, inventive compounds have $^{Cell}IC_{50}$ values $\leq 50$ µM. In certain other embodiments, inventive compounds have $^{Cell}IC_{50}$ values $\leq 25$ µM. In certain other embodiments, inventive compounds have $^{Cell}IC_{50}$ values $\leq 10$ µM. In certain other embodiments, inventive compounds have $^{Cell}IC_{50}$ values $\leq 7.5$ µM. In certain other embodiments, inventive compounds have $^{Cell}IC_{50}$ values $\leq 5$ µM. In certain other embodiments, inventive compounds have $^{Cell}IC_{50}$ values $\leq 2.5$ µM. In certain other embodiments, inventive compounds have $^{Cell}IC_{50}$ values $\leq 1$ µM. In certain other embodiments, inventive compounds have $^{Cell}IC_{50}$ values $\leq 800$ nM. In certain other embodiments, inventive compounds have $^{Cell}IC_{50}$ values $\leq 600$ nM. In certain other embodiments, inventive compounds have $^{Cell}IC_{50}$ values $\leq 500$ nM. In certain other embodiments, inventive compounds have $^{Cell}IC_{50}$ values $\leq 300$ nM. In certain other embodiments, inventive compounds have $^{Cell}IC_{50}$ values $\leq 200$ nM. In certain other embodiments, inventive compounds have $^{Cell}IC_{50}$ values $\leq 100$ nM.

In yet another aspect, a method for the treatment or lessening the severity of an Aurora-mediated disease or condition is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of an Aurora-mediated disease or condition. The compounds and compositions, according to the method of the present invention, may be administered using any amount and any route of administration effective for treating or lessening the severity of an Aurora-mediated disease or condition. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are Aurora kinase inhibitors, and thus, without wishing to be bound by any particular theory, the compounds and compositions are particularly useful for treating or lessening the severity of a disease, condition, or disorder where activation of Aurora kinase is implicated in the disease, condition, or disorder. When activation of Aurora kinase is implicated in a particular disease, condition, or disorder, the disease, condition, or disorder may also be referred to as "Aurora-mediated disease" or disease symptom. Accordingly, in another aspect, the present invention provides a method for treating or lessening the severity of a disease, condition, or disorder where activation of Aurora kinase is implicated in the disease state.

The activity of a compound utilized in this invention as an Aurora kinase inhibitor, may be assayed in vitro, in vivo or in a cell line. In vitro assays include assays that determine inhibition of either the phosphorylation activity or ATPase activity of activated Aurora A, B and/or C. Alternate in vitro assays quantitate the ability of the inhibitor to bind to Aurora A, B and/or C. Inhibitor binding may be measured by radiolabelling the inhibitor prior to binding, isolating the inhibitor/Aurora A, B and/or C, complex and determining the amount of radiolabel bound. Alternatively, inhibitor binding may be determined by running a competition experiment where new inhibitors are incubated with Aurora A, B and/or C bound to known radioligands.

The term "measurably inhibit", as used herein means a measurable change in Aurora A, B and/or C activity between a sample comprising said composition and a Aurora A, B and/or C kinase and an equivalent sample comprising Aurora A, B and/or C kinase in the absence of said composition.

The term "Aurora-mediated disease" or "Aurora-mediated condition", as used herein, means any disease or other deleterious condition in which Aurora is known to play a role. The terms "Aurora-mediated disease" or "Aurora-mediated condition" also mean those diseases or conditions that are alleviated by treatment with an Aurora inhibitor. Such conditions include, without limitation, colon, breast, stomach, and ovarian cancer. The term "Aurora-mediated disease", as used herein, means any disease or other deleterious condition or disease in which Aurora is known to play a role. Such diseases or conditions include, without limitation, cancers such as colon and breast cancer.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, other therapies, chemotherapeutic agents or other anti-proliferative agents may be combined with the compounds of this invention to treat proliferative diseases and cancer. Examples of therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe—See Appendix).

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat.

Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting Aurora A, B and/or C activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Aurora A, B and/or C kinase activity in a biological sample is useful for a variety of purposes that are known to one of skill in the art. Examples of such purposes include, but are not limited to, blood transfusion, organ-transplantation, biological specimen storage, and biological assays.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

Example 1

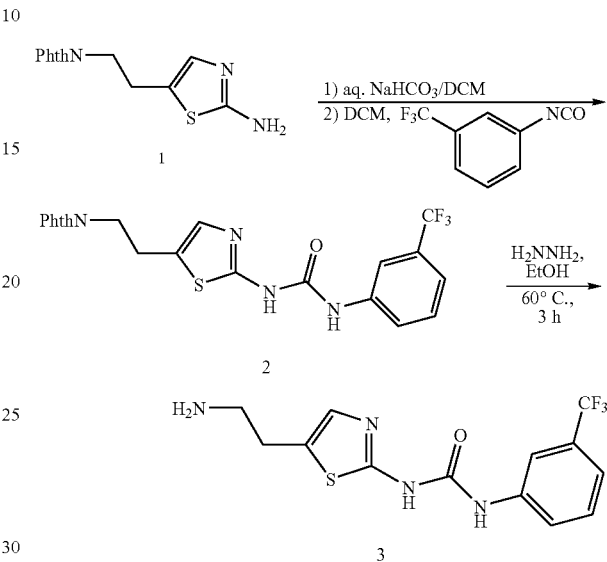

Compound 2: A mixture of 1 (15.5 g, 44.0 mmol, Eriks, J. C. et al. *J. Med. Chem.*, 1992, 3239.) in 250 mL aqueous sat. NaHCO₃ and 150 mL water was extracted three times with dichloromethane. The combined organic layers were dried (Na₂SO₄) and concentrated. The residue was dissolved in dichloromethane (500 mL) and carefully treated with 3-trifluoromethylphenyl isocyanate (6.1 mL, 44.3 mmol). After 3 h at room temperature, another 0.50 mL of the isocyanate was added. After 5 h, the resulting white precipitate was filtered off and washed with dichloromethane to afford 2, ES (+) MS m/e=461 (M+1).

Compound 3: The solid (2) obtained in the previous step was taken up in ethanol and treated with hydrazine (8.5 mL). The mixture was heated at 60° C. for 5 h. After cooling to ambient temperature, the mixture was filtered and concentrated to yield 12.4 g (61% for 2 steps) of a white solid 3, ES (+) MS m/e=331 (M+1).

Example 2

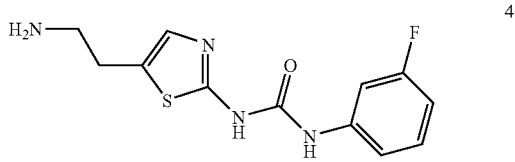

Compound 4: This compound was made according to procedures towards the synthesis of 2 and 3 except that 3-fluorophenyl isocyanate was used in place of 3-trifluoromethylphenyl isocyanate in the first step in preparation of 2.

Example 3

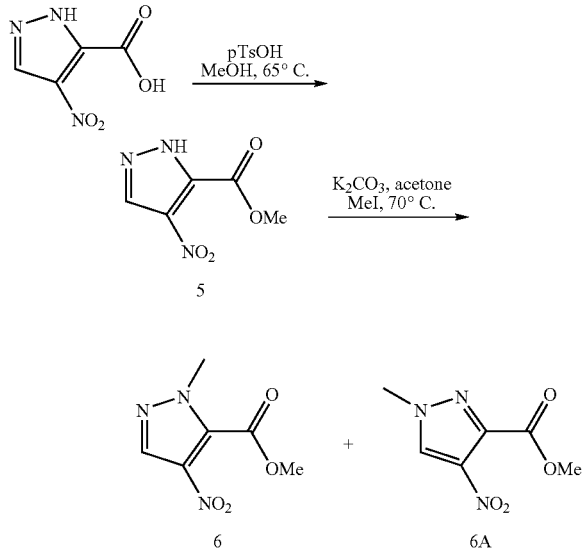

Compound 5: p-Toluene sulfonic acid monohydrate (0.3 g, 1.6 mmol) was added to a solution of 4-nitro-3-pyrazole carboxylic acid (5.0 g, 31.8 mmol) in 60 mL of methanol. The reaction mixture was heated and stirred overnight at 65° C. After the reaction mixture was cooled to room temperature, saturated sodium bicarbonate solution was added and the mixture was extracted with ethyl acetate (×3). The combined organics were washed with brine, dried (MgSO$_4$), and concentrated under reduced pressure to afford 5 (4.79 g, 88%) as white solid. $^1$H NMR (d6-DMSO) δ 3.85 (s, 3H) 8.81 (s, 1H); ES (+) MS m/e=172 (M+1).

Compound 6 and 6A: To a mixture containing 5 (3.1 g, 18.1 mmol) and potassium carbonate (5.0 g, 36.2 mmol) in 60 mL of acetone was added methyl iodide (2.2 mL, 36.2 mmol). The resulting solution was heated and stirred at 70° C. for 2 hours. After the reaction mixture was cooled to room temperature, water was added and the mixture was extracted with ethyl acetate (×3). The combined organics were washed with brine, dried (MgSO$_4$), and concentrated under reduced pressure. The crude residue was purified by column chromatography on silica gel using 20% ethyl acetate in hexanes as the eluent to afford 6 (1.1 g, 33%) as white solid. $^1$H NMR (d6-DMSO) δ 3.96 (s, 3H) 3.98 (s, 3H) 8.36 (s, 1H); ES (+) MS m/e=186 (M+1) and using 30% ethyl acetate in hexanes to afford 6A (2.2 g, 66%) as white solid. $^1$H NMR (d-CDCl$_3$) δ 3.98 (s, 3H) 4.00 (s, 3H) 8.13 (s, 1H); ES (+) MS m/e=186 (M+1).

Example 4

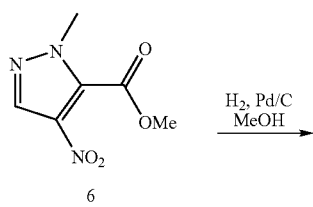

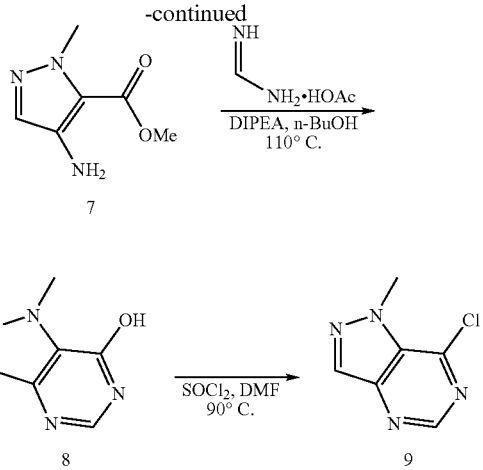

Compound 7: 10% wt. Pd/C (0.15 g, 0.14 mmol) was added to a solution containing 6 (0.26 g, 1.4 mmol) in 10 mL of methanol. The mixture was stirred under a hydrogen atmosphere at ambient temperature. After 3 hours, the reaction mixture was filtered thru a plug of Celite. The resulting filtrate was concentrated under reduced pressure to afford 7 (0.20 g, 91%), ES (+) MS m/e=156 (M+1).

Compound 8: To a solution of 7 (0.92 g, 5.9 mmol) in 5 mL of Hunig's base and 5 mL of n-butanol was added formamidine acetate (0.68 g, 6.5 mmol). The reaction mixture was heated and stirred at 110° C. for 1 hour. After cooling to room temperature, the white precipitate was collected by filtration and washed with diethyl ether. The resulting white precipitate was dried under reduced pressure to afford 8 (0.83 g, 94%). $^1$H NMR (d6-DMSO) δ 4.33 (s, 3H) 8.50 (s, 1H) 8.80 (s, 1H); ES (+) MS m/e=151 (M+1).

Compound 9: To a solution of 8 (0.835 g, 5.5 mmol) in 10 mL thionyl chloride was added 0.5 mL DMF. The resulting mixture was heated to 90° C. under nitrogen for 1 hour. After cooling to room temperature, the solvents were removed under reduced pressure. Water was added to the resulting residue and the mixture was extracted with dichloromethane (×3). The combined organics were dried (MgSO$_4$) and concentrated under reduced pressure to afford 9 (0.94 g, 100%), ES (+) MS m/e=169 (M+1).

Example 5

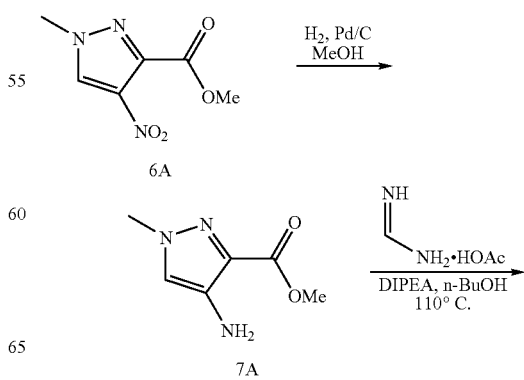

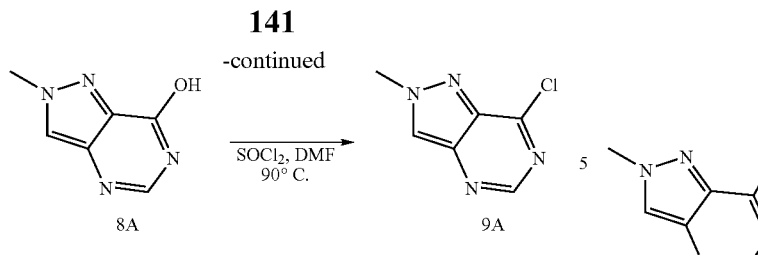

Compound 7A: This compound was made according to procedures towards the synthesis of 7, except that 6A was used in place of 6, ES (+) MS m/e=156 (M+1).

Compound 8A: This compound was made according to procedures towards the synthesis of 8, except that 7A was used in place of 7, ES (+) MS m/e=151 (M+1).

Compound 9A: This compound was made according to procedures towards the synthesis of 9, except that 8A was used in place of 8, ES (+) MS m/e=169 (M+1).

Example 6

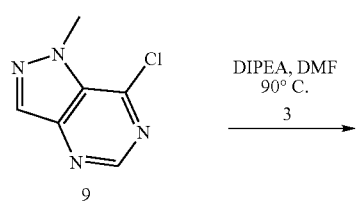

Compound 10: To a solution of 3 (0.33 g, 1.0 mmol) and Hunig's base (0.52 mL, 3.0 mmol) in 3 mL of DMF was added 9 (0.169 g, 1.0 mmol). The resulting mixture was heated and stirred at 90° C. for 1 hour. After the reaction was cooled to room temperature, water was added and washed with ethyl acetate (×3). The combined organics were washed with brine, dried (MgSO$_4$), and concentrated under reduced pressure. The crude residue was purified by prep RP-HPLC. The fractions containing pure compound were consolidated and concentrated. The residue thus obtained was lyophilized under high-vacuum to yield 10 (59 mg, 9%) as the bis TFA salt. $^1$H NMR (d6-DMSO) δ 3.10-3.13 (m, 2H) 3.90-3.92 (m, 2H) 4.33 (s, 3H) 7.19 (s, 1H) 7.36 (m, 1H) 7.51-7.55 (m, 1H) 7.62-7.64 (m, 1H) 8.01 (s, 1H) 8.16 (s, 1H) 8.72 (s, 1H) 9.02 (bs, 1H) 9.57 (s, 1H); ES (+) MS m/e=463 (M+1).

Example 7

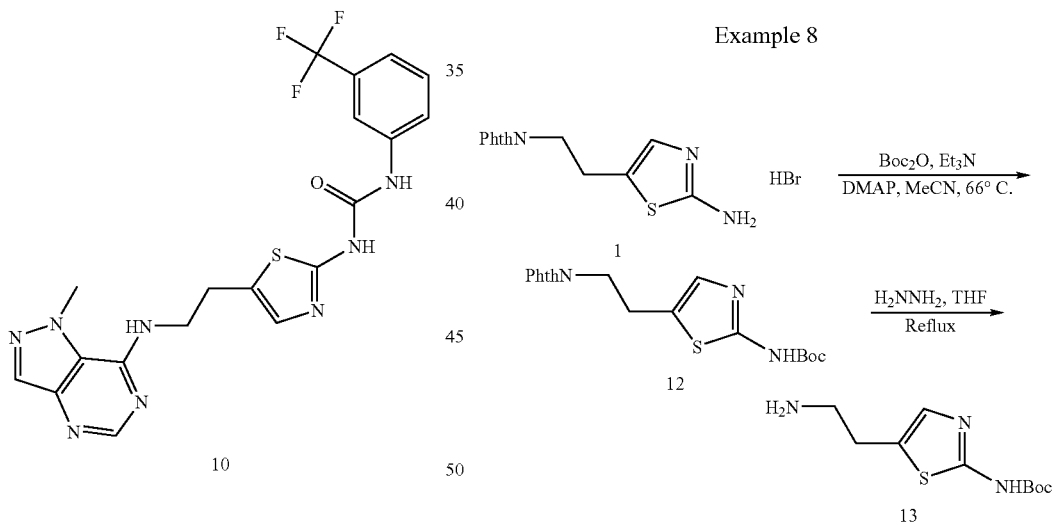

Compound 11: This compound was made according to procedures towards the synthesis of 10, except that 9A was used in place of 9, ES (+) MS m/e=463 (M+1).

Example 8

Compound 12: 1 (60 g, 170 mmol) was slurried in 190 ml acetonitrile. DMAP (0.05 eq, 1 g) and Et$_3$N (1.1 eq, 26 ml) were added, turning the reaction yellow, forming more precipitate and raising the reaction temperature to 31° C. Boc$_2$O (1.2 eq, 44 g) was added and the reaction heated to reflux at 66° C. As the temperature rose, the thick reaction mixture became easier to stir. After 45 min, the yellow color had disappeared and the reaction was done by TLC (50/50 EtOAc/hexane.) The reaction was cooled to 0° C., the solid collected via filtration and washed with cold ACN. The solid was then slurried with water, collected via filtration. Drying in vacuo gave 55 g white solid (86% yield.).

Compound 13: 12 (40 g, 107 mmol) were slurried in 500 ml THF and heated to reflux, dissolving almost all of the phthalimide. Anhydrous hydrazine (2 eq., 6.7 ml) was added and the reaction stirred 2 hr at which time TLC (50/50 EtOAc/hexane) showed the reaction to be ~75% complete. 1 eq. hydrazine was added and after 1 more hr at reflux the reaction was complete by TLC. The reaction was cooled to 40° C. and the white precipitate was filtered off and washed with 200 ml THF. The filtrate was concentrated in vacuo to ~200 ml at which time a little white solid forms. The mixture was diluted with 200 ml hexane, giving a milky solution, and let stand overnight. The solid was removed via filtration (4 g of 1:1 product:phthalic hydrazide) and the filtrate concentrated in vacuo to give 23 g white solid (88% yield.).

Example 9

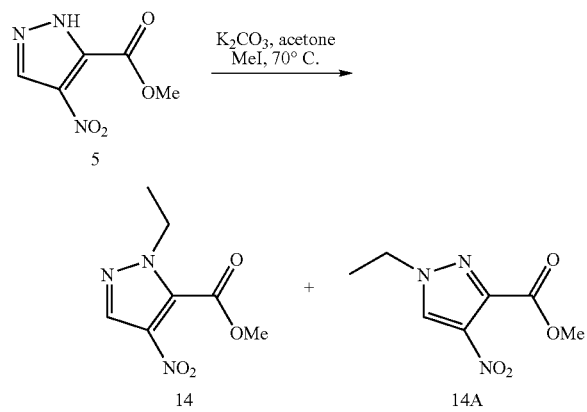

Compound 14 and 14A: To a mixture of 5 (1.9 g, 11.1 mmol) and potassium carbonate (3.07 g, 22.2 mmol) in 100 mL of acetone was added iodoethane (3.46 g, 22.2 mmol). The reaction was heated and stirred for 2 hours at 70° C. After cooling to room temperature, the mixture was diluted with water extracted with ethyl acetate (×2). The combined organics were washed with brine, dried with MgSO$_4$, filtered, and concentrated. The resulting residue was purified by silica gel column chromatography using 20% ethyl acetate in hexanes to afford 14 (0.65 g, 29%). $^1$H NMR (d6-DMSO) δ 1.37 (t, 3H, J=7.3 Hz) 3.97 (s, 3H) 4.28 (q, 2H, J=7.3 Hz) 8.39 (s, 1H); ES (+) MS m/e=200 (M+1) and using 30% ethyl acetate in hexanes to afford 14A (1.3 g, 58%). $^1$H NMR (d6-DMSO) δ 1.40 (t, 3H, J=7.3 Hz) 3.87 (s, 3H) 4.22 (q, 2H, J=7.3 Hz) 9.00 (s, 1H); ES (+) MS m/e=200 (M+1)

Example 10

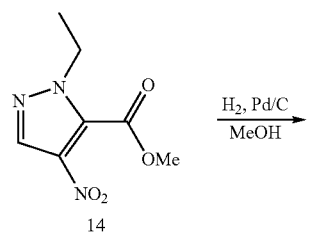

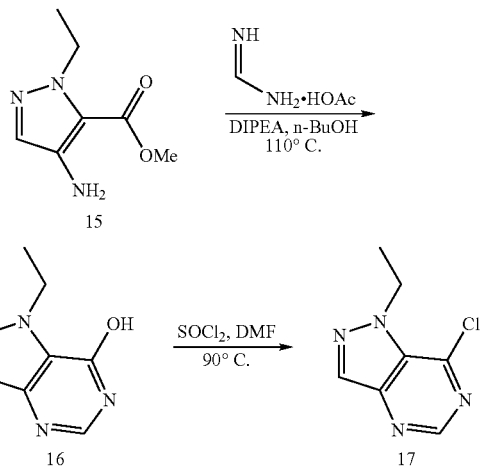

Compound 15: 10% wt. Pd/C (0.35 g, 0.33 mmol) was added to a solution containing 14 (0.65 g, 3.3 mmol) in 30 mL of methanol. Atmospheric hydrogen pressure was introduced via balloon. After stirring for 3 hours, the reaction mixture was filtered thru a plug of Celite. The resulting filtrate was concentrated under reduced pressure to afford 15 (0.55 g, 100%), ES (+) MS m/e=170 (M+1).

Compound 16: Formamidine acetate (0.37 g, 3.6 mmol) was added to a solution of 15 (0.55 g, 3.3 mmol) in 5 mL of Hunig's base and 5 mL of n-butanol. The reaction mixture was heated and stirred at 110° C. for 1 hour. After the reaction mixture was cooled, brine water was added and washed with ethyl acetate (×3). The combined organics were dried with MgSO$_4$, filtered, and concentrated to afford 16 (0.51 g, 97%). ES (+) MS m/e=165 (M+1).

Compound 17: 0.2 mL of DMF was added to a solution containing 16 (0.51 g, 3.1 mmol) in 6 mL of thionyl chloride. The reaction mixture was heated to 90° C. for 1 hour. After the reaction mixture was cooled to room temperature, the solvents were removed under reduced pressure. Water was added to the resulting residue and extracted with dichloromethane (×3). The combined organics were dried with MgSO$_4$, filtered and concentrated to afford 17 (0.57 g, 100%), ES (+) MS m/e=183 (M+1).

Example 11

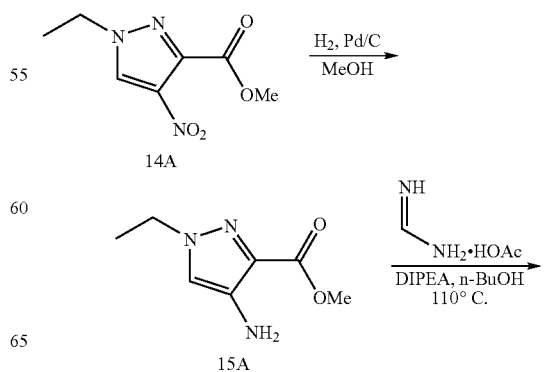

-continued

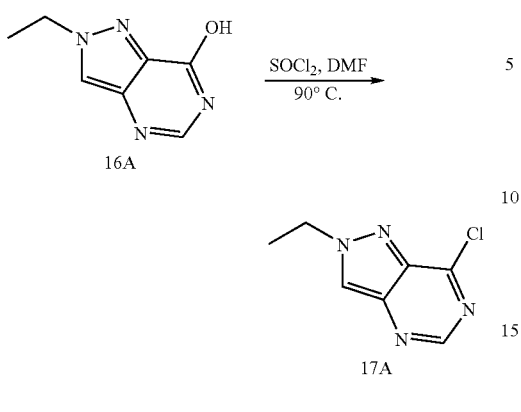

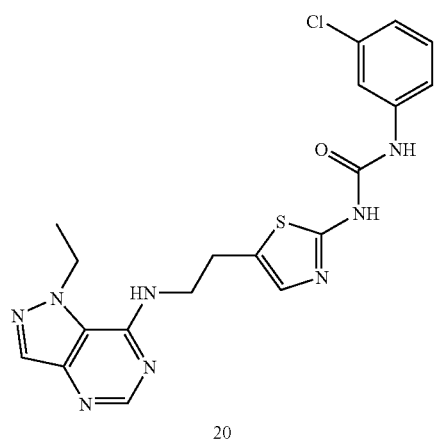

Compound 15A: This compound was made according to procedures towards the synthesis of 15, except that 14A was used in place of 14, ES (+) MS m/e=170 (M+1).

Compound 16A: This compound was made according to procedures towards the synthesis of 16, except that 15A was used in place of 15, ES (+) MS m/e=165 (M+1).

Compound 17A: This compound was made according to procedures towards the synthesis of 17, except that 16A was used in place of 16, ES (+) MS m/e=183 (M+1).

Example 12

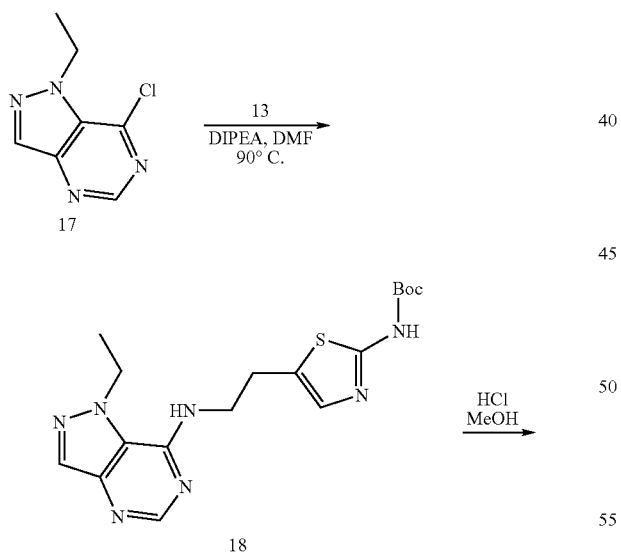

Compound 18: To a solution containing 13 (0.75 g, 3.1 mmol) and Hunig's base (1.6 mL, 9.3 mmol) in 3 mL of DMF was added 17 (0.57 g, 3.1 mmol). The resulting mixture was heated and stirred at 90° C. for 1 hour. After cooling to room temperature, the mixture was diluted with water and extracted with ethyl acetate (×3). The combined organics were washed with brine, dried (MgSO$_4$), and concentrated under reduced pressure. The resulting residue was purified by silica gel column chromatography using 10% MeOH in DCM to afford 18 (0.726 g, 60%). ES (+) MS m/e=390 (M+1).

Compound 19: To a solution of 18 (0.73 g, 1.9 mmol) in 1 mL MeOH was added 5 mL of 4.0M HCl in dioxanes. The reaction mixture was stirred for 1 hour then concentrated under reduced pressure to afford 19 (0.74 g, 100%). ES (+) MS m/e=290 (M+1).

Compound 20: 3-chlorophenyl isocyanate (64 mgs, 0.42 mmol) was added to a solution containing 19 (80 mgs, 0.21 mmol) and triethylamine (0.14 mL, 1.0 mmol) in 3 mL of THF. The reaction mixture was stirred for 30 minutes, concentrated, and purified by prep RP-HPLC to afford 20. $^1$H NMR (d6-DMSO) δ 1.32-1.36 (t, 3H, J=6.8 Hz) 3.12-3.15 (m, 2H) 3.92-3.93 (m, 2H) 4.67-4.72 (q, 2H, J=7.4 Hz) 7.06 (bs, 1H) 7.15 (s, 1H) 7.30-7.32 (m, 1H) 7.70 (s, 1H) 8.21 (s, 1H) 8.74 (s, 1H) 8.91 (bs, 1H) 9.37 (s, 1H); ES (+) MS m/e=443 (M+1).

Example 13

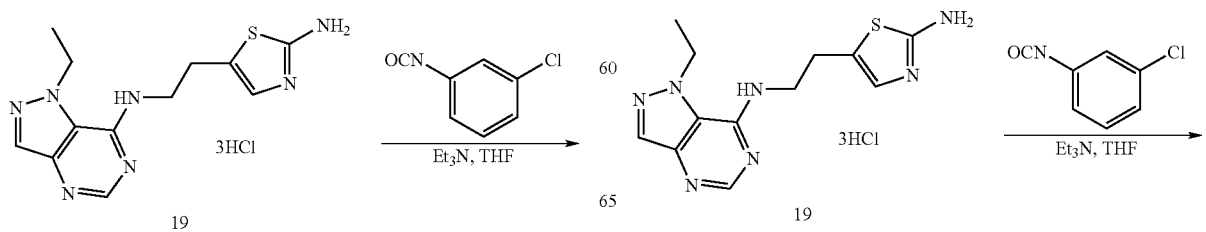

147
-continued

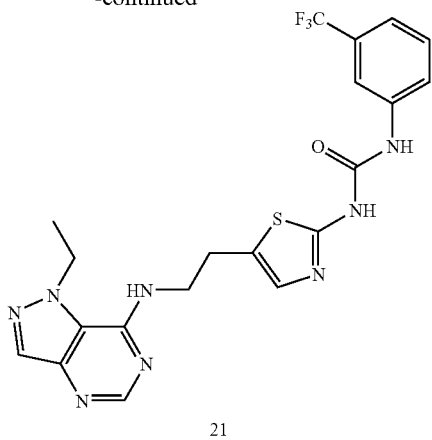

21

Compound 21: 3-trifluorophenyl isocyanate (77 mgs, 0.42 mmol) was added to a solution containing 19 (0.21 mmol, 80 mgs) and triethylamine (0.14 mL, 1.0 mmol) in 3 mL of THF. The reaction mixture was stirred for 30 minutes, concentrated, and purified by prep RP-HPLC to afford 21. $^1$H NMR (d6-DMSO) δ 1.32-1.35 (t, 3H, J=7.4 Hz) 3.12-3.15 (m, 2H) 3.92-3.93 (m, 2H) 4.67-4.72 (q, 2H, J=7.4 Hz) 7.16 (bs, 1H) 7.34-7.36 (m, 1H) 7.50-7.52 (m, 1H) 7.61-7.63 (m, 1H) 8.02 (s, 1H) 8.21 (s, 1H) 8.74 (s, 1H) 8.91 (bs, 1H) 9.55 (s, 1H); ES (+) MS m/e=477 (M+1).

Example 14

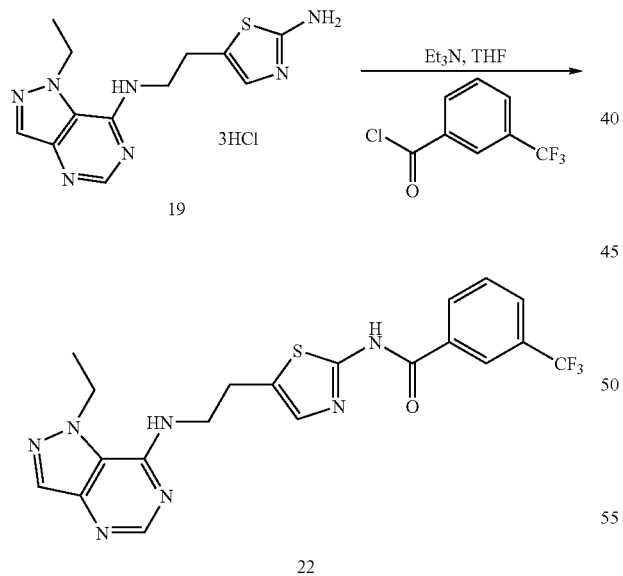

Compound 22: To a mixture of 19 (0.072 g, 0.18 mmol) and triethylamine (0.13 mL, 0.9 mmol) in 3 mL of THF was added 3-(trifluoromethyl)-benzoyl chloride (0.038 g, 0.18 mmol). After stirring for 0.5 h, the reaction was quenched with methanol and concentrated under reduced pressure to yield an oily residue. The crude was purified by prep RP-HPLC to afford 22. ES (+) MS m/e=462 (M+1).

148

Example 15

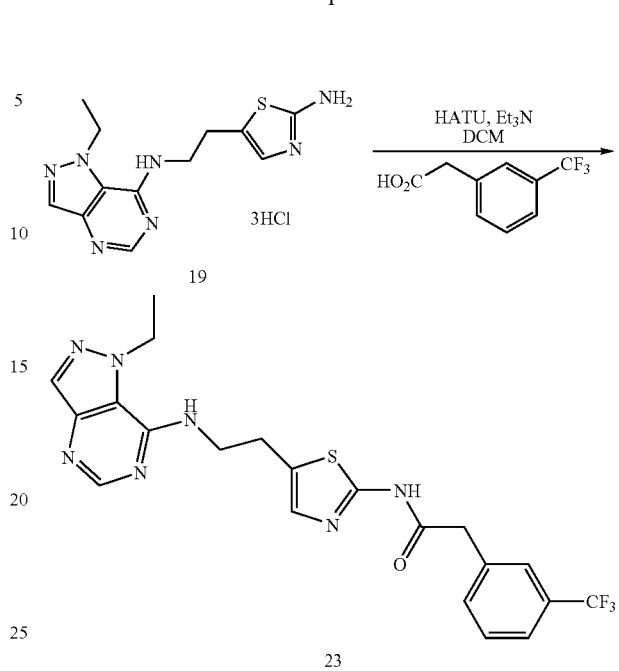

Compound 23: HATU (0.085 g, 0.22 mmol) was added to a solution containing trifluoro-m-tolyl acetic acid (0.046 g, 0.22 mmol), 19 (0.089 g, 0.22 mmol) and triethylamine (0.16 mL, 1.1 mmol) in 3 mL of DCM. The reaction mixture was stirred for 30 minutes and quenched with methanol. The reaction mixture was then concentrated under reduced pressure resulting in an oily residue. The crude was purified by prep HPLC to afford 23. ES (+) MS m/e=476 (M+1).

Example 16

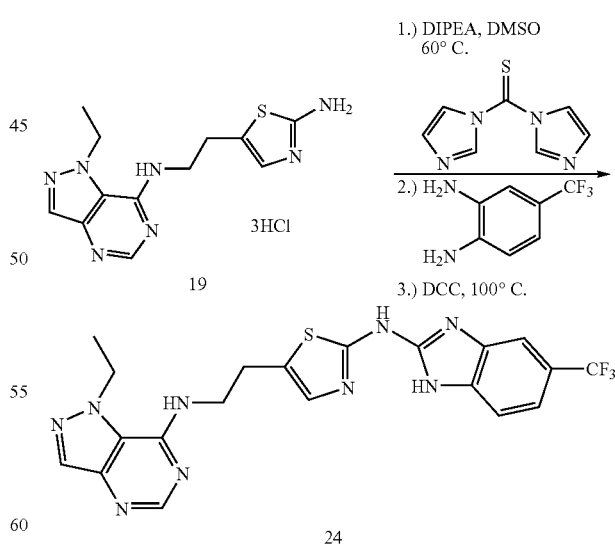

Compound 24: 1,1'-thiocarbonyldiimidazole (0.054 g, 0.3 mmol) was added to a solution containing 19 (0.12 g, 0.3 mmol) and Hunig's base (0.2 mL, 1.2 mmol) in 3 mL of DMSO. The reaction mixture was heated at 60° C. After 30 minutes, 4-(trifluoromethyl)-o-phenylenediamine (0.053 g, 0.3 mmol) was added. The reaction mixture continued to be stirred and heated at 60° C. overnight. DCC (0.062 g, 0.33 mmol) was added and the reaction was heated to 100° C. After 1 hour, the reaction mixture was cooled to room temperature. Water was added and the heterogeneous solution was stirred for 15 minutes. The dark brown precipitate was collected and purified by prep RP-HPLC to afford 24. ES (+) MS m/e=474 (M+1).

Example 17

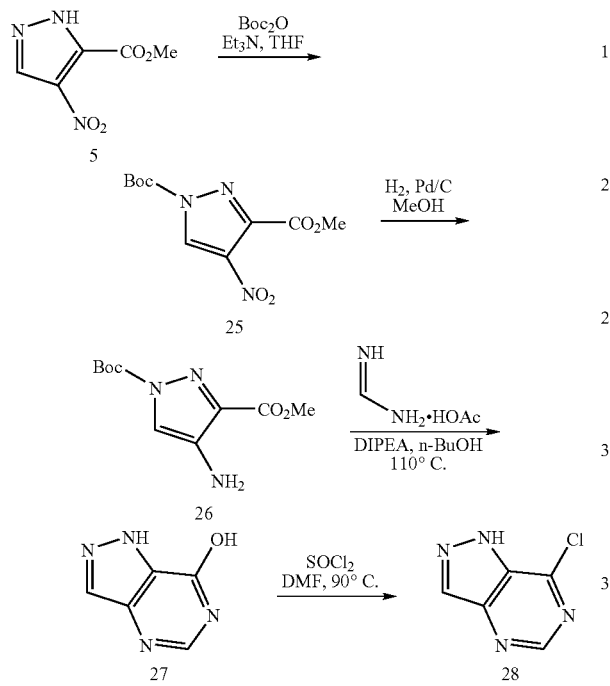

Compound 25: Boc$_2$O (12.75 g, 58.4 mmol) was added to a solution containing 5 (10.0 g, 58.4 mmol) and Et$_3$N (8.1 mL, 58.4 mmol) in THF (200 mL). The reaction mixture was stirred at room temperature for 1 hour and was then diluted with water. The aqueous layer was extracted with ethyl acetate. The combined organic phases were dried with MgSO$_4$, filtered and concentrated to afford 25 (14.7 g, 93%), ES(+) MS m/e=272 (M+1).

Compound 26: 10% wt Pd/C (2.88 g, 2.7 mmol) was added to a solution containing 25 (14.7 g, 54.2 mmol) in MeOH (200 mL). The reaction mixture was stirred under 1 atm H$_2$ pressure for 4 hours. The mixture was then filtered thru a plug of Celite and concentrated to afford 26 (11.1 g, 85%), ES (+) MS m/e=242 (M+1).

Compound 27: Formamidine acetate (40.3 mmol, 4.2 g) was added to a solution containing 26 (8.85 g, 36.7 mmol) in Hunig's base (40 mL) and n-BuOH (40 mL). The stirred solution was heated at 110° C. for 1 hour. After cooling to ambient temperature the resulting solid was collected, washed with dichloromethane, and dried under reduced pressure to afford 27 (4.46 g, 89%), ES (+) MS m/e=137.

Compound 28: DMF (1.05 mL) was added to a solution containing 27 (1.0 g, 7.3 mmol) in thionyl chloride (21 mL). Heated the stirring solution to 90° C. for 1 hour. Cooled the homogeneous reaction mixture to room temperature. Concentrated to remove volatiles and diluted the reaction mixture with EtOAc followed by ice. Extracted the aqueous layer with EtOAc. Combined the organics, washed with saturated NaHCO$_3$, dried with MgSO$_4$, filtered and concentrated to afford 28 (0.73 g, 64%), ES (+) MS m/e=155.

Example 18

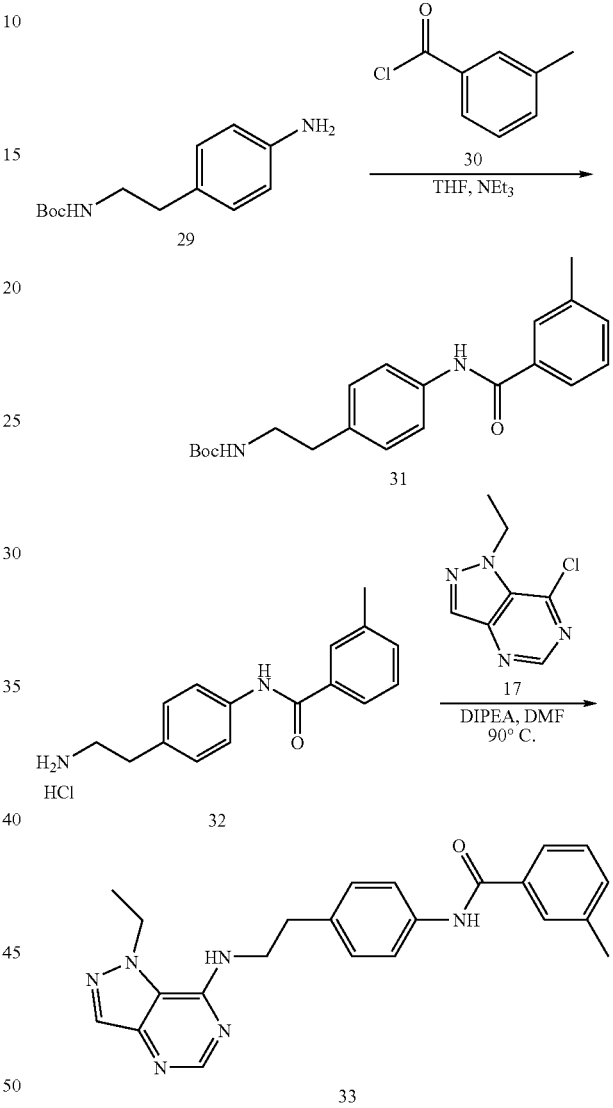

Compound 31: Add 30 (1.0 mmol) drop-wise to a solution of 29 (1.0 mmol) and NEt$_3$ (2.0 mmol) in THF 10.0 mL under nitrogen at 0° C. When the reaction is completed, dilute with ethyl acetate. Wash with 1.0 M HCl, aqueous sat. NaHCO$_3$, and brine. Dry with Na$_2$SO$_4$, concentrate, and purify by flash column chromatography to obtain 31.

Compound 32: Stir a mixture of 31 (0.5 mmol) in 4.0M HCl in dioxane. After completion, concentrate the mixture and dry the residue under high-vacuum to afford 32.

Compound 33: Add 17 (1.0 mmol) to a solution containing 32 (1.0 mmol), Hunig's base (2.0 mmol) in 10 mL of DMF. Heat the stirring solution to 90° C. for 1 hour. Cool the reaction mixture to room temperature and dilute with water. Extract the aqueous layer with ethyl acetate (×3). Combine organics, dry with MgSO₄, filter, and concentrate to obtain crude residue. Purify using prep. RP-HPLC to afford 33.

Example 19

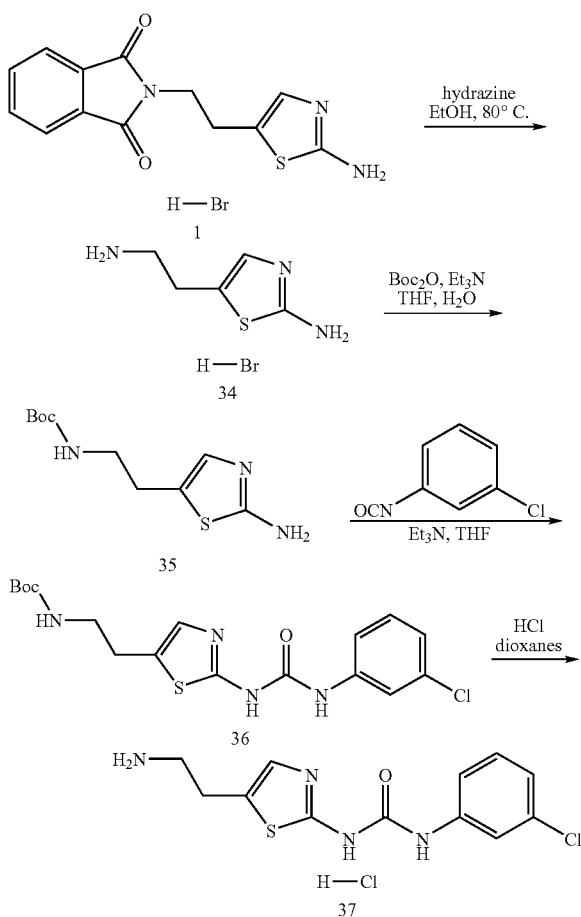

Compound 34: Hydrazine monohydrate (8.4 mL, 173.6 mmol) was added to a heterogeneous solution of 1 (15.37 g, 43.4 mmol, Eriks, J. C. et al. *J. Med. Chem.*, 1992, 3239.) in THF (150 mL) and EtOH (150 mL). The reaction mixture was stirred and heated to 80° C. for 5 hours. The reaction mixture was cooled to room temperature and filtered. The resulting white solid was washed with methanol. The filtrate was then concentrated to obtain 34 (9.72 g, 100%) as a white solid, ES (+) MS m/e=144 (M+1).

Compound 35: Boc₂O (10.4 g, 47.7 mmol) was added to a solution of 34 (9.72 g, 43.4 mmol) in Et₃N (12.1 mL, 86.7 mmol), THF (220 mL) and H₂O (20 mL). The reaction mixture was stirred for 1 hour and was then diluted with water/EtOAc (1:1, 600 mL). The layers were separated and the aqueous layer was extracted with EtOAc (150 mL×2). The combined organic phases were dried (MgSO₄) and concentrated under reduced pressure to afford 35 (10.55 g, 100%) as a white solid, ES (+) MS m/e=244 (M+1).

Compound 36: 3-Chlorophenyl isocyanate (5.2 mL, 43.3 mmol) was added to a solution of 35 (10.55 g, 43.3 mmol), Et₃N (12.7 mL, 91.0 mmol), and THF (220 mL). The reaction mixture was stirred for 3 hours and concentrated under reduced pressure. The resulting solid was triturated with 1:1 DCM:hexanes to afford 36 (16 g, 93%) as a white solid, ES (+) MS m/e=397 (M+1).

Compound 37: HCl (50 mL, 4M in dioxanes) was added to a solution of 36 (16 g, 40.3 mmol) in MeOH (200 mL). The reaction mixture was stirred for 1 hour and concentrated to afford 37 (13.43 g, 100%) as a white solid, ES (+) MS m/e=297 (M+1).

Example 20

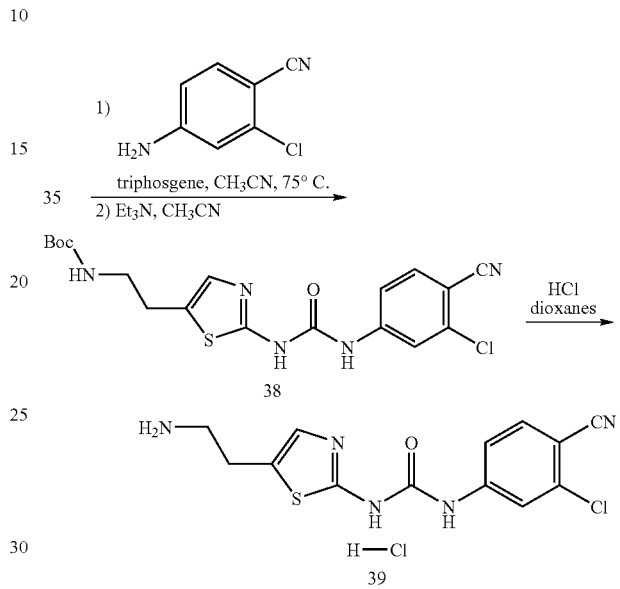

Compound 38: Triphosgene (0.48 g, 1.61 mmol) was added to a solution of 4-amino-2-chlorobenzonitrile (0.62 g, 4.1 mmol) in CH₃CN (10 mL). The reaction mixture was heated to 75° C. for 1.5 hours and then slowly cooled to room temperature. A solution containing 35 (0.99 g, 4.1 mmol), Et₃N (2.2 mL, 16.3 mmol) and CH₃CN (10 mL) was added and stirred for 15 minutes. The reaction mixture was diluted with H₂O and extracted with EtOAc. The combined organics were dried with MgSO₄, filtered, concentrated and purified by column chromatography on silica gel using 20% MeOH in DCM to afford 6 (0.43 g, 30%).

Compound 39: HCl (2 mL, 4M in dioxanes) was added to a solution of 38 (0.43 g, 1.0 mmol) in MeOH (5 mL). The reaction mixture was stirred for 1 hour and concentrated to afford 39 (0.37 g, 100%) as a white solid, ES (+) MS m/e=322 (M+1).

Example 21

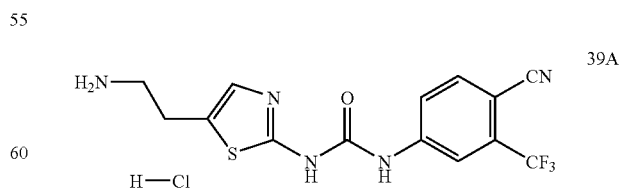

Compound 39A: This compound was made according to procedures towards the synthesis of 38 and 39 except that 4-amino-2-trifluoromethylbenzonitrile was used in place of 4-amino-2-chlorobenzonitrile, ES (+) MS m/e=356 (M+1).

Example 22

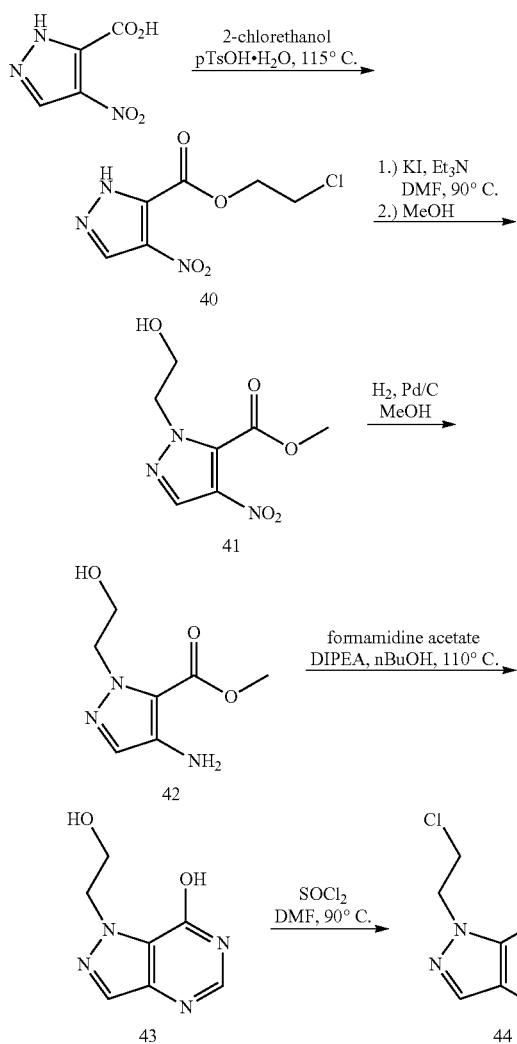

Compound 40: pTsOH monohydrate (1.2 g, 6.4 mmol) was added to a solution containing 4-nitro-3-pyrazole carboxylic acid (10 g, 63.7 mmol) in 2-chloroethanol (64 mL). The reaction mixture was heated to 115° C. for 2 hours and cooled to room temperature. The bulk solvent was removed under reduced pressure. The residue was diluted with EtOAc and aqueous saturated NaHCO$_3$. The layers were separated and the aqueous phase was extracted with EtOAc. The combined organic layers were dried (MgSO$_4$), filtered, and concentrated to afford 40 (14 g, 100%), ES (+) MS m/e=220 (M+1).

Compound 41: Et$_3$N (18 mL, 127.5 mmol) was added to a solution of 40 (14 g, 63.8 mmol) and KI (1.0 g, 6.4 mmol) in DMF (200 mL). The reaction mixture was heated to 90° C. and stirred for 16 hours. Methanol (100 mL) was added and stirred at 90° C. for 1 hour. The reaction mixture was cooled to room temperature. Excess methanol was removed under reduced pressure. The reaction mixture was diluted with H$_2$O. The aqueous layer was extracted with EtOAc, the combined organics were dried with MgSO$_4$, filtered, and concentrated. The crude residue was purified by column chromatography on silica gel using 50% EtOAc in hexanes to afford 41 (6.08 g, 44%), ES (+) MS m/e=216 (M+1).

Compound 42: 41 (6.0 g, 27.9 mmol) was placed in a flask containing 10% wt Pd/C (1.48 g, 1.4 mmol) in MeOH (100 mL) with 1 atm H$_2$, via balloon. After stirring overnight, the reaction mixture was filtered thru a plug of Celite and concentrated to afford 42 (5.16 g, 100%), ES (+) MS m/e=186 (M+1).

Compound 43: Formamidine acetate (3.34 g, 30.7 mmol) was added to a solution containing 42 (5.16 g, 27.9 mmol), Hunig's base (30 mL) and n-butanol (30 mL). The reaction mixture was heated to 110° C. for 1 hour. The reaction mixture was cooled to room temperature. Et$_2$O (30 mL) was added and the resulting solid was collected, washed with Et$_2$O, and dried under vacuum to afford 43 (4.3 g, 85%), ES (+) MS m/e=181 (M+1).

Compound 44: DMF (8 mL) was added to a solution containing 43 (4.32 g, 24.0 mmol) in SOCl$_2$ (80 mL). The heterogeneous reaction mixture was heated to 90° C. for 30 minutes and the homogeneous solution was cooled to room temperature. The solvents were removed under reduced pressure. The resulting residue was diluted with EtOAc, followed by ice. The layers were separated and the aqueous layer was extracted with EtOAc. The combined organics were washed with saturated NaHCO$_3$, followed by brine. The resulting organics were dried with MgSO$_4$, filtered, and concentrated to afford 44 (3.02 g, 58%), ES (+) MS m/e=218 (M+1).

Example 23

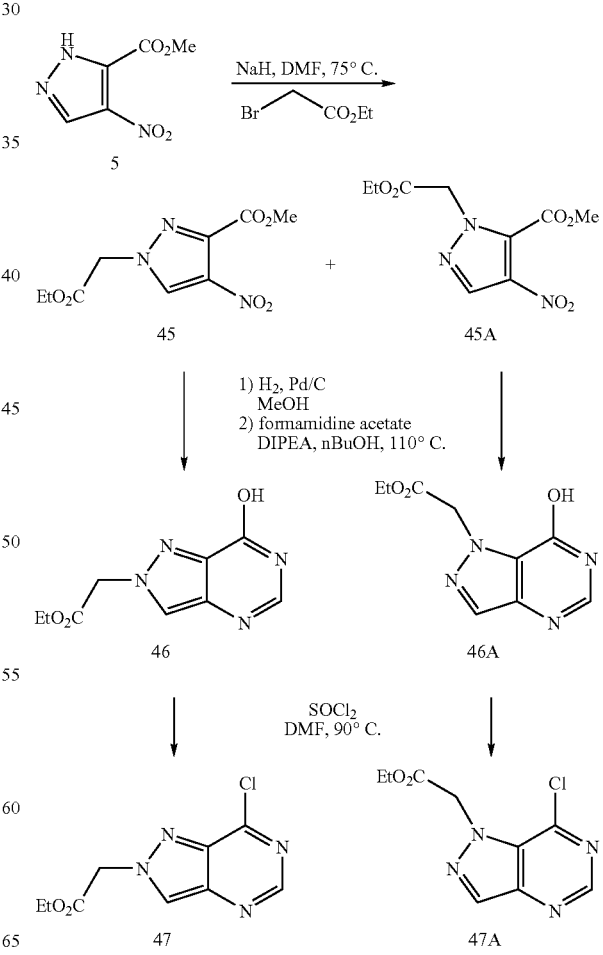

Compound 45 and 45A: Ethyl bromoacetate (3.9 mL, 35.0 mmol) was added to a preheated solution of 5 (4.0 g, 23.4 mmol) and 60% wt of NaH (1.4 g, 35.0 mmol) in DMF (50 mL) at 75° C. The reaction mixture was stirred for 30 minutes and then cooled to room temperature. The reaction mixture was diluted with H$_2$O. The layers were separated and the aqueous layer was extracted with EtOAc. The combined organics were dried (MgSO$_4$) and concentrated. The residue was purified by column chromatography on silica gel using 20% EtOAc in hexanes to afford 45A (0.79 g, 13%), ES (+) MS m/e=258 (M+1) and using 30% EtOAc in hexanes to afford 45 (3.3 g, 55%), ES (+) MS m/e=258 (M+1).

Compound 46: 45 (6.12 g, 23.8 mmol) was placed in a flask containing 10% wt Pd/C (1.27 g, 1.2 mmol) in MeOH (30 mL) with 1 atm H$_2$, via balloon. The reaction was stirred overnight. Filtered thru a plug of Celite and concentrated to afford oily residue. The residue was diluted with n-butanol (50 mL) followed by Hunig's base (50 mL). Formamidine acetate (2.72 g, 26.2 mmol) was added and the reaction was heated to 110° C. for 1 hour. The reaction was cooled to room temperature and concentrated to remove solvents. The resulting residue was diluted with H$_2$O. The aqueous layer was extracted with EtOAc. The combined organics were dried with MgSO$_4$, filtered, and concentrated to afford 46 (3.86 g, 73%), ES (+) MS m/e=223 (M+1).

Compound 46A: 45A (0.79 g, 3.1 mmol) was placed in a flask containing 10% wt Pd/C (0.32 g, 0.3 mmol) in MeOH (30 mL) with 1 atm H$_2$, via balloon. The reaction was stirred overnight. Filtered thru a plug of Celite and concentrated to afford oily residue. The residue was diluted with n-butanol (6 mL) followed by Hunig's base (6 mL). Formamidine acetate (0.33 g, 3.1 mmol) was added and the reaction was heated to 110° C. for 1 hour. The reaction was cooled to room temperature and concentrated to remove solvents. The resulting residue was diluted with H$_2$O. The aqueous layer was extracted with EtOAc. The combined organics were dried with MgSO$_4$, filtered, and concentrated to afford 46A (0.63 g, 95%), ES (+) MS m/e=223 (M+1).

Compound 47: DMF (2.5 mL) was added to a solution containing 46 (1.69 g, 7.6 mmol) in SOCl$_2$ (25 mL). The heterogeneous reaction mixture was heated to 90° C. for 30 minutes and the homogeneous solution was cooled to room temperature. The solvents were removed under reduced pressure. The resulting residue was diluted with EtOAc, followed by ice. The layers were separated and the aqueous layer was extracted with EtOAc. The combined organics were washed with saturated NaHCO$_3$, followed by brine. The resulting organics were dried with MgSO$_4$, filtered, and concentrated to afford 47 (1.56 g, 92%), ES (+) MS m/e=241 (M+1).

Compound 47A: DMF (1.0 mL) was added to a solution containing 46A (0.63 g, 2.8 mmol) in SOCl$_2$ (10 mL). The heterogeneous reaction mixture was heated to 90° C. for 30 minutes and the homogeneous solution was cooled to room temperature. The solvents were removed under reduced pressure. The resulting residue was diluted with EtOAc, followed by ice. The layers were separated and the aqueous layer was extracted with EtOAc. The combined organics were washed with saturated NaHCO$_3$, followed by brine. The resulting organics were dried with MgSO$_4$, filtered, and concentrated to afford The resulting organics were dried with MgSO$_4$, filtered, and concentrated to afford 18 (0.52 g, 76%), ES (+) MS m/e=241 (M+1).

Example 24

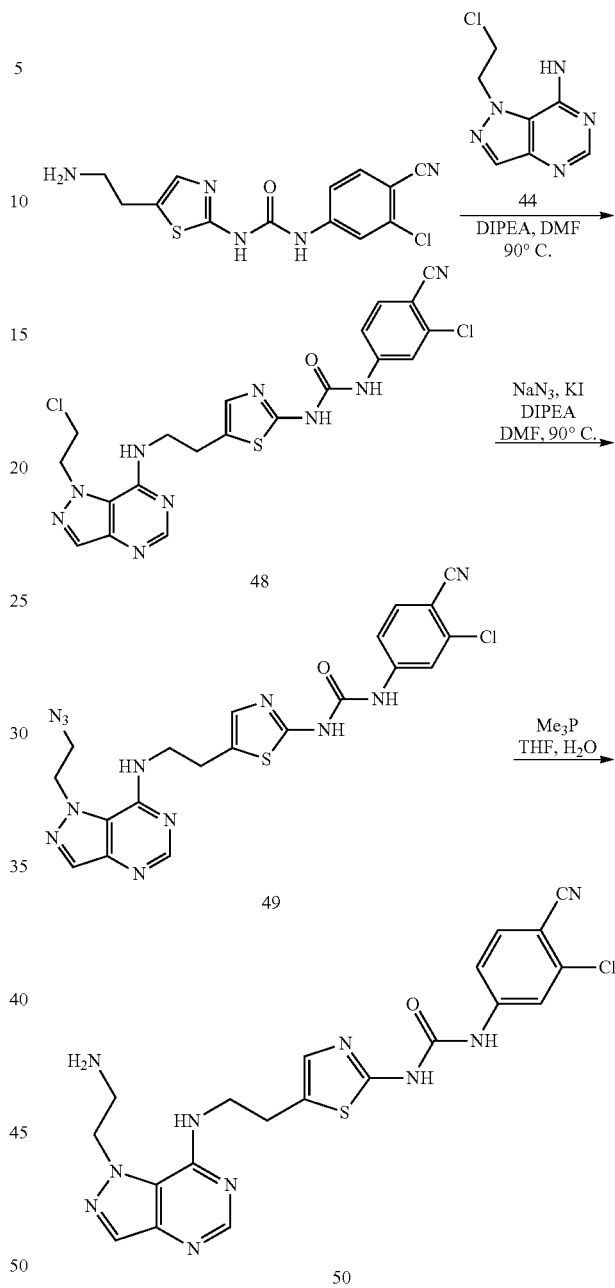

Compound 48: 39 (3.07 g, 8.6 mmol) was added to a solution containing 44 (1.86 g, 8.6 mmol) and Hunig's base (5.9 mL, 34.3 mmol) in DMF (30 mL). The reaction mixture was heated to 90° C. and stirred for 1 hour. The reaction was cooled to room temperature. The reaction was diluted with H$_2$O and extracted aqueous layer with EtOAc. The combined organics were dried with MgSO$_4$, filtered, and concentrated. Purification on silica gel using 10% MeOH in DCM afforded 48 (1.78 g, 41%), ES (+) MS m/e=503 (M+1).

Compound 49: Sodium azide (0.15 g, 2.4 mmol) was added to a solution containing 48 (0.6 g, 1.2 mmol), KI (0.02 g, 0.1 mmol), and Hunig's base (0.64 mL, 3.6 mmol) in DMF (5 mL). The reaction mixture was heated to 90° C. and stirred for 1 hour. The reaction mixture was cooled to room temperature. The reaction was diluted with H$_2$O and extracted aqueous layer with EtOAc. The combined organics were dried with MgSO₄, filtered, and concentrated. Purification on silica gel using 10% MeOH in DCM afforded 49 (0.33 g, 54%), ES (+) MS m/e=510 (M+1).

Compound 50: Trimethylphosphine (1.3 mL, 1.0M in THF) was added to a solution containing 49 (0.33 g, 0.6 mmol) in THF (5 mL) and H₂O (0.5 mL). The reaction mixture was stirred overnight. The reaction mixture was concentrated and triturated with DCM and hexanes to afford 50 (0.31 g, 100%), ES (+) MS m/e=484 (M+1).

Example 25

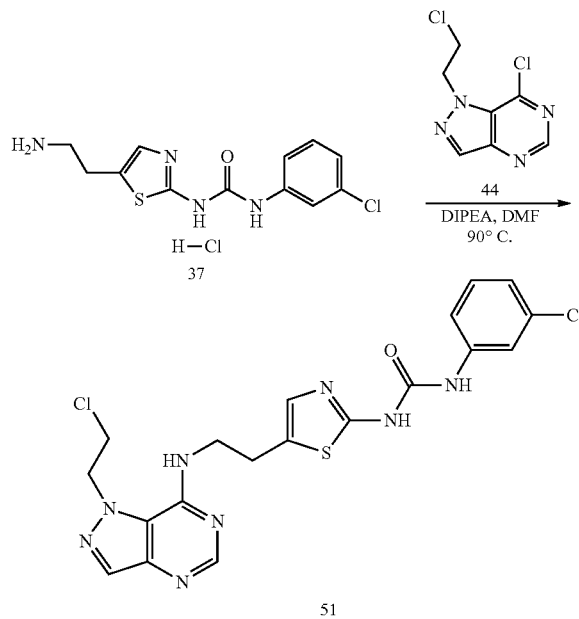

Compound 51: 37 (0.35 g, 1.6 mmol) was added to a solution containing 44 (0.54 g, 1.6 mmol) and Hunig's base (1.1 mL, 6.4 mmol) in DMF (16 mL). The reaction mixture was heated to 90° C. and stirred for 1 hour. The reaction was cooled to room temperature. The reaction was diluted with H₂O and extracted aqueous layer with EtOAc. The combined organics were dried with MgSO₄, filtered, and concentrated. Purification on silica gel using 10% MeOH in DCM afforded 51 (0.41 g, 54%), ES (+) MS m/e=478 (M+1).

Example 26

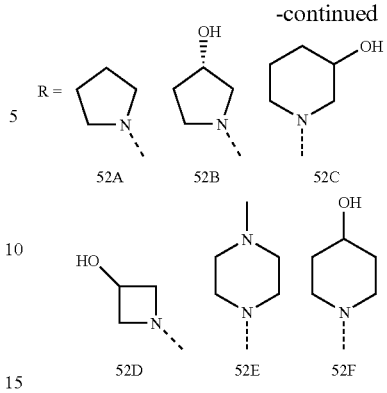

Compound 52A: Pyrrolidine (16 mgs, 0.02 mmol) was added to a solution containing 51 (55 mgs, 0.01 mmol), Hunig's base (0.05 mL, 0.3 mmol), and KI (2 mgs) in DMF (3 mL). The reaction mixture was heated to 90° C. overnight. The reaction mixture was cooled to room temperature. The solvent was removed under reduced pressure. The crude residue was purified by prep RP-HPLC. The fractions containing pure compound were consolidated and concentrated. The residue thus obtained was lyophilized under high-vacuum to yield 52A as the tris TFA salt, ES (+) MS m/e=513 (M+1).

Compound 52B: This compound was made according to procedures towards the synthesis of 52A except that S(+)-3-pyrrolidinol was used in place of pyrrolidine, ES (+) MS m/e=528 (M+1).

Compound 52C: This compound was made according to procedures towards the synthesis of 52A except that 3-hydroxypiperidine was used in place of pyrrolidine, ES (+) MS m/e=542 (M+1).

Compound 52D: This compound was made according to procedures towards the synthesis of 52A except that 3-hydroxyazetidine was used in place of pyrrolidine, ES (+) MS m/e=514 (M+1).

Compound 52E: This compound was made according to procedures towards the synthesis of 52A except that 4-methylpiperazine was used in place of pyrrolidine, ES (+) MS m/e=541 (M+1).

Compound 52F: This compound was made according to procedures towards the synthesis of 52A except that 4-hydroxypiperidine was used in place of pyrrolidine, ES (+) MS m/e=542 (M+1).

Example 27

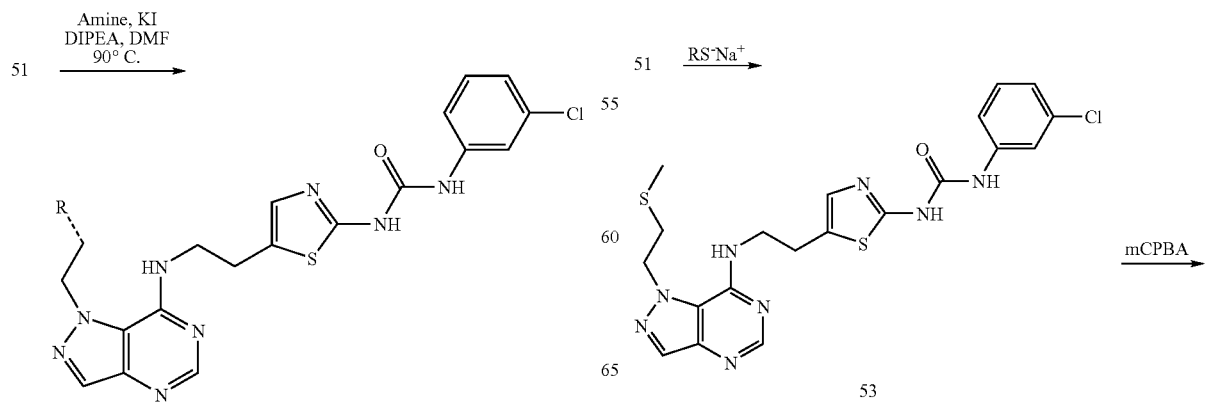

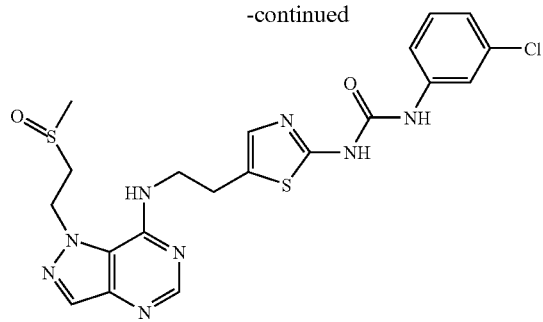

54A

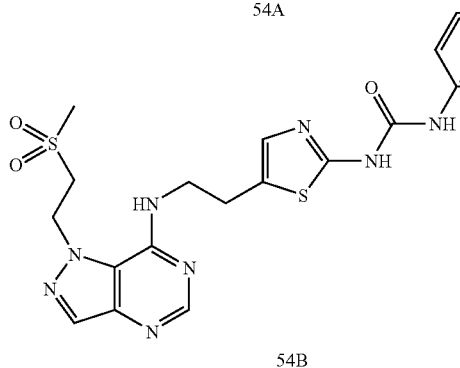

54B

Compound 53: Sodium thiomethoxide (57 mgs, 0.81 mmol) was added to a solution containing 51 (0.31 g, 0.65 mmol) in DMF (3 mL). The reaction mixture was stirred for 30 minutes. The solvent was removed under reduced pressure and purified by column chromatography on silica gel using 10% MeOH in DCM to afford 53 (0.21 g, 66%), ES (+) MS m/e=489 (M+1).

Compound 54A and 54B: 77% wt of mCPBA (0.13 g, 0.74 mmol) was added to a solution containing 51 (0.26 g, 0.53 mmol) in DCM. The reaction mixture was stirred overnight. Diluted reaction mixture with saturated NaHCO₃ and extracted aqueous layer with EtOAc. The combined organics were dried, filtered, and concentrated. The crude residue was purified by prep RP-HPLC. The fractions containing pure compounds were consolidated and concentrated. The residue thus obtained was lyophilized under high-vacuum to yield 54A as the bis TFA salt, ES (+) MS m/e=505 (M+1) and 54B as the bis TFA salt, ES (+) MS m/e=521 (M+1).

Example 28

48 →(Amine, KI, DIPEA, DMF, 90° C.)

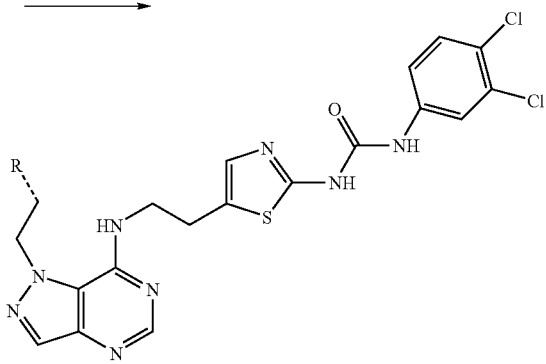

+

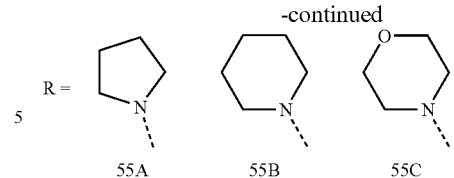

Compound 55A: Pyrrolidine (0.033 mL, 0.4 mmol) was added to a solution containing 48 (0.1 g, 0.2 mmol), Hunig's base (0.1 mL, 0.6 mmol) and KI (3 mgs) in DMF (3 mL). The reaction mixture was heated to 90° C. overnight. The reaction mixture was cooled to room temperature. The solvent was removed under reduced pressure. The crude residue was purified by prep RP-HPLC. The fractions containing pure compound were consolidated and concentrated. The residue thus obtained was lyophilized under high-vacuum to yield 55A as the tris TFA salt, ES (+) MS m/e=538 (M+1).

Compound 55B: Piperidine (0.04 mL, 0.4 mmol) was added to a solution containing 48 (0.1 g, 0.2 mmol), Hunig's base (0.1 mL, 0.6 mmol) and KI (3 mgs) in DMF (3 mL). The reaction mixture was heated to 90° C. overnight. The reaction mixture was cooled to room temperature. The solvent was removed under reduced pressure. The crude residue was purified by prep RP-HPLC. The fractions containing pure compound were consolidated and concentrated. The residue thus obtained was lyophilized under high-vacuum to yield 55B as the tris TFA salt, ES (+) MS m/e=552 (M+1).

Compound 55C: Morpholine (0.035 mL, 0.4 mmol) was added to a solution containing 48 (0.1 g, 0.2 mmol), Hunig's base (0.1 mL, 0.6 mmol) and KI (3 mgs) in DMF (3 mL). The reaction mixture was heated to 90° C. overnight. The reaction mixture was cooled to room temperature. The solvent was removed under reduced pressure. The crude residue was purified by prep RP-HPLC. The fractions containing pure compound were consolidated and concentrated. The residue thus obtained was lyophilized under high-vacuum to yield 55C as the tris TFA salt, ES (+) MS m/e=554 (M+1).

Example 29

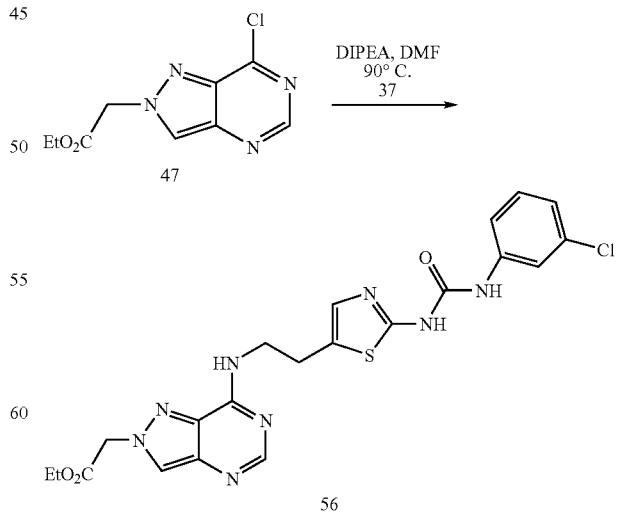

Compound 56: 37 (1.44 g, 4.2 mmol) was added to a solution containing 47 (1.04 g, 4.2 mmol) and Hunig's base (2.2 mL, 13.0 mmol) in DMF (10 mL). The reaction mixture was heated to 90° C. for 1 hour. The reaction was cooled to room temperature. The reaction mixture was diluted with water and extracted three times with EtOAc. The combined organics were dried (MgSO$_4$) and concentrated. The crude residue was purified by column chromatography on silica gel using 10% MeOH in DCM to afford 56 (1.0 g, 46%), ES (+) MS m/e=502 (M+1).

Example 30

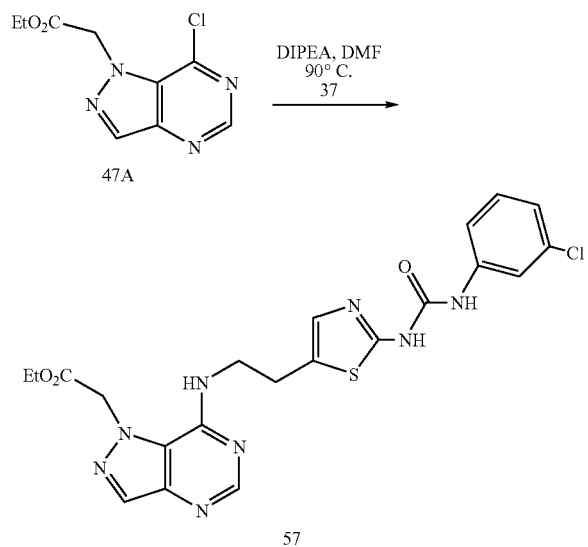

Compound 57: 37 (0.72 g, 2.1 mmol) was added to a solution containing 47A (0.52 g, 2.1 mmol) and Hunig's base (1.1 mL, 6.5 mmol) in DMF (3 mL). The reaction mixture was heated to 90° C. for 1 hour. The reaction was cooled to room temperature. The reaction mixture was diluted with water and extracted three times with EtOAc. The combined organics were dried (MgSO$_4$) and concentrated. The crude residue was purified by column chromatography on silica gel using 10% MeOH in DCM to afford 57 (0.3 g, 28%), ES (+) MS m/e=502 (M+1).

Example 31

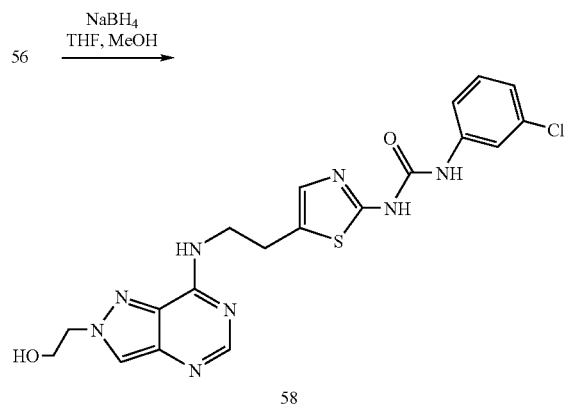

Compound 58: Sodium borohydride (8 mgs, 0.2 mmol) to a solution containing 56 (0.05 g, 0.1 mmol) in THF (3 mL) and MeOH (0.3 mL). The reaction mixture was stirred for 1 hour. The reaction mixture was diluted with and extracted three times with EtOAc. The combined organics were dried (MgSO$_4$) and concentrated. The crude residue was purified by prep RP-HPLC. The fractions containing pure compound were consolidated and concentrated. The residue thus obtained was lyophilized under high-vacuum to yield 58 as the bis TFA salt, ES (+) MS m/e=460 (M+1).

Example 32

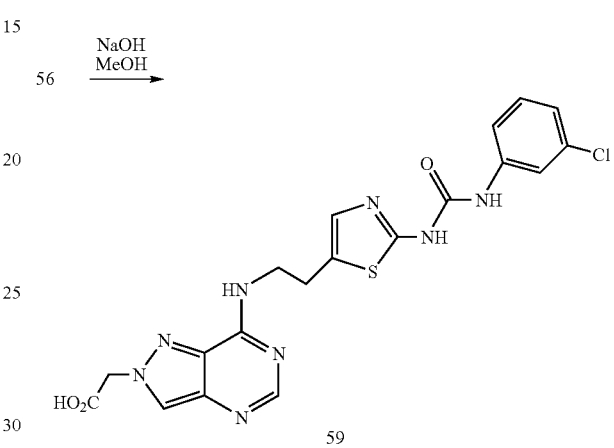

Compound 59: 2M NaOH (1 mL) was added to a solution containing 56 (0.6 g, 1.2 mmol) in MeOH (10 mL). The reaction mixture was stirred for 10 minutes. The mixture was then concentrated followed by the addition of water (3 mL). Aqueous 1M HCl was added until solid precipitated from the solution. The solid was collected and dried to yield 59 (0.4 g, 70%), ES (+) MS m/e=474 (M+1).

Example 33

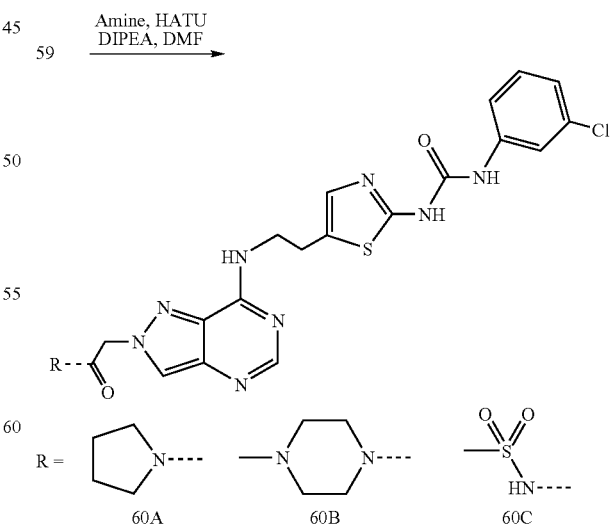

Compound 60A: HATU (0.136 g, 0.36 mmol) was added to a solution containing 59 (0.085 g, 0.18 mmol), Hunig's base (0.16 mL, 0.9 mmol), pyrrolidine (26 mgs, 0.36 mmol) in DMF (3 mL). The reaction mixture was heated to 70° C. and stirred for 1 hour. The reaction was cooled to room temperature. The reaction mixture was diluted with H₂O. The aqueous layer was extracted twice with EtOAc. The combined organic phases were dried with MgSO₄, filtered, and concentrated. The crude residue was purified by prep RP-HPLC. The fractions containing pure compound were consolidated and concentrated. The residue thus obtained was lyophilized under high-vacuum to yield 60A as the bis TFA salt, ES (+) MS m/e=527 (M+1).

Compound 60B: HATU (0.136 g, 0.36 mmol) was added to a solution containing 59 (0.085 g, 0.18 mmol), Hunig's base (0.16 mL, 0.9 mmol), N-methyl piperazine (36 mgs, 0.36 mmol) in DMF (3 mL). The reaction mixture was heated to 70° C. and stirred for 1 hour. The reaction was cooled to room temperature. The reaction mixture was diluted with H₂O. Extracted the aqueous layer with EtOAc. Combined the organics, dried with MgSO₄, filtered, and concentrated. The crude residue was purified by prep RP-HPLC. The fractions containing pure compound were consolidated and concentrated. The residue thus obtained was lyophilized under high-vacuum to yield 60B as the tris TFA salt, ES (+) MS m/e=556 (M+1).

Compound 60C: HATU (0.136 g, 0.36 mmol) was added to a solution containing 59 (0.085 g, 0.18 mmol), Hunig's base (0.16 mL, 0.9 mmol), methanesulfonamide (30 mgs, 0.36 mmol) in DMF (3 mL). The reaction mixture was heated to 70° C. and stirred for overnight. The reaction was cooled to room temperature. The reaction mixture was diluted with H₂O. Extracted the aqueous layer with EtOAc. Combined the organics, dried with MgSO₄, filtered, and concentrated. The crude residue was purified by prep RP-HPLC. The fractions containing pure compound were consolidated and concentrated. The residue thus obtained was lyophilized under high-vacuum to yield 60C as the bis TFA salt, ES (+) MS m/e=551 (M+1).

Example 34

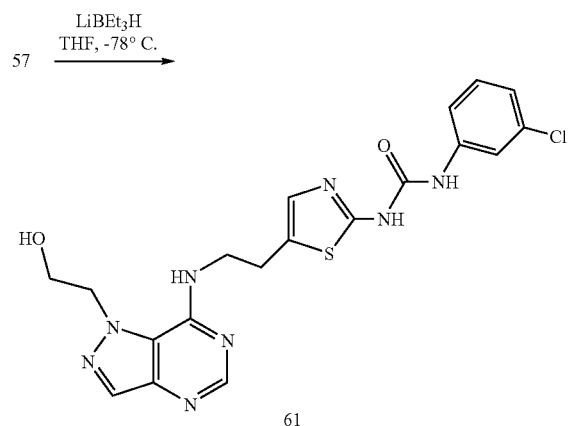

Compound 61: LiBEt₃H (0.3 mL, 1.0M in THF) was added to a pre-cooled solution of 57 (73 mgs, 0.15 mmol) in THF (5 mL) at −78° C. The reaction mixture was stirred at −78° C. for 1 hour and warmed to room temperature. The reaction mixture was diluted with 1M NaHCO₃ and extracted with EtOAc. The combined organics were dried with MgSO₄, filtered, and concentrated. The crude residue was purified by prep RP-HPLC. The fractions containing pure compound were consolidated and concentrated. The residue thus obtained was lyophilized under high-vacuum to yield 61 as the bis TFA salt, ES (+) MS m/e=460 (M+1).

Example 35

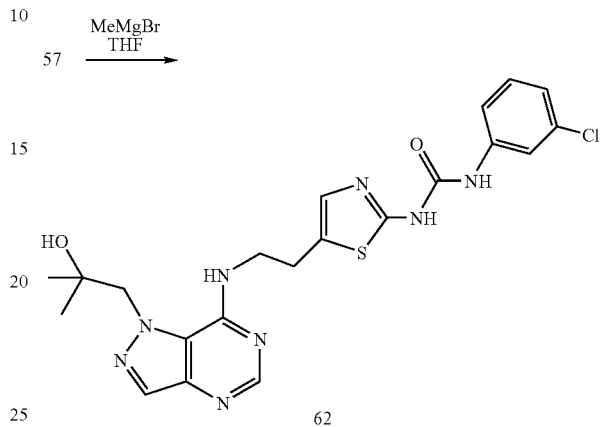

Compound 62: Methyl magnesium bromide (0.2 mL, 3.0M in Et₂O) was added to a solution of 57 (75 mgs, 0.15 mmol) in THF. The reaction mixture was stirred for 30 minutes. The reaction mixture was diluted with H₂O and extracted with EtOAc. The combined organics were dried with MgSO₄, filtered, and concentrated. The crude residue was purified by prep RP-HPLC. The fractions containing pure compound were consolidated and concentrated. The residue thus obtained was lyophilized under high-vacuum to yield 62 as the bis TFA salt, ES (+) MS m/e=488 (M+1).

Example 36

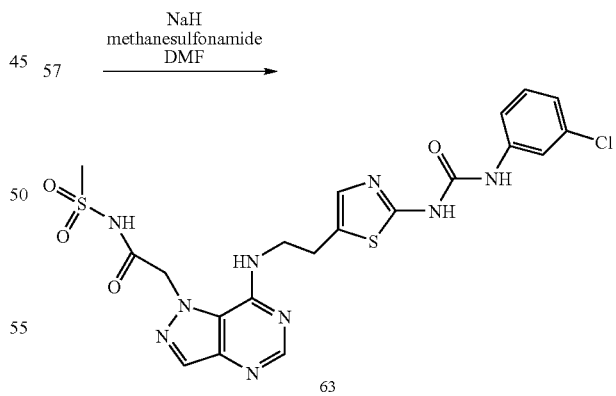

Compound 63: 60% wt of NaH (20 mgs, 0.5 mmol) was added to a solution containing 57 (50 mgs, 0.1 mmol) and methanesulfonamide (20 mgs, 0.2 mmol) in DMF (3 mL). The reaction mixture was stirred for 30 minutes. The reaction mixture was diluted with H₂O and extracted with EtOAc. The combined organics were dried with MgSO₄, filtered, and concentrated. The crude residue was purified by prep RP-HPLC. The fractions containing pure compound were consolidated and concentrated. The residue thus obtained was lyophilized under high-vacuum to yield 63 as the bis TFA salt, ES (+) MS m/e=552 (M+1).

Example 37

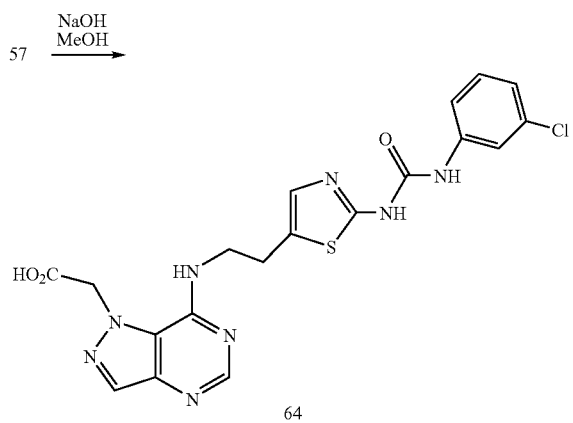

Compound 64: 2M NaOH (2.6 mL) was added to a solution of 57 (1.28 g, 2.6 mmol) in MeOH (20 mL). The reaction mixture was stirred for 10 minutes. Concentrated to remove methanol and added H$_2$O (3 mL). Added 1M HCl until solid precipitated from the solution. Filtered, collected, and dried precipitate as 64 (1.2 g, 99%), ES (+) MS m/e=474 (M+1).

Example 38

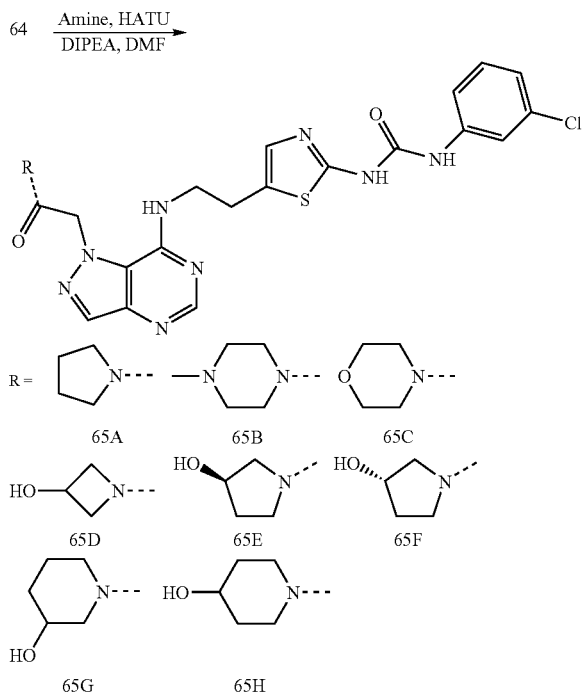

Compound 65A: HATU (0.1 g, 0.27 mmol) was added to a solution containing 64 (0.07 g, 0.13 mmol), Hunig's base (0.12 mL, 0.69 mmol), pyrrolidine (19 mgs, 0.27 mmol) in DMF (2 mL). The reaction mixture was heated to 70° C. and stirred for 1 hour. The reaction was cooled to room temperature. The reaction mixture was diluted with H$_2$O. Extracted the aqueous layer with EtOAc. Combined the organics, dried with MgSO$_4$, filtered, and concentrated. The crude residue was purified by prep RP-HPLC. The fractions containing pure compound were consolidated and concentrated. The residue thus obtained was lyophilized under high-vacuum to yield 65A as the bis TFA salt, ES (+) MS m/e=527 (M+1).

Compound 65B: HATU (0.1 g, 0.27 mmol) was added to a solution containing 64 (0.07 g, 0.13 mmol), Hunig's base (0.12 mL, 0.69 mmol), N-methyl piperazine (28 mgs, 0.27 mmol) in DMF (2 mL). The reaction mixture was heated to 70° C. and stirred for 1 hour. The reaction was cooled to room temperature. The reaction mixture was diluted with H$_2$O. Extracted the aqueous layer with EtOAc. Combined the organics, dried with MgSO$_4$, filtered, and concentrated. The crude residue was purified by prep RP-HPLC. The fractions containing pure compound were consolidated and concentrated. The residue thus obtained was lyophilized under high-vacuum to yield 65B as the tris TFA salt, ES (+) MS m/e=556 (M+1).

Compound 65C: HATU (0.1 g, 0.27 mmol) was added to a solution containing 64 (0.07 g, 0.13 mmol), Hunig's base (0.12 mL, 0.69 mmol), morpholine (24 mgs, 0.27 mmol) in DMF (2 mL). The reaction mixture was heated to 70° C. and stirred for 1 hour. The reaction was cooled to room temperature. The reaction mixture was diluted with H$_2$O. Extracted the aqueous layer with EtOAc. Combined the organics, dried with MgSO$_4$, filtered, and concentrated. The crude residue was purified by prep RP-HPLC. The fractions containing pure compound were consolidated and concentrated. The residue thus obtained was lyophilized under high-vacuum to yield 65C as the bis TFA salt, ES (+) MS m/e=543 (M+1).

Compound 65D: HATU (0.1 g, 0.27 mmol) was added to a solution containing 64 (0.07 g, 0.13 mmol), Hunig's base (0.12 mL, 0.69 mmol), 3-hydroxyazetidine hydrochloride (30 mgs, 0.27 mmol) in DMF (2 mL). The reaction mixture was heated to 70° C. and stirred for 1 hour. The reaction was cooled to room temperature. The reaction mixture was diluted with H$_2$O. Extracted the aqueous layer with EtOAc. Combined the organics, dried with MgSO$_4$, filtered, and concentrated. The crude residue was purified by prep RP-HPLC. The fractions containing pure compound were consolidated and concentrated. The residue thus obtained was lyophilized under high-vacuum to yield 65D as the bis TFA salt, ES (+) MS m/e=529 (M+1).

Compound 65E: HATU (0.1 g, 0.27 mmol) was added to a solution containing 64 (0.07 g, 0.13 mmol), Hunig's base (0.12 mL, 0.69 mmol), R(+)-3-pyrrolidinol (24 mgs, 0.27 mmol) in DMF (2 mL). The reaction mixture was heated to 70° C. and stirred for 1 hour. The reaction was cooled to room temperature. The reaction mixture was diluted with H$_2$O. Extracted the aqueous layer with EtOAc. Combined the organics, dried with MgSO$_4$, filtered, and concentrated. The crude residue was purified by prep RP-HPLC. The fractions containing pure compound were consolidated and concentrated. The residue thus obtained was lyophilized under high-vacuum to yield 65E as the bis TFA salt, ES (+) MS m/e=543 (M+1).

Compound 65F: HATU (0.1 g, 0.27 mmol) was added to a solution containing 64 (0.07 g, 0.13 mmol), Hunig's base (0.12 mL, 0.69 mmol), S(+)-3-pyrrolidinol (24 mgs, 0.27 mmol) in DMF (2 mL). The reaction mixture was heated to 70° C. and stirred for 1 hour. The reaction was cooled to room temperature. The reaction mixture was diluted with H$_2$O. Extracted the aqueous layer with EtOAc. Combined the organics, dried with MgSO₄, filtered, and concentrated. The crude residue was purified by prep RP-HPLC. The fractions containing pure compound were consolidated and concentrated. The residue thus obtained was lyophilized under high-vacuum to yield 65F as the bis TFA salt, ES (+) MS m/e=543 (M+1).

Compound 65G: HATU (0.1 g, 0.27 mmol) was added to a solution containing 64 (0.07 g, 0.13 mmol), Hunig's base (0.12 mL, 0.69 mmol), 3-hydroxypiperidine (29 mgs, 0.27 mmol) in DMF (2 mL). The reaction mixture was heated to 70° C. and stirred for 1 hour. The reaction was cooled to room temperature. The reaction mixture was diluted with H₂O. Extracted the aqueous layer with EtOAc. Combined the organics, dried with MgSO₄, filtered, and concentrated. The crude residue was purified by prep RP-HPLC. The fractions containing pure compound were consolidated and concentrated. The residue thus obtained was lyophilized under high-vacuum to yield 65G as the bis TFA salt, ES (+) MS m/e=557 (M+1).

Compound 65H: HATU (0.1 g, 0.27 mmol) was added to a solution containing 64 (0.07 g, 0.13 mmol), Hunig's base (0.12 mL, 0.69 mmol), R(+)-3-pyrrolidinol (24 mgs, 0.27 mmol) in DMF (2 mL). The reaction mixture was heated to 70° C. and stirred for 1 hour. The reaction was cooled to room temperature. The reaction mixture was diluted with H₂O. Extracted the aqueous layer with EtOAc. Combined the organics, dried with MgSO₄, filtered, and concentrated. The crude residue was purified by prep RP-HPLC. The fractions containing pure compound were consolidated and concentrated. The residue thus obtained was lyophilized under high-vacuum to yield 65H as the bis TFA salt, ES (+) MS m/e=543 (M+1).

Example 39

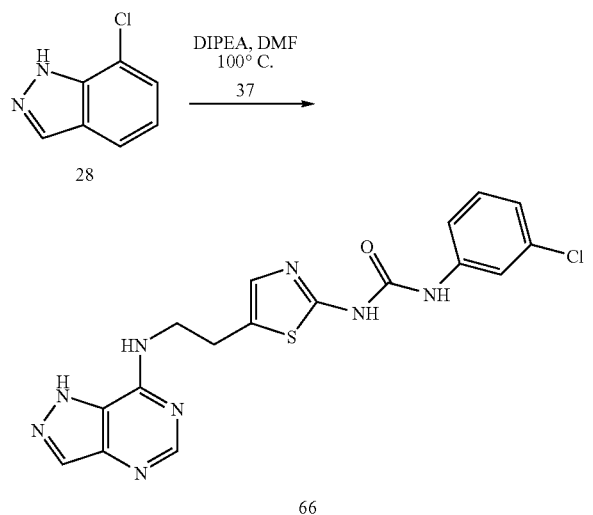

Compound 66: 37 (0.67 g, 2.0 mmol) was added to a solution containing 28 (0.67 g, 2.0 mmol) and Hunig's base (1.4 mL, 8.0 mmol) in DMF (15 mL). The reaction mixture was heated to 100° C. for 1 hour. The reaction was cooled to room temperature. The reaction mixture was diluted with H₂O. Extracted the aqueous layer with EtOAc. Combined the organics, dried with MgSO₄, filtered, and concentrated. The crude residue was purified by column chromatography on silica gel using 10% MeOH in DCM to afford 66 (0.45 g, 54%), ES (+) MS m/e=416 (M+1).

Example 40

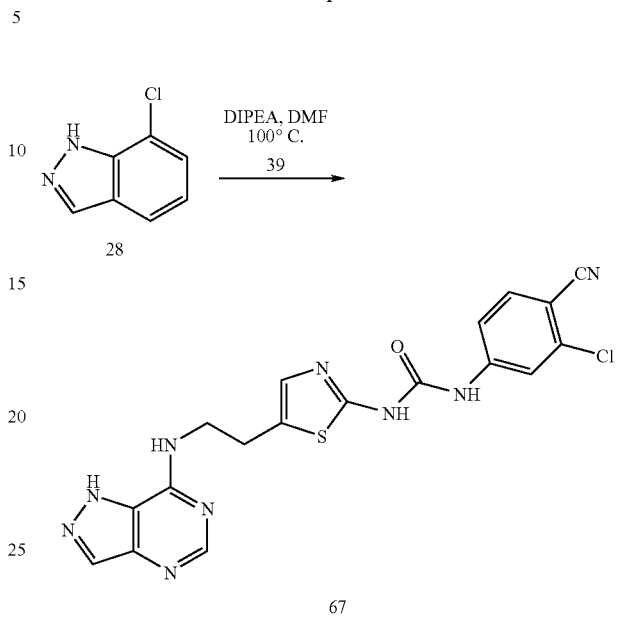

Compound 67: 39 (0.69 g, 2.0 mmol) was added to a solution containing 28 (0.67 g, 2.0 mmol) and Hunig's base (1.4 mL, 8.0 mmol) in DMF (15 mL). The reaction mixture was heated to 100° C. for 1 hour. The reaction was cooled to room temperature. The reaction mixture was diluted with H₂O. Extracted the aqueous layer with EtOAc. Combined the organics, dried with MgSO₄, filtered, and concentrated. The crude residue was purified by column chromatography on silica gel using 10% MeOH in DCM to afford 67 (0.40 g, 49%), ES (+) MS m/e=440 (M+1).

Example 41

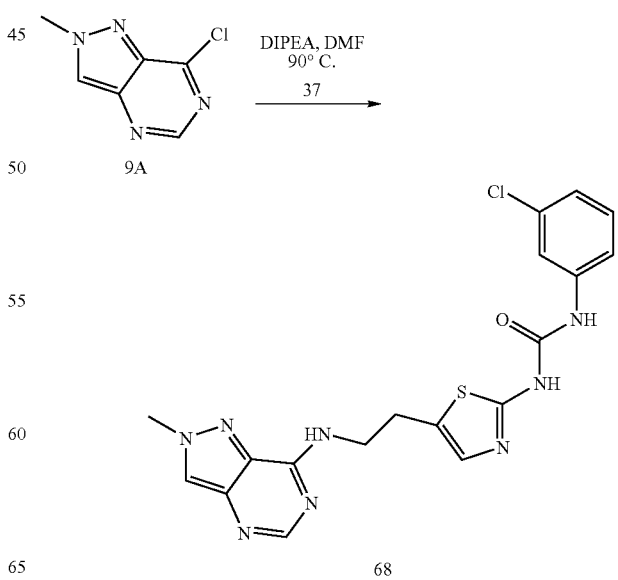

Compound 68: This compound was made according to procedures towards the synthesis of 10, except that 9A and 37 was used in place of 9 and 3 respectively, ES (+) MS m/e=429 (M+1).
Example 42
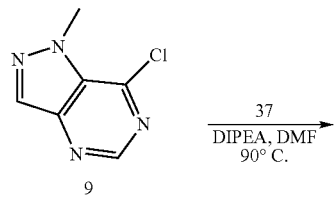
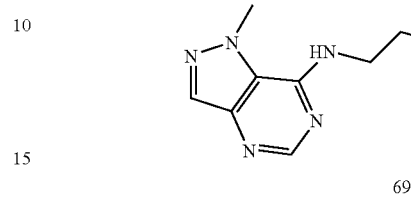
Compound 69: This compound was made according to procedures towards the synthesis of 10, except that 37 was used in place of 3, ES (+) MS m/e=429 (M+1).
Example 43
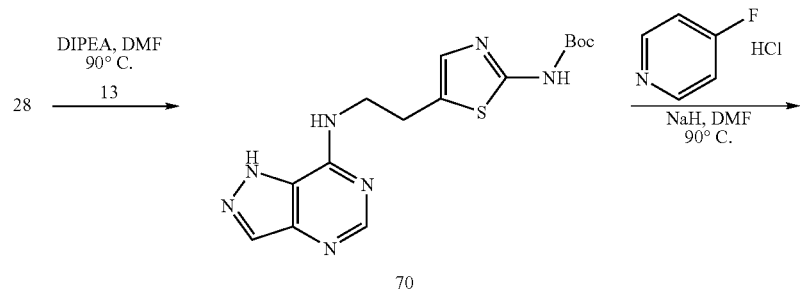
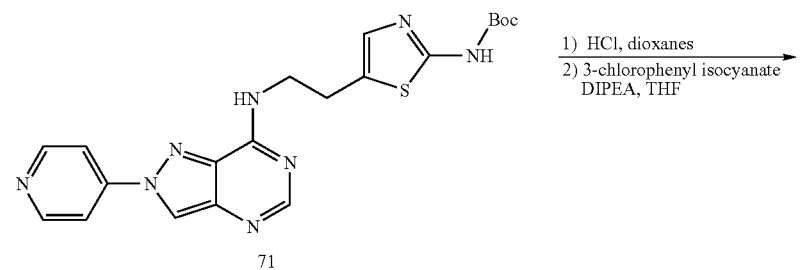

Compound 70: 13 (0.86 g, 3.5 mmol) was added to a solution containing 28 (0.55 g, 3.5 mmol) and Hunig's base (1.2 mL, 7.1 mmol) in DMF (12 mL). The reaction mixture was heated to 90° C. and stirred for 1 hour. The reaction mixture was cooled to room temperature. The reaction mixture was diluted with $H_2O$. Extracted the aqueous layer with EtOAc. Combined the organics, dried with $MgSO_4$, filtered, and concentrated. The crude residue was purified by column chromatography on silica gel using 100% EtOAc to afford 70 (0.5 g, 39%), ES (+) MS m/e=362 (M+1).

Compound 71: 60% wt of NaH (0.11 g, 0.66 mmol) was added to a solution containing 70 (0.2 g, 0.55 mmol) and 4-fluoropyridine hydrochloride (0.09 g, 0.66 mmol) in DMF (2 mL). The reaction mixture was heated to 90° C. and stirred overnight. The reaction mixture was cooled to room temperature. The reaction mixture was diluted with $H_2O$. Extracted the aqueous layer with EtOAc. Combined the organics, dried with $MgSO_4$, filtered, and concentrated. The crude residue was purified by column chromatography on silica gel using 100% EtOAc to afford 71 (0.09 g, 36%), ES (+) MS m/e=439 (M+1).

Compound 72: HCl (1 mL, 4.0M in dioxanes) was added to a solution of 71 (0.09 g, 0.2 mmol) in dioxanes (1 mL). The reaction mixture was stirred for 1 hour and concentrated. The resulting residue was dissolved in Hunig's base (0.21 mL) and THF (5 mL). 3-chlorophenyl isocyanate (56 mgs, 0.36 mmol) was added and the reaction stirred for 3 hours. The reaction mixture was concentrated. The crude residue was purified by prep RP-HPLC. The fractions containing pure compound were consolidated and concentrated. The residue thus obtained was lyophilized under high-vacuum to yield 72 as the bis TFA salt, ES (+) MS m/e=492 (M+1).

Example 44

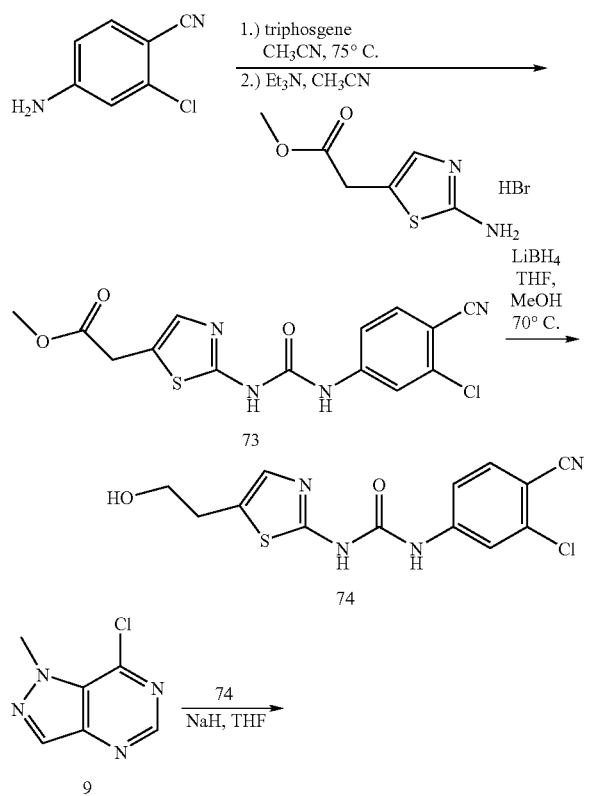

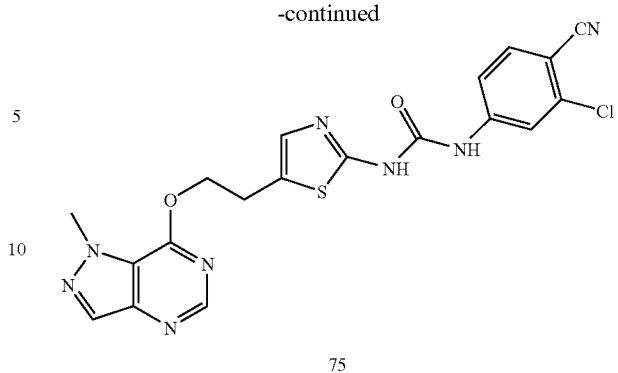

75

Compound 73: Triphosgene (0.74 g, 2.5 mmol) was added to a solution containing 4-amino-2-chlorobenzonitrile (1.05 g, 6.9 mmol) in acetonitrile (28 mL). The reaction mixture was heated to 75° C. and stirred for 1.5 hours. The reaction was cooled to room temperature. A solution containing (2-amino-thiazol-5-yl)-acetic acid methyl ester hydrobromide (1.58 g, 6.2 mmol) [See Patent Application Publication US 2006/0035908], and $Et_3N$ (4.4 mL, 31.2 mmol) in acetonitrile (12 mL) was added to the reaction mixture and stirred for 15 minutes. The reaction mixture was diluted with $H_2O$. The aqueous layer was extracted with EtOAc. The combined organics were dried with $MgSO_4$, filtered, and concentrated. The crude residue was triturated with DCM and hexanes to afford 73 (1.9 g, 87%), ES (+) MS m/e=351 (M+1).

Compound 74: $LiBH_4$ (0.48 g, 21.6 mmol) was added to a solution containing 73 (1.9 g, 5.4 mmol) in THF (50 mL) and MeOH (5 mL). The reaction mixture was heated to 70° C. for overnight. The reaction mixture was cooled to room temperature. The reaction mixture was diluted with $H_2O$ and the aqueous layer was extracted with EtOAc. The combined organics were dried with $MgSO_4$, filtered, and concentrated to afford 74 (1.7 g, 97%), ES (+) MS m/e=323 (M+1).

Compound 75: 60% wt of NaH (52 mgs, 1.3 mmol) was added to a solution of 4-chlorothieno[3,2-d]pyrimidine (63 mgs, 0.4 mmol) and 74 (0.12 g, 0.4 mmol) in THF (4 mL). The reaction mixture was stirred for overnight. The reaction mixture was diluted with $H_2O$ and extracted aqueous layer with EtOAc. The combined organics were dried with $MgSO_4$, filtered, and concentrated. The crude residue was purified by prep RP-HPLC. The fractions containing pure compound were consolidated and concentrated. The residue thus obtained was lyophilized under high-vacuum to yield 75 as the bis TFA salt, ES (+) MS m/e=457 (M+1).

Example 45

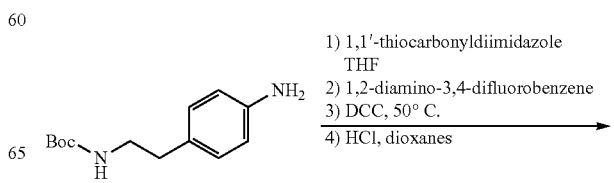

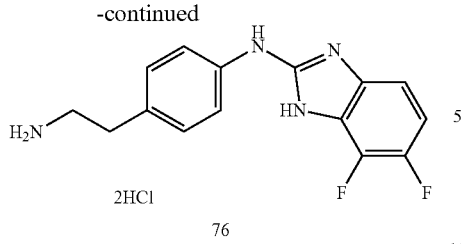

2HCl

76

Compound 76: 1,1'-thiocarbonyldiimidazole (0.68 g, 4.6 mmol) was added to a solution containing [2-(4-amino-phenyl)-ethyl]-carbamic acid t-butyl ester (1.1 g, 4.6 mmol). The reaction mixture was stirred for 30 minutes. 1,2-diamino-3,4-difluorobenzene (0.66 g, 4.6 mmol) was added to the reaction mixture and stirred for 3 hours. DCC (0.94 g, 4.6 mmol) was added and the reaction mixture was heated to 50° C. for 2 hours. The reaction mixture was cooled to room temperature and stirred overnight. The reaction mixture was diluted with H$_2$O and extracted the aqueous layer with EtOAc. Combined the organics, dried with MgSO$_4$, filtered, and concentrated. The crude residue was purified by column chromatography on silica gel using 40% EtOAc in hexanes to obtain solid. The resulting solid was dissolved in dioxanes (5 mL) and HCl (3 mL, 4.0M in dioxanes) was added. The reaction mixture was stirred for overnight and concentrated to afford 76 (1.45 g, 87%), ES (+) MS m/e=289 (M+1).

Example 46

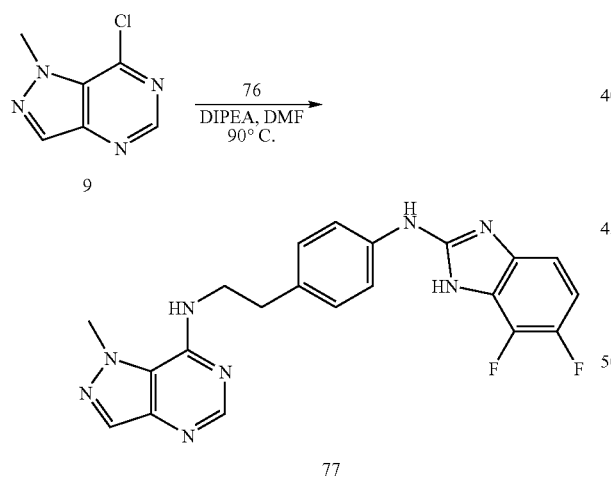

Compound 77: 76 (0.3 g, 0.84 mmol) was added to a solution containing 9 (0.14 g, 0.84 mmol) and Hunig's base (0.7 mL, 4.2 mmol) in DMF (5 mL). The reaction mixture was heated to 90° C. and stirred for 1 hour. The reaction mixture was cooled to room temperature. The reaction mixture was diluted with H$_2$O and extracted the aqueous layer with EtOAc. Combined the organics, dried with MgSO$_4$, filtered, and concentrated. The crude residue was purified by column chromatography on silica gel using 5% CH$_3$CN in EtOAc to afford 77 (0.11 g, 31%), ES (+) MS m/e=421 (M+1).

Example 47

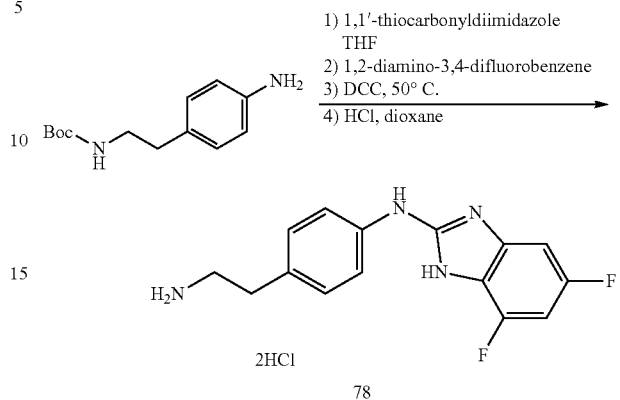

Compound 78: This compound was made according to procedures towards the synthesis of 76 except that 1,2-diamino-3,5-difluorobenzene was used in place of 1,2-diamino-3,4-difluorobenzene, ES (+) MS m/e=289 (M+1).

Example 48

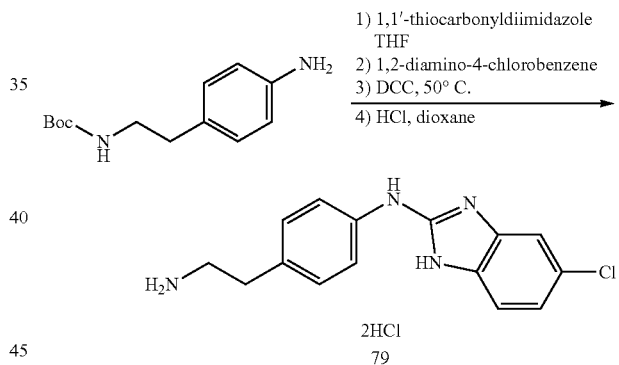

Compound 79: This compound was made according to procedures towards the synthesis of 76 except that 1,2-diamino-4-chlorobenzene was used in place of 1,2-diamino-3,4-difluorobenzene, ES (+) MS m/e=287 (M+1).

Example 49

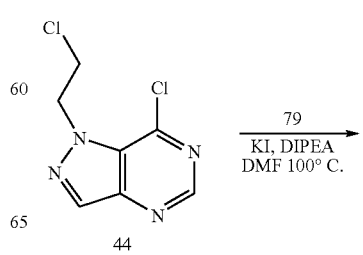

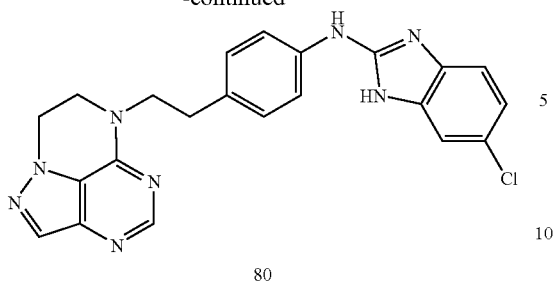

80

Compound 80: 79 (0.11 g, 0.3 mmol) was added to a solution containing 44 (0.066 g, 0.3 mmol), KI (51 mgs, 0.3 mmol) and Hunig's base (0.27 mL, 1.5 mmol) in DMF (5 mL). The reaction mixture was heated to 100° C. for overnight. The reaction was cooled to room temperature. The reaction mixture was diluted with $H_2O$. Extracted the aqueous layer with EtOAc. Combined the organics, dried with $MgSO_4$, filtered, and concentrated. The crude residue was purified by prep RP-HPLC. The fractions containing pure compound were consolidated and concentrated. The residue thus obtained was lyophilized under high-vacuum to yield 80 as the bis TFA salt, ES (+) MS m/e=431 (M+1).

Example 50

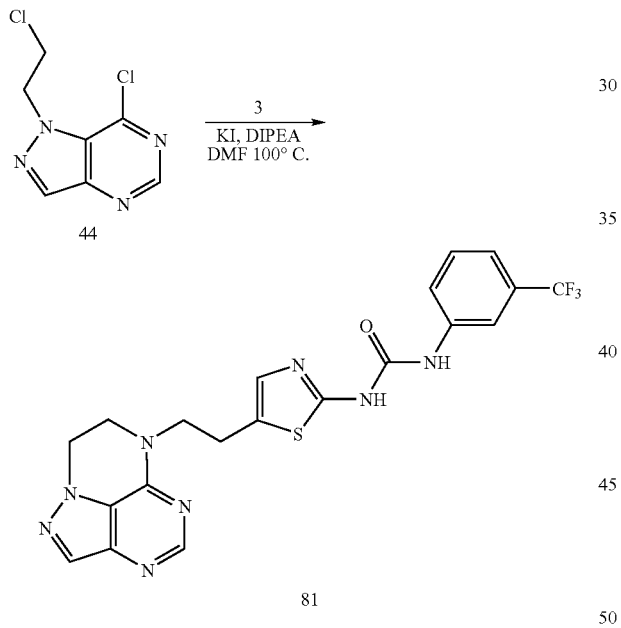

81

Compound 81: This compound was made according to procedures towards the synthesis of 80, except that 3 was used in place of 79, ES (+) MS m/e=475 (M+1).

Example 51

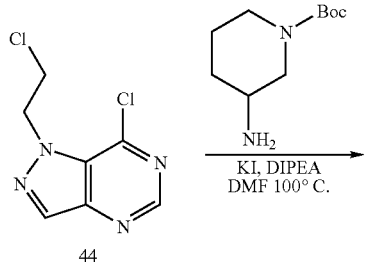

44

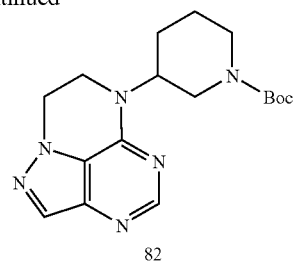

82

Compound 82: This compound was made according to procedures towards the synthesis of 80, except that 3-amino-piperidine-1-carboxylic acid t-butyl ester was used in place of 79, ES (+) MS m/e=345 (M+1).

Example 52

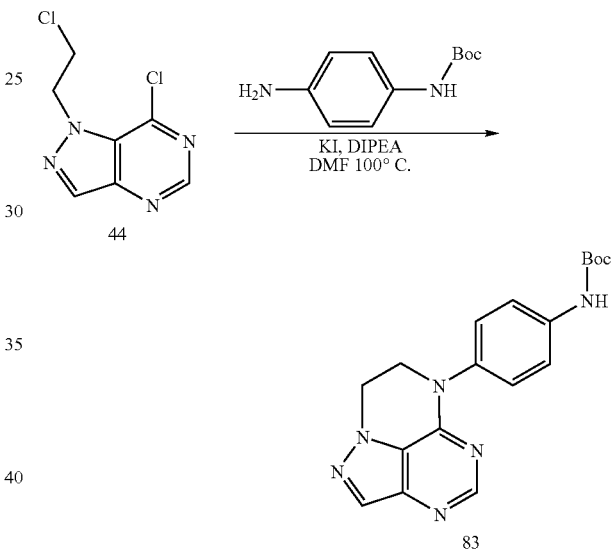

83

Compound 83: This compound was made according to procedures towards the synthesis of 80 except that (4-aminophenyl)-carbamic acid t-butyl ester was used in place of 79, ES (+) MS m/e=353 (M+1).

Example 53

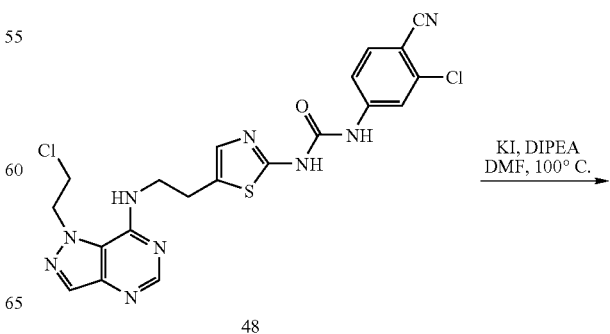

48

-continued

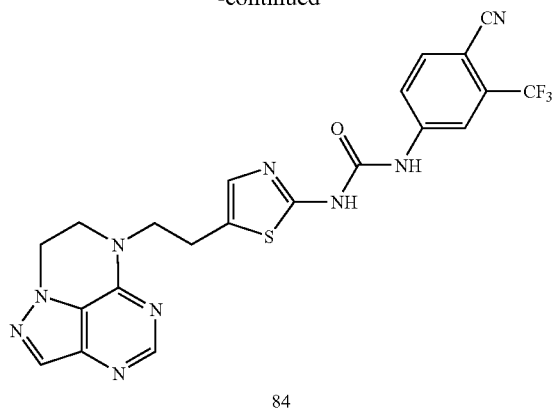

84

Compound 84: This compound was made according to procedures towards the synthesis of 80, ES (+) MS m/e=466 (M+1).

Example 54

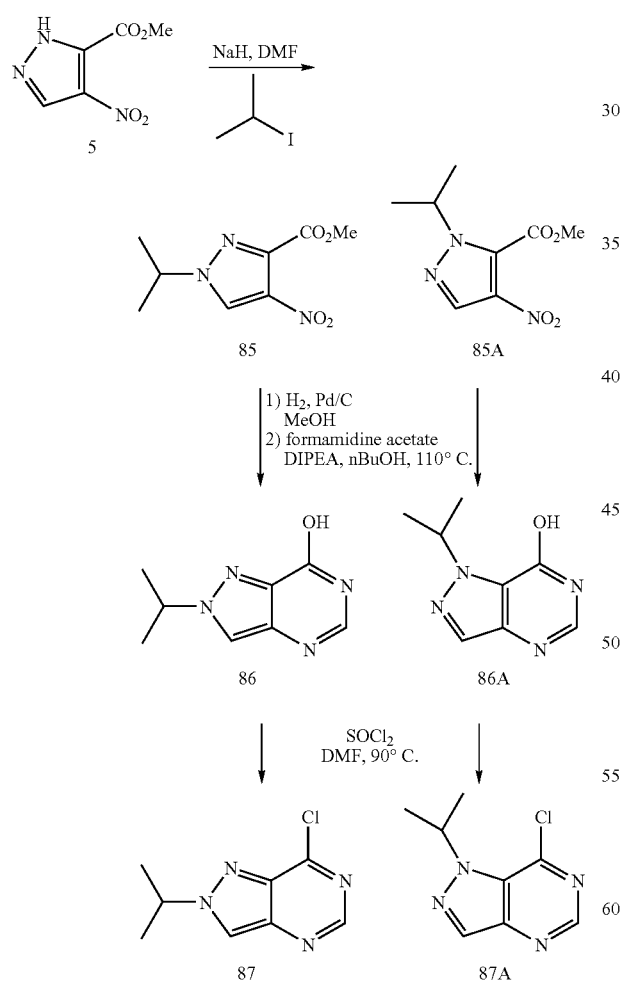

Compound 85 and 85A: 2-iodopropane (4.0 mL, 40.0 mmol) was added to a solution of 5 (2.3 g, 13.5 mmol) and 60% wt of NaH (0.68 g, 16.9 mmol) in DMF (50 mL). The reaction mixture was stirred for 2 hours. The reaction mixture was diluted with H₂O. Separated the layers and the aqueous layer was extracted with EtOAc. The combined organics were dried with MgSO₄, filtered, and concentrated. Purified the residue by column chromatography on silica gel using 30% EtOAc in hexanes to afford 85A (0.66 g, 23%), ES (+) MS m/e=214 (M+1) and using 40% EtOAc in hexanes to afford 85 (1.09 g, 38%), ES (+) MS m/e=214 (M+1).

Compound 86: This compound was made according to procedures towards the synthesis of 46, except that 85 was used in place of 45, ES (+) MS m/e=179 (M+1).

Compound 86A: This compound was made according to procedures towards the synthesis of 46, except that 85A was used in place of 45, ES (+) MS m/e=179 (M+1).

Compound 87: This compound was made according to procedures towards the synthesis of 47, except that 86 was used in place of 46, ES (+) MS m/e=197 (M+1).

Compound 87A: This compound was made according to procedures towards the synthesis of 47, except that 86A was used in place of 46, ES (+) MS m/e=197 (M+1).

Example 55

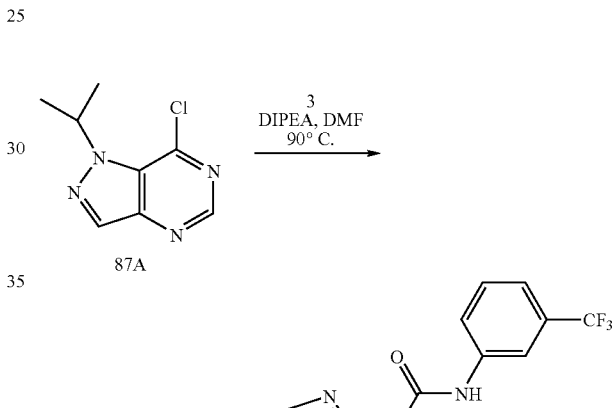

Compound 88: This compound was made according to procedures towards the synthesis of 10, except that 87A was used in place of 9, ES (+) MS m/e=491 (M+1).

Example 56

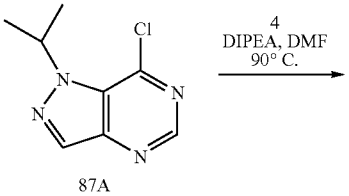

-continued

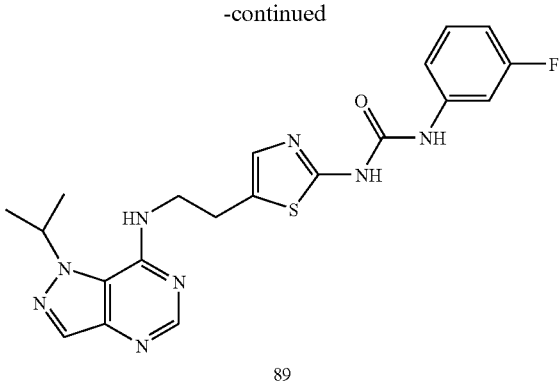

89

Compound 89: This compound was made according to procedure towards the synthesis of 10, except that 87A and 4 were used in place of 9 and 3 respectively, ES (+) MS m/e=441 (M+1).

Example 57

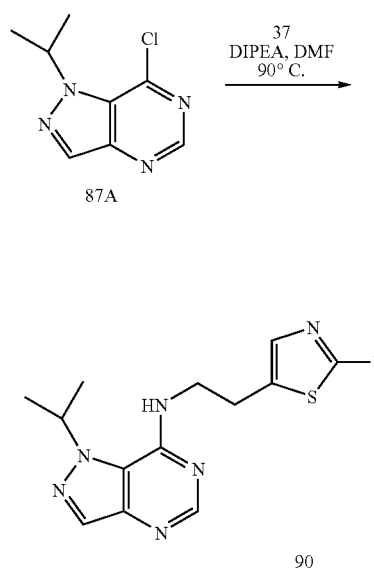

90

Compound 90: This compound was made according to procedures towards the synthesis of 10, except that 87A and 37 were used in place of 9 and 3 respectively, ES (+) MS m/e=457 (M+1).

Example 58

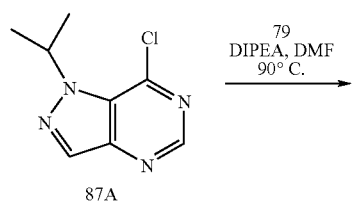

87A

-continued

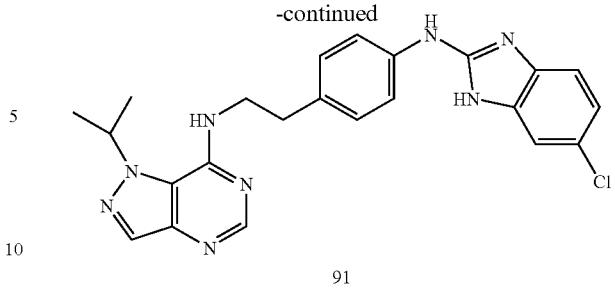

91

Compound 91: This compound was made according to procedures towards the synthesis of 10, except that 87A and 79 were used in place of 9 and 3 respectively, ES (+) MS m/e=447 (M+1).

Example 59

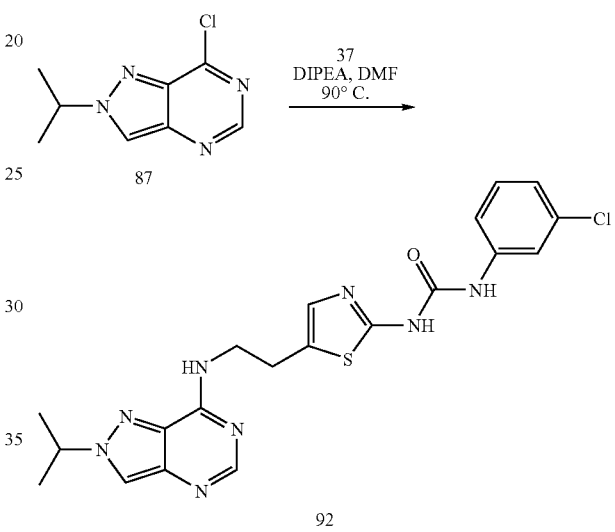

92

Compound 92: This compound was made according to procedures towards the synthesis of 10, except that 87 and 37 were used in place of 9 and 3 respectively, except for using 46 in place of 1.8 and 5 in place of 1.3. ES (+) MS m/e=457 (M+1).

Example 60

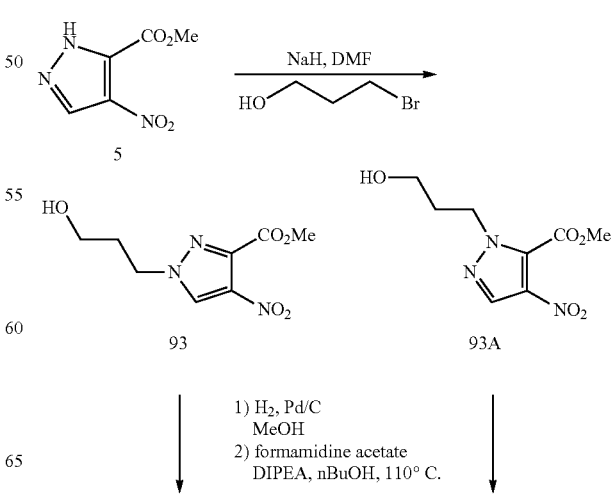

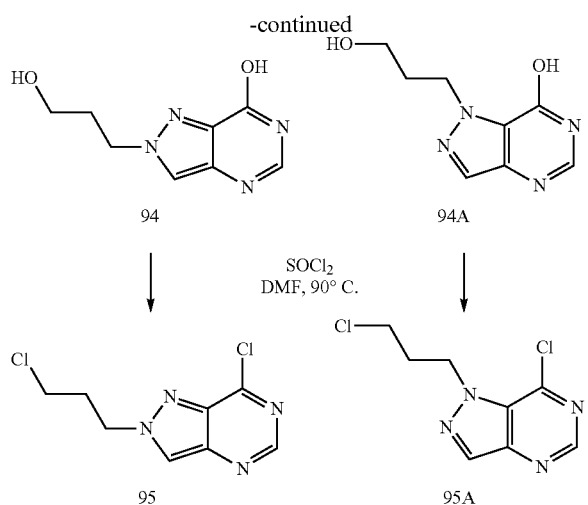

Compound 93 and 93A: These compounds were made according to procedures towards the synthesis of 44 and 44A except that 3-bromo-1-propanol was used in place of 2-iodopropane, ES (+) MS m/e=230.

Compound 94: This compound was made according to procedures towards the synthesis of 46, except that 93 was used in place of 45, ES (+) MS m/e=195 (M+1).

Compound 94A: This compound was made according to procedures towards the synthesis of 46, except that 93A was used in place of 45, ES (+) MS m/e=195 (M+1).

Compound 95: This compound was made according to procedures towards the synthesis of 47, except that 94 was used in place of 46, ES (+) MS m/e=231 (M+1).

Compound 95A: This compound was made according to procedures towards the synthesis of 47, except that 94A was used in place of 46, ES (+) MS m/e=231 (M+1).

Example 61

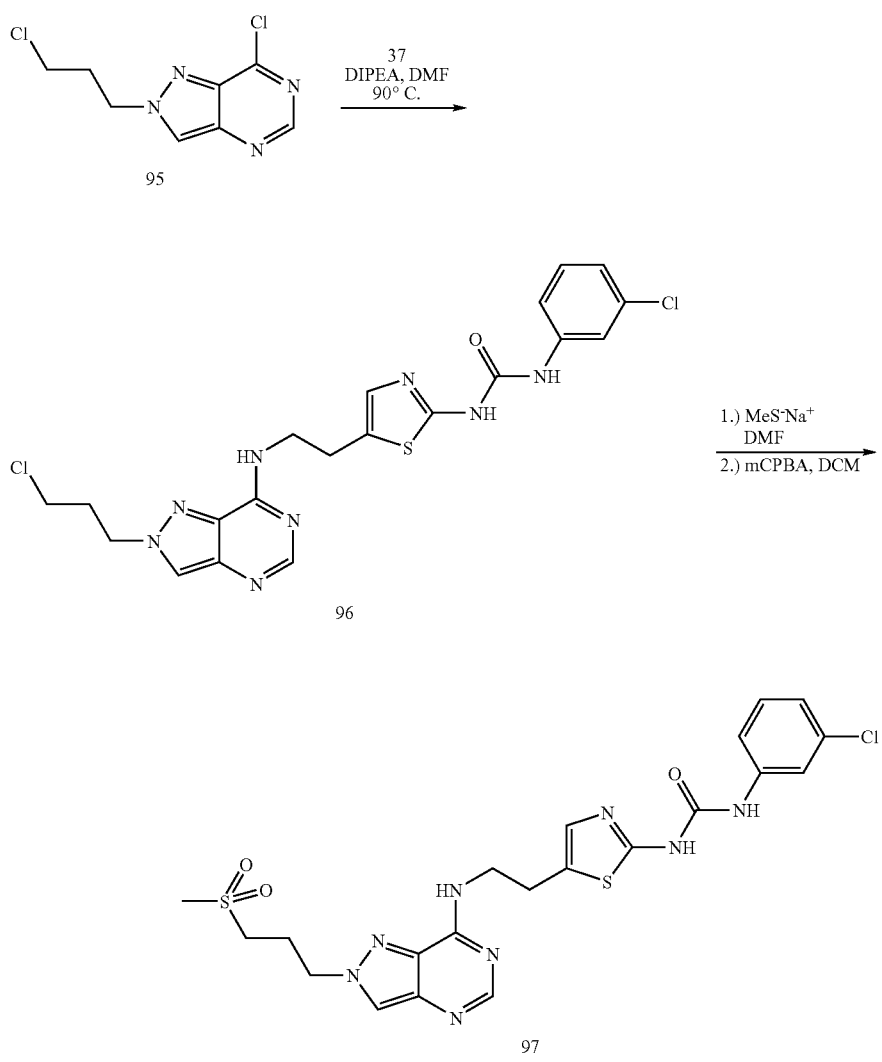

Compound 96: This compound was made according to procedures towards the synthesis of 51, except that 95 was used in place of 44, ES (+) MS m/e=491 (M+1).

Compound 97: This compound was made according to procedures towards the synthesis of 53 and 54B, except that 96 was used in place of 51, ES (+) MS m/e=535 (M+1).

Example 62

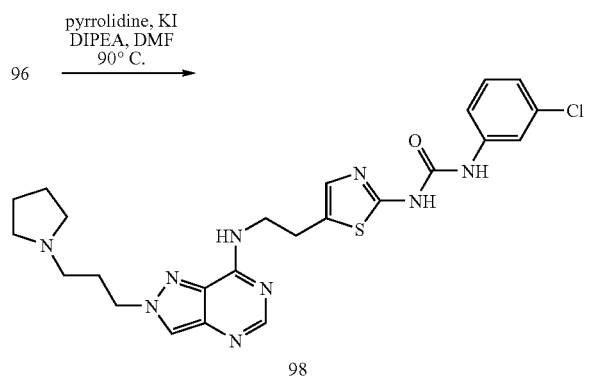

Compound 98: Pyrrolidine (16 mgs, 0.02 mmol) was added to a solution containing 96 (60 mgs, 0.01 mmol), Hunig's base (0.05 mL, 0.3 mmol), and KI (2 mgs) in DMF (3 mL). The reaction mixture was heated at 90° C. overnight. The reaction mixture was cooled to room temperature and the solvent was removed under reduced pressure. The crude residue was purified by prep RP-HPLC. The fractions containing pure compound were consolidated and concentrated. The residue thus obtained was lyophilized under high-vacuum to yield 98 as the tris TFA salt, ES (+) MS m/e=526 (M+1).

Example 63

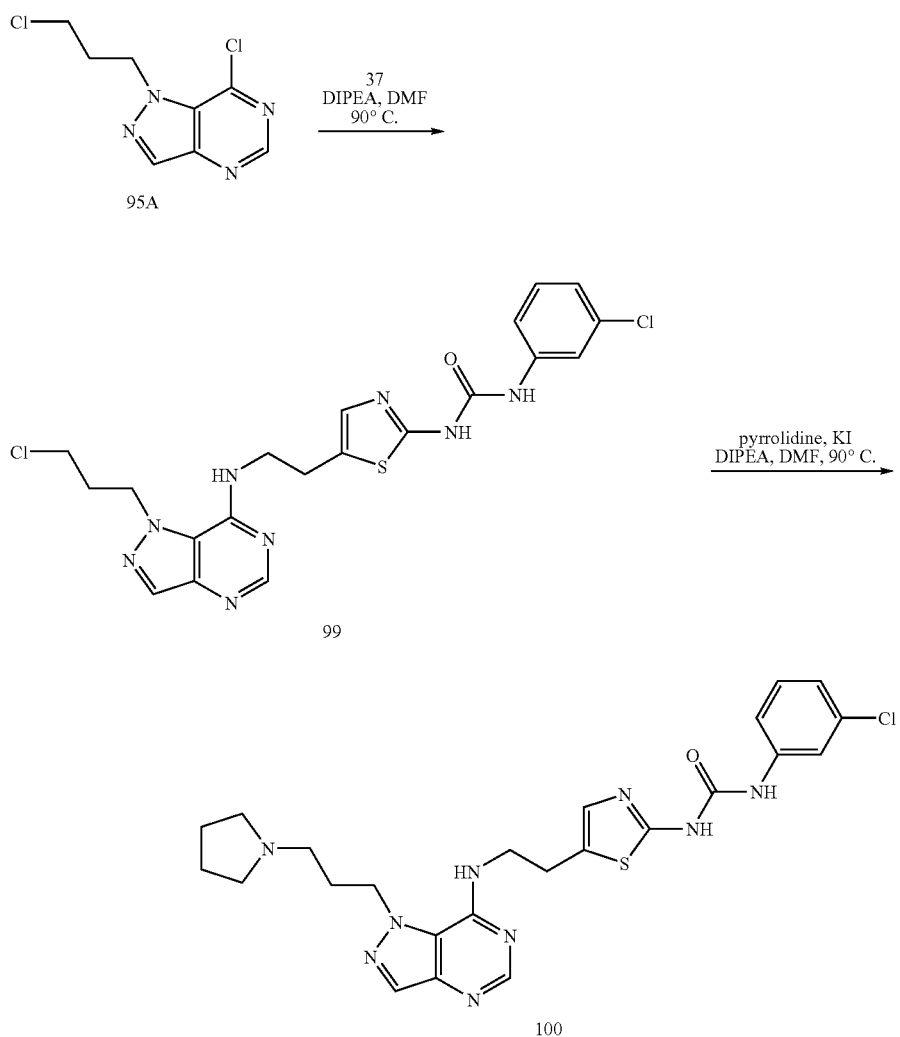

Compound 99: This compound was made according to procedures towards the synthesis of 51, except that 95A was used in place of 44, ES (+) MS m/e=491 (M+1).

Compound 100: This compound was made according to procedures towards the synthesis of 98, except that 99 was used in place of 96, ES (+) MS m/e=526 (M+1).

Example 64

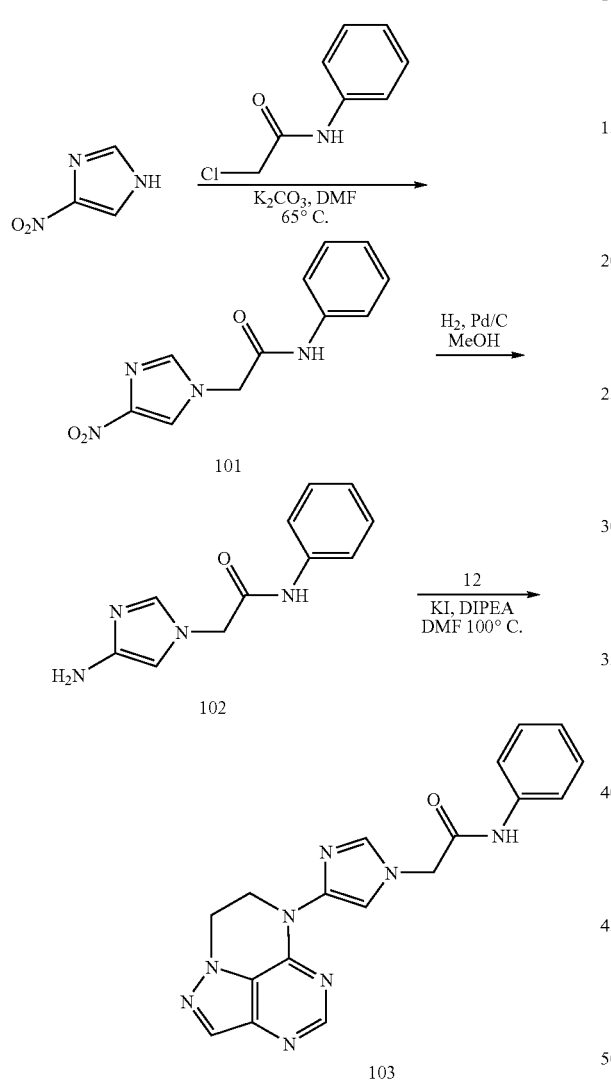

Example 65

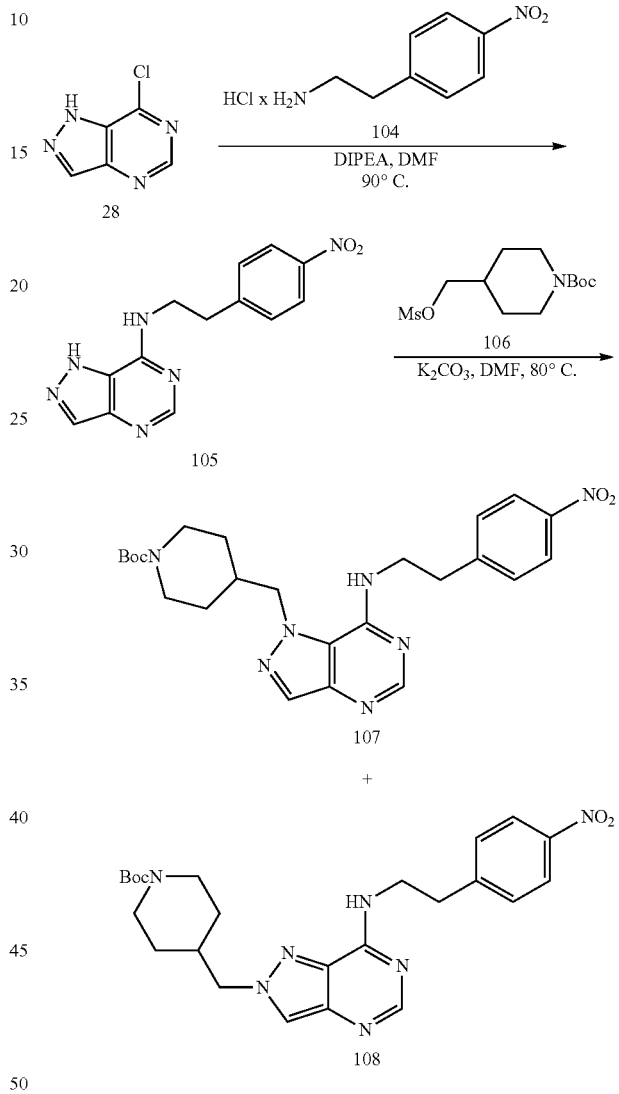

Compound 101: 2-chloro-N-phenylacetamide (0.15 g, 0.9 mmol) was added to a solution containing 4-nitroimidazole (0.1 g, 0.9 mmol) in DMF (5 mL). The reaction mixture was heated to 65° C. for 1 hour. The reaction mixture was diluted with H$_2$O. Separated the layers and the aqueous layer was extracted with EtOAc. The combined organics were dried with MgSO$_4$, filtered, and concentrated to afford 101 (0.22 g, 100%), ES (+) MS m/e=247 (M+1).

Compound 102: 10% wt. Pd/C (0.1 g, 0.09 mmol) was added to a solution containing 101 (0.22 g, 0.88 mmol) in 10 mL of methanol. The mixture was stirred under a hydrogen atmosphere at ambient temperature. After 3 hours, the reaction mixture was filtered thru a plug of Celite. The resulting filtrate was concentrated under reduced pressure to afford 102 (0.19 g, 100%).

Compound 105: This compound was made according to example 10 except that 28 and 104 sere used in place of 9 and 3, respectively. ES (+) MS m/e=285 (M+1).

Compounds 107 and 108: A mixture of 105, 106, and K$_2$CO$_3$ in DMF was heated at 80 C. After 4.5 h, the mixture was concentrated and the residue was partitioned between water and EtOAc. The aqueous layer was extracted twice with EtOAc and the combined organic phases were dried (Na$_2$SO$_4$) and concentrated. The crude residue thus obtained was purified by column chromatography (SiO$_2$; 0 to 5% MeOH in EtOAc) to yield 50 mg of 107 and 108 mg of 108. 107: R$_f$ 0.59 (SiO; 5% MeOH in EtOAc), ES (+) MS m/e=482 (M+1). 108: R$_f$ 0.47 (SiO; 5% MeOH in EtOAc), ES (+) MS m/e=482 (M+1).

Example 66

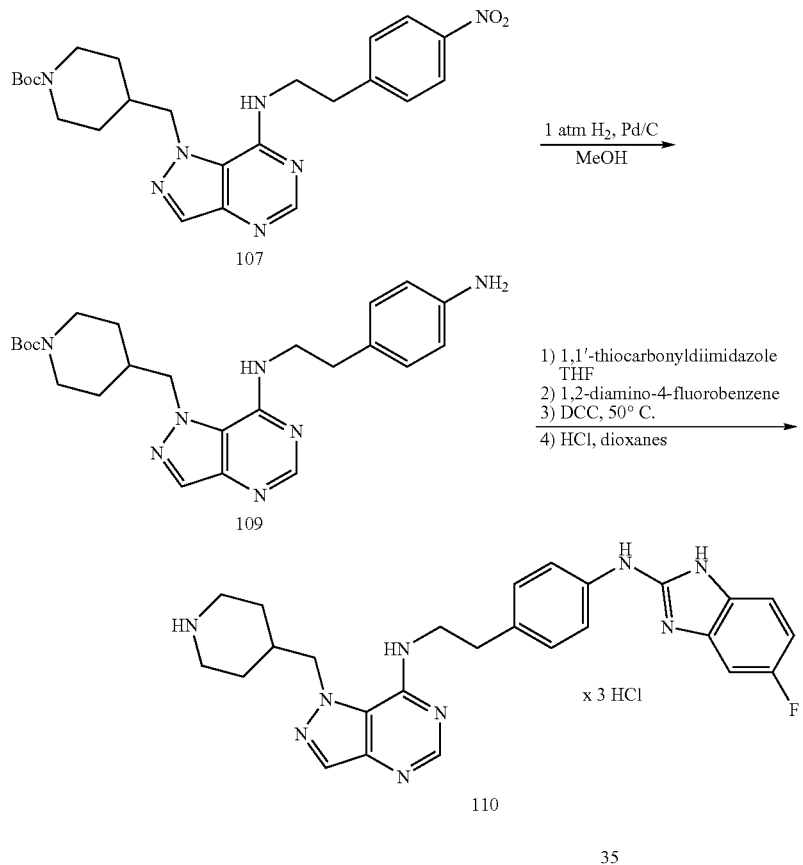

Compound 109: This compound was made according to procedures towards the synthesis of 15 except that 107 was used in place of 14. ES (+) MS m/e=452 (M+1).

Compound 110: This compound was made according to procedures towards the synthesis of 76 except that 109 was used in place of [2-(4-amino-phenyl)-ethyl]-carbamic acid t-butyl ester and 1,2-diamino-4-fluorobenzene was used in place of 1,2-diamino-3,4-difluorobenzene. ES (+) MS m/e=586 (M+1).

Example 67

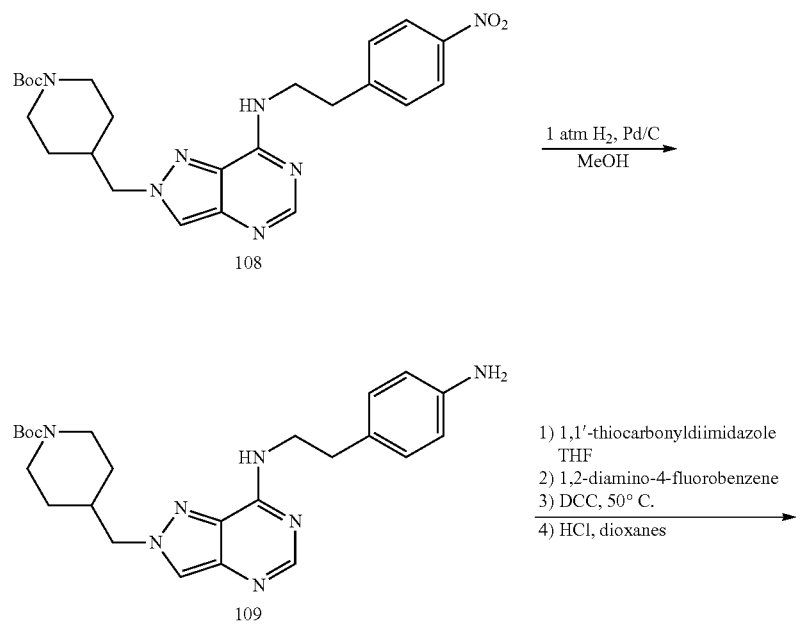

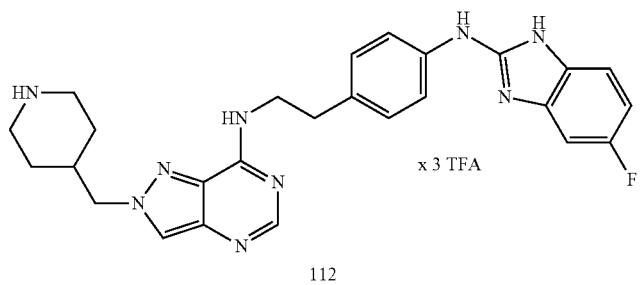

112

Compound 111: This compound was made according to procedures towards the synthesis of 15 except that 108 was used in place of 14. ES (+) MS m/e=452 (M+1).

Compound 112: This compound was made according to procedures towards the synthesis of 76 except that 111 was used in place of [2-(4-amino-phenyl)-ethyl]-carbamic acid t-butyl ester and 1,2-diamino-4-fluorobenzene was used in place of 1,2-diamino-3,4-difluorobenzene. The crude product was purified using RP-preparative HPLC. ES (+) MS m/e=586 (M+1).

Example 68

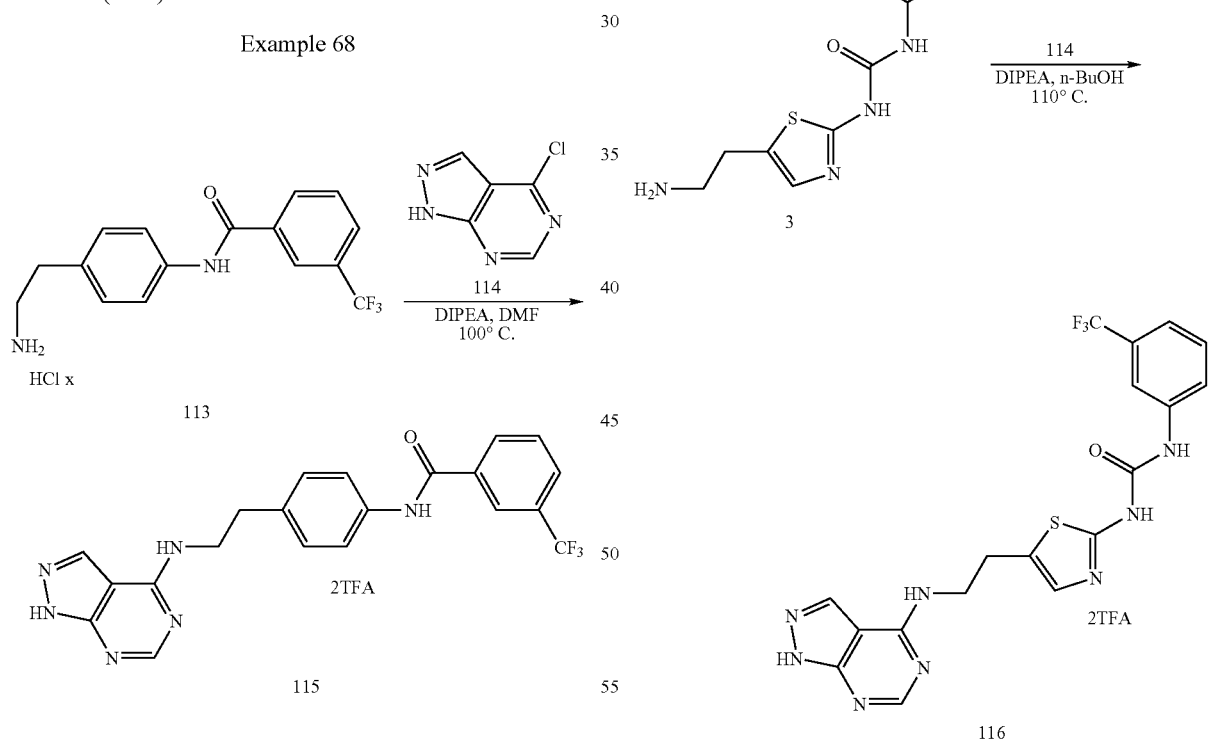

Compound 115: To a solution of 114 (0.22 g, 0.6 mmol) and DIPEA (0.34 mL, 1.9 mmol) in DMF (3.0 mL) was added 114 (0.10 g, 0.60 mmol, Chern, J.-H. et al. *Bioorg. Med. Chem. Lett.*, 2004, 2519). The resulting solution was stirred at 100° C. for 1 hour and was then cooled to room temperature. The solvents were removed under reduced pressure using high-vacuum and a heated water bath. The resulting residue was diluted with methanol and purified by prep HPLC to afford 115 (40 mg, 10%) as a white solid. ES (+) MS m/e=427 (M+1).

Example 69

Compound 116: A mixture of 3 (100 mg, 0.303 mmol), 114 (47 mg, 0.303 mmol), and DIPEA (1.0 mL) in n-butanol (1.0 mL) was stirred at 110° C. for 2 hours. The solution was then concentrated and the residue was purified by prep. RP-HPLC. The fractions containing pure compound were combined and concentrated. The residue thus obtained was lyophilized under high-vacuum to yield 40 mg of a solid. ES (+) MS m/e=449 (M+1).

Example 70

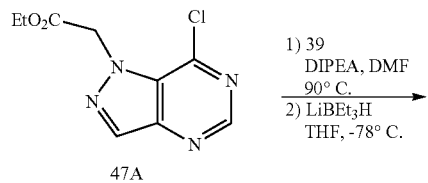

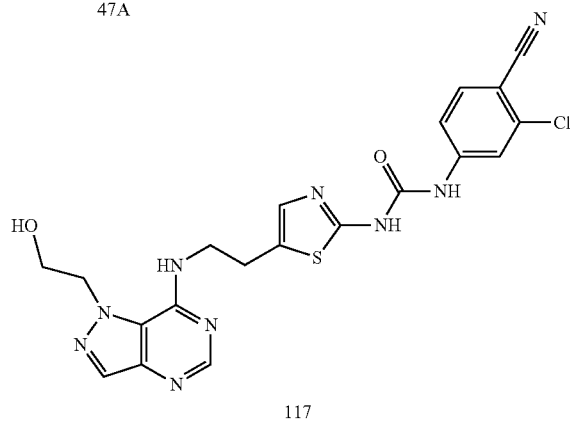

117

Compound 117: Add 39 (1.0 mmol) to a solution containing 47A (1.0 mmol) and Hunig's base (3.0 mmol) in DMF (10 mL). Heat the reaction mixture to 90° C. for 1 hour and cool to room temperature. Dilute the reaction mixture with $H_2O$. Extract the aqueous layer with EtOAc. Combine organics, dry with $MgSO_4$, filter and concentrate. Purify by column chromatography on silica gel using 10% MeOH in hexanes. Dilute the resulting residue with THF (10 mL) and cool to −78° C. Add $LiBEt_3H$ (2.0 mL, 1.0M in THF) to the reaction mixture. Stir the reaction mixture at −78° C. for 1 hour and warm to room temperature. Dilute the reaction mixture with 1M $NaHCO_3$ and extract with EtOAc. Combine organics, dry with $MgSO_4$, filter, and concentrate. Purify resulting residue by prep RP-HPLC to afford 117.

Example 71

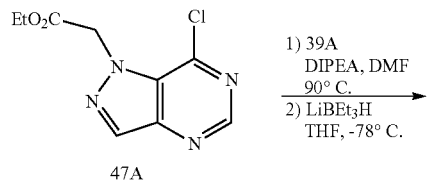

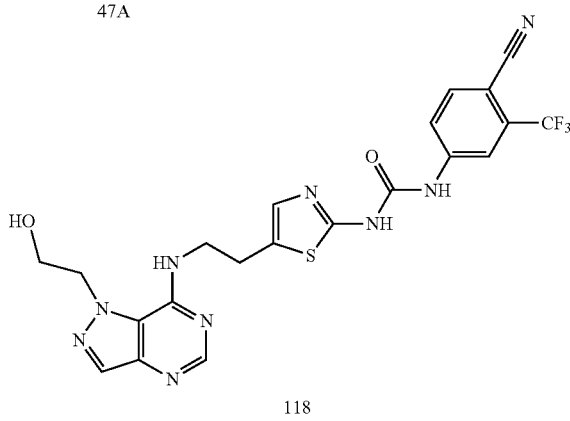

118

Compound 118: Add 39A (1.0 mmol) to a solution containing 47A (1.0 mmol) and Hunig's base (3.0 mmol) in DMF (10 mL). Heat the reaction mixture to 90° C. for 1 hour and cool to room temperature. Dilute the reaction mixture with $H_2O$. Extract the aqueous layer with EtOAc. Combine organics, dry with $MgSO_4$, filter and concentrate. Purify by column chromatography on silica gel using 10% MeOH in hexanes. Dilute the resulting residue with THF (10 mL) and cool to −78° C. Add $LiBEt_3H$ (2.0 mL, 1.0M in THF) to the reaction mixture. Stir the reaction mixture at −78° C. for 1 hour and warm to room temperature. Dilute the reaction mixture with 1M $NaHCO_3$ and extract with EtOAc. Combine organics, dry with $MgSO_4$, filter, and concentrate. Purify resulting residue by prep RP-HPLC to afford 118.

Example 72

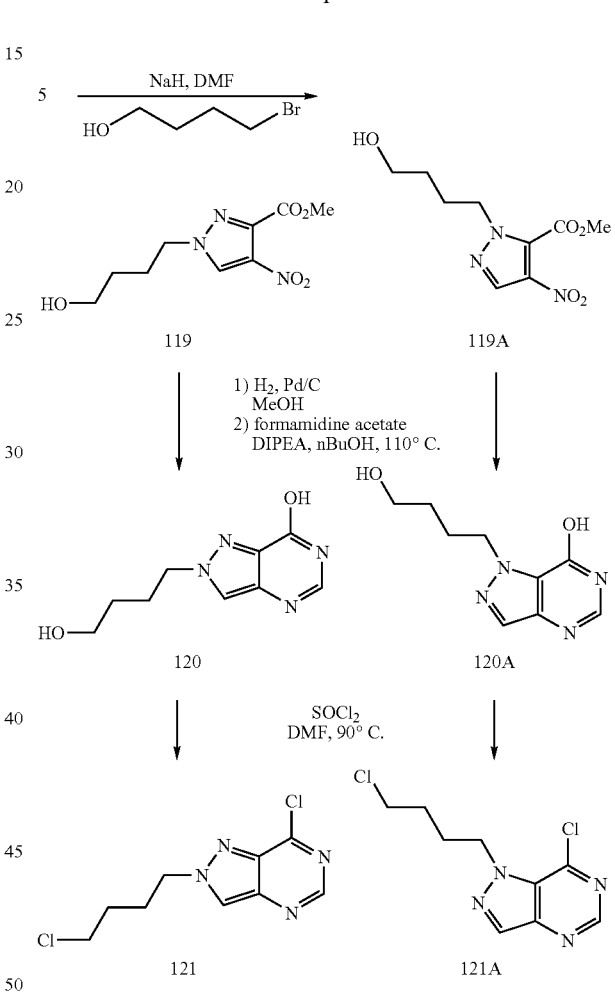

Compound 119 and 119A: Add 4-bromo-1-butanol (35.0 mmol) to a solution containing 1.4 (23.4 mmol) and 60% wt of NaH (35.0 mmol) in DMF (50 mL). Stir the reaction mixture for 2 hours. Dilute the reaction mixture with $H_2O$. Extract the aqueous layer with EtOAc. Combine organics, dry with $MgSO_4$, filter and concentrate. Purify the residue with column chromatography on silica gel to isolate both 63 and 64.

Compound 120: Combine 119 (12 mmol) and 10% wt of Pd/C (0.6 mmol) in MeOH (30 mL) with 1 atm $H_2$, via balloon. Stir the reaction mixture overnight. Filter the reaction mixture thru a plug of Celite and concentrate to afford residue. Dilute residue with n-butanol (25 mL) followed by Hunig's base (25 mL). Add formamidine acetate (13 mmol) and heat the reaction mixture to 110° C. for 1 hour. Cool the reaction mixture to room temperature and concentrate. Dilute the reaction mixture with H$_2$O and extract the aqueous layer with EtOAc. Combine organics, dry with MgSO$_4$, filter, and concentrate to afford 120.

Compound 120A: Combine 119A (6 mmol) and 10% wt of Pd/C (0.3 mmol) in MeOH (15 mL) with 1 atm H$_2$, via balloon. Stir the reaction mixture overnight. Filter the reaction mixture thru a plug of Celite and concentrate to afford residue. Dilute residue with n-butanol (13 mL) followed by Hunig's base (13 mL). Add formamidine acetate (8 mmol) and heat the reaction mixture to 110° C. for 1 hour. Cool the reaction mixture to room temperature and concentrate. Dilute the reaction mixture with H$_2$O and extract the aqueous layer with EtOAc. Combine organics, dry with MgSO$_4$, filter, and concentrate to afford 120A.

Compound 121: Add DMF (2.5 mL) to a solution containing 120 (7.6 mmol) in SOCl$_2$ (25 mL). Heat the heterogeneous reaction mixture to 90° C. for 30 minutes. Cool the homogeneous solution for room temperature. Concentrate the reaction mixture. Dilute with EtOAc, followed by ice. Separate the layers and extract the aqueous layer with EtOAc. Combine organics and wash with saturated NaHCO$_3$, followed by brine. Dry with MgSO$_4$, filter, and concentrate to afford 121.

Compound 121A: Add DMF (1.3 mL) to a solution containing 120A (3.8 mmol) in SOCl$_2$ (13 mL). Heat the heterogeneous reaction mixture to 90° C. for 30 minutes. Cool the homogeneous solution for room temperature. Concentrate the reaction mixture. Dilute with EtOAc, followed by ice. Separate the layers and extract the aqueous layer with EtOAc. Combine organics and wash with saturated NaHCO$_3$, followed by brine. Dry with MgSO$_4$, filter, and concentrate to afford 121A.

Example 73

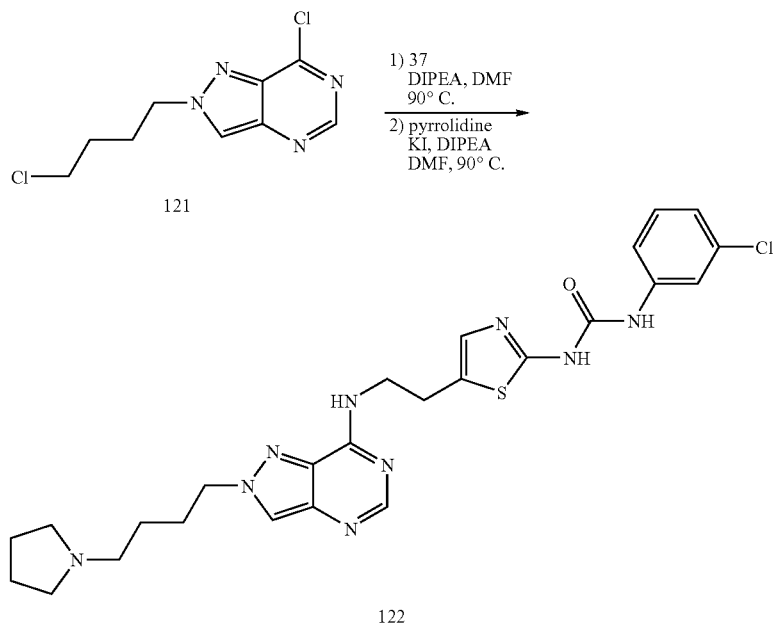

Compound 122: Add 37 (1.0 mmol) to a solution containing 121 (1.0 mmol) and Hunig's base (3.0 mmol) in DMF (10 mL). Heat the reaction mixture to 90° C. for 1 hour and cool to room temperature. Dilute the reaction mixture with H$_2$O. Extract the aqueous layer with EtOAc. Combine organics, dry with MgSO$_4$, filter and concentrate. Purify by column chromatography on silica gel using 10% MeOH in hexanes. Dilute the resulting residue in DMF (10 mL). Add KI (1.0 mmol), Hunig's base (1.0 mmol), and pyrrolidine (2.0 mmol). Heat the reaction mixture to 90° C. Cool the reaction mixture to room temperature. Dilute the reaction mixture with H$_2$O. Extract the aqueous layer with EtOAc. Combine organics, dry with MgSO$_4$, filter and concentrate. Purify resulting residue by prep RP-HPLC to afford 122.

Example 74

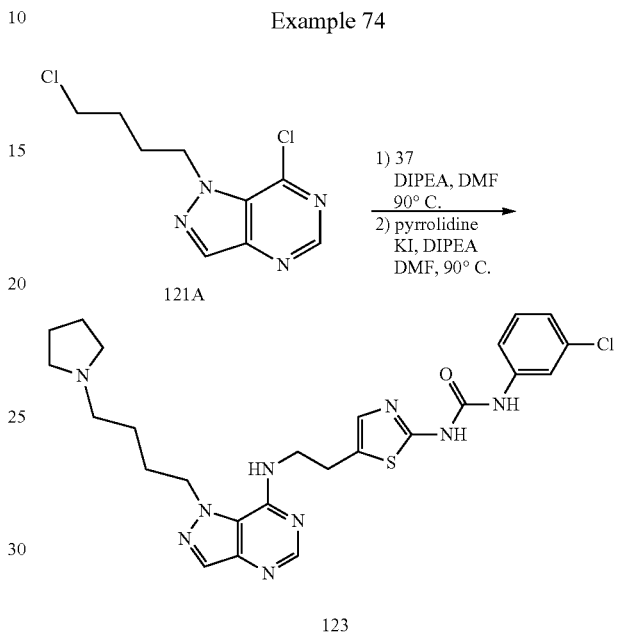

Compound 123: Add 37 (1.0 mmol) to a solution containing 121A (1.0 mmol) and Hunig's base (3.0 mmol) in DMF (10 mL). Heat the reaction mixture to 90° C. for 1 hour and cool to room temperature. Dilute the reaction mixture with H$_2$O. Extract the aqueous layer with EtOAc. Combine organics, dry with MgSO$_4$, filter and concentrate. Purify by column chromatography on silica gel using 10% MeOH in hexanes. Dilute the resulting residue in DMF (10 mL). Add KI (1.0 mmol), Hunig's base (1.0 mmol), and pyrrolidine (2.0 mmol). Heat the reaction mixture to 90° C. Cool the reaction mixture to room temperature. Dilute the reaction mixture with H$_2$O. Extract the aqueous layer with EtOAc. Combine organics, dry with MgSO$_4$, filter and concentrate. Purify resulting residue by prep RP-HPLC to afford 123.

Example 75

Formulation of Compounds

The solubility of poorly soluble compounds are improved by making them as acid salts. Illustrative examples of such acids include methane sulfonic acid and citric acid. Solubility of these compounds can be additionally improved by the addition of solubility enhancing agents such as Tween-80 and PEG-400. Illustrative formulations of poorly soluble compounds of the present invention include 10%/30%/60%, 5%/30%/65%, and 2.5%/30%/67.5% respectively of Tween-80, PEG-400 and water. The pH of these formulations can also be varied to identify a range for optimal solubility.

Example 76

Biochemical Assays (See FIG. 2)

Aurora A Kinase Assay

Aurora A protein kinase assays contained 10 mM Tris HCl, pH7.2, 10 mM MgCl$_2$, 0.1% BSA, 0.01% Triton X-100, 1 mM DTT, 20 µM ATP, 120 nM H3 peptide substrate, compound inhibitor (5% final DMSO concentration) and 25 nM Aurora A protein in a total volume of 40 µl. Reactions were incubated at room temperature for 60 min, stopped with 28 µl of 50 mM EDTA pH9, and further incubated at room temperature for 60 min. An equal volume of stopped reaction was incubated with detection buffer containing 50 mM HEPES pH 7.0, 0.5M KF, 0.1% BSA, 0.25 µg/mL α-Phospho H3 antibody, and 0.016 µM StreptAvidin-XL665 for 60 min, and subsequently read on the Analyst (LjL BioSystems) at excitation 330-370 nm, and detection 665 nm, 620 nm.

Aurora B Kinase Assay

Aurora B protein kinase assays contained 10 mM Tris HCl, pH7.2, 10 mM MgCl$_2$, 0.1% BSA, 0.01% Triton X-100, 1 mM DTT, 80 µM ATP, 120 nM H3 peptide substrate, compound inhibitor (5% final DMSO concentration) and 1.5 nM Aurora B protein in a total volume of 40 µl. Reactions were incubated at room temperature for 60 min, stopped with 28 µl of 50 mM EDTA pH9, and further incubated at room temperature for 60 min. An equal volume of stopped reaction was incubated with detection buffer containing 50 mM HEPES pH 7.0, 0.5M KF, 0.1% BSA, 0.25 µg/mL α-Phospho H3 antibody, and 0.016 µM StreptAvidin-XL665 for 60 min, and subsequently read on the Analyst (LjL BioSystems) at excitation 330-370 nm, and detection 665 nm, 620 nm.

HCS Cell Cycle Assay

The HCS Cell Cycle assay is used to measure the amount of cells with DNA content of 4N or greater. Inhibiting Aurora kinases in cells can cause failed mitosis and endoreduplication. This yields cells with 4N DNA content or greater.

Protocol: Plate 10,000 cells per well in a 96 well, clear bottom plate. (This assay is routinely done with HCT-116 cells, but has also been performed with a number of other adherent human cell lines.) Grow overnight. The next day, add compound to each well at the desired concentration. Incubate at 37° C. for 16 hours. Remove compound and fix cells with 4% Formaldehyde for 12 minutes at room temperature. Remove Formaldehyde and wash once with PBS. Add DNA stain in blocking solution (10% FBS in PBS) to the cells, and incubate for one hour at 37° C. Remove stain solution and wash cells one time with PBS. Visualize the cells on a high content imager to quantitate the DNA content of the cells.

Phospho-Histone H3 HCS Assay

The Phospho-Histone H3 HCS assay is done to measure a compounds ability to inhibit Aurora B in tumor cell lines. As Aurora B is inhibited, it is unable to phosphorylate Histone H3 on Serine 10, and this lack of phosphorylation can be measured by a high content imager.

Protocol: Plate 10,000 cells per well in a 96 well, clear bottom plate. (This assay is routinely done with HCT-116 cells, but has also been performed with a number of other adherent human cell lines.) Grow overnight. The next day, add compound to each well at the desired concentration. Incubate at 37° C. for one hour. Remove compound and fix cells with 4% Formaldehyde for 12 minutes at room temperature. Remove Formaldehyde and permeabilize cells with 0.1% Triton X-100 for 5 minutes at room temperature. Remove Triton X-100 and wash once with PBS. Block cells overnight with blocking solution (10% FBS in PBS) at 4° C. Remove blocking agent and add phospho-histone H3 Serine 10 antibody in blocking solution to the cells, and incubate for two hours at 37° C. Remove primary antibody solution and wash cells twice with PBS. Add a fluorescent antibody and DNA stain in blocking solution to the cells, and incubate for one hour at room temperature. Remove secondary antibody solution and wash cells three times with PBS. Visualize the cells on a high content imager to quantitate the levels of phospho-histone H3 Serine 10 in the cells.

Example 77

Target Modulation Studies (See FIG. 1).

Nu/nu mice are subcutaneously injected into their hind flank with human HCT-116 cells and 50% Matrigel (Becton-Dickinson). Human HCT-116 tumors are then allowed to grow to 400 mm$^3$. The tumor bearing mice are then either given an administration of SPD or vehicle (Sigma-Aldrich) (orally, intravenously or intraperitoneally). At prescribed time points post dose, mice are anesthetized and blood taken via terminal cardiac puncture, and sacrificed. The HCT-116 tumors are excised from the mice, pulverized using liquid nitrogen-cooled mortar and pestle, and flash-frozen in liquid nitrogen. Tumor lysates are made from the pulverized samples by addition of lysis buffer.

For detection of response markers by Western blotting, the protein concentration of the lysates is determined by calorimetric detection. Twenty-five micrograms of protein is loaded per lane on an SDS-PAGE gel. Proteins are separated by gel electrophoresis, blotted onto nitrocellulose membranes, and probed using anti-Histone H3 and anti-phosphorylated Histone H3 antibodies, (both from Cell Signaling Technology)

Example 78

Maximum Tolerated Dose Studies

Maximum Tolerated Dose (MTD) is defined as the dose at which the mouse is no longer able to function normally and is determined by either significant toxicity (e.g. body weight loss) or mortality. Mice (nu/nu) are sorted according to weight and randomized into groups prior to being dosed with a test compound, by oral, intravenous or intraperitoneal routes. Escalating doses of a test compound are used. Animal weights are measured daily for 5 days and about every 3 days after that until the animal is removed from the study due to body weight loss of >20% or any alterations in physiological function that would affect normal function. Clinical observations are performed throughout the study to note any toxicity and mice are monitored until the end of the study.

Example 79

Efficacy Studies

Nu/nu mice are subcutaneously injected into their hind flank with human HCT-116 cells and 50% Matrigel (Becton-Dickinson). Human HCT-116 tumors are allowed to grow to 150-200 mm$^3$. The tumor bearing mice are then either given an administration of a test compound or a vehicle control. The tumor dimensions (length [1 mm] and width [w mm]) are measured by electronic calipers and the tumor volume (mm$^3$) determined from the equation ([w$^2$×1]÷2). Weights of the mice and their respective tumor volumes are measured twice weekly until the animal is removed from the study, either because there is a body weight loss of greater than 20% or a tumor volume greater than 2000 mm$^3$. Clinical observations are performed throughout the study, which usually lasted for up to 70 days after the initial implantation of the tumor cells. Tumor volume increases are compared to negative (vehicle) and positive controls. Percentage tumor growth inhibition (TGI) is calculated from the equation [(tumor volume T−tumor volume)÷tumor volume C]×100, where T=treatment group and C=control or vehicle group. The tumor volume for both groups is usually determined at defined times after the administration of the last dose of compound. Survival plots (Kaplan-Maier) are also performed to examine the pattern of survival.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A compound having the structure:

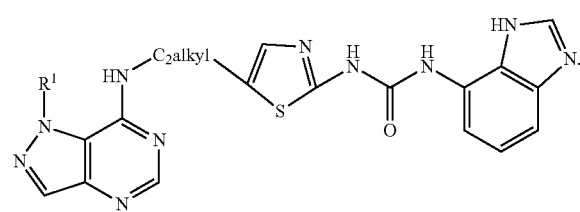

or a pharmaceutically acceptable salt thereof, wherein R$^1$ is hydrogen or phenyl.

2. A compound having the structure:

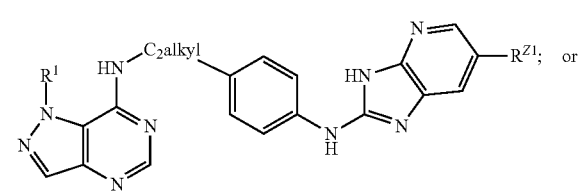

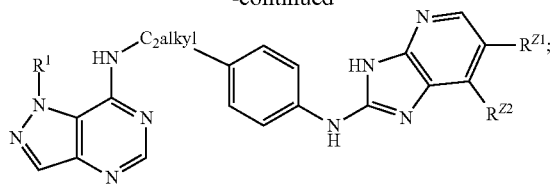

or a pharmaceutically acceptable salt thereof;
wherein R$^1$ is hydrogen or phenyl; and
R$^{Z1}$ and R$^{Z2}$ are independently halogen, lower alkyl or lower haloalkyl.

3. A compound having the structure:

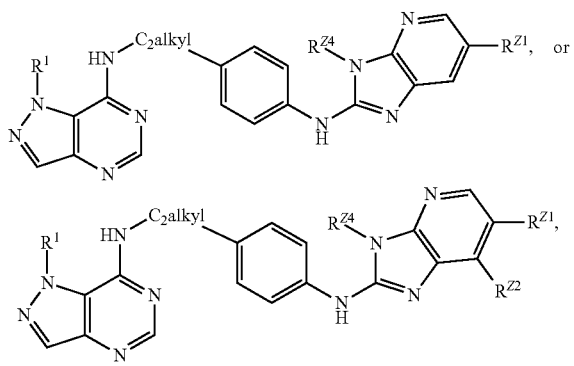

or a pharmaceutically acceptable salt thereof;
wherein R$^1$ is hydrogen or phenyl; and
R$^{Z1}$ and R$^{Z2}$ are independently halogen, lower alkyl or lower haloalkyl and R$^{Z4}$ is hydrogen or lower alkyl.

4. The compound of claim 3 wherein R$^{Z1}$ and R$^{Z2}$ are each Cl, F, methyl or —CF$_3$.

5. The compound of claim 3 wherein R$^{Z4}$ is hydrogen or isopropyl.

6. A compound having the structure:

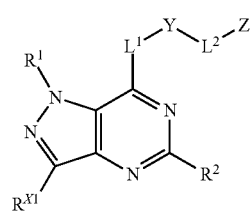

or a pharmaceutically acceptable salt thereof;
R$^1$ is hydrogen or phenyl;
R$^2$ is hydrogen, methyl, tert-butyl, or phenyl;
R$^{X1}$ is hydrogen or methyl;
L$^1$ is a 2-8 atom heteroaliphatic linker having at least one —NH—, —O— or —S— in the heteroaliphatic main chain;
L$^2$ is —NR$^{L2A}$—, —C(=O)NR$^{L2A}$—, —OC(=O)NR$^{L2A}$—, —NR$^{L2A}$NR$^{L2B}$—, —NR$^{L2A}$NR$^{L2B}$C(=O)—, —NR$^{L2A}$C(=O)—, —NR$^{L2A}$CO$_2$—, NR$^{L2A}$C(=O)NR$^{L2B}$—, —NR$^{L2A}$C(=O)NR$^{L2B}$CR$^{L2C}$R$^{L2D}$, —CR$^{L2C}$R$^{L2D}$C(=O)NR$^{L2B}$, —NR$^{L2A}$SO$_2$—, —SO$_2$NR$^{L2A}$—, —NR$^{L2A}$SO$_2$NR$^{L2B}$—, wherein each occurrence of R$^{L2A}$, R$^{L2B}$, R$^{L2C}$ and R$^{L2D}$ is independently hydrogen, C$_{1-6}$ alkyl, C$_{1-6}$ heteroalkyl, heterocyclyl, aryl, heteroaryl or acyl;

Y is an aromatic or heteroaromatic moiety; and
Z is an aliphatic or heteroaliphatic moiety; or
Z is cycloalkyl, cycloalkenyl, or a heterocyclyl, aryl or heteroaryl moiety having one of the structures:

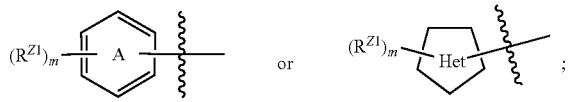

wherein the "A" cyclic moiety is a 6- to 10-membered mono- or fused bicyclic aromatic ring comprising from 0-4 nitrogen atoms; the "Het" moiety represents a fully or partially saturated or unsaturated 5- to 8-membered mono- or fused bicyclic ring comprising 1-4 heteroatoms selected from nitrogen, oxygen, and sulfur;

m is an integer from 0-6;

each $R^{Z1}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —$C(=O)N(R^{Z2})_2$, halogen, —CN, —$NO_2$, —C(=O)$OR^{Z2}$, —$N(R^{Z2})C(=O)R^{Z3}$ or —$N(R^{Z2})SO_2R^{Z4}$, or:

any two adjacent occurrence of $R^{Z1}$ may form a fused 5- to 6-membered aryl, heteroaryl or heterocyclic ring;

each $R^{Z2}$ and $R^{Z3}$ is independently hydrogen, $C_{1-6}$ alkyl, $C_{1-6}$ heteroalkyl, aryl, heteroaryl, -(alkyl)aryl, -(alkyl)heteroaryl, or acyl; or any two occurrences of $R^{Z2}$, taken together with the nitrogen atom to which they are attached, form a substituted or unsubstituted heterocyclic moiety; and $R^{Z4}$ is alkyl, heteroalkyl, aryl, heteroaryl, -(alkyl)aryl, or -(alkyl)heteroaryl.

7. The compound of claim 6 having the structure:

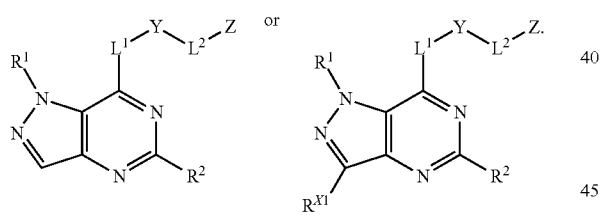

8. The compound of claim 6 wherein $R^1$ is hydrogen.
9. The compound of claim 6 wherein $L^2$ is —NHC(=O)NH—, —$CH_2$—C(=O)NH—, or —NHC(=O)NHCH$_2$—.
10. The compound of claim 6 wherein Z has one of the following structures:

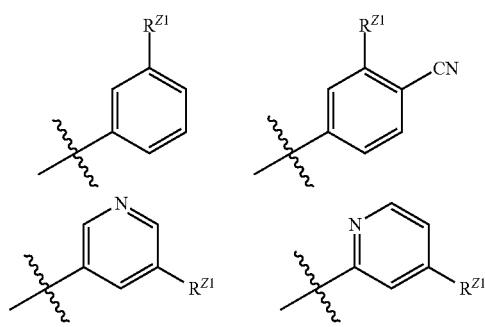

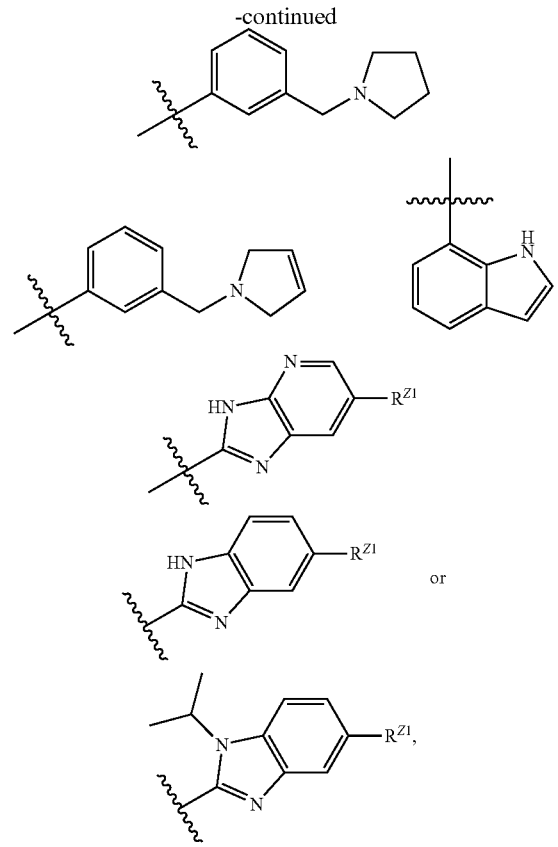

wherein $R^{Z1}$ is —Cl, —F, or —$CH_3$.

11. A compound having the structure:

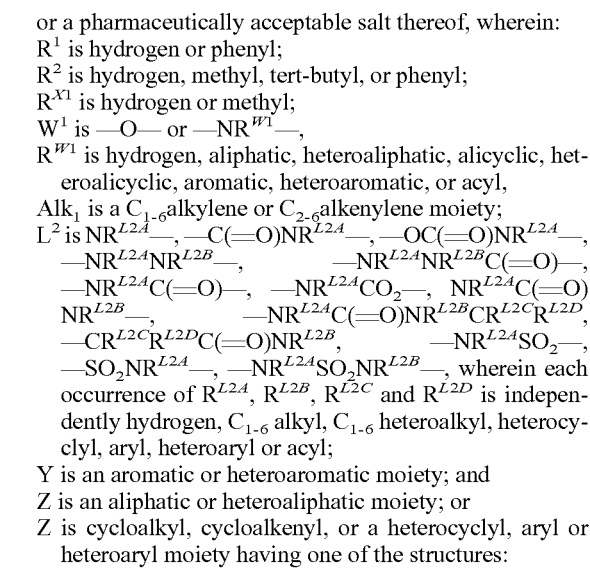

or a pharmaceutically acceptable salt thereof, wherein:
$R^1$ is hydrogen or phenyl;
$R^2$ is hydrogen, methyl, tert-butyl, or phenyl;
$R^{X1}$ is hydrogen or methyl;
$W^1$ is —O— or —$NR^{W1}$—,
$R^{W1}$ is hydrogen, aliphatic, heteroaliphatic, alicyclic, heteroalicyclic, aromatic, heteroaromatic, or acyl,
$Alk_1$ is a $C_{1-6}$alkylene or $C_{2-6}$alkenylene moiety;
$L^2$ is $NR^{L2A}$—, —C(=O)$NR^{L2A}$—, —OC(=O)$NR^{L2A}$—, —$NR^{L2A}NR^{L2B}$—, —$NR^{L2A}NR^{L2B}$C(=O)—, —$NR^{L2A}$C(=O)—, —$NR^{L2A}CO_2$—, $NR^{L2A}$C(=O)$NR^{L2B}$—, —$NR^{L2A}$C(=O)$NR^{L2B}CR^{L2C}R^{L2D}$, —$CR^{L2C}R^{L2D}$C(=O)$NR^{L2B}$, —$NR^{L2A}SO_2$—, —$SO_2NR^{L2A}$—, —$NR^{L2A}SO_2NR^{L2B}$—, wherein each occurrence of $R^{L2A}$, $R^{L2B}$, $R^{L2C}$ and $R^{L2D}$ is independently hydrogen, $C_{1-6}$ alkyl, $C_{1-6}$ heteroalkyl, heterocyclyl, aryl, heteroaryl or acyl;
Y is an aromatic or heteroaromatic moiety; and
Z is an aliphatic or heteroaliphatic moiety; or
Z is cycloalkyl, cycloalkenyl, or a heterocyclyl, aryl or heteroaryl moiety having one of the structures:

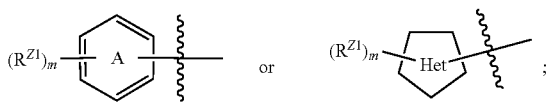

wherein the "A" cyclic moiety is a 6- to 10-membered mono- or fused bicyclic aromatic ring comprising from 0-4 nitrogen atoms;

the "Het" moiety represents a fully or partially saturated or unsaturated 5- to 8-membered mono- or fused bicyclic ring comprising 1-4 heteroatoms selected from nitrogen, oxygen, and sulfur;

m is an integer from 0-6; and each $R^{Z1}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —$C(=O)N(R^{Z2})_2$, halogen, —CN, —$NO_2$, —$C(=O)OR^{Z2}$, —$N(R^{Z2})C(=O)R^{Z3}$ or —$N(R^{Z2})SO_2R^{Z4}$, or:

any two adjacent $R^{Z1}$ groups may form a fused 5- to 6-membered aryl, heteroaryl or heterocyclic ring;

each $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached, form a substituted or unsubstituted heterocyclic moiety; and $R^{Z4}$ is alkyl, heteroalkyl, aryl, heteroaryl, -(alkyl)aryl, or -(alkyl)heteroaryl.

12. The compound of claim 11 having the structure:

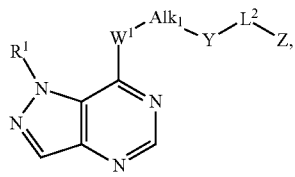

wherein:
$W^1$ is —O— or —$NR^{W1}$—; and
$R^{W1}$ is hydrogen, $C_{1-6}$ alkyl, $C_{1-6}$ heteroalkyl, aryl, heteroaryl, -(alkyl)aryl, -(alkyl)heteroaryl, or acyl.

13. The compound of claim 12 wherein —$W^1$-$Alk_1$- is —NH—$C_{1-6}$alkyl- or —O—$C_{1-6}$alkyl-.

14. The compound of claim 13 wherein —$W^1$-$Alk_1$- is —$NHCH_2CH_2$— or —$OCH_2CH_2$—.

15. The compound of claim 11 wherein $L^2$ is —NHC(=O)NH—, —$CH_2$—C(=O)NH—, or —NHC(=O)$NHCH_2$—.

16. The compound of claim 11 having the structure:

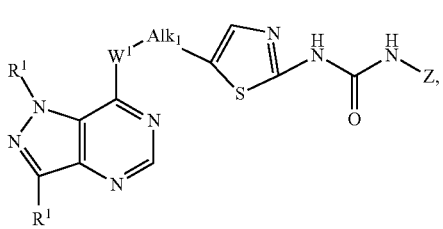

wherein:
$W^1$ is —O— or —$NR^{W1}$—,
$R^{W1}$ is hydrogen, $C_{1-6}$ alkyl, $C_{1-6}$ heteroalkyl, aryl, heteroaryl, -(alkyl)aryl, -(alkyl)heteroaryl, or acyl;

Z is a heterocyclyl, aryl or heteroaryl moiety having one of the structures:

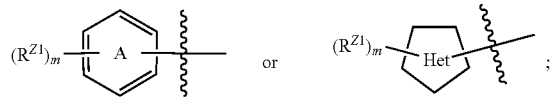

wherein the "A" cyclic moiety is a 6- to 10-membered mono- or fused bicyclic aromatic ring comprising from 0-4 nitrogen atoms;

the "Het" moiety represents a fully or partially saturated or unsaturated 5- to 8-membered mono- or fused bicyclic ring comprising 1-4 heteroatoms selected from nitrogen, oxygen, and sulfur;

m is an integer from 0-6; and each $R^{Z1}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —$C(=O)N(R^{Z2})_2$, halogen, —CN, —$NO_2$, —$C(=O)OR^{Z2}$, —$N(R^{Z2})C(=O)R^{Z3}$ or —$N(R^{Z2})SO_2R^{Z4}$, or:

any two adjacent $R^{Z1}$ groups may form a fused 5- to 6-membered aryl, heteroaryl or heterocyclic ring;

each $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached, form a substituted or unsubstituted heterocyclic moiety; and $R^{Z4}$ is alkyl, heteroalkyl, aryl, heteroaryl, -(alkyl)aryl, or -(alkyl)heteroaryl.

17. The compound of claim 16 wherein $R^{X1}$ is hydrogen.

18. The compound of claim 16 having the structure:

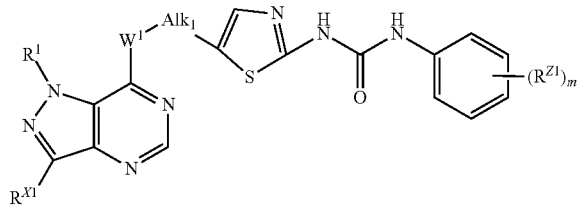

wherein:
m is an integer from 0 to 3; and
each $R^{Z1}$ is independently hydrogen, alkyl, heteroalkyl, aryl, heteroaryl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —$C(=O)N(R^{Z2})_2$, halogen, —CN, —$NO_2$, —$C(=O)OR^{Z2}$, or —$N(R^{Z2})C(=O)R^{Z3}$.

19. The compound of claim 18, wherein $W^1$ is —$NR^{W1}$—.

20. The compound of claim 18 having the structure:

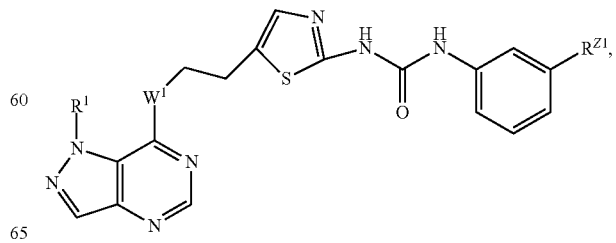

wherein:

W¹ is —O— or —NH—; and $R^{Z1}$ is halogen or $C_{1-6}$ alkyl.

21. The compound of claim 20 wherein W¹ is —NH—.

22. The compound of claim 16 having the structure:

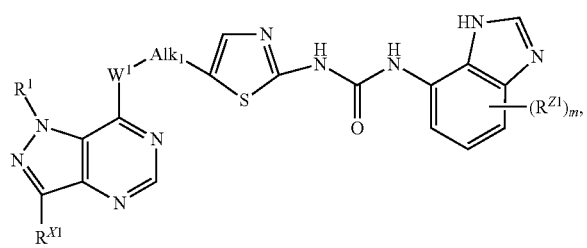

wherein:

m is an integer from 0 to 3; and each $R^{Z1}$ is independently hydrogen, alkyl, heteroalkyl, aryl, heteroaryl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —C(=O)N$(R^{Z2})_2$, halogen, —CN, —$NO_2$, —C(=O)$OR^{Z2}$, or —N$(R^{Z2})$C(=O)$R^{Z3}$.

23. The compound of claim 22, wherein R¹ is hydrogen and m is 0.

24. The compound of claim 11 having the structure:

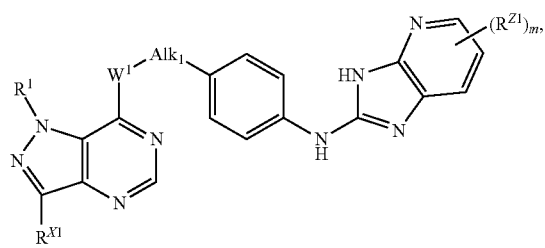

wherein:

m is an integer from 0 to 3; and each $R^{Z1}$ is independently hydrogen, alkyl, heteroalkyl, aryl, heteroaryl, -(alkyl)aryl, -(alkyl)heteroaryl, —$OR^{Z2}$, $SR^{Z2}$, —$N(R^{Z2})_2$, —$SO_2N(R^{Z2})_2$, —$SO_2R^{Z4}$, —C(=O)N$(R^{Z2})_2$, halogen, —CN, —$NO_2$, —C(=O)$OR^{Z2}$, or —N$(R^{Z2})$C(=O)$R^{Z3}$.

25. The compound of claim 24, wherein W¹ is $NR^{W1}$.

26. A compound having the structure:

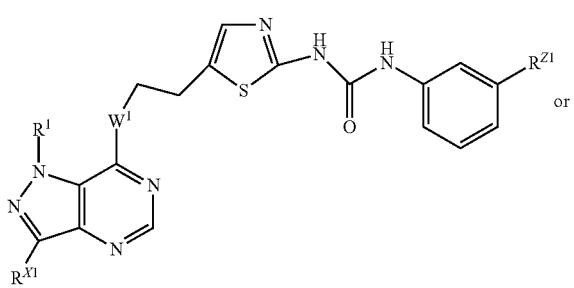

or

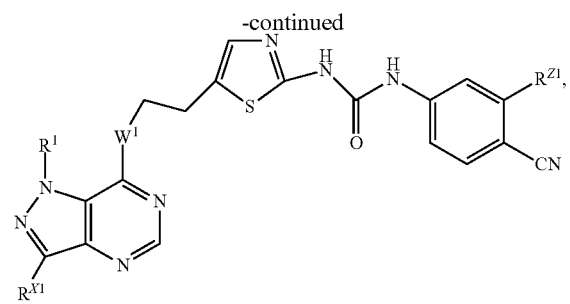

-continued or a pharmaceutically acceptable salt thereof, wherein:

R¹ is hydrogen;

$R^{X1}$ is hydrogen or methyl;

W¹ is —NH— or —O—; and $R^{Z1}$ is halogen, $C_{1-6}$ alkyl, or $C_{1-6}$ haloalkyl.

27. The compound of claim 26, wherein $R^{Z1}$ is —Cl, —F, —$CH_3$, or —$CF_3$.

28. A compound having the structure:

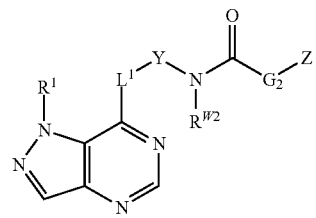

or a pharmaceutically acceptable salt thereof, wherein:

R¹ is hydrogen or phenyl;

L¹ is a 2-8 atom heteroaliphatic linker having at least one —NH—, —O— or —S— in the heteroaliphatic main chain;

Y is an aromatic or heteroaromatic moiety;

Z is an aliphatic or heteroaliphatic moiety; or

Z is cycloalkyl, cycloalkenyl, or a heterocyclyl, aryl or heteroaryl moiety having one of the structures:

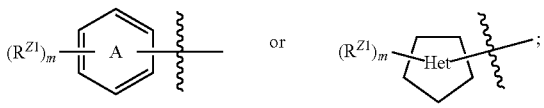

wherein the "A" cyclic moiety is a 6- to 10-membered mono- or fused bicyclic aromatic ring comprising from 0-4 nitrogen atoms; the "Het" moiety represents a fully or partially saturated or unsaturated 5- to 8-membered mono- or fused bicyclic ring comprising 1-4 heteroatoms selected from nitrogen, oxygen, and sulfur;

m is an integer from 0-6;

each $R^{Z1}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —C(=O)N$(R^{Z2})_2$, halogen, —CN, —$NO_2$, —C(=O)$OR^{Z2}$, —N$(R^{Z2})$C(=O)$R^{Z3}$ or —N$(R^{Z2})SO_2R^{Z4}$, or:

any two adjacent occurrence of $R^{Z1}$ may form a fused 5- to 6-membered aryl, heteroaryl or heterocyclic ring;

each $R^{Z2}$ and $R^{Z3}$ is independently hydrogen, $C_{1-6}$ alkyl, $C_{1-6}$ heteroalkyl, aryl, heteroaryl, -(alkyl)aryl, -(alkyl)heteroaryl, or acyl; or any two occurrences of $R^{Z2}$, taken together with the nitrogen atom to which they are attached, form a substituted or unsubstituted heterocyclic moiety; and $R^{Z4}$ is alkyl, heteroalkyl, aryl, heteroaryl, -(alkyl)aryl, or -(alkyl)heteroaryl;

$G_2$ is a bond, O or $NR^{G2}$; and $R^{W2}$ and $R^{G2}$ are independently hydrogen, lower alkyl, lower heteroalkyl, heterocyclyl, aryl, heteroaryl, -(alkyl)aryl, -(alkyl)heteroaryl or acyl.

29. The compound of claim 28, wherein —N($R^{W2}$)C(═O)$G_2$- is —NHC(═O)—, —NHC(═O)O—, or —NHC(═O)NH—.

30. The compound of claim 29, wherein —N($R^{W2}$)C(═O)$G_2$- is —NHC(═O)NH—.

31. A compound having the structure:

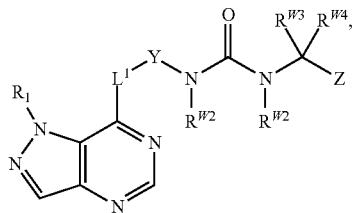

or a pharmaceutically acceptable salt thereof, wherein:
$R^1$ is hydrogen or phenyl;
$L^1$ is a 2-8 atom heteroaliphatic linker having at least one —NH—, —O— or —S— in the heteroaliphatic main chain;
Y is an aromatic or heteroaromatic moiety;
Z is an aliphatic or heteroaliphatic moiety; or
Z is cycloalkyl, cycloalkenyl, or a heterocyclyl, aryl or heteroaryl moiety having one of the structures:

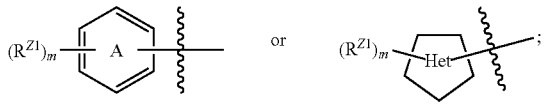

wherein the "A" cyclic moiety is a 6- to 10-membered mono- or fused bicyclic aromatic ring comprising from 0-4 nitrogen atoms; the "Het" moiety represents a fully or partially saturated or unsaturated 5- to 8-membered mono- or fused bicyclic ring comprising 1-4 heteroatoms selected from nitrogen, oxygen, and sulfur;
m is an integer from 0-6;
each $R^{Z1}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —$OR^{Z2}$, —$SR^{Z2}$, —N($R^{Z2}$)$_2$, —$SO_2$N($R^{Z2}$)$_2$, —$SO_2R^{Z4}$, —C(═O)N($R^{Z2}$)$_2$, halogen, —CN, —$NO_2$, —C(═O)$OR^{Z2}$, —N($R^{Z2}$)C(═O)$R^{Z3}$ or —N($R^{Z2}$)$SO_2R^{Z4}$, or:
any two adjacent occurrences of $R^{Z1}$ may form a fused 5- to 6-membered aryl, heteroaryl or heterocyclic ring;
each $R^{Z2}$ and $R^{Z3}$ is independently hydrogen, $C_{1-6}$ alkyl, $C_{1-6}$ heteroalkyl, aryl, heteroaryl, -(alkyl)aryl, -(alkyl)heteroaryl, or acyl; or any two occurrences of $R^{Z2}$, taken together with the nitrogen atom to which they are attached, form a substituted or unsubstituted heterocyclic moiety; and
$R^{Z4}$ is alkyl, heteroalkyl, aryl, heteroaryl, -(alkyl)aryl, or -(alkyl)heteroaryl; and
$R^{W2}$, $R^{W3}$ and $R^{W4}$ are independently hydrogen, lower alkyl, lower heteroalkyl, heterocyclyl, aryl, heteroaryl, -(alkyl)aryl, -(alkyl)heteroaryl, or acyl.

32. The compound of claim 31, wherein —N($R^{W2}$)C(═O)N($R^{W2}$)$CR^{W3}R^{W4}$— is —NHC(═O)NHCH$_2$—.

33. A compound having the structure:

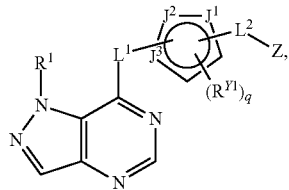

or a pharmaceutically acceptable salt thereof, wherein:
q is an integer from 0-2;
$R^1$ is hydrogen or phenyl;
$L^1$ is a 2-8 atom heteroaliphatic linker having at least one —NH—, —O— or —S— in the heteroaliphatic main chain;
$L^2$ is $NR^{L2A}$—, —C(═O)$NR^{L2A}$—, —OC(═O)$NR^{L2A}$—, —$NR^{L2A}NR^{L2B}$—, —$NR^{L2A}NR^{L2B}$C(═O)—, —$NR^{L2A}$C(═O)—, —$NR^{L2A}CO_2$—, —$NR^{L2A}$C(═O)$NR^{L2B}$—, —$NR^{L2A}$C(═O)$NR^{L2B}CR^{L2C}R^{L2D}$—, —$CR^{L2C}R^{L2D}$C(═O)$NR^{L2B}$—, —$NR^{L2A}SO_2$—, —$SO_2NR^{L2A}$—, —$NR^{L2A}SO_2NR^{L2B}$—, wherein each occurrence of $R^{L2A}$, $R^{L2B}$, $R^{L2C}$ and $R^{L2D}$ is independently hydrogen, $C_{1-6}$ alkyl, $C_{1-6}$ heteroalkyl, heterocyclyl, aryl, heteroaryl or acyl;
Z is an aliphatic or heteroaliphatic moiety; or
Z is cycloalkyl, cycloalkenyl, or a heterocyclyl, aryl or heteroaryl moiety having one of the structures:

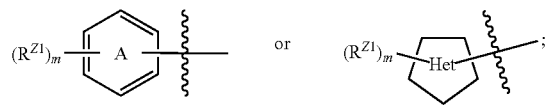

wherein the "A" cyclic moiety is a 6- to 10-membered mono- or fused bicyclic aromatic ring comprising from 0-4 nitrogen atoms; the "Het" moiety represents a fully or partially saturated or unsaturated 5- to 8-membered mono- or fused bicyclic ring comprising 1-4 heteroatoms selected from nitrogen, oxygen, and sulfur;
m is an integer from 0-6;
each $R^{Z1}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —$OR^{Z2}$, —$SR^{Z2}$, —N($R^{Z2}$)$_2$, —$SO_2$N($R^{Z2}$)$_2$, —$SO_2R^{Z4}$, —C(═O)N($R^{Z2}$)$_2$, halogen, —CN, —$NO_2$, —C(═O)$OR^{Z2}$, —N($R^{Z2}$)C(═O)$R^{Z3}$ or —N($R^{Z2}$)$SO_2R^{Z4}$, or:
any two adjacent occurrences of $R^{Z1}$ may form a fused 5- to 6-membered aryl, heteroaryl or heterocyclic ring;
each $R^{Z2}$ and $R^{Z3}$ is independently hydrogen, $C_{1-6}$ alkyl, $C_{1-6}$ heteroalkyl, aryl, heteroaryl, -(alkyl)aryl, -(alkyl)heteroaryl, or acyl; or any two occurrences of $R^{Z2}$, taken together with the nitrogen atom to which they are attached, form a substituted or unsubstituted heterocyclic moiety; and
$R^{Z4}$ is alkyl, heteroalkyl, aryl, heteroaryl, -(alkyl)aryl, or -(alkyl)heteroaryl; and
$J^1$, $J^2$ and $J^3$ are independently O, S, N, $NR^{Y1}$ or $CR^{Y1}$;
each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —C(═O)$NR^{Y2}R^{Y3}$, halogen, —CN, —$NO_2$, —C(═O)$OR^{Y3}$, —N($R^{Y2}$)C(═O)$R^{Y3}$;

each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or:

$R^{Y2}$ and $R^{Y3}$ taken together with the nitrogen atom to which they are attached form a 5-6 membered heterocyclic ring.

34. The compound of claim 33 having the structure:

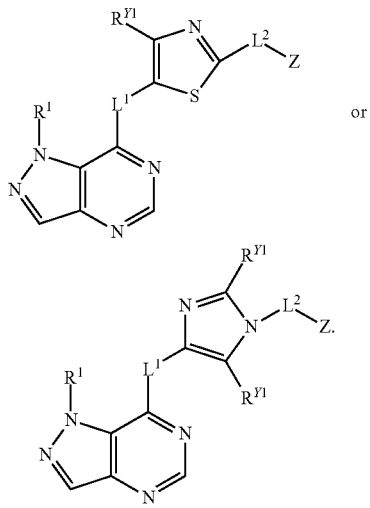

or

35. A compound having the structure:

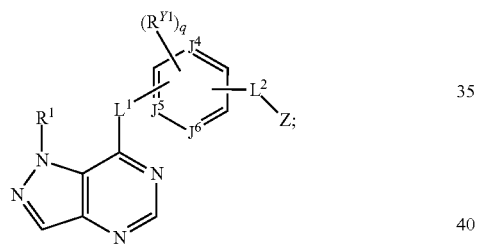

or a pharmaceutically acceptable salt thereof, wherein:

$R^1$ is hydrogen or phenyl;

$L^1$ is a 2-8 atom heteroaliphatic linker having at least one —NH—, —O— or —S— in the heteroaliphatic main chain;

$L^2$ is $NR^{L2A}$—, —C(=O)$NR^{L2A}$—, —OC(=O)$NR^{L2A}$—, —$NR^{L2A}NR^{L2B}$—, —$NR^{L2A}NR^{L2B}$C(=O)—, —$NR^{L2A}$C(=O)—, —$NR^{L2A}CO_2$—, $NR^{L2A}$C(=O)$NR^{L2B}$—, —$NR^{L2A}$C(=O)$NR^{L2B}CR^{L2C}R^{L2D}$—, —$CR^{L2C}R^{L2D}$C(=O)$NR^{L2B}$—, —$NR^{L2A}SO_2$—, —$SO_2NR^{L2A}$—, —$NR^{L2A}SO_2NR^{L2B}$—, wherein each occurrence of $R^{L2A}$, $R^{L2B}$, $R^{L2C}$ and $R^{L2D}$ is independently hydrogen, $C_{1-6}$ alkyl, $C_{1-6}$ heteroalkyl, heterocyclyl, aryl, heteroaryl or acyl;

Z is an aliphatic or heteroaliphatic moiety; or

Z is cycloalkyl, cycloalkenyl, or a heterocyclyl, aryl or heteroaryl moiety having one of the structures:

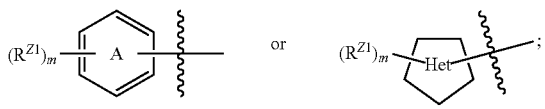

wherein the "A" cyclic moiety is a 6- to 10-membered mono- or fused bicyclic aromatic ring comprising from 0-4 nitrogen atoms; the "Het" moiety represents a fully or partially saturated or unsaturated 5- to 8-membered mono- or fused bicyclic ring comprising 1-4 heteroatoms selected from nitrogen, oxygen, and sulfur;

m is an integer from 0-6;

each $R^{Z1}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —C(=O)$N(R^{Z2})_2$, halogen, —CN, —$NO_2$, —C(=O)$OR^{Z2}$, —$N(R^{Z2})C(=O)R^{Z3}$ or —$N(R^{Z2})SO_2R^{Z4}$, or:

any two adjacent occurrences of $R^{Z1}$ may form a fused 5- to 6-membered aryl, heteroaryl or heterocyclic ring;

each $R^{Z2}$ and $R^{Z3}$ is independently hydrogen, $C_{1-6}$ alkyl, $C_{1-6}$ heteroalkyl, aryl, heteroaryl, -(alkyl)aryl, -(alkyl)heteroaryl, or acyl; or any two occurrences of $R^{Z2}$, taken together with the nitrogen atom to which they are attached, form a substituted or unsubstituted heterocyclic moiety; and $R^{Z4}$ is alkyl, heteroalkyl, aryl, heteroaryl, -(alkyl)aryl, or -(alkyl)heteroaryl; and $J^4$, $J^5$ and $J^6$ are independently N or $CR^{Y1}$;

q is an integer from 0-3;

each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —C(=O)$NR^{Y2}R^{Y3}$, halogen, —CN, —$NO_2$, —C(=O)$OR^{Y3}$, —$N(R^{Y2})C(=O)R^{Y3}$;

each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or:

$R^{Y2}$ and $R^{Y3}$ taken together with the nitrogen atom to which they are attached form a 5-6 membered heterocyclic ring.

36. The compound of claim 35 having the structure:

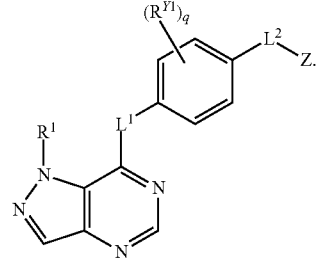

37. The compound of claim 35 having the structure:

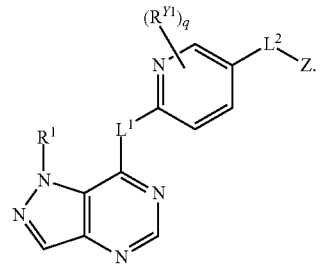

38. A composition comprising an effective amount of a compound of any one of claim 2, 3, 6, 11, 26, 28, 31, 33, or 35, and a pharmaceutically acceptable carrier, adjuvant, or vehicle.

39. The composition of claim 38, wherein the compound is in an amount to detectably inhibit Aurora protein kinase activity.

* * * * *